(12) United States Patent
Rees

(10) Patent No.: US 9,549,740 B2
(45) Date of Patent: Jan. 24, 2017

(54) DEVICE AND METHOD FOR FILLING OF ANEURYSM OR BODY CAVITY

(71) Applicant: Interventco LLC, Dallas, TX (US)

(72) Inventor: Chet R. Rees, Dallas, TX (US)

(73) Assignee: Interventco LLC, Dallas, TX (US)

( * ) Notice: Subject to any disclaimer, the term of this patent is extended or adjusted under 35 U.S.C. 154(b) by 120 days.

(21) Appl. No.: 13/887,777

(22) Filed: May 6, 2013

(65) Prior Publication Data
US 2013/0296917 A1 Nov. 7, 2013

Related U.S. Application Data

(60) Provisional application No. 61/642,762, filed on May 4, 2012, provisional application No. 61/660,930, filed on Jun. 18, 2012.

(51) Int. Cl.
*A61M 29/00* (2006.01)
*A61B 17/12* (2006.01)

(52) U.S. Cl.
CPC ....... *A61B 17/1215* (2013.01); *A61B 17/1214* (2013.01); *A61B 17/12022* (2013.01);
(Continued)

(58) Field of Classification Search
CPC ............... A61B 2017/12063; A61B 17/12022; A61B 17/12068; A61B 17/12081; A61B 17/12086; A61B 17/1209; A61B 2017/1205; A61B 2017/12054; A61B 2017/1209; A61B 2017/12059; A61B 2017/12068; A61B 17/12113; A61B 17/1214; A61B 2018/1266; A61F 2/95; A61F 2/2427; A61F 2/2466; A61F 2002/011; A61N 1/18; A61N 1/20; A61N 1/32; A61N 1/44
(Continued)

(56) References Cited

U.S. PATENT DOCUMENTS 5,122,136 A 6/1992 Guglielmi et al.
5,540,680 A 7/1996 Guglielmi
(Continued)

FOREIGN PATENT DOCUMENTS

EP 2 216 068 A1 8/2010
JP 2009 285151 A 12/2009
(Continued)

OTHER PUBLICATIONS

International Search Report for corresponding application PCT/US2013/039600 dated Sep. 17, 2013.
(Continued)

*Primary Examiner* — Melanie Tyson
*Assistant Examiner* — Majid Jamialahmadi
(74) *Attorney, Agent, or Firm* — Woodard, Emhardt, Moriarty, McNett & Henry LLP

(57) ABSTRACT

The invention relates generally to embolic agents and embolic delivery systems more specifically it relates to a device and method for filling of aneurysm or body cavity. In various embodiments, segmented and monolithic embolic agents provide the operator with the ability to select and detach the length of embolic agent, either extracorporeally or intracorporeally as desired by the operator, for implantation into the aneurysm or body cavity. Linking elements and detachment elements may be utilized by the operator to connect and detach variable lengths of embolic agents either extracorporeally or intracorporeally utilizing electrolytic, chemical, and mechanical detachment mechanisms. Embolic delivery systems are disclosed providing for constant and steady propulsion of the embolic agent.

29 Claims, 89 Drawing Sheets

(52) U.S. Cl.
CPC .. *A61B 17/12113* (2013.01); *A61B 17/12154* (2013.01); *A61B 17/12163* (2013.01); *A61B 2017/1205* (2013.01); *A61B 2017/12054* (2013.01); *A61B 2017/12059* (2013.01); *A61B 2017/12063* (2013.01); *A61B 2017/12068* (2013.01); *A61B 2017/12081* (2013.01); *A61B 2017/12095* (2013.01)

(58) Field of Classification Search
USPC ............... 606/108, 200, 191; 623/1.11, 2.11
See application file for complete search history.

(56) References Cited

U.S. PATENT DOCUMENTS

| | | | |
|---|---|---|---|
| 5,941,888 A * | 8/1999 | Wallace | A61B 17/12022 606/108 |
| 6,059,779 A | 5/2000 | Mills | |
| 6,077,260 A * | 6/2000 | Wheelock et al. | 606/32 |
| 6,159,206 A | 12/2000 | Ogawa | |
| 6,299,619 B1 | 10/2001 | Greene | |
| 6,312,421 B1 | 11/2001 | Boock | |
| 6,692,510 B2 | 2/2004 | West | |
| 6,984,240 B1 | 1/2006 | Ken | |
| 7,410,482 B2 * | 8/2008 | Murphy et al. | 606/1 |
| 8,048,104 B2 | 11/2011 | Monstadt | |
| 2001/0056281 A1 | 12/2001 | Wallace et al. | |
| 2002/0138096 A1 | 9/2002 | Hieshima | |
| 2004/0186464 A1 | 9/2004 | Mamayek et al. | |
| 2004/0225279 A1 | 11/2004 | Raymond | |
| 2006/0135986 A1 * | 6/2006 | Wallace | A61B 17/12113 606/200 |
| 2007/0060879 A1 | 3/2007 | Weitzner et al. | |
| 2007/0083226 A1 | 4/2007 | Bruiser et al. | |
| 2007/0123928 A1 * | 5/2007 | Farnan | A61B 17/12022 606/200 |
| 2008/0109057 A1 | 5/2008 | Calabria et al. | |
| 2009/0024133 A1 | 1/2009 | Keady et al. | |
| 2009/0062726 A1 | 3/2009 | Ford et al. | |
| 2009/0143786 A1 | 6/2009 | Bashiri et al. | |
| 2009/0177261 A1 * | 7/2009 | Teoh | A61B 17/12022 623/1.11 |
| 2010/0076479 A1 | 3/2010 | Monstadt | |
| 2010/0174290 A1 | 7/2010 | Wuebbeling et al. | |
| 2010/0268204 A1 | 10/2010 | Tieu et al. | |
| 2011/0028941 A1 | 2/2011 | Nagano et al. | |
| 2011/0238148 A1 | 9/2011 | Monstadt et al. | |
| 2012/0071752 A1 | 3/2012 | Sewell et al. | |
| 2012/0158034 A1 * | 6/2012 | Wilson | A61B 17/12113 606/192 |

FOREIGN PATENT DOCUMENTS

| | | |
|---|---|---|
| WO | WO 83/04182 | 12/1983 |
| WO | WO 98/30266 | 7/1998 |
| WO | WO 99/42038 | 8/1999 |
| WO | WO 99/55239 | 11/1999 |
| WO | WO 02/096301 A1 | 12/2002 |
| WO | WO 2004/045363 A2 | 6/2004 |
| WO | WO 2005/070308 A2 | 8/2005 |
| WO | WO 2006/076537 A2 | 7/2006 |

OTHER PUBLICATIONS

Written Opinion of the International Searching Authority for corresponding application PCT/US2013/039600 dated Sep. 17, 2013.

* cited by examiner

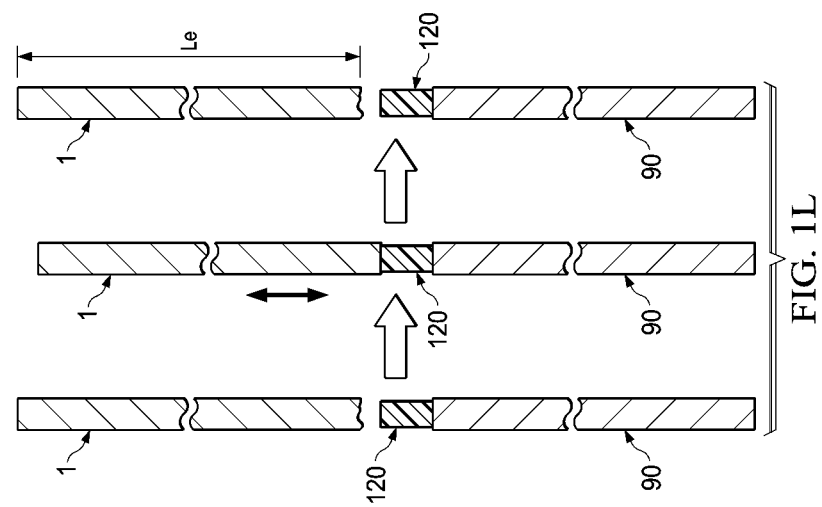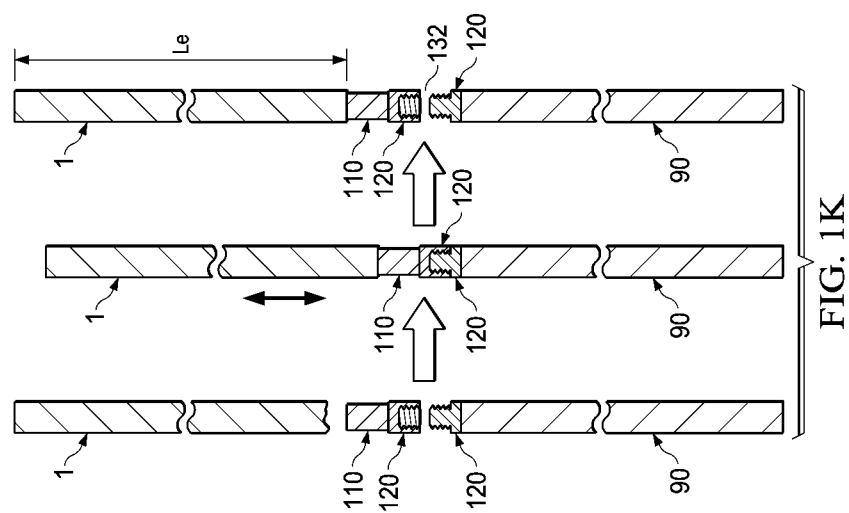

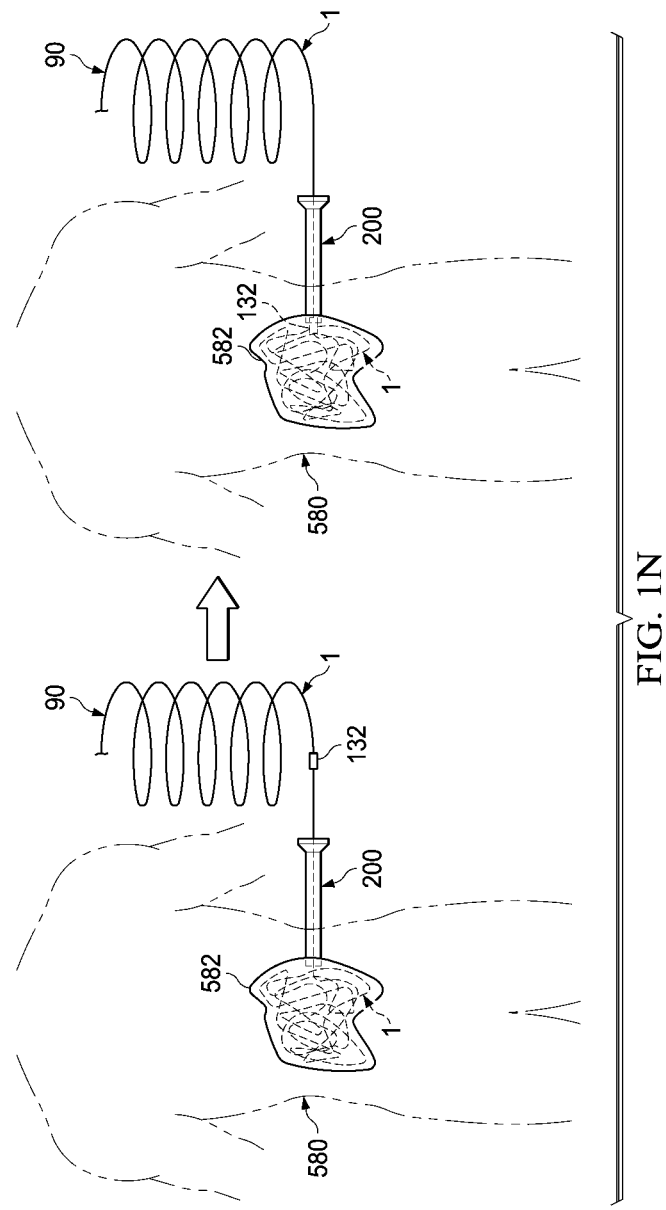

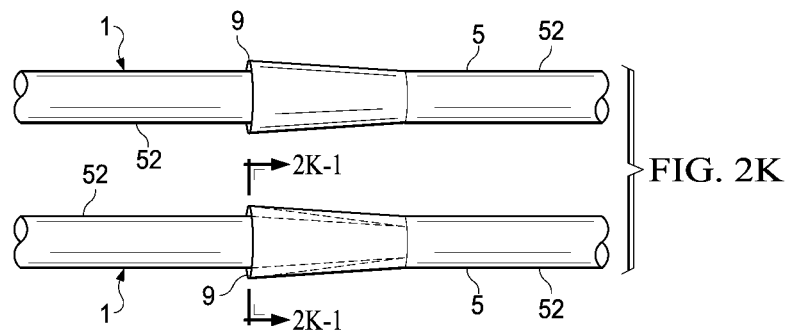
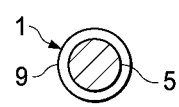
FIG. 2K-1
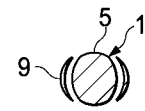
FIG. 2L-1
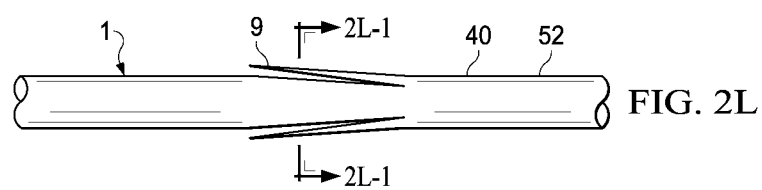
FIG. 2L
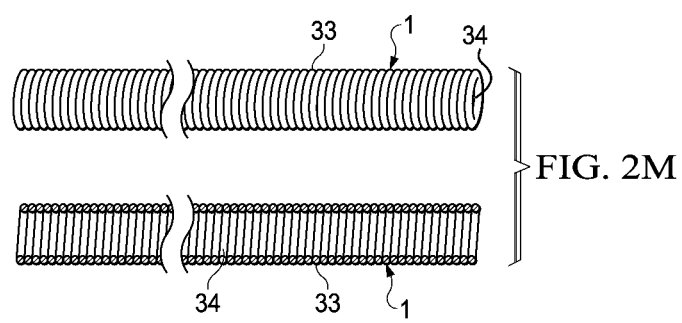
FIG. 2M

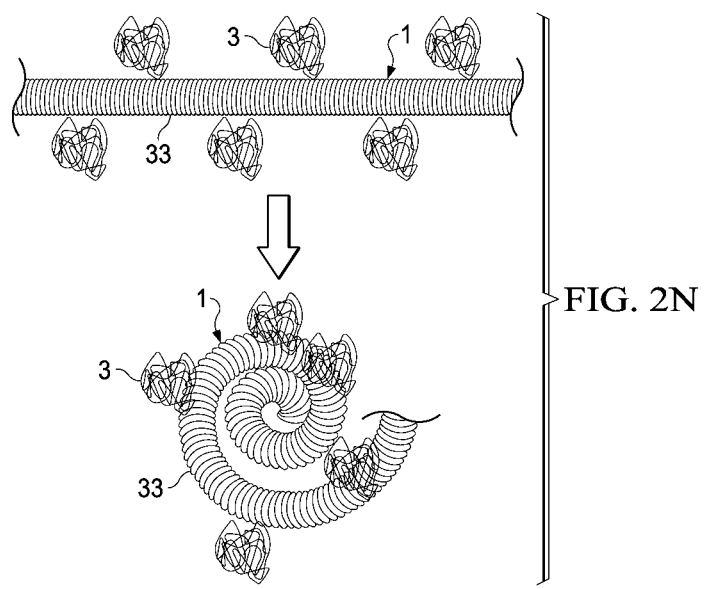
FIG. 2N
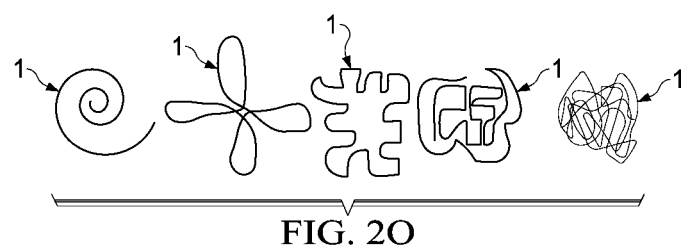
FIG. 2O
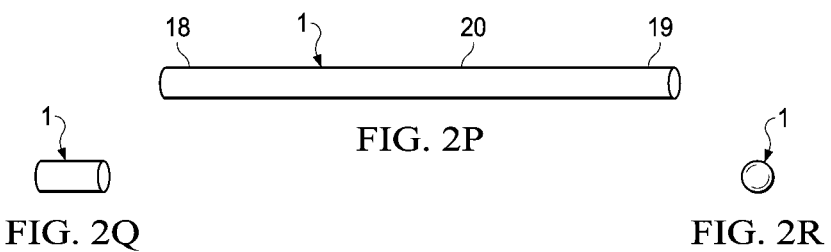
FIG. 2P
FIG. 2Q
FIG. 2R

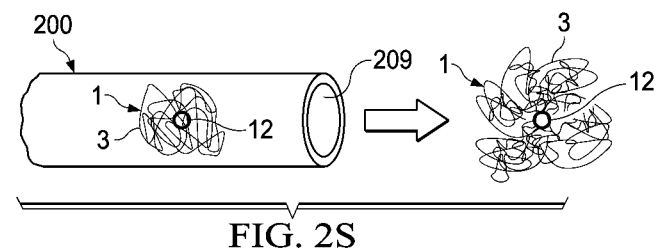
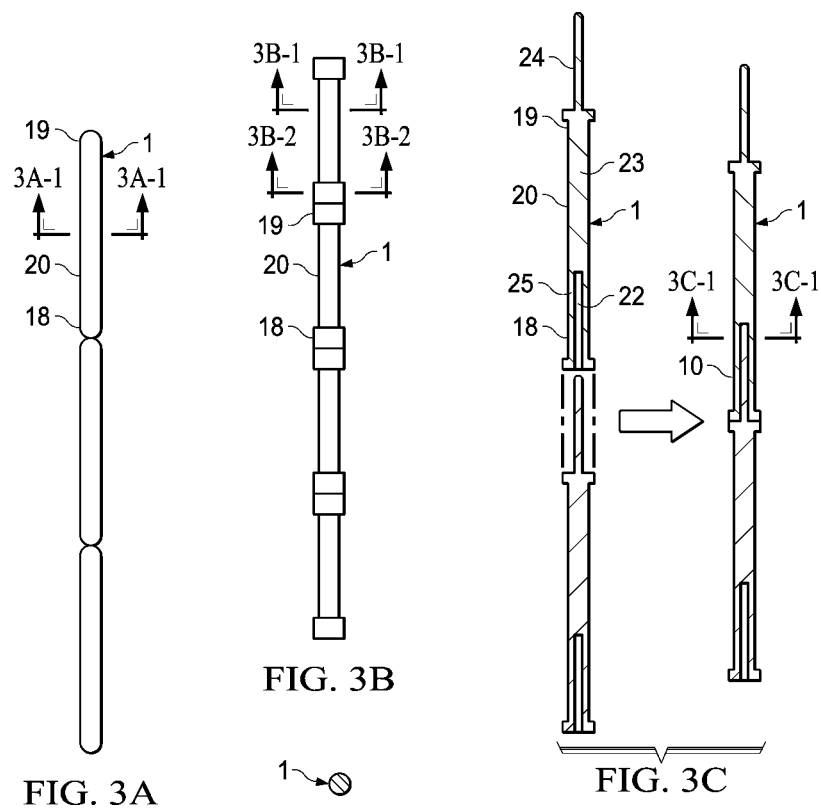
FIG. 2S
FIG. 3A
FIG. 3B
FIG. 3C
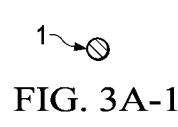
FIG. 3A-1
FIG. 3B-1
FIG. 3B-2
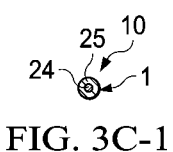
FIG. 3C-1

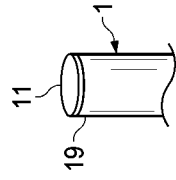
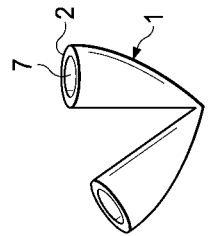
FIG. 3G
FIG. 3H
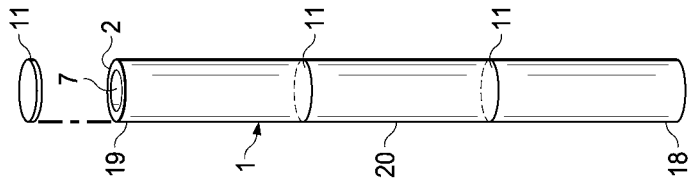
FIG. 3F
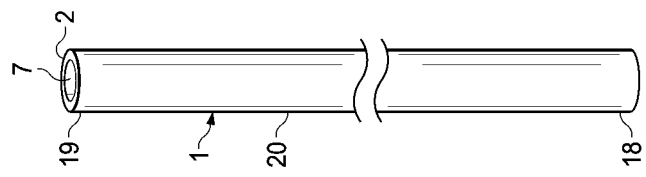
FIG. 3E
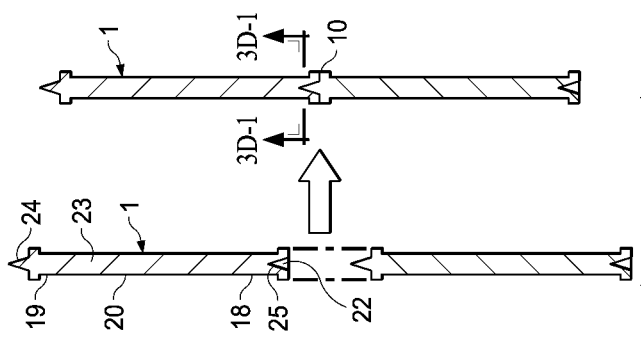
FIG. 3D
FIG. 3D-1

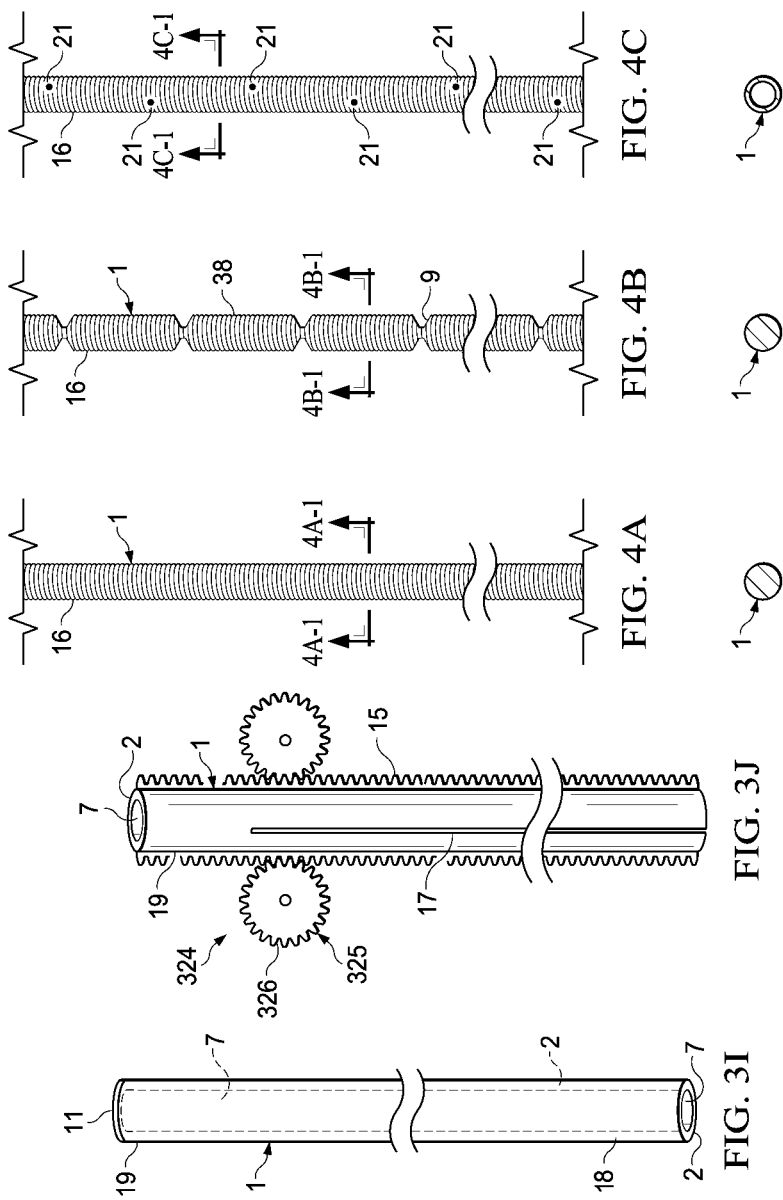

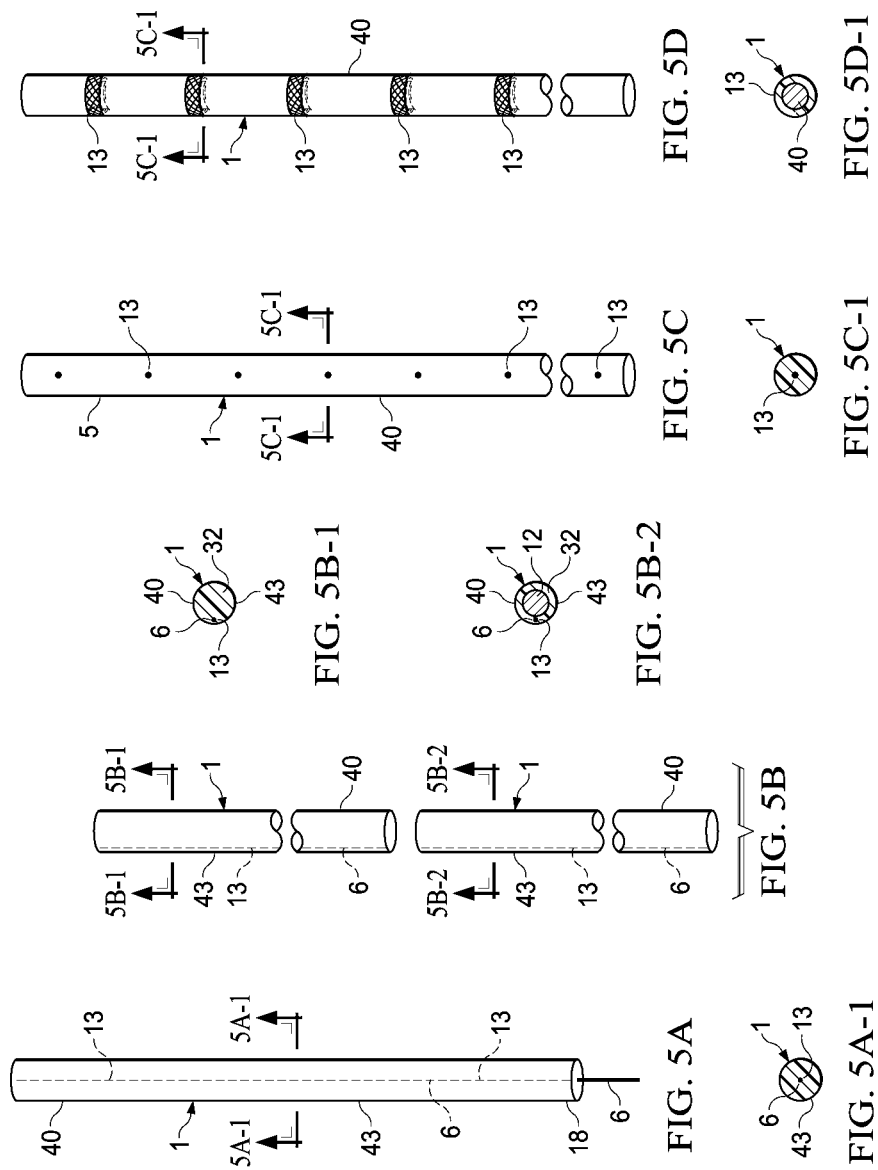

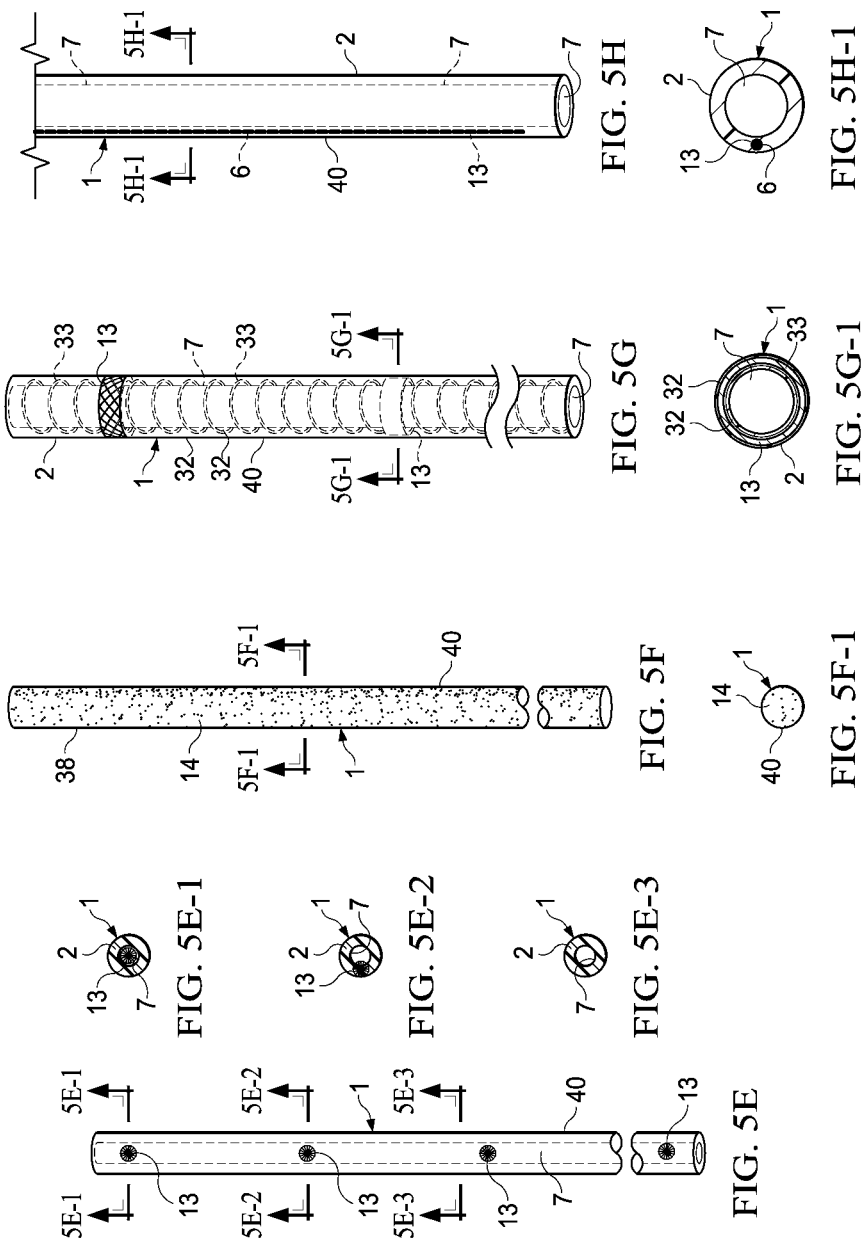

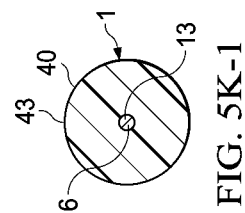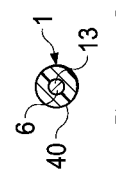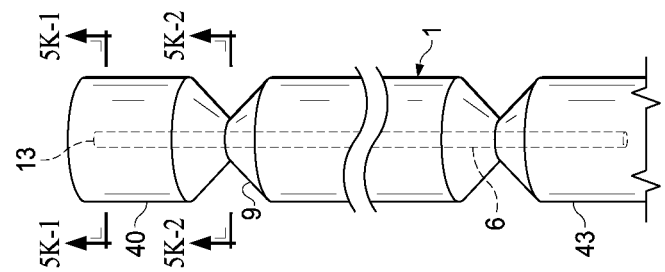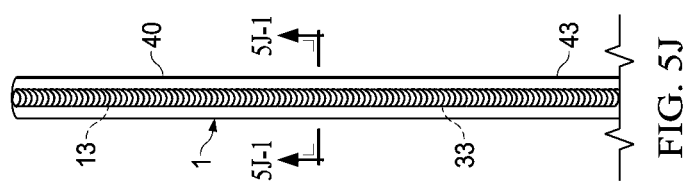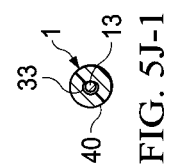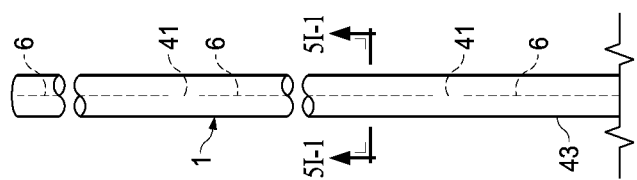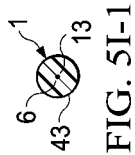

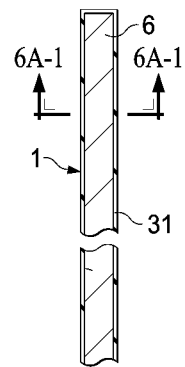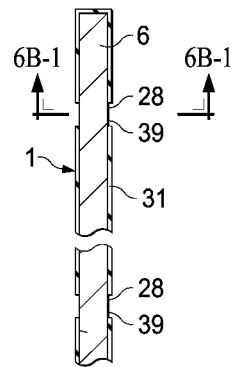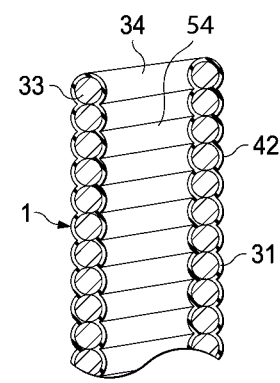
FIG. 6A  FIG. 6B  FIG. 6C
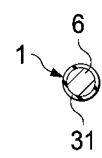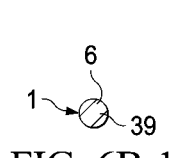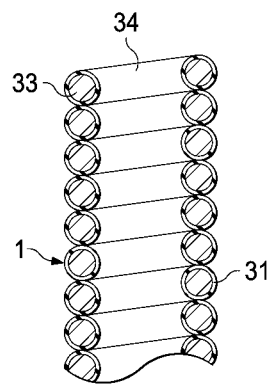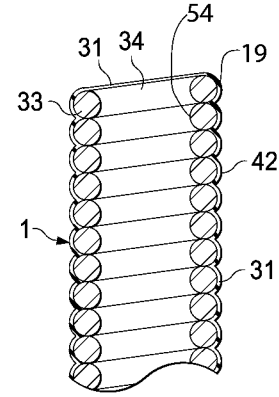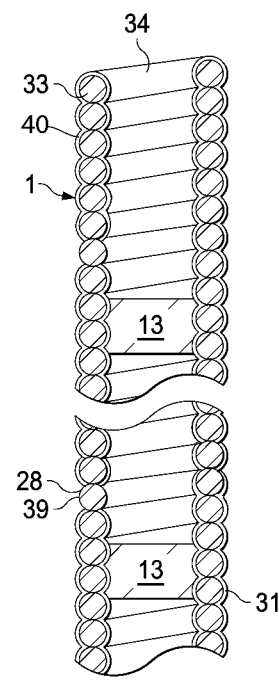
FIG. 6A-1  FIG. 6B-1
FIG. 6D  FIG. 6E  FIG. 6F

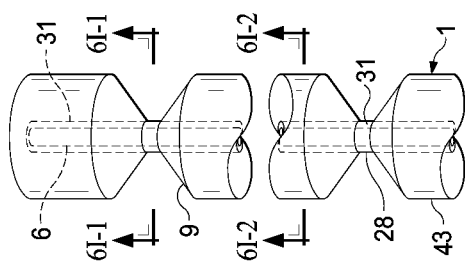
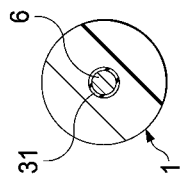
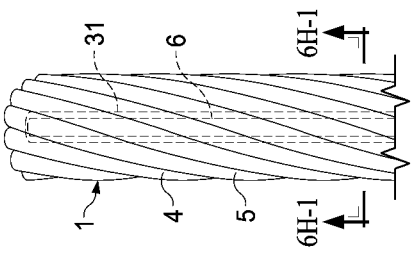
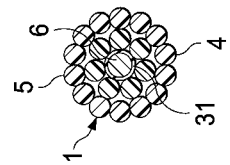
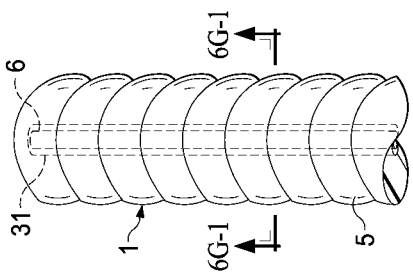
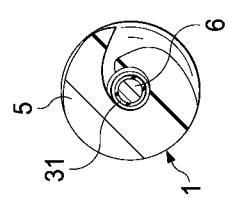

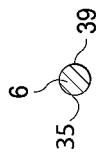
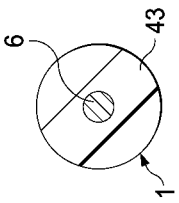
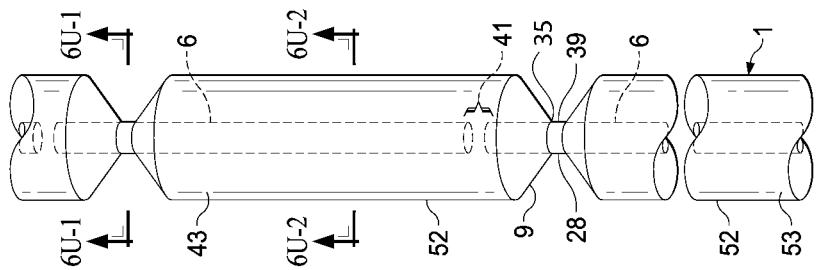
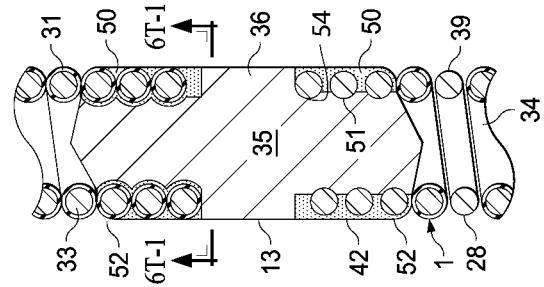
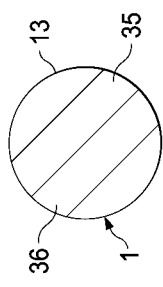
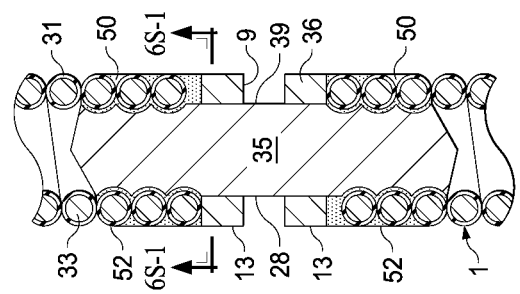
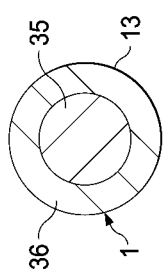

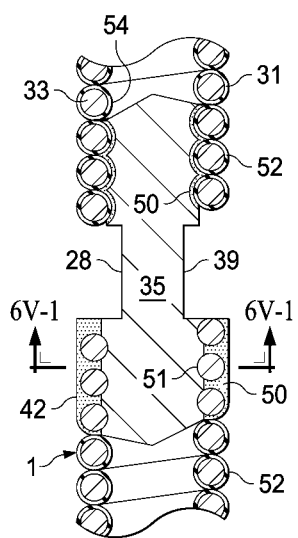
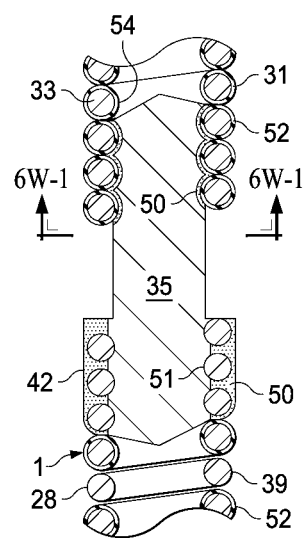
FIG. 6V            FIG. 6W
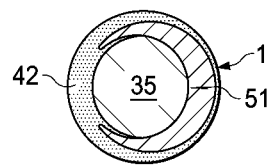
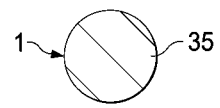
FIG. 6V-1          FIG. 6W-1

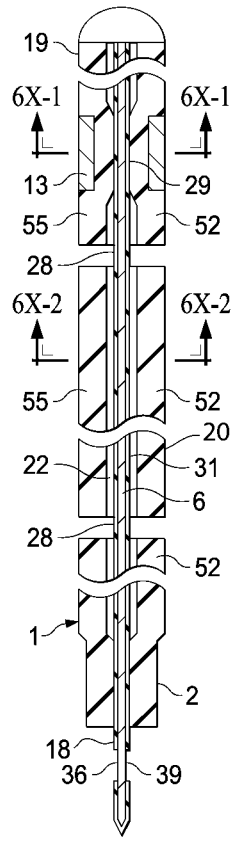
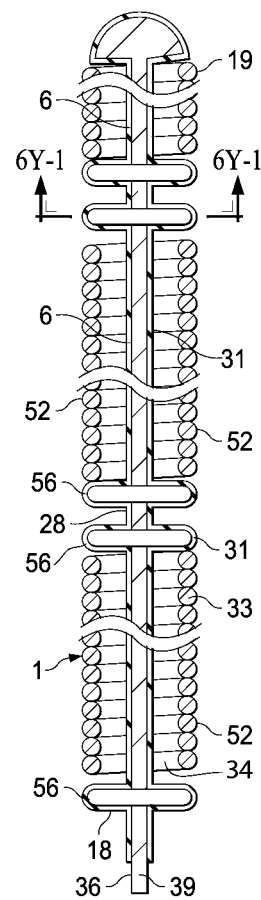
FIG. 6X  FIG. 6Y
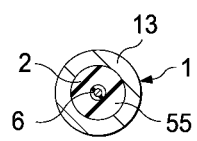
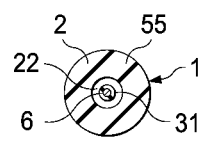
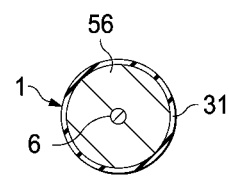
FIG. 6X-1   FIG. 6X-2   FIG. 6Y-1

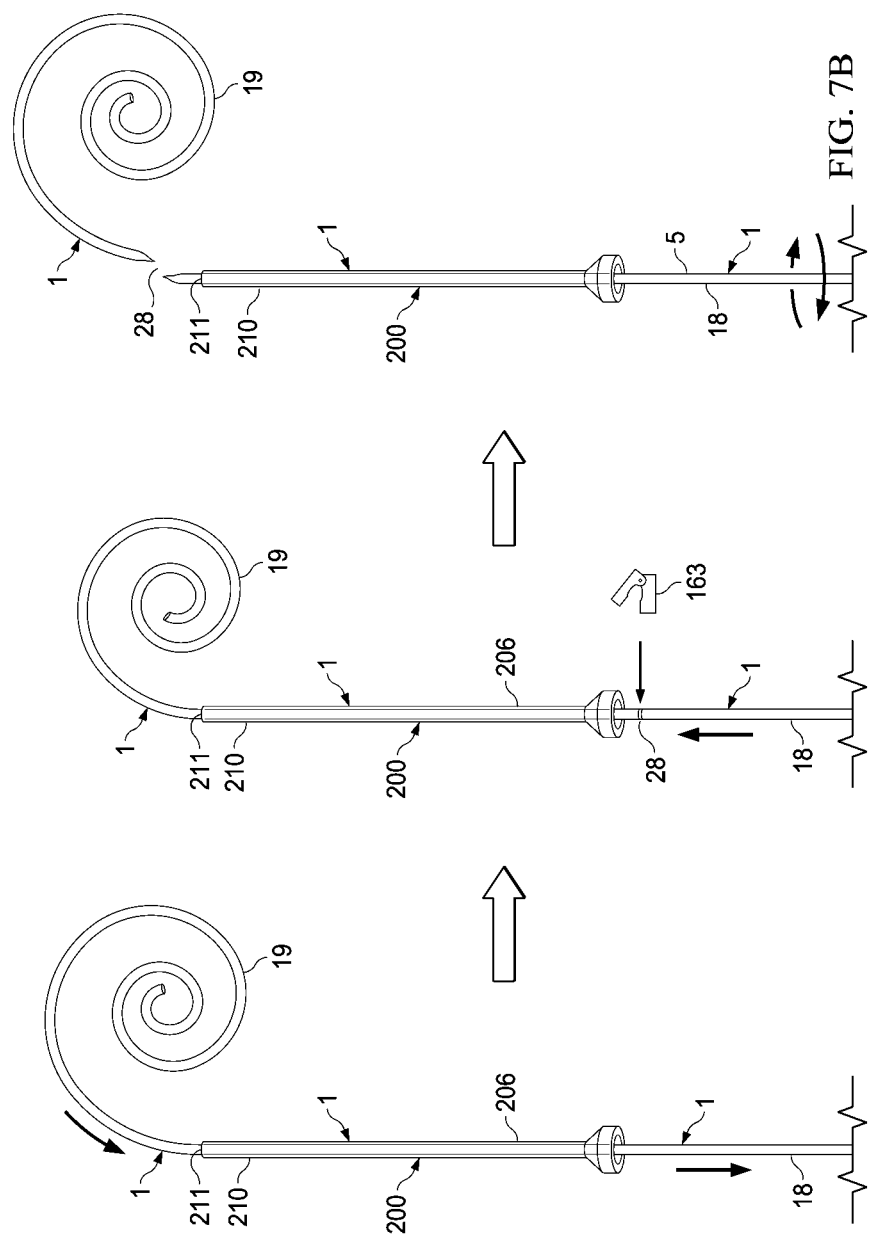

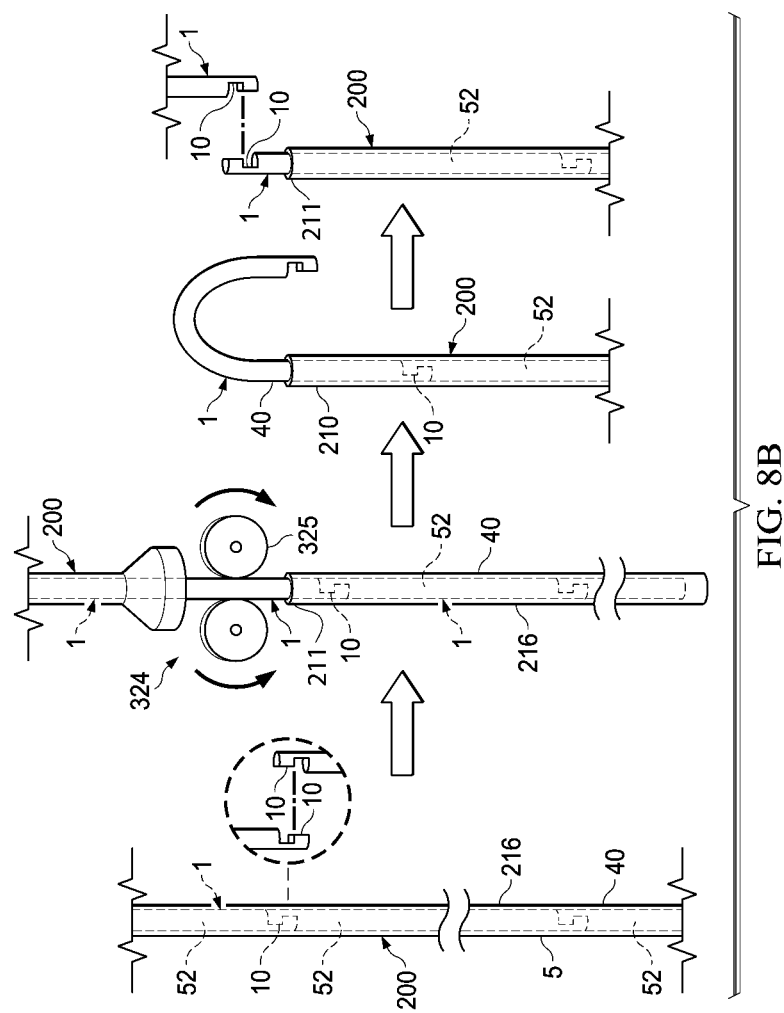

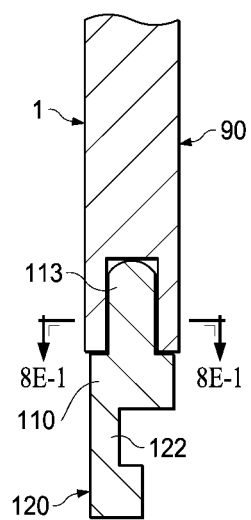
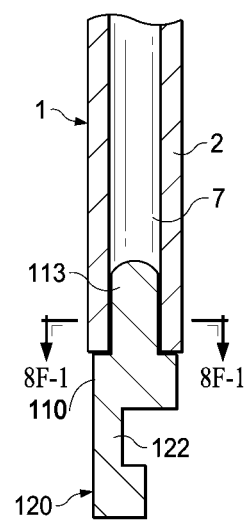
FIG. 8E  FIG. 8F
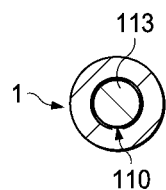
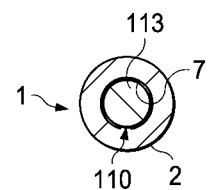
FIG. 8E-1  FIG. 8F-1

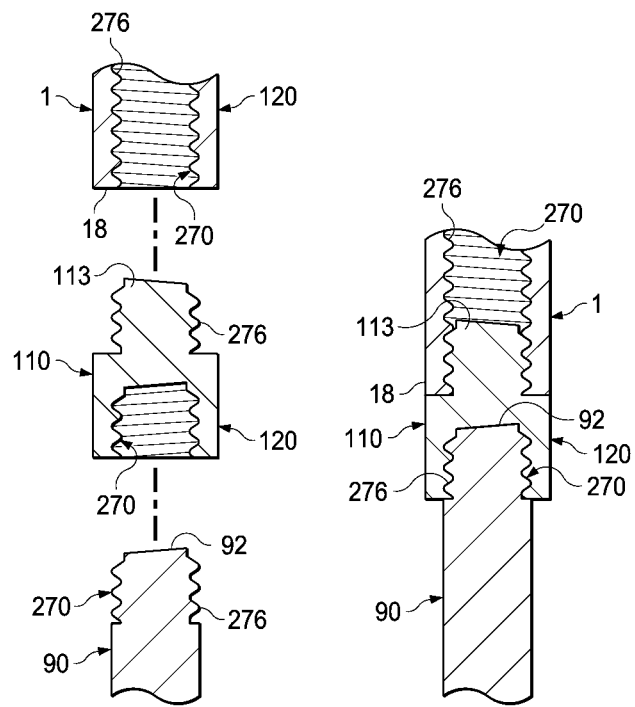
FIG. 8H
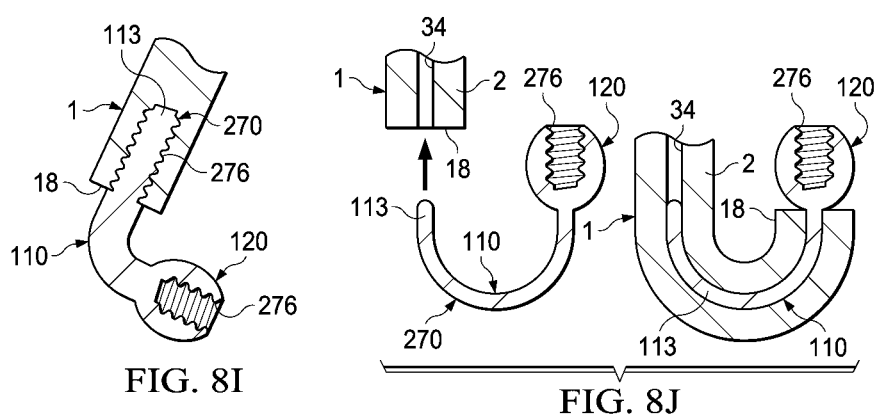
FIG. 8I
FIG. 8J

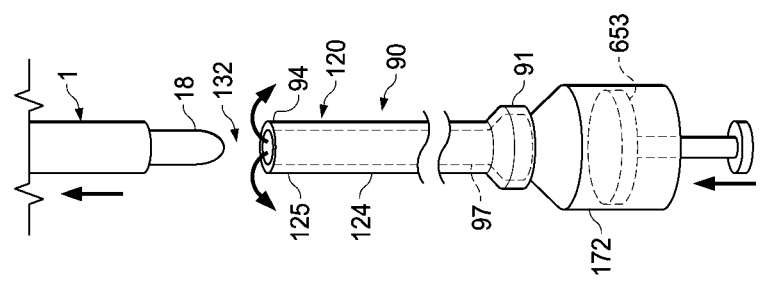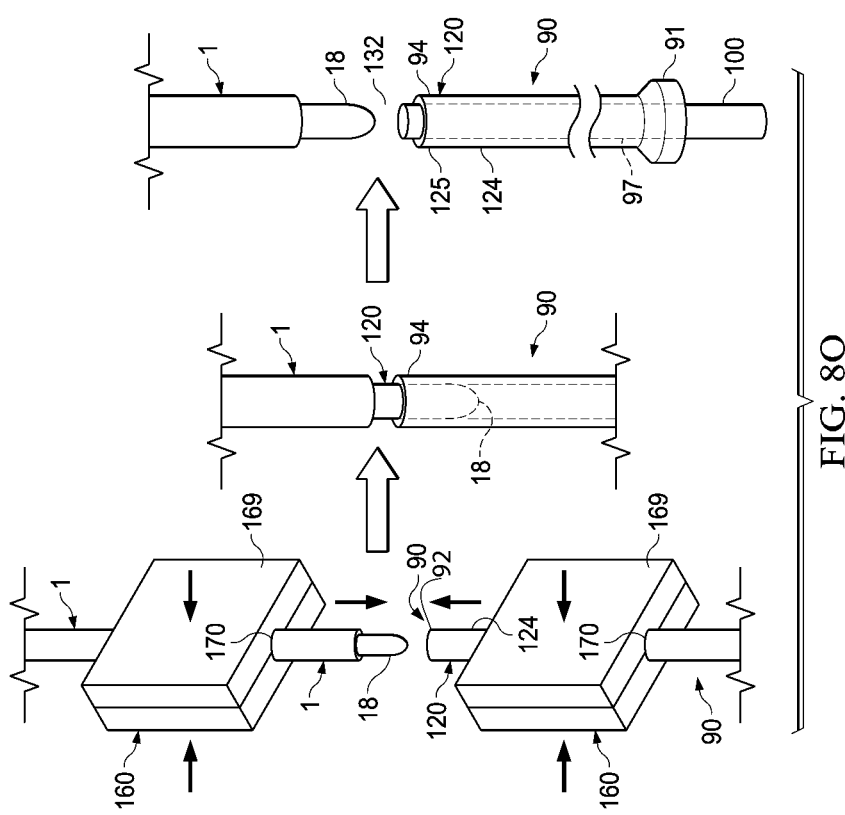

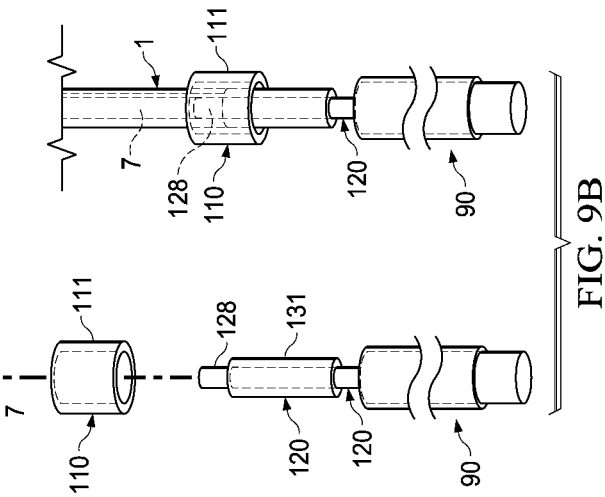

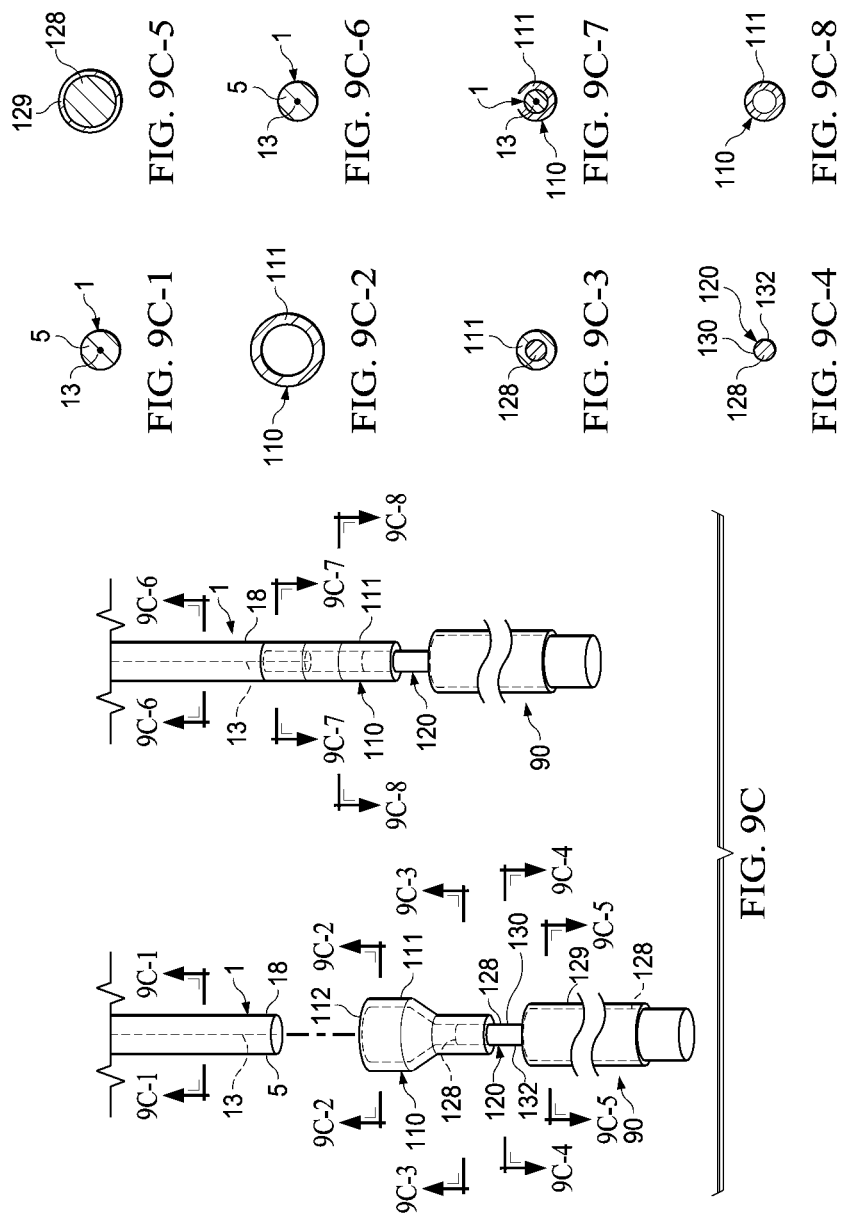

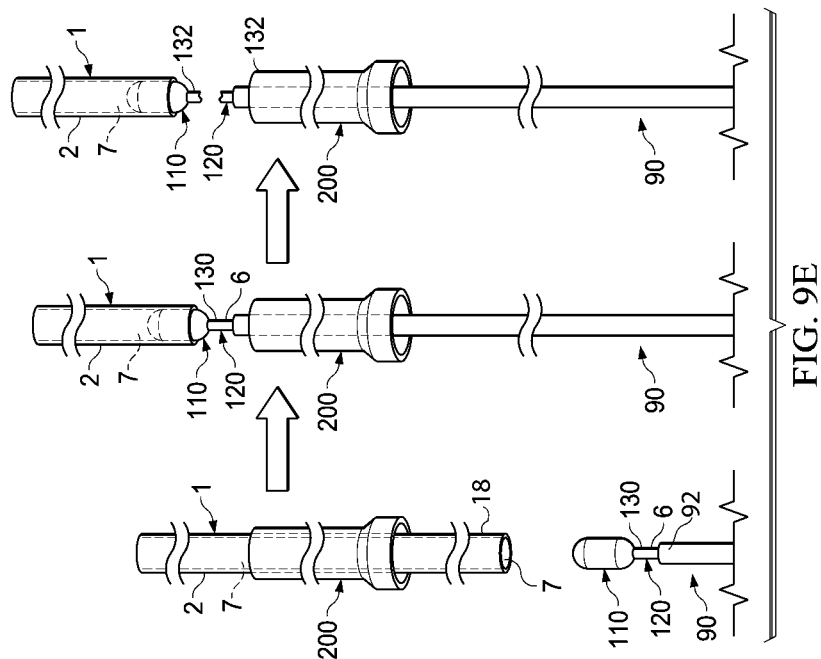
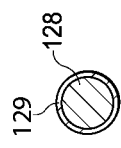
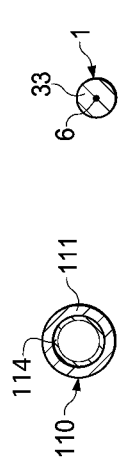
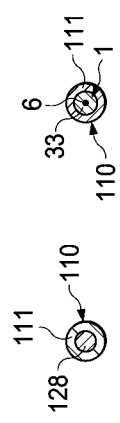
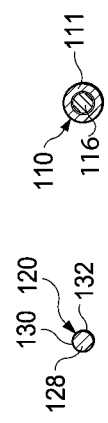
FIG. 9E

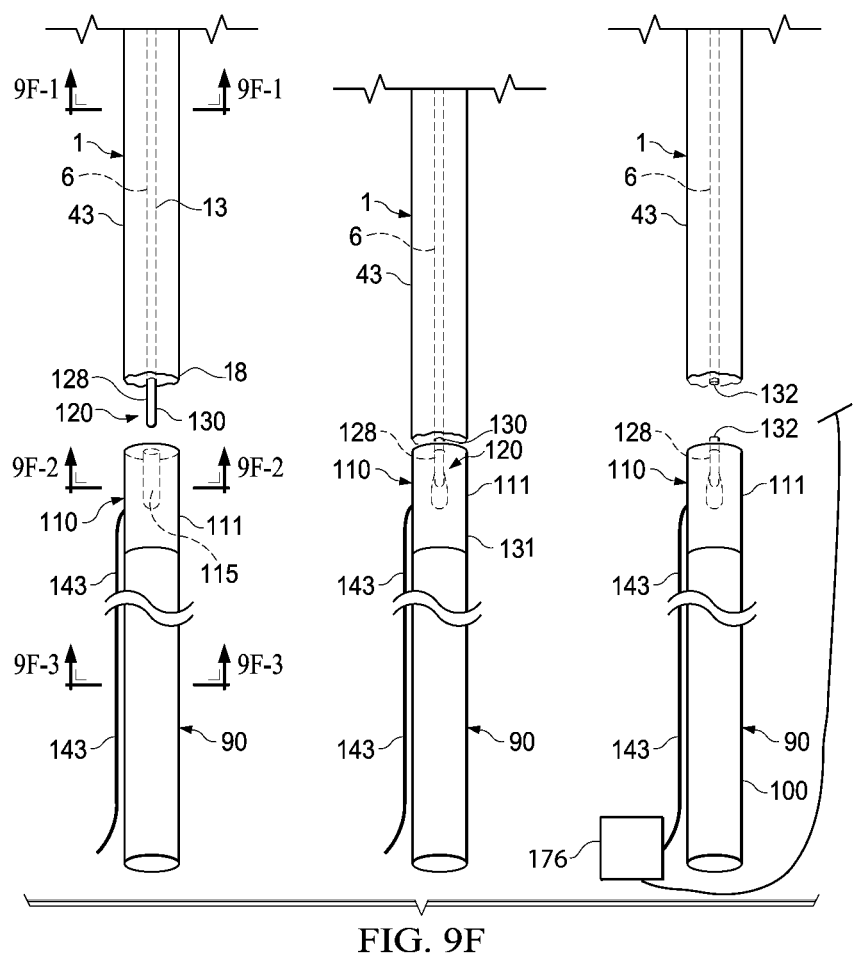
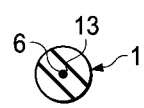
FIG. 9F-1
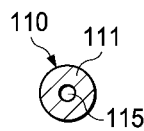
FIG. 9F-2
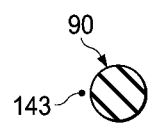
FIG. 9F-3
FIG. 9F

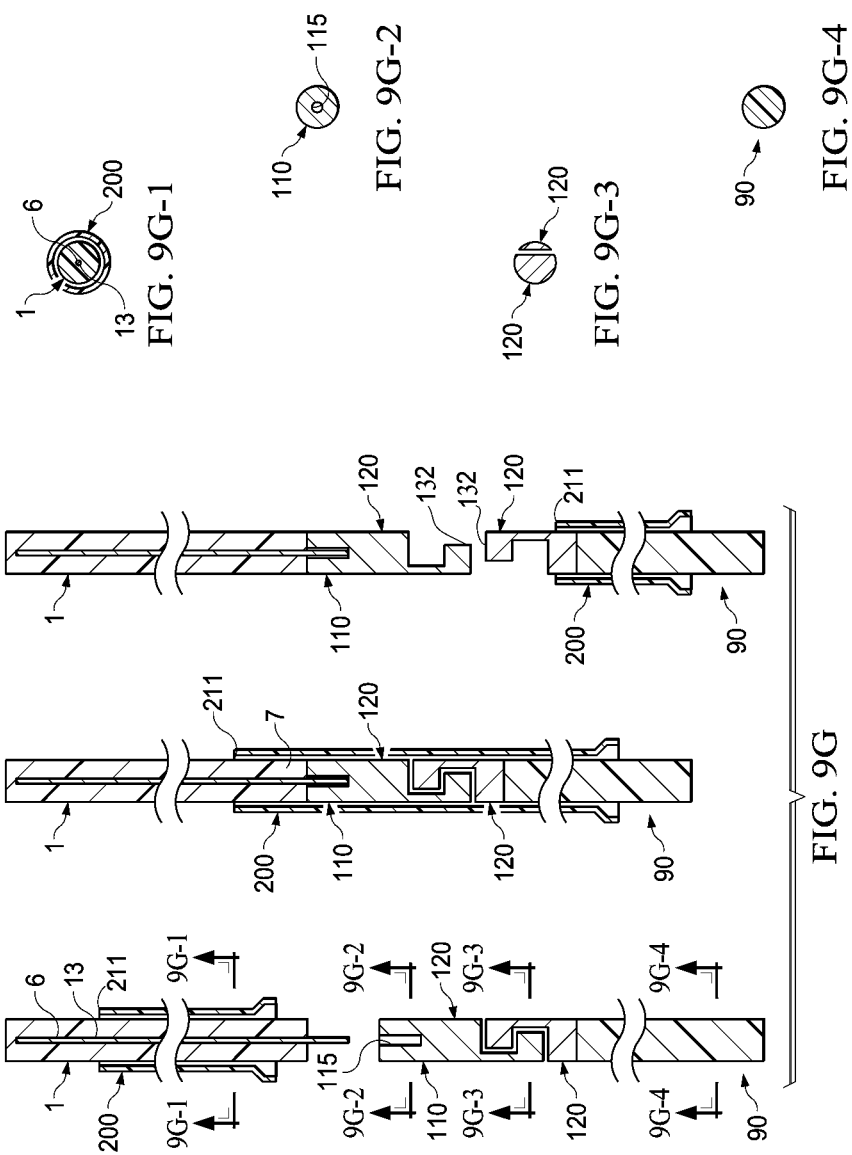

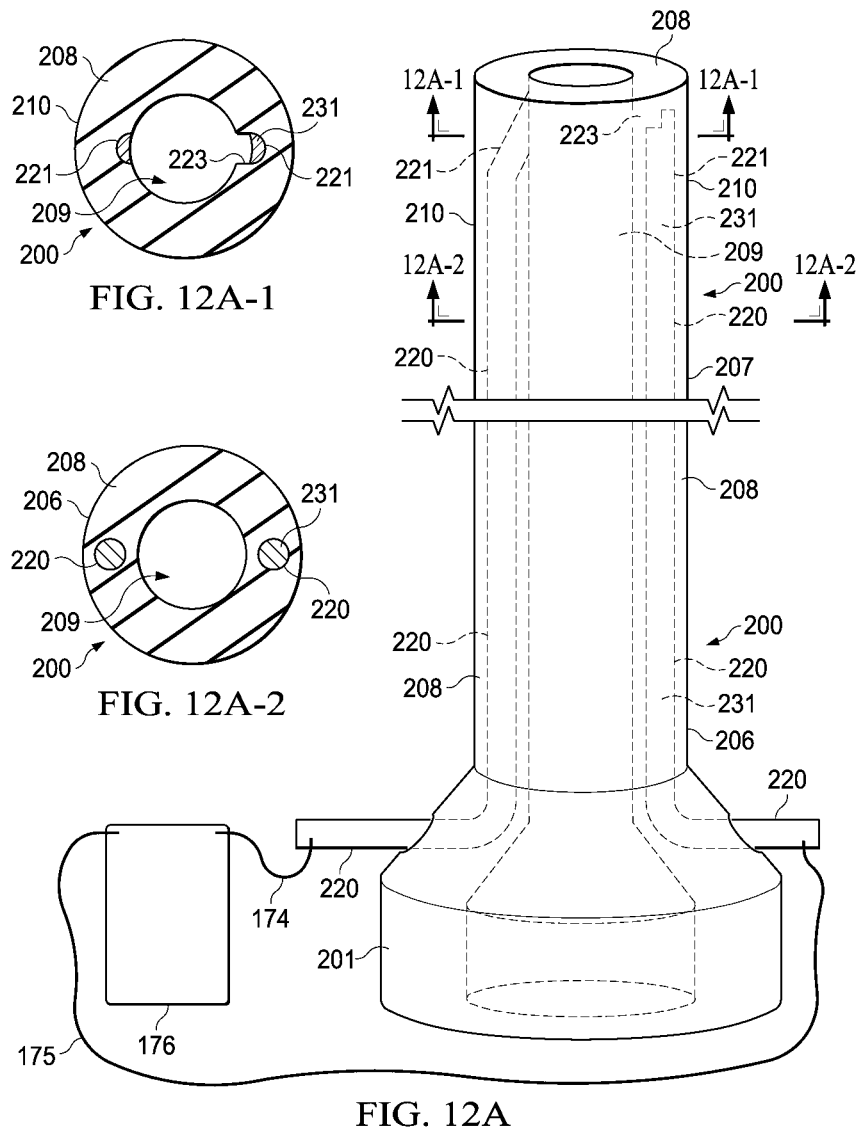

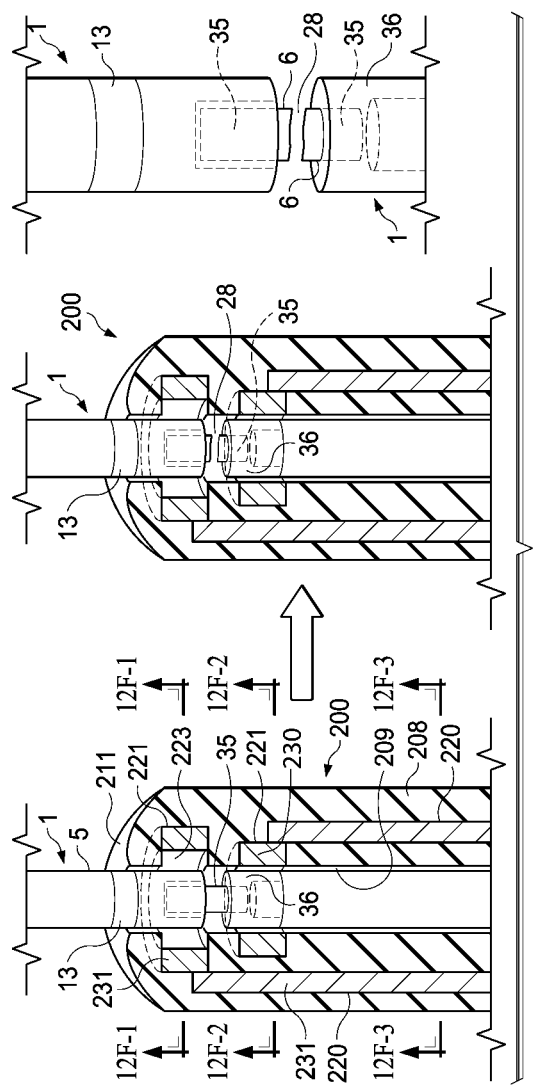

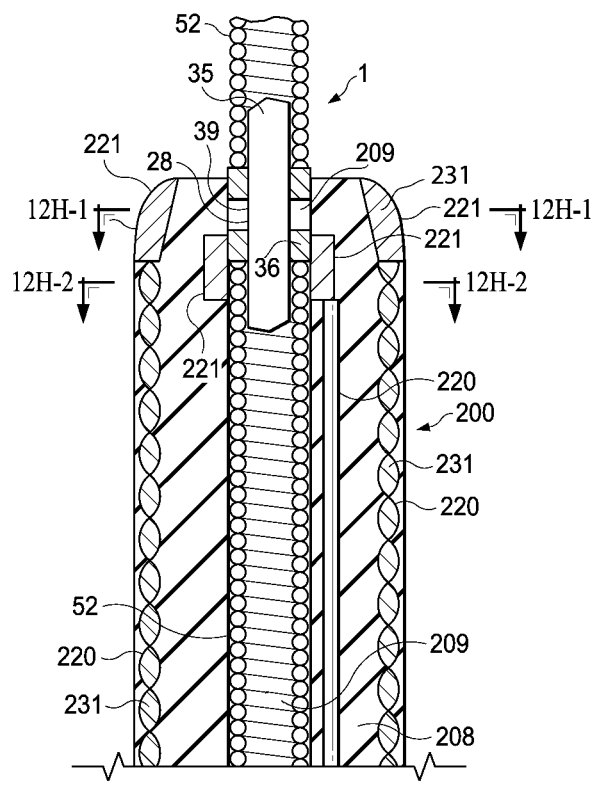
FIG. 12H
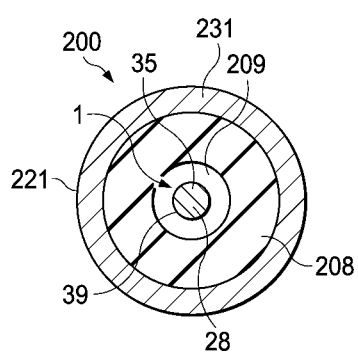
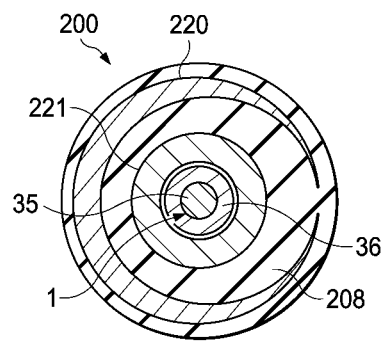
FIG. 12H-1          FIG. 12H-2

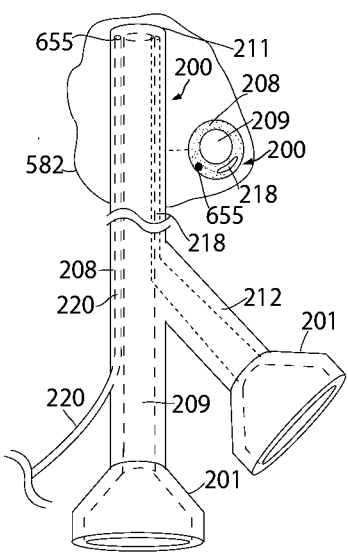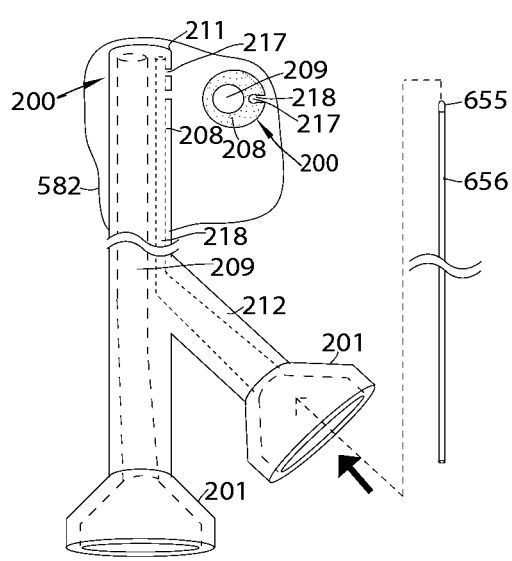
FIG. 15A   FIG. 15B
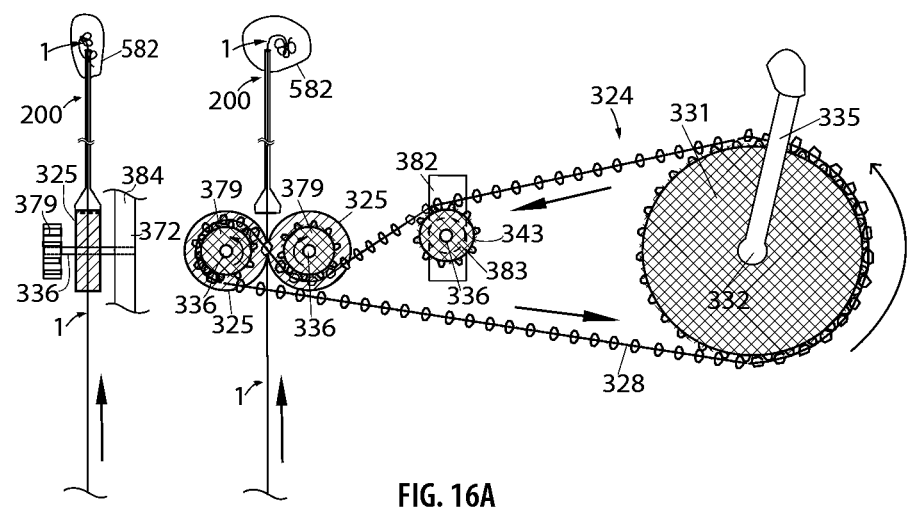
FIG. 16A

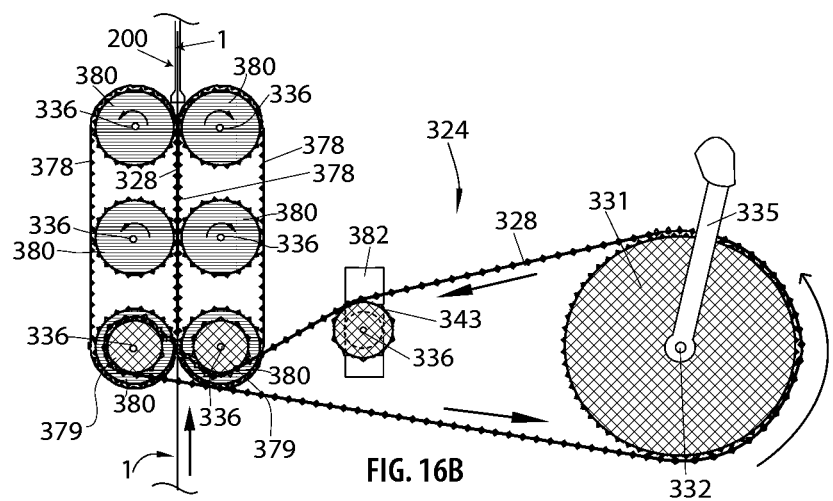
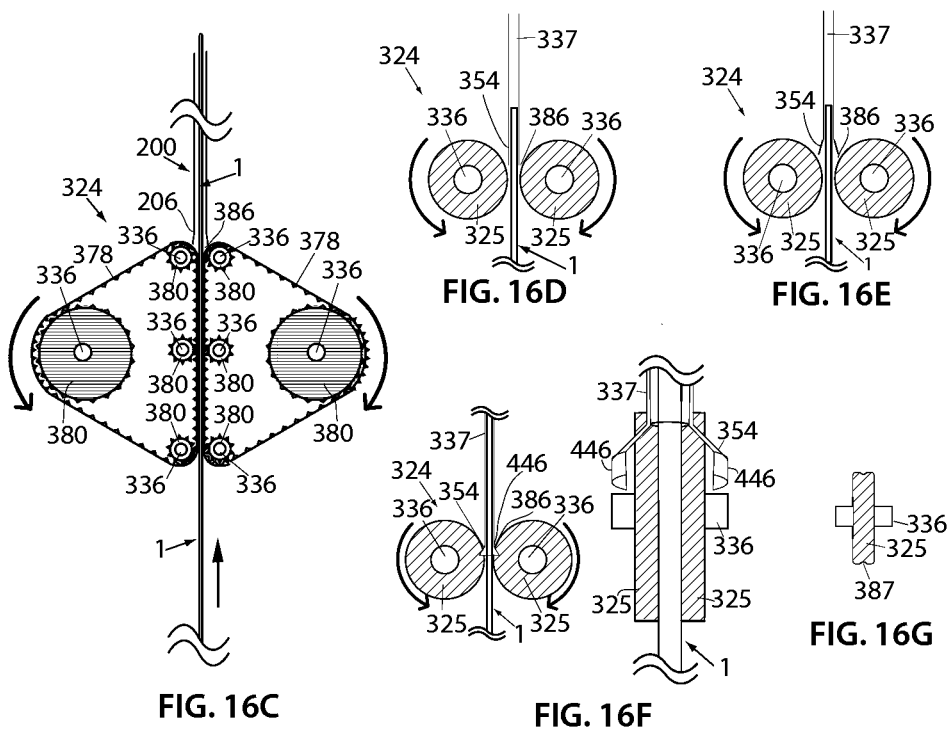

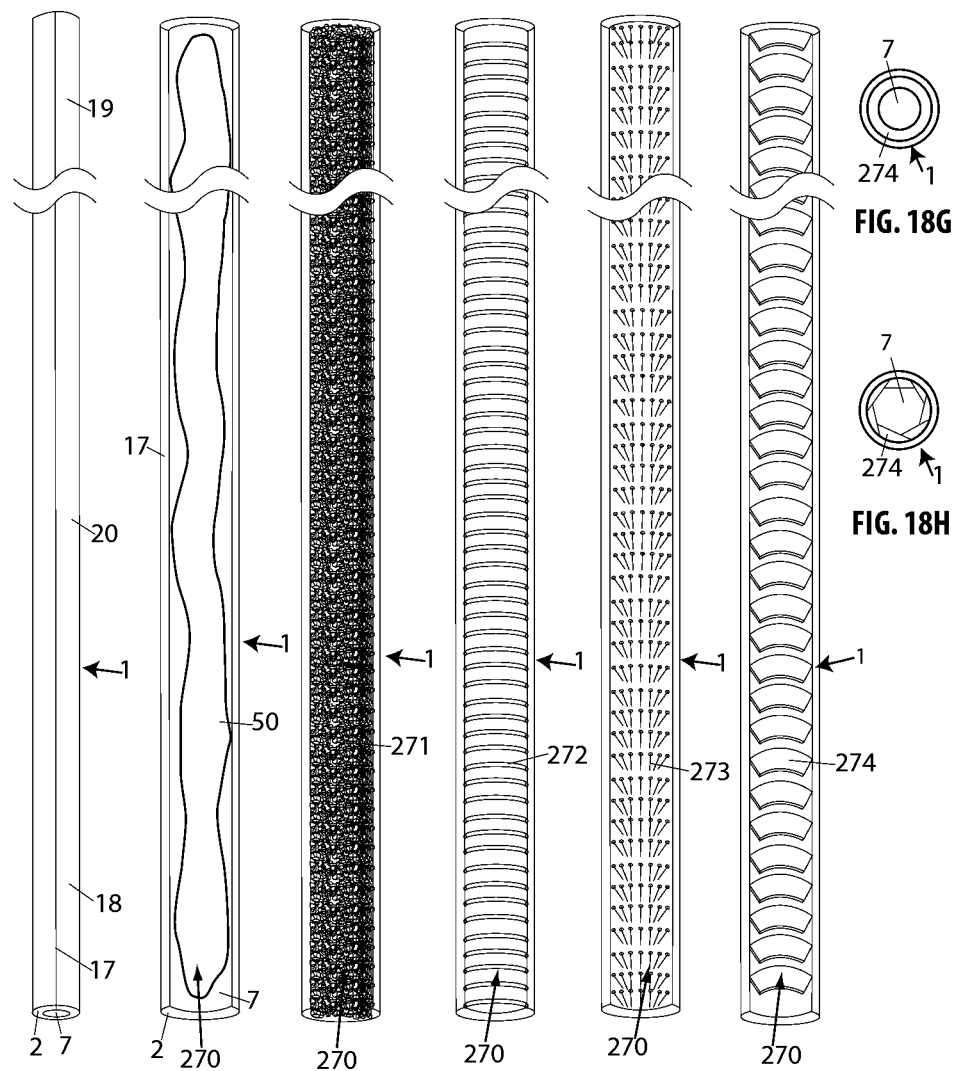

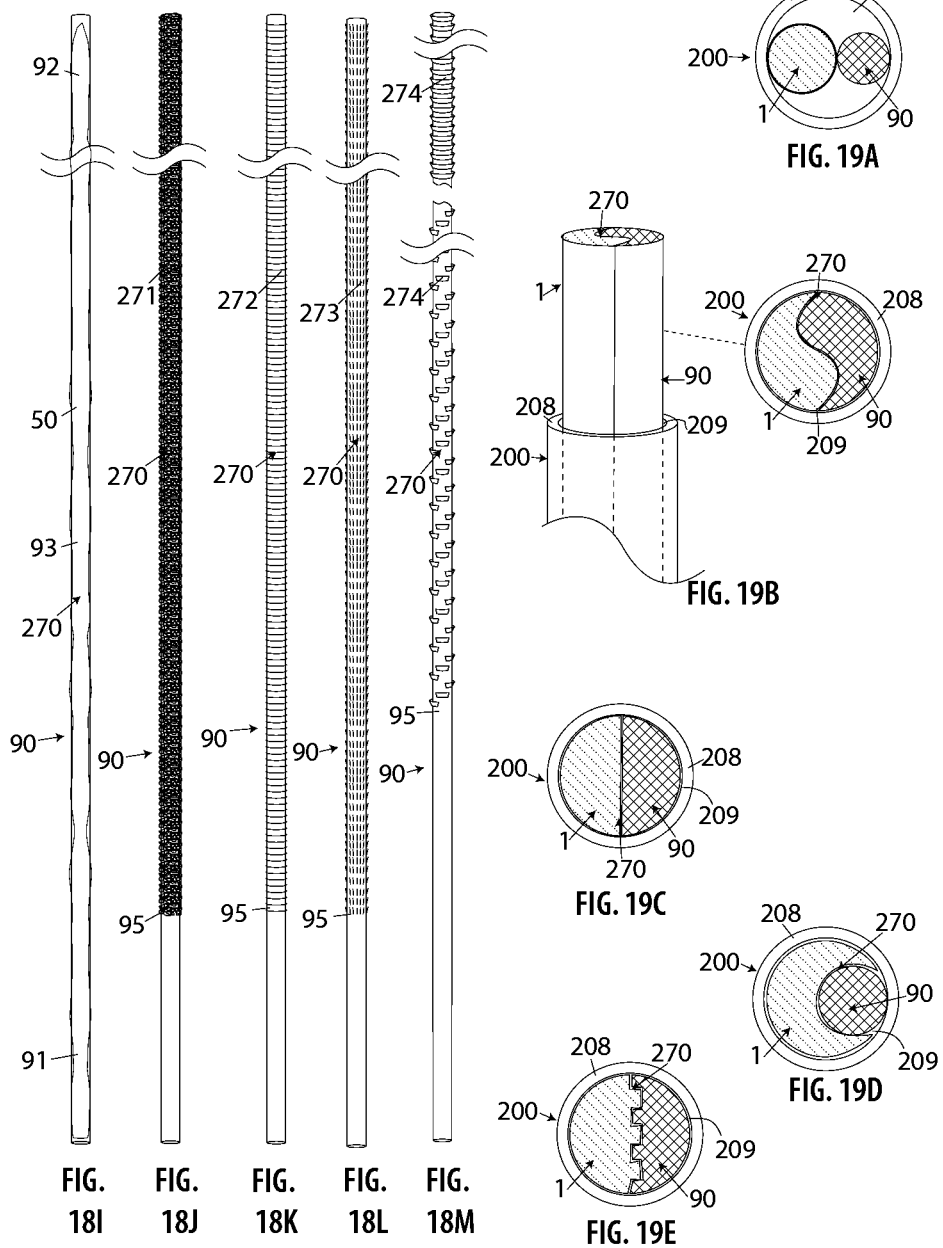

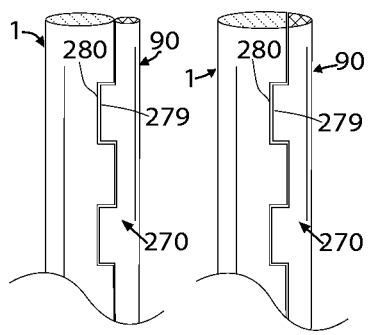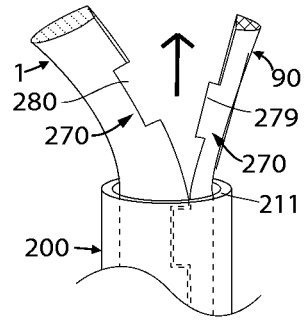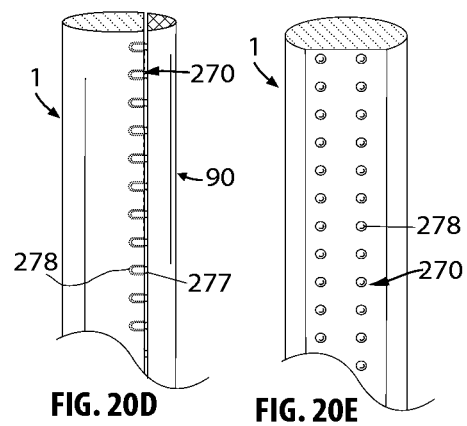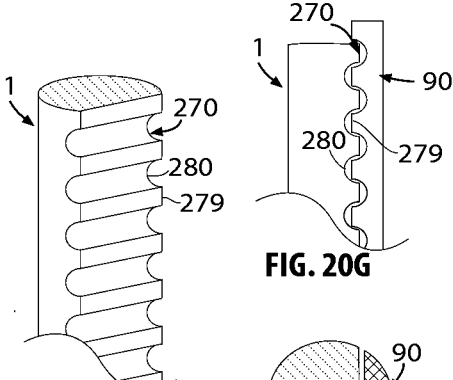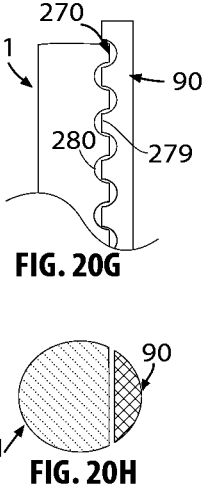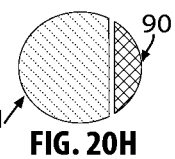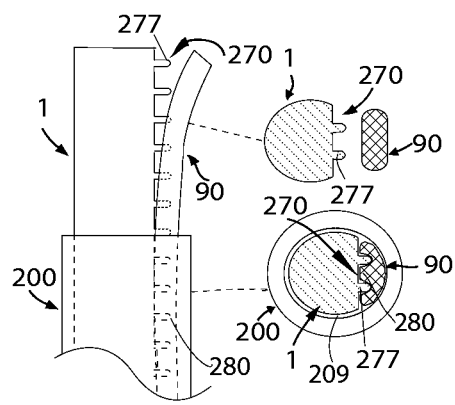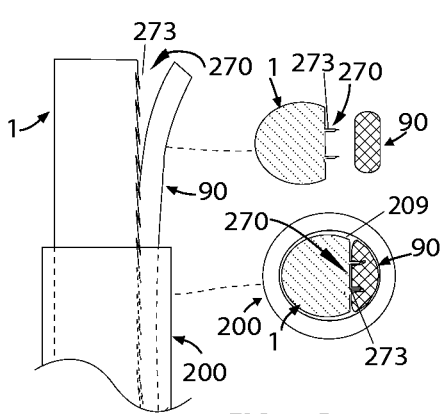

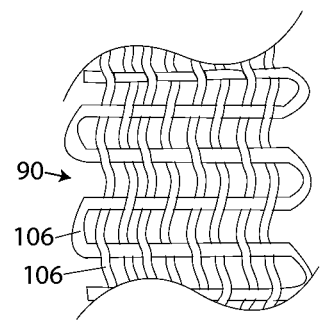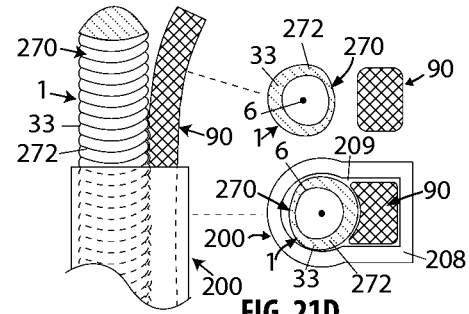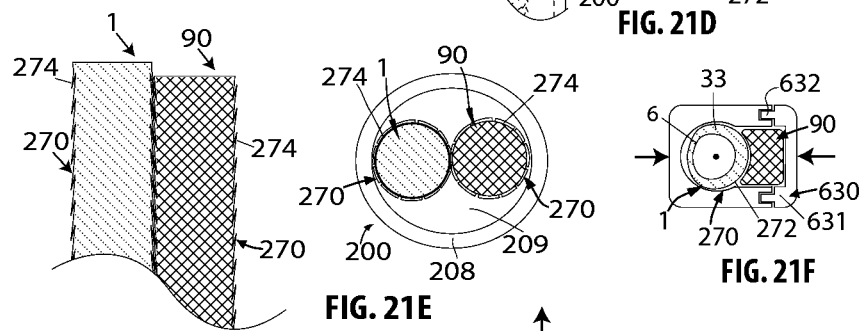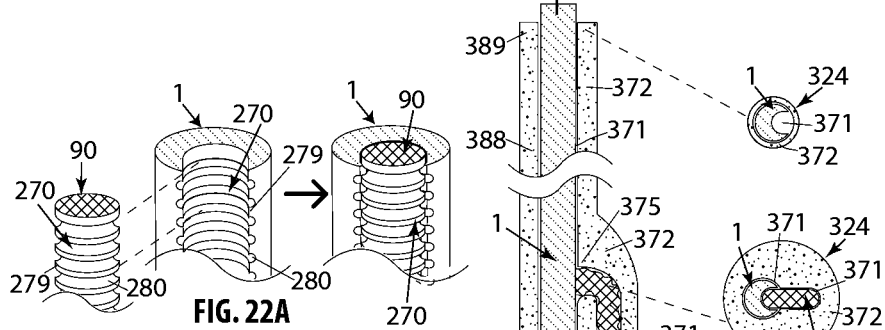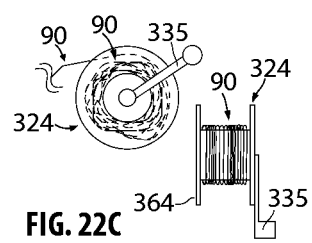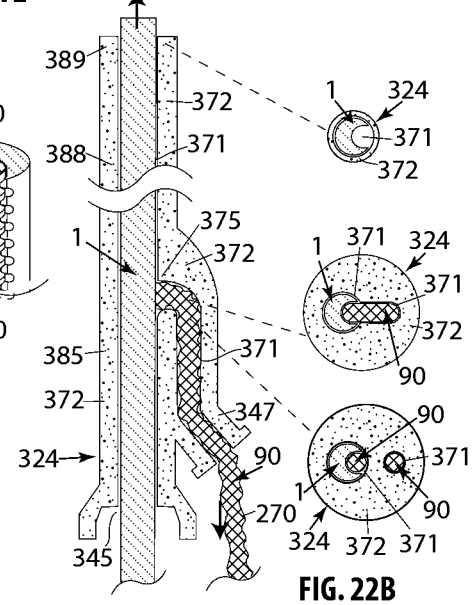

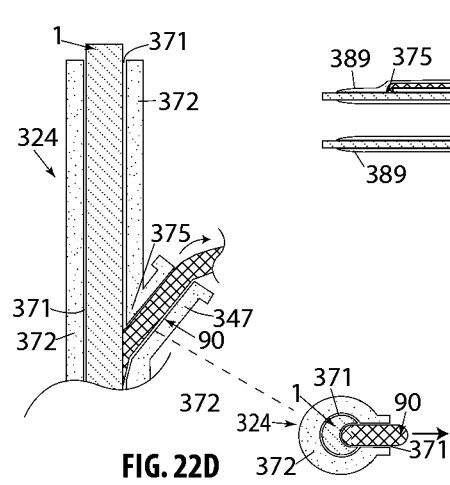
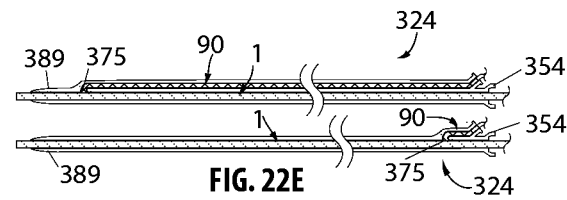
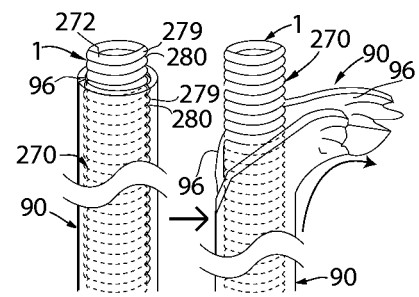
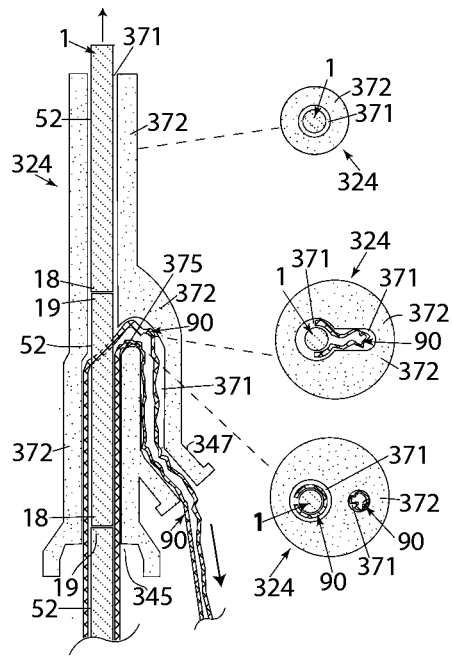
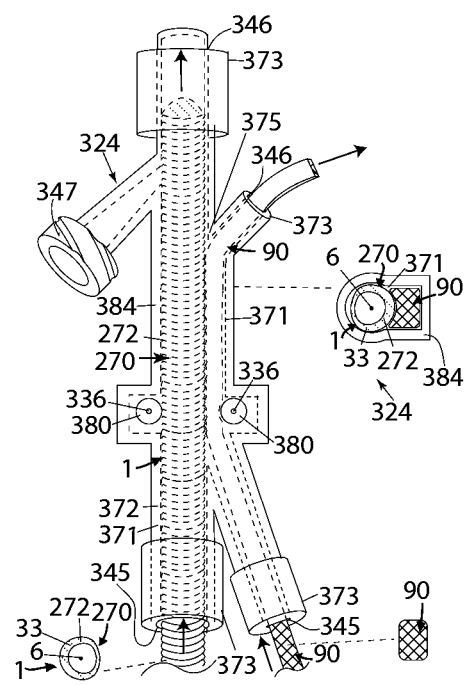

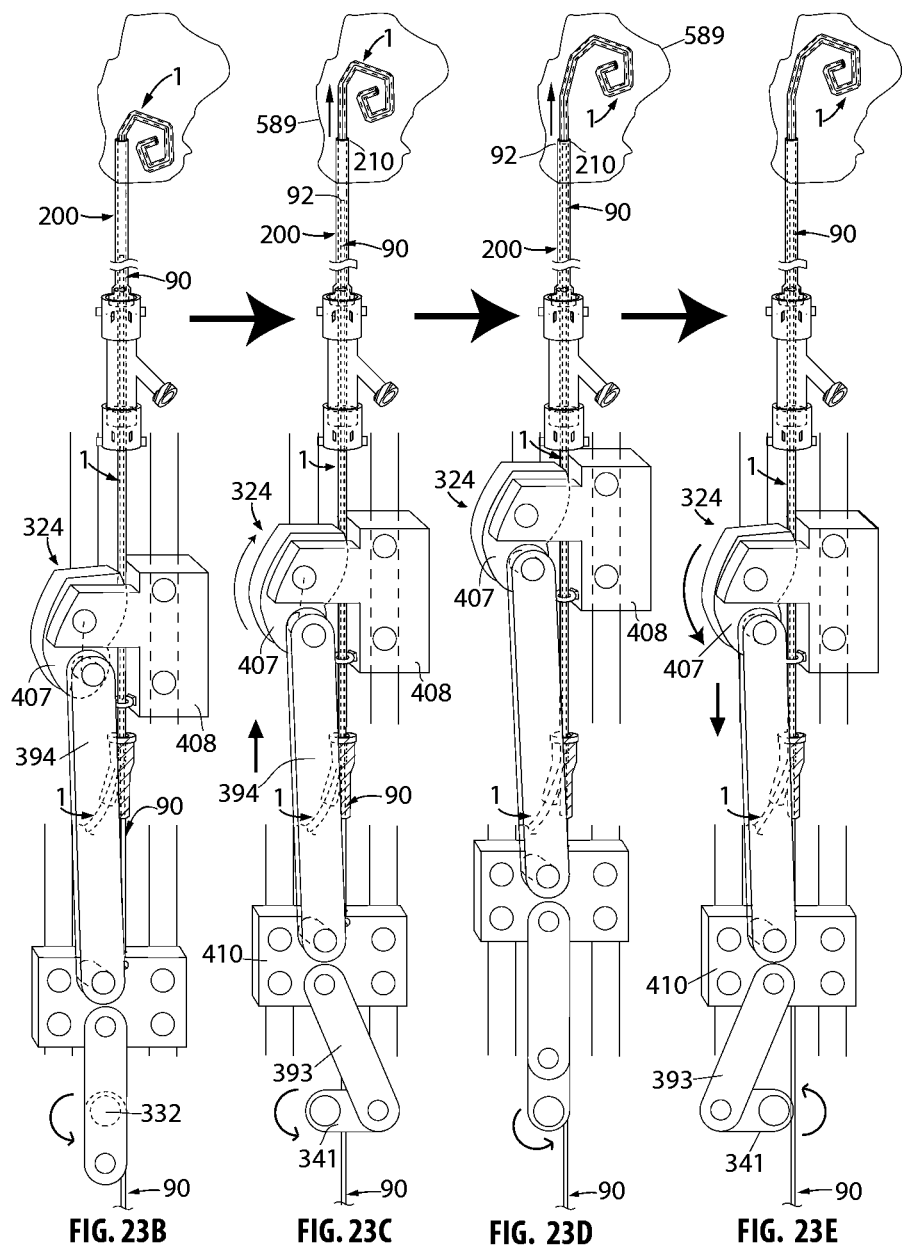

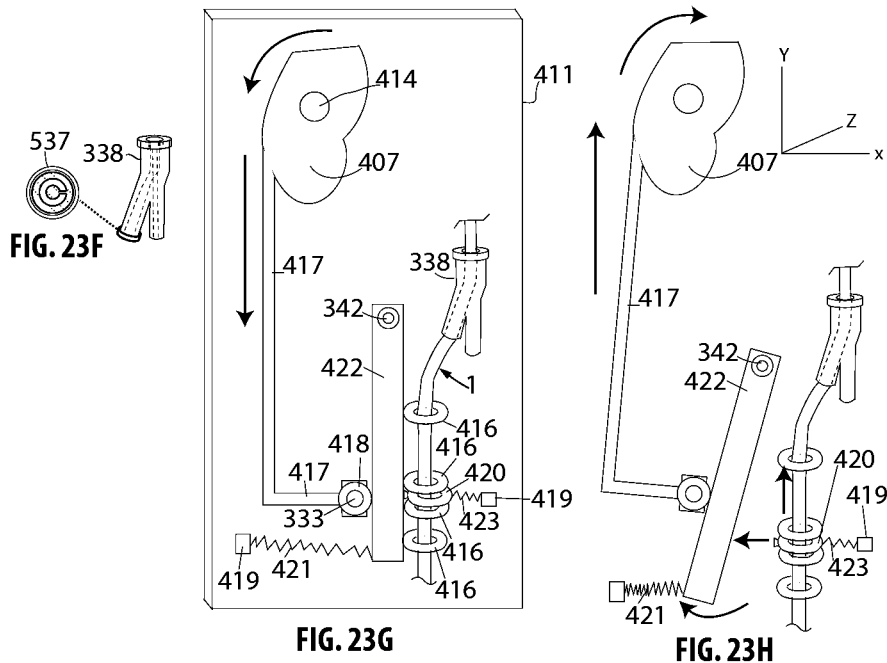
FIG. 23F  FIG. 23G  FIG. 23H
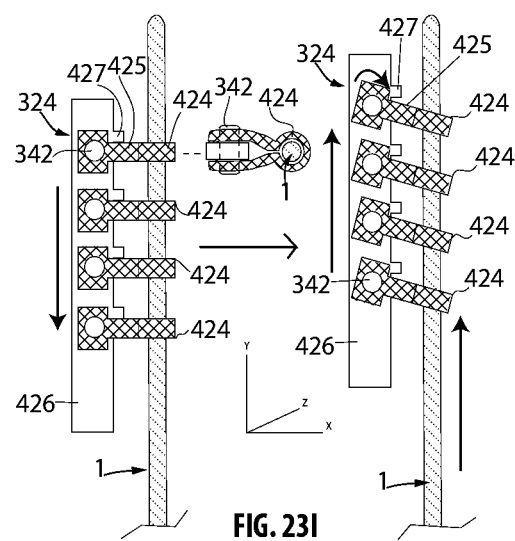
FIG. 23I

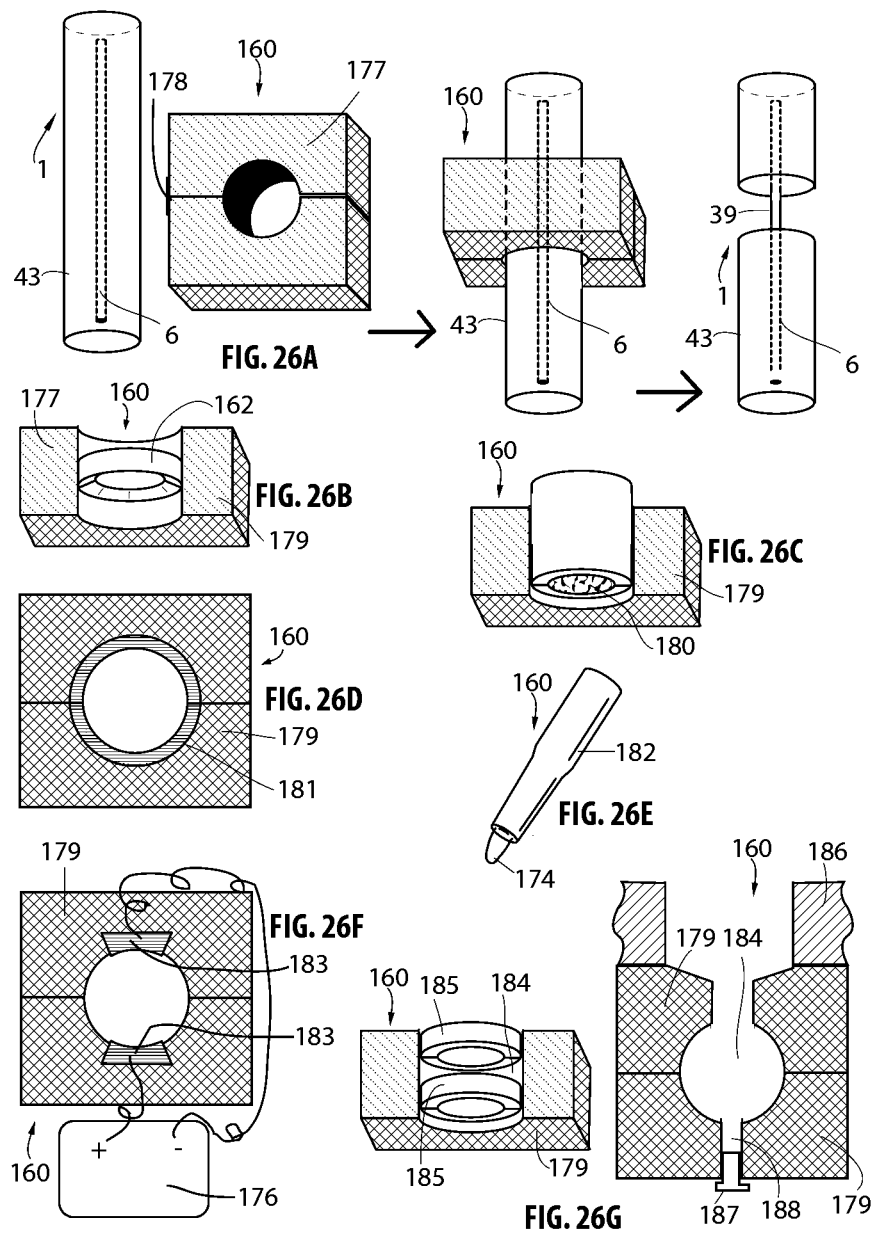

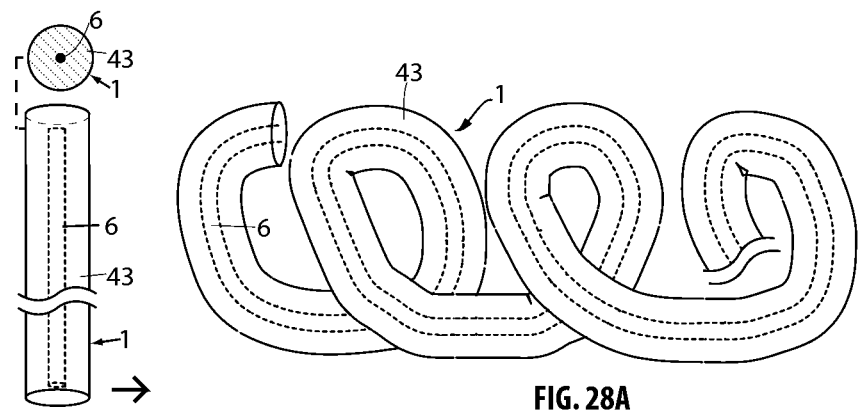
FIG. 28A
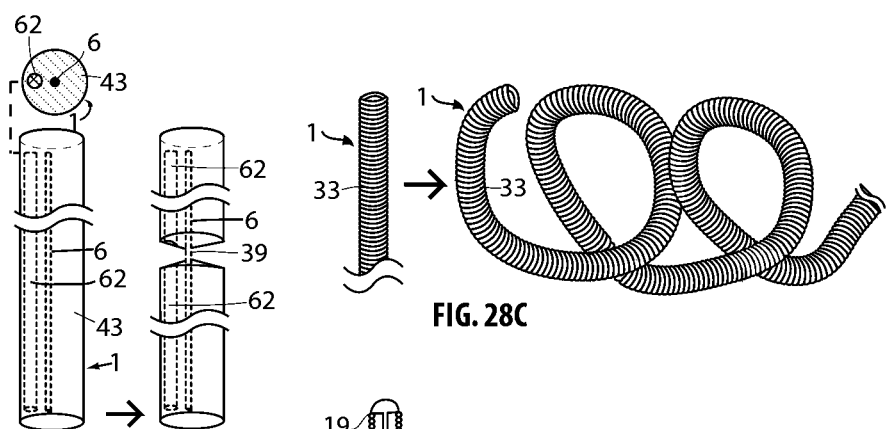
FIG. 28B
FIG. 28C
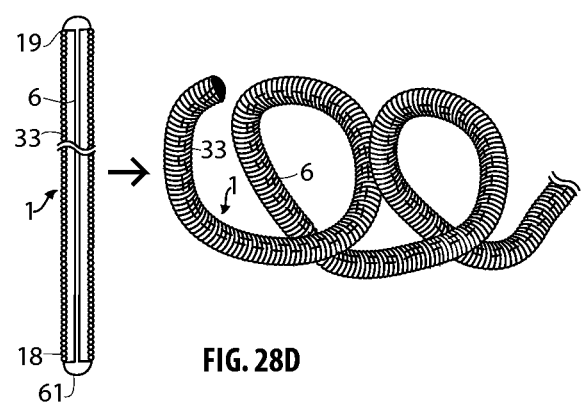
FIG. 28D

DEVICE AND METHOD FOR FILLING OF ANEURYSM OR BODY CAVITY

CROSS-REFERENCE TO RELATED APPLICATIONS

This application claims priority to and the benefit of U.S. provisional patent application Ser. No. 61/642,762, filed on May 4, 2012. This application also claims priority to and the benefit of U.S. provisional patent application Ser. No. 61/660,930, filed on Jun. 18, 2012. The disclosures of U.S. Ser. No. 61/642,762 and U.S. Ser. No. 61/660,930 are incorporated by reference herein as if fully set forth at length.

BACKGROUND OF THE INVENTION

The present invention relates generally to embolic materials and more specifically it relates to a device and method for filling of an aneurysm or body cavity. The purpose of this invention is to provide a device and method for filling of a small or large aneurysm or other body cavity with material to prevent flow of blood or bodily fluids and promote blood clot or scarring in the tissues to prevent undesirable conditions such as bleeding or fluid leakage.

BRIEF SUMMARY OF THE INVENTION

The invention generally relates to an embolic material and method for its delivery into the body. The elements of the invention in the various described embodiments may include an introducer sheath, an introducer catheter, a micro-catheter, an embolic agent, a linking element, a detachment element, an embolic delivery apparatus, an embolic containment apparatus, a guide wire, a pusher element, traction elements, a stopcock, a side port adaptor, embolic detachment tools, and in certain environments an endograft or stent. The operator selects the elements of the invention as necessary to perform the procedure as may be required.

In one embodiment, the invention comprises a device and method for filling of a small or large aneurysm or other body cavity with material to prevent flow of blood or bodily fluids and promote blood clot or scarring in the tissues to prevent undesirable conditions such as bleeding or fluid leakage. In one embodiment, the invention comprises a device and method for filling of an aneurysm or body cavity that may be used for many sizes of aneurysm or cavity, including very large ones that may be difficult or impossible to treat with other means or with conventional embolic agents.

In one embodiment, the invention comprises a device and method for filling of an aneurysm or body cavity that provides rapid filling of the aneurysm or cavity that might otherwise take substantially more time to fill or to prevent flow of body fluids or blood using other means. In one embodiment, the invention comprises a device and method for filling of an aneurysm or body cavity with a high degree of safety due to small instrument sizes and use of embolic materials that are biocompatible and may be accurately delivered to target tissue without inadvertent delivery to non-target tissues. Smaller diameters may be possible due to the longer lengths of embolic agent possible with this invention, resulting in great volume despite small diameter.

In one embodiment, the invention comprises a mechanical and/or hydraulic means of advancement of embolic agent(s) through introducer catheters that provide more rapid and controlled deliveries that are not currently possible with current conventional delivery means and to enable the advancement of very flexible embolic agents that might be difficult to push manually due to kinking. An object of this invention is to provide such a delivery means to advance a very long single embolic agent with speed and control and another object of other embodiments of this invention provide a means for very rapid and controlled delivery and advancement of a great plurality of shorter or more conventionally proportioned embolic agents in order to provide a great bulk of embolic material in their summation.

In one embodiment, the invention comprises a means of providing a very long strand of embolic agent which may be reduced in its length during the operative procedure using safe and effective means, giving the operator flexibility to utilize the advantages of a very long single embolic agent while also having the advantage of tailoring the length to a very specific desired length, with the determination of the desired length being possible after the procedure has already begun and considerable length of embolic material has already been deployed into the affected tissues.

In one embodiment, the invention comprises an electrolytic method of detaching and shortening the embolic agent during the procedure at one of many possible locations along the embolic agent instead of being limited to one specific detachment location or point as with current conventional electrolytic agents. In one embodiment, the invention comprises an introducer catheter with electrical means to facilitate detachment or shortening of the embolic agent at or near the tip of the introducer catheter deep within the body of the subject in.

In one embodiment, the invention provides precision control of the position of the embolic agent deep within the body of the subject by manipulation of attached parts accessible to the operators hands extra-corporeally, with ability to advance or retract until the time of detachment. In one embodiment, the invention comprises embolic agents that are modifiable by the operator to facilitate objectives of determination of total length and location of detachment. In one embodiment, the invention provides the means to enable electrolytic methods with greater utility than other known systems by being applicable to variable-length embolic agents and also directed to a specific detachment area. In one embodiment, the invention comprises means to enhance the utility of existing mechanical detachment configurations to be compatible with a variable-length embolic agent.

In this respect, before explaining the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting. To the accomplishment of the above and related objects, this invention may be embodied in the form illustrated in the accompanying drawings, attention being called to the fact, however, that the drawings are illustrative only, and that changes may be made in the specific construction illustrated and described within the scope of this application.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein:

FIGS. 9A-G depict novel linking elements and their use to provide for shortening and detachment of embolic agents;

FIGS. 12A-H depict various embodiments of novel catheters containing electrical elements comprising two electrodes which are utilized in conjunction with the embolic agents and embolic delivery systems to provide for electrolytic detachment as described herein;

FIGS. 15A-B depict various embodiments of venting catheters which are utilized in conjunction with the embolic agents and embolic delivery systems described herein;

FIGS. 16A-17 show an embodiment of a novel embolic delivery system propelling the embolic agent using feeder wheels or belts as described herein;

FIGS. 18A-M show various embodiments of traction elements which may be formed or fashioned on to or within embolic agents as described herein;

FIGS. 19A-E and FIGS. 20A-H depict various embodiments of novel traction elements as described herein;

FIGS. 21A-F depict various embodiments of novel traction elements and pusher elements as described herein;

FIGS. 22A-H depict various embodiments of embolic delivery systems that utilize a principle of an attached flexible member such as a string or filament or tape that may be pulled to force an embolic agent through a catheter and then are stripped away from the agent in a running manner, as disclosed in various embodiments of the invention;

FIGS. 23A-I show various embodiments of novel embolic delivery systems that use bidirectional linear motion elements combined with traction elements to provide unidirectional linear motion of embolic agents as described herein;

FIGS. 26A-G depict various embodiments of tools providing for modification of an embolic agent intra-procedurally as described herein;

FIGS. 28A-D depict various embodiments of novel embolic agents with shape memory features useful to some embodiments of delivery system as described herein.

DETAILED DESCRIPTION OF THE INVENTION

Figure 1A:
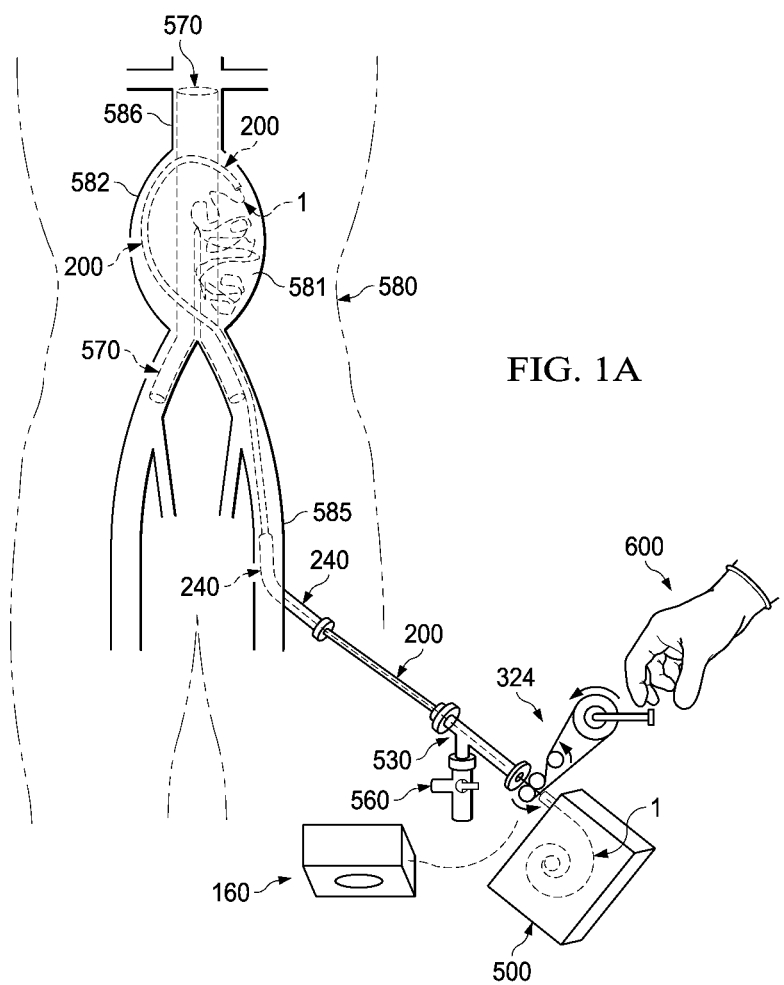
FIGS. 1A-C are simplified block diagrams in the front view illustrating the overall elements for embolization in one embodiment of the present invention.

Before proceeding with a detailed description of the invention, some commonly used terms will be defined to aid the reader in the understanding and practice of the invention disclosed herein.

The introducer sheath is a hollow tube of semi-rigid material with a thin wall. It permits introduction of other elements described below into the body. The other elements, such as the introducer catheter, may pass through the lumen, or hollow core, of the introducer sheath. The tip of the introducer sheath will usually be positioned inside the body, such as in the artery in FIG. 1, while the proximal end will usually be outside the body. Once it is in position, it may be left in place for most of the procedure, and thus provides a channel for passage of instruments from the outside to the inside of the body. Several introducer sheaths may be in place at one time, and some may be used for passage of instruments that are not part of this invention, as well as for instruments composing this invention. Introducer sheaths are conventional elements known in the art. An introducer catheter may be used without an introducer sheath in some instances.

The introducer catheter is a hollow shaft of semi-rigid material with a thin wall, but is generally longer in length than an introducer sheath and often smaller in caliber so that it can fit co-axially inside an introducer sheath. It may be manipulated by a user or operator into the desired part of the body, often under fluoroscopic imaging for guidance. In FIG. 1 it is seen to have its distal tip inside the body in an aortic aneurysm, and can be seen to be in close proximity and adjacent to the endograft inside the body aneurysm, but does not pass inside the hollow endograft. It may be passed over a guide wire for more control, and to facilitate the desired placement. The introducer catheter may be used to pass the embolic agent, such as a long filament, from outside the body, into the body where treatment is needed. Although the introducer catheter may enter the body through the introducer sheath, it may also be introduced through the tissues without the introducer sheath using means well known in the art. Introducer catheters are conventional elements commonly used in the art for many purposes including the introduction of embolic agents. Novel variations are described in this invention, including introducer catheters that provide elements and functions relating to detachment of the embolic agents as described below, sometimes including electrolytic mechanisms that are partially located within the introducer catheter.

Embolic agents are used in conventional practice of the art, often using conventional introducer sheaths and introducer catheters. In this invention, novel embolic agents are described in detail elsewhere herein. Various embodiments of novel embolic agents are depicted. The embolic agents described in this invention are solids, and longer in the longitudinal axis than in width, like strings or wires or filaments of various lengths and widths and shapes depicted in detail elsewhere herein. They may be flexible, but have enough stiffness to be capable of being pushed by a pusher element or embolic delivery system. In FIG. 1, a long, narrow filamentous embolic agent is seen housed in an embolic containment apparatus outside of the body, being pushed into an introducer catheter by an embolic delivery system, and exiting the distal end of the introducer catheter inside the body; in this example into an aneurysm of the abdominal aorta where it kinks and folds into a complex shape, thus filling much of the space within the aneurysm cavity in the body. Many details and variations of embolic agents comprise many of the novel aspects of this invention.

Figure 1B:
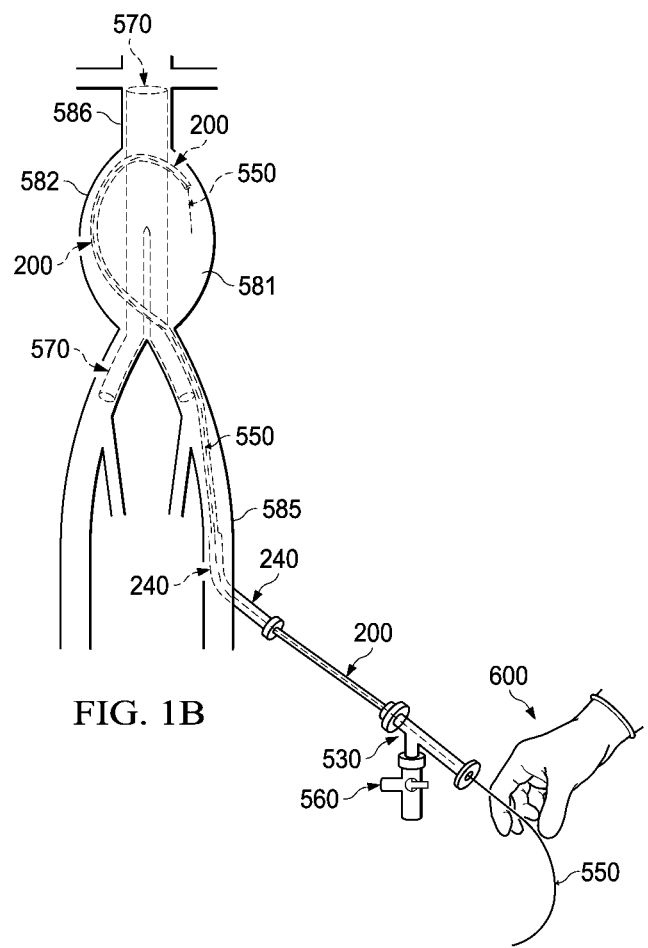
Figure 1C:
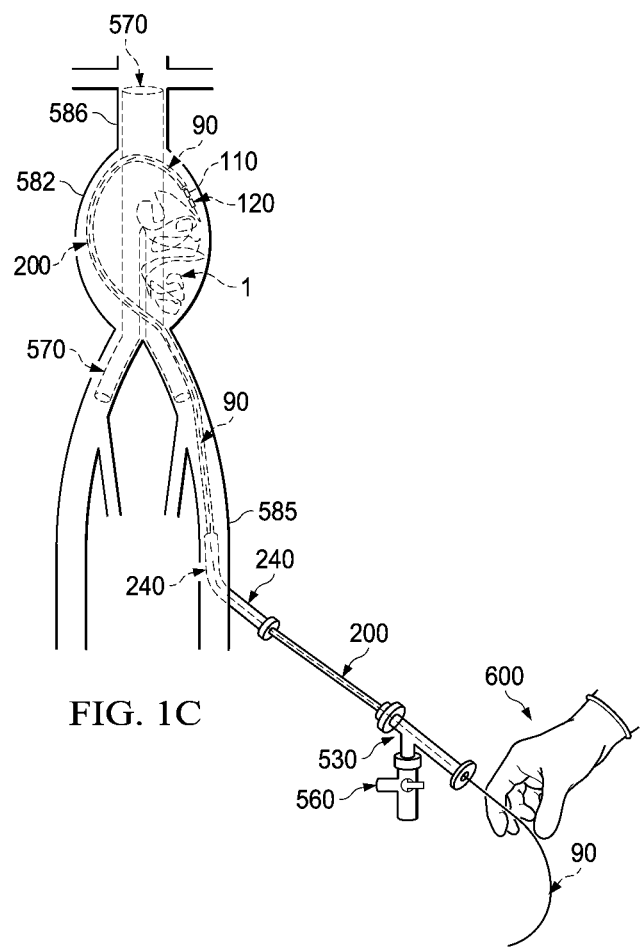
Figure 1F:
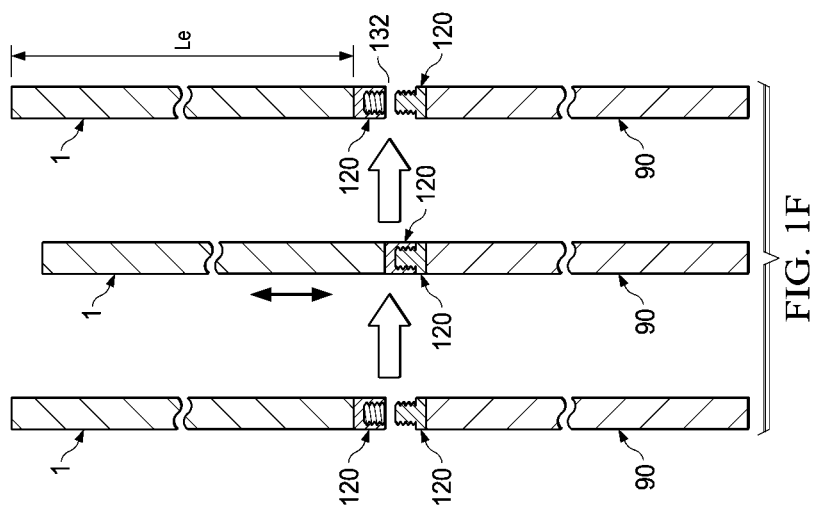
FIGS. 1D-L are schematic representations of different categories of detachment systems including conventional and novel.
Figure 1E:
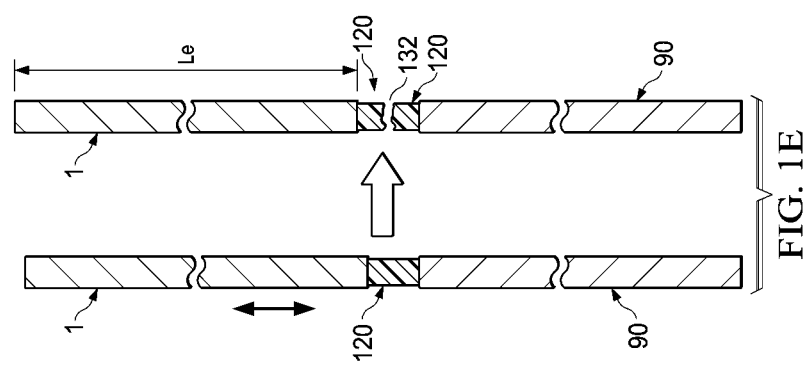
Figure 1D:
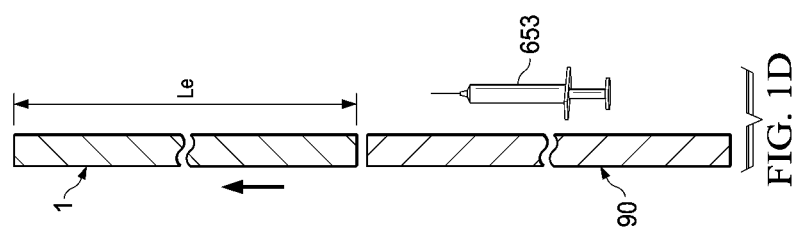
Figure 1H:
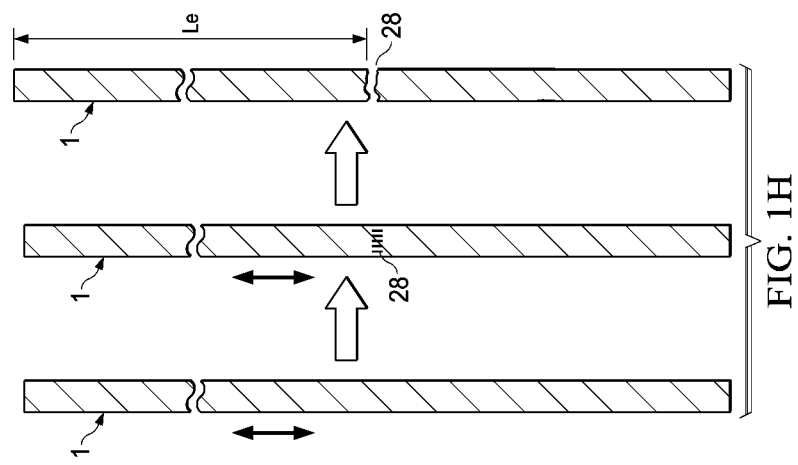
Figure 1G:
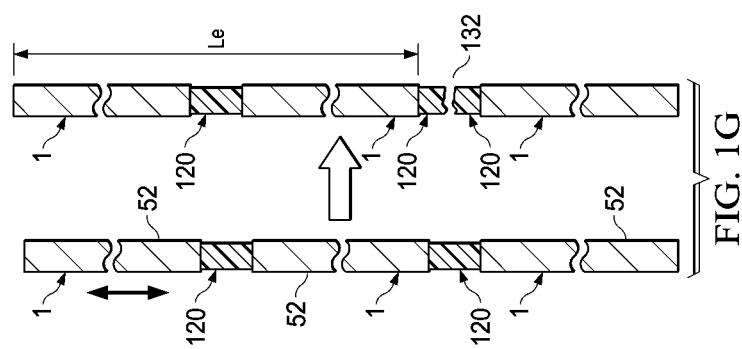
Figure 1I:
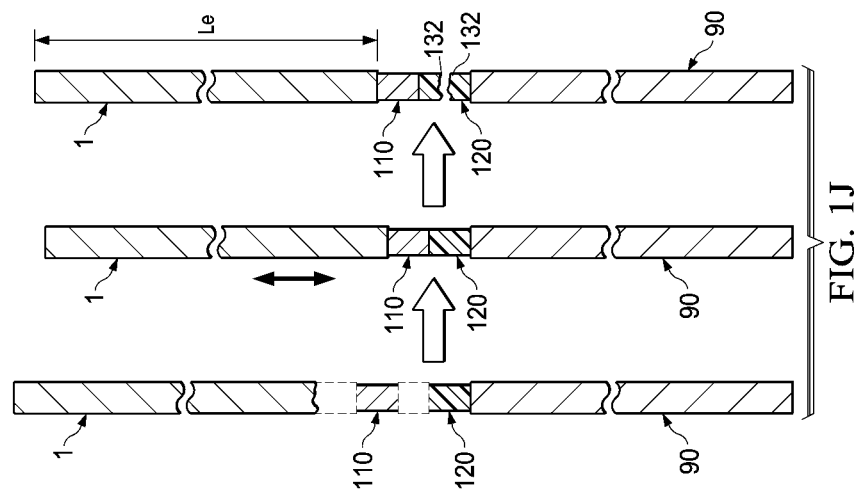
Figure 1J:
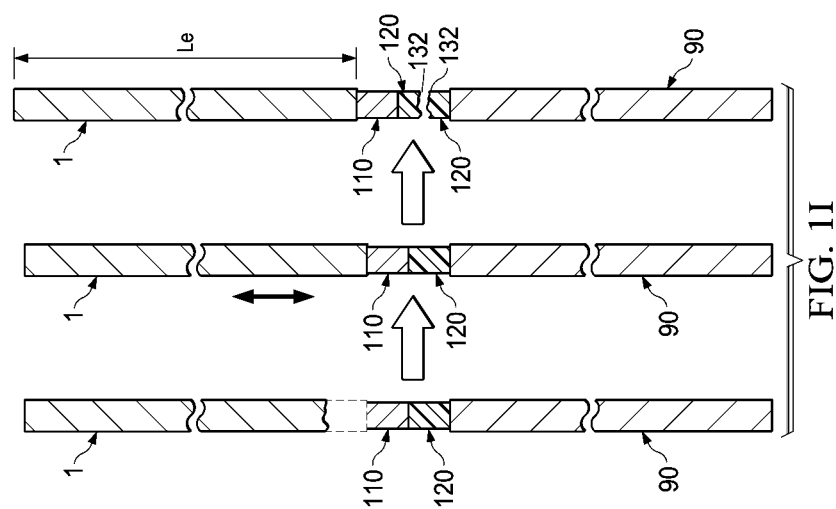

A novel linking element is used by the operator to modify the manufacturer-supplied elements by linking, defined as connecting linearly (i.e. "end-to-end"), other elements with a non-detachable attachment as seen in FIGS. 1I and 1J. The linking site is separate from the detachment site, and is not located on the linking element. Usually the elements that are linked by the linking element are the embolic agent (on its proximal aspect) to the detachment element (on its distal aspect) with the result of and end-to-end series of connected elements that may be advanced or retracted in unison by operator-manipulation of the proximal aspect of the proximal component, i.e. the pusher element. In this invention linking elements are used in conjunction with detachment elements to enable operator-controlled detachment of the embolic agent from the pusher element. Although linking elements do not detach, their function provides the operator with the novel ability to apply the detachment element and pusher elements at the location of their choice on the embolic agent, thereby enabling the novel aspects of variable length as determined by operator after partial completion of procedure when ideal final length becomes evident. Concepts of linking elements are demonstrated in FIGS. 1D-1L.

Detachment elements are elements that provide a detachable attachment between other elements arrayed end-to-end so that one element, usually an embolic agent, may be positionally controlled by operator manipulation of another element, usually the pusher element, until the operator wishes to separate the detachment element, or separate between two detachment elements which were attached together, thereby separating the other two elements from each other, such as the embolic agent from the pusher element. There are many different embodiments of previously described detachment elements, with several commercially available, corresponding to configurations and limitations described in FIGS. 1D-F. The invention disclosed herein additionally describes detachment elements with configurations and properties described herein. At the time of manufacture the detachment elements in this invention are non-detachably attached to the embolic agent and/or the linking or pusher element depending on embodiment.

The embolic delivery systems described herein are machines made of solid materials that can withstand wetness without losing function, such as metal, plastic, and rubber or rubber-like flexible compounds. They may also contain electrical components and a motor with speed controls, and an electrical power source such as battery. The system serves to drive the embolic agent to the target tissue in the body. It may drive the embolic agent though a side port adaptor and then through the through the introducer catheter before it reaches the target tissue in the body as seen in FIG. 1, although many variations are described herein where different components and configurations are different to achieve a similar result of driving the embolic agent to the target tissue. In some examples described later herein, and as shown in FIG. 1, the embolic delivery system includes a system of pulleys and a toothed belt, whereby the drive system, in this case the hand of the operator, turns a hand crank to drive the large pulley, which in turn drives the feeder rollers, which then move the embolic agent. The embolic delivery systems are all novel elements of this invention, and include many variations that include different sub-elements and mechanisms. Also described herein are embolic delivery systems that utilize hydraulic propulsion mechanisms to drive embolic agents. Also described is system using a combination of feeder rollers and hydraulic mechanisms. Also described herein are embolic delivery systems that include traction elements and a to-and-fro motion of the driving mechanism, sometimes in combination with a clamp, to drive the embolic agent to its target tissue in the body. The pusher element can be an adjunct to the embolic delivery system, and as such can serve to function as an embolic delivery system or in conjunction with an embolic delivery system. Also described are systems that provide for rapid sequential delivery of a plurality of short or medium length embolic agents.

The pusher element exists in simple forms conventionally in the art, but is described in this invention in novel forms. They are generally a long and narrow, and flexible enough to pass through a catheter with curves, but rigid enough to push an embolic agent through the catheter, such as the introducer catheter. Such characteristics may be aided by transitions in stiffness along their length. There are many possible variations of pusher elements 90. They may be composed of different metals or plastics or other compounds, with varying degrees of stiffness of the various parts. Some have no transition 95 and are of similar composition throughout entire length. Some are helically wound, some are mono-filamentous or mandrel wire composition. This is conventionally manipulated by the hands of the operator, and is used to push an embolic agent through a catheter into the target area in the body. Conventional pusher elements are either attached to the embolic agent or not attached. Those that are not attached may push the embolic agent when both are constrained within the lumen of a catheter whose inner diameter is roughly similar to the outer diameters of the embolic agent and pusher element, much like a piston pushing another piston through a hollow cylinder. This type may not retract the embolic agent as they are not connected. Pusher elements that are attached to embolic agents are detachably attached since the pusher elements are not left inside the body after use. Before detachment, there two elements are connected and the embolic agent may be pushed or retracted by manipulation of the pusher element. In novel embodiments of this invention, it may be detachably or non-detachably connected to the embolic delivery system to affect the proper movement of the pusher element. The pusher element can be an adjunct to the embolic delivery system, and as such can serve to function as an embolic delivery system or in conjunction with an embolic delivery system. The pusher element may also contain traction elements in some novel forms of this invention, which may enable novel functions such as application of a to-and-fro motion of the pusher element resulting in a net forward advancement of the embolic agent, or retraction of the embolic agent effected by manipulation of the pusher element without a rigid attachment between the two elements. Conventional pusher elements may be the same composition and structure as a guide wire, and in some instances they are interchangeable, although in most instances they will have slightly different characteristics to facilitate their goals.

The embolic containment apparatus is a container for the embolic agent to store it and prepare it for delivery into the body. Its structure depends on the embodiment as described later, and may even be optional in some embodiments. A simple embolic containment apparatus could consist of a solid spool, such as is commonly used to store wire or cable or string, in which case it can be as simple as a cylindrical spool of many different types of materials. A slightly more complex embodiment could include a rigid tank-like container which contains the spool and the filament, as seen in FIG. 1, and allows dispensing of the filament out through an opening to the embolic delivery system. This tank could be fluid-tight and contain a solution to bathe the filament, or it could be air filled and not be water tight. Such an embodiment as depicted in FIG. 1 would be a novel aspect of this invention. Other more complex structures such as a Side Port Adaptor may be detachably or permanently connected to the embolic containment apparatus to allow injection or aspiration of contents. A simple embodiment could include a conventional bag, such as a plastic bag, which contains a coiled or otherwise compacted embolic agent. More complex and novel embodiments will be described later herein, and can include an integration of the elements of the embolic containment apparatus with the embolic delivery system. For example, a rigid container, similar to a tank, can contain embolic agent in such a manner as to permit hydraulic pressure to force the embolic agent out of the containment apparatus and into the introducer catheter or other component that will lead to the goal of ultimate delivery of embolic agent to the target tissue in the body. Another embodiment also involves an integration of the embolic containment apparatus with the embolic delivery system, and utilizes a solid plunger or piston to force the embolic agent out of the embolic containment apparatus for purposes described above. In some embodiments, the embolic delivery systems and the embolic containment apparatus are integrated in such a manner that the mechanical driver, for example the feeder rollers of the embolic delivery systems, are housed within the embolic containment apparatus, where they may be sealed within the fluid-tight system. Many other variations and combinations of these novel elements are possible. In some embodiments the embolic containment apparatus is fluid-tight, but in others it is not. It is usually rigid in most embodiments, but could also be flexible in some embodiments where rigidity is not necessary. The embolic containment apparatus and its variations are novel aspects of this invention.

A side port adaptor is a conventional device used commonly in the art. It is usually rigid and composed of plastic or metal, has one or more lumens, or channels that extends from one end along its longitudinal axis, to the other end, permitting flow of a fluid through them. It often has connector hubs on both ends that may detachably or non-detachably connect to another device such as an introducer catheter and/or an embolic delivery system or embolic containment apparatus. Such connections are usually fluid-tight. The side port adaptor also includes a side port that also contains one or more lumens that permit a 3-way communication of the lumens with the other ports.

A stop cock is a conventional device commonly used in the art, which is composed of a rigid material, usually plastic or metal, that has one or more lumens, 2 or more ports that communicate via the lumen, and a handle or switch mechanism that permits flow or restriction of flow through the lumens. Thus flow of fluid into or out of any port is controllable by the operator by manipulating the switch. The ports may be connected to other devices such as introducer catheter or embolic delivery system to permit or restrict flow of fluids or embolic agent between them. The stopcock is usually fluid-tight, not permitting leakage of contents to the environment, when the ports are attached to other components, or when the switch mechanism is configured to restrict flow.

The embolic detachment tools function to detach or fragment the embolic agent to separate the portion intended to be delivered to the target tissue inside the body from the portion to remain unused outside of the body. There are many variations of possible embolic detachment tools some of which are simple, conventional devices such as a common pair of scissors seen in FIG. 1, or a knife blade, whereas others are novel devices specific to this invention. Some examples score the embolic agent, or alter it in ways that permit its fragmentation and deployment as described in more detail elsewhere herein. More complex embolic detachment tools may include hydraulic means as described elsewhere herein, melting devices, hot wires or burners, spark generators, sanders, shapers, wire strippers, dissolution chamber (where a solvent is used to dissolve an element), swaging tools, adhesives, embolic agent modification tools, electricity sources such as a battery, and heat chambers that provide heat within a specific range. In some variations, the embolic detachment tool is attached to another component such as the introducer catheter, so that it can detach the embolic agent in a location remote from the operator, and/or outside of the body. For example it could be integrated with the distal end or tip of the introducer catheter. The embolic detachment tool may also include a method for detachment that is mostly accomplished by the Operator using his hands, such as weakening techniques that utilize manipulations such as bending or twisting that may be followed by rapid pulling or kinking to enable detachment.

Traction Elements provide traction or friction to various elements of the invention to enable an engagement of the members such that motion of one member, possibly effected by the operator or embolic delivery system will subsequently effect a desired motion, in a desired direction, of another member. An example is the presence of traction elements on an embolic agent such as a filament, which engage the traction elements on another member, such as a pusher element, so that manipulation of the pusher element by the operator will direct the embolic agent through an introducer catheter into the target tissues in the body. Traction elements have many different possible shapes and compositions including those described in more detail elsewhere herein for embolic agents. They are rigid or semi-rigid. Some function by using friction combined with mechanical elements creating a slidable engagement between the two members allowing them to move in relation to each other when desired, whereas others create a stronger mechanical engagement where relational motion between the two engaged members is very restricted, so that they move in unison, until they are disengaged. Traction elements form attachments that vary from easily detachable to substantially non-detachable. Some traction elements or their manner of use are novel aspects of this invention.

Guide wires are conventional elements, shaped as a long, narrow, semi-rigid elements that fit within the lumens of catheters, introducer catheters, introducer sheaths, or other elements. It may be used to help guide the other element to its target, or stabilize it, or hold an established path for passage of an element later. Ideally, the guide wire is stiff enough to perform the above functions, yet flexible enough to move forward around curves, and to prevent damage to tissues in the body.

Guide wires are usually composed of metals such as stainless steel, nickel-titanium alloys, platinum, or gold, among others, and often have a coating of other substances such as a hydrophilic polymer or other non-metallic compound to provide the desired coefficient of friction and reduction of tendency to induce blood clots when in contact with blood within the patient body.

There are many possible variations of guide wires. They may be composed of different metals or plastics or other compounds, with varying degrees of stiffness of the various parts. Some have no transition and are of similar composition throughout entire length. Some are braided, some are mono-filamentous or mandrel composition. The guide wire may be the same composition and structure as a pusher element, and in some instances they are interchangeable, although in most instances they will have slightly different characteristics to facilitate their goals. Many types of guide wire and pusher elements are commonly used in the art. In this invention, guide wires may have many different functions. It can be advanced through the lumen of catheter into the desired location inside the body, and then facilitate the passage of the catheter to its desired location, and then withdrawn to permit the use of the lumen for passage of fluids or embolic agent or other materials. It may be used to maintain a pathway that has been achieved through many elements such as stop cock, introducer catheter, side port adaptor, embolic delivery system, and others, so that a catheter or other agent may be passed over it co-axially (guide wire inside lumen of agent), to its desired location. After passing through these elements, it may then pass into the body, and therefore maintain a path through the elements outside the body to the target area inside the body.

An endograft is a conventional element, typically composed of one or more tubes composing wide-caliber lumens that permit the flow of blood, with a wall that prevents blood from passing anywhere except the lumens. It may be a simple tube with one lumen and 2 open ends that permit flow of blood in one end and out the other, or it may be more complex, such as the commonly used shape of a Y, or upside-down Y, where two tubes join to one tube, and their lumens join, so that blood may flow into or out of 3 separate lumen openings at the ends, as seen in FIG. 1. The endograft is often composed of a metal skeleton for support, which results in a flexible structure than could stand on its own, but may pass around corners and bends in the body. Integrated with the metal skeleton is usually a fabric wall made of woven polyester or expanded polytetrafluoroethylene. The endograft is usually inserted into the patient's body through a catheter that is inserted into an artery, in a compacted form that reduces its diameter considerably to permit passage through a much smaller hole than its ultimate fully expanded diameter will become after deployment. Once deployed, it is allowed to open to its full diameter, and attach to the inside of the vessel by various means such as hooks or friction. It will then permit flow of blood through its lumens, but not through its wall, thus preventing flow into abnormal structures such as an aneurysm in the patient's body as seen in FIG. 1.

Detachment mechanisms provide a detachable attachment between an embolic agent and a pusher element or something that functions as a pusher element, possible with other elements in a line, said pusher remaining partially within the operating field where the operator may manipulate it, providing control of the embolic agent indirectly, which may be deep within the body beyond the reach of the operator during crucial procedural steps. Electrolytic detachment of embolic agents is a principle and technique used in conventional embolic systems whereby electrical current is passed through components and ionic fluid medium or blood in a manner that takes advantage of well described electrolytic effect of corrosion of a metallic component of the circuit. The corrosion leads to disintegration of a segment of the wire-shaped structure, which then results in disconnection, fragmentation, or detachment, of the two newly separated components. The configuration of polarity will determine the type of electrochemical reaction that occurs and the desired effects of corrosion of the detachment element. The choice of metals determines the results as well. Stainless steel is a common metal in medical products which is susceptible to rapid electrolytic corrosion and is utilized in this invention. Nickel Titanium alloys are used as well. "Non-corrodible" metals are referred to in this document for simplification, but may actually be minimally or slowly corrodible to degrees that are not significant when used in the manners described herein. A common example of this is platinum, which is commonly used in medical devices due to this effect as well as its malleability, flexibility, and X-ray density. Some embodiments of the embolic agent in this invention utilize electrolysis to enable precise positioning of the distal portion of the embolic agent within the body, to enable the operator to choose the total length of the embolic agent, and to facilitate the pushing of the embolic agent to the desired endpoint by allowing it to remain continuous until in final position, and then fragmented, and then proximal portion removed. Most of the electrolytic systems described herein are novel due to inventions required to enable the desired functions which were not conventionally available. Mechanical detachment systems described herein achieve similar results as described above but use mechanical means to provide the detachable attachments necessary. Many mechanical systems have been previously described, and herein we disclose new novel systems as well as novel adaptations of existing detachment components to achieve the novel functions we describe.

The operator is the specialist trained in the art who performs the procedure using the elements of this invention for its purpose. Most of the relevant manipulations and device controls are performed by the hands of the operator as seen in FIG. 1. The operator's hands are generally outside of the patient, since this invention is predominantly used with techniques that permit passage of materials into the body through small bore elements such as introducer catheter and introducer sheath, although it may also be amenable to open techniques, whereby the operator will perform a larger surgical incision and use her hands and/or other instruments to deploy the embolic agent using some or all of the elements of this invention, in which case the operator's hands and/or some of the elements of this invention will be inside of the body. In any case these devices must enable delicate control of the elements deep within the body that are outside of the direct reach of the operator, through the other elements that extend into the operator's field.

Turning now to the drawings, in which similar reference characters denote similar elements throughout the several views, the figures illustrate the main elements of this invention. Many elements of the invention are seen in FIG. 1A and include an introducer sheath 240, an introducer catheter 200, an embolic agent 1, an embolic delivery system 324, an embolic containment apparatus 500, a stopcock 560, a side port adaptor 530, an embolic detachment tool 160, an operator 600, a body containing an abnormal cavity or aneurysm 582, and an endograft 570. The embolic agent 1 is spooled in the embolic containment apparatus 500, and fed by the embolic delivery system 324, which is controlled by the operator 600, into the side port adaptor 530 which has a stopcock 560 on its side port, then into the introducer catheter 200, which passes into the body 580 through an introducer sheath 240 that traverses the skin and enters the femoral artery 585. The introducer catheter 200 passes up the arteries into the abnormal aneurysm 582, which involves the aorta 586 in this example. The embolic agent 1 passes through and beyond the introducer catheter 200 to fill the cavity 581 (aka sac) of the aneurysm 582. Embolic detachment tool 160 was used to modify the embolic agent 1 prior to completion. FIG. 1B contains main element guide wire 550 which is shown being used to help pass the introducer catheter 200 into the aneurysm 582 prior to introducing the embolic agent. FIG. 1C shows a pusher element 90 being used to advance the final portion of the embolic agent 1 into the aneurysm 582. A linking element 110 and a detachment element 120 are seen in line between the pusher element 90 and the embolic agent 1, enabling advancement and retraction of the embolic agent 1 until the operator 600 is satisfied with the position, when detachment is initiated in the detachment element 120, and then the embolic agent 1 and, in some embodiments, a portion of the detachment element 120 is left in the aneurysm 582 and all other components are pulled out. Traction elements are too small to visualize in these overview drawings and are used in some embodiments where they are described.

FIGS. 1D-L are longitudinal section schematic views teaching some important concepts contrasting the prior art with some of the novel aspects of this invention especially in reference to the embolic agents. The embolic agents 1 and pusher elements 90 are much longer than easily represented so smooth wavy lines are used to represent continuity of the elements. Jagged lines indicate detachment points 132. FIG. 1D represents a common conventional embolic agent 1 and pusher element 90 commonly referred to as a "pushable" embolic, usually a helically coiled wire. When both elements are in the introducer catheter (not shown) which passes from the extra-corporeal field to the intra-corporeal tissues the operator may push the embolic agent deep into the body by pushing the pusher element 90, but they may not retract it once pushed (indicated by the one-way arrow pointing up). If the embolic agent 1 goes to a non-desired location in the body, it must remain there because it cannot be pulled out or repositioned. The length ("Le") of the embolic agent 1 is pre-determined by the manufacturer, and is limited by practical necessity to be relatively short, generally not longer than approximately 30 cm. as explained in more detail in FIG. 1M-N. This may lead to use of a great number of embolic agents at great cost and is technically impractical for large aneurysms. Sometimes embolic agents 1 of this type are pushed hydraulically instead of with a pusher element 90, e.g. by a syringe 653 which is a commonly used simple device for creating hydraulic pressure. FIG. 1E is a two part sequence depicting a conventional system that gives the operator the freedom to advance or retract the embolic agent 1 by manipulating the pusher 90 (indicated by bidirectional arrow) because they are securely attached together by a detachment element 120 as on the left. When the embolic 1 is in the desired position, detachment may be initiated at the detachment point 132 as seen on the right, relinquishing control over the embolic agent 1. Finally the pusher 90 is removed. This imposes two important limitations of conventional agents. The length ("Le") of the embolic agent 1 must be pre-determined by the manufacturer, and is limited by practical necessity to be relatively short, generally not longer than approximately 30 cm. as explained in more detail in FIGS. 1M-N. FIG. 1F is a 3 part sequential schematic that represents another conventional embolic device which involves operator modification during the procedure. On the left, an embolic agent 1 with a detachment element 120 and a pusher element 90 with a mating detachment element 120 are available to the operator. In the middle, the operator has modified the device in the operating field by attaching the detachment elements 120 to each other, and now has bidirectional control over the embolic agent 1 indirectly by controlling the pusher element 90. In the final drawing, the embolic agent has been pushed into the body, and the operator detaches the components at the detachment point 132 between the detachment elements 120. Note that the detachment point 132 is also the location of operator modification, i.e. the joining of the separate elements. The detachment elements are schematically depicted as a screw-type system to broadly represent any type of reversible mechanical attachment mechanism described. This configuration is also subject to the limitations described in FIG. 1E and FIGS. M-N.

FIG. 1G depicts and demonstrates principles of variable, operator-determined length (Le) of embolic agent 1 and the practical capacity for lengths that are vastly greater than conventional embolic agents, possibly over a hundred meters in some embodiments, in addition to full operator control over advancement and retraction of embolic agent 1. Such long lengths would not be possible with conventional agents because the operator cannot possibly predetermine the exact length that would be needed in such a large cavity, so would have to use many conventional agents until the endpoint was achieved. As shown in FIG. 1G, embolic agent 1 includes a series of repeating segments 52, each of which includes a detachment element 120. The embolic agent 1 is pushed into the body without a separate pusher element as the operator may push directly on the embolic agent until the desired amount is in the body cavity, at which point detachment is initiated at a selected detachment point 132. In some embodiments, the detachment point 132 will be limited to that most proximate to the operator's field of manual manipulation extra-corporeally, whereas in other embodiments the detachment element 120 adjacent to, and distal to, said proximate detachment element 120 may also be used for detachment, and in other embodiments any detachment point 132 may be chosen for detachment, although usually requiring modification of the desired detachment element 120 by the operator prior to passage of said modified detachment element 120 to the place of detachment if deep within the body.

FIG. 1H is a sequential view depicting embolic agent 1 that also has operator-determined length (Le) of embolic agent 1, and the practical capacity for lengths that are vastly greater than conventional agents, in addition to full operator control over advancement and retraction of embolic agent 1. In addition, embolic agents 1 in this category have infinite choices of detachment points 28 without discrete detachment elements 120 (not shown) in the manufacture-provided embolic agent 1. This is made possible in part by embolic agents 1 that are modifiable extra-corporeally by the operator in the manual operating field. In the second drawing, after modification which is schematically shown as four vertical lines at detachment point 28, the embolic agent 1 remains intact and the operator retains control over advancement or retraction of the embolic agent 1 by manipulating its trailing portion extra-corporeally. When the desired position of the modified embolic agent 1 is achieved, detachment may be initiated as seen in the third drawing at detachment point 28.

FIG. 1I is a sequential view introducing the novel concept of operator-controlled linking elements 110 in the extracorporeal operating field to provide the functions of operator-determined length (Le) of embolic agent 1, and practical capacity for lengths that are vastly greater than conventional embolic agents, in addition to full operator control over advancement and retraction of embolic agent 1, and the presence of infinite choices of detachment points 132 without the need for discrete detachment elements 110 in the manufacture-provided embolic agent 1, with potential manufacturing simplification. Once the desired length of embolic agent 1 is determined by the operator, possibly after much of it is already deployed within the body, it may be severed using tools, with severed end schematically represented as jagged edge. On the left, the severed embolic agent 1 is not yet linked to the detachment element 120 which is already securely attached to the pusher element 90 by manufacturer. In the center drawing, the operator has used the linking element 110 to link the detachment element 110 to the embolic agent 1. The operator now has control over the embolic agent 1 outside or inside the body by manipulating the extracorporeal aspect of pusher element 90. When desired position of embolic agent 1 is achieved, detachment at detachment point 132 is initiated as described previously. Because only one detachment element 120 is needed, and because it does not need to be manufactured into the embolic agent 1, this category permits the use of a very wide variety of detachment element types, including conventional types that have been modified in novel ways to suit function in this novel manner, thereby greatly expanding their utility beyond conventional systems. Nearly any described detachment mechanism which has been thus far restrained to usage in the limited manners of FIG. 1D-F may become the basis for novel modifications that permit the greatly expanded utility of the novel devices in the category described in FIG. 1I.

FIG. 1J is a three part sequential view of a category of embolic agents 1 and related elements that permit roughly the same functionality as described for FIG. 1I, however in FIG. 1J the linking element 110 is manufactured as a separate piece, which is used by the operator to link two other separate pieces including the severed embolic agent 1, and the pusher element 90 with attached detachment element 120. Once linked, the functionality is similar to FIG. 1I. The separate linking element 110 seen in FIG. 1J provides some different functionalities that are explained in more detail for each embodiment herein. FIG. 1K is a three part sequential view of a category of embolic agents 1 and related elements that permit roughly the same functionality as described for FIG. 1I and FIG. 1J. It resembles conventional configuration in FIG. 1F except that in FIG. 1K there is a linking element 110 which is non-detachably attached to a detachment element 120 by the manufacturer seen on the left. Once linked to the severed embolic agent 1 by the operator, the functionality is similar to the novel devices in FIG. 1I or FIG. 1J, with variable, operator-determined length and full control of embolic agent 1 through manipulation of pusher element 90 in the middle drawing, which is detached at will as shown on the right. The detachment elements are schematically depicted as a screw-type system to broadly represent any type of reversible mechanical attachment mechanism described FIG. 1L is a 3 part sequential view of another category of this invention where on the left is an embolic agent 1 that has been severed to desired length by the operator, and a detachment element 120 non-detachably attached to a pusher element 90. The severed end of the embolic agent 1, with or without further modifications, is detachably attached by the operator to the detachment element 120 without the need of a linking element, as shown in the center, giving operator control of embolic agent 1 via pusher element 90. On the right, when desired, the detachment element 120 and embolic agent 1 are separated at the same place as initial attachment not substantially altered relative to before they were attached together.

Figure 1M:
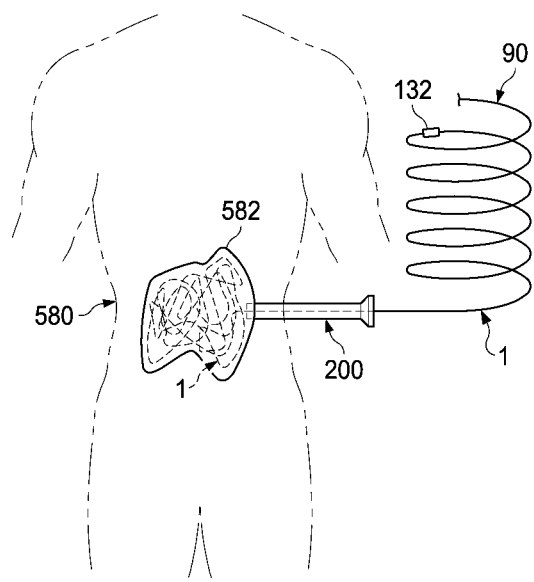
FIGS. 1M-N are schematic demonstrations of the limitations of conventional systems for treatment of large cavities, and the advantages of the novel systems disclosed herein; depict various novel embolic agents according to the various embodiments of the disclosed invention.

FIGS. 1M-N schematically demonstrate important limitations of conventional embolic devices and their solution by this invention, and demonstrate why conventional embolic agents may not be provided in very long lengths which are possible in this invention. In FIG. 1M, a scenario is depicted which would very frequently arise if a conventional detachable embolic agent 1 of the type described in FIG. 1E or FIG. 1F were hypothetically manufactured in very long lengths as is possible for our invention. The detachment point 132 is near the end of the assembly of embolic agent 1 and pusher element 90. The embolic agent 1 has been partially deployed into the aneurysm 582 within the body 580, but the endpoint of maximal embolization has been achieved before the detachment point 132 has reached the aneurysm 582. No viable options are now available. The remainder of embolic agent 1 cannot be passed into the aneurysm 582, it cannot be severed or left dangling partially out of the aneurysm 582 or the body 580, and it would be dangerous to remove the great length of already deployed embolic agent 1, as well as rendering the procedure useless. FIG. 1N is a two part sequence that shows how this invention addresses this type of scenario due its length being variable and operator-determined. The operator may decide, based on the progress of the procedure in real time, where to position the detachment point 132 along the great length of the embolic agent 1, or in some embodiments, to choose from among many possible detachment points 132 along the entire embolic agent 1. In this example the operator chose to enable a detachment point 132 at the position shown. The detachment point 132 of the embolic agent 1 is passed into the aneurysm 5982, where detachment will occur, followed by the removal of un-needed portions from the body.

FIGS. 2A-6Y depict different inventive embodiments of the embolic agent 1 as described herein. The depicted embolic agents 1 are stiff enough to push through the lumen of a catheter, but flexible enough to fold or kink or bend in order to compact into the cavity of the target tissue such an aneurysm. They have a proximal end 18 which is the last to enter the body, or to be detached from the remainder and discarded. There is also a distal end 19 which is the first to enter the body, and middle 20 in between. Their main function is to occupy the cavity to promote a desired biologic effect such as blood clotting, or tissue healing or scarring to permanently fill the space that was once occupied by gas or fluid with clot, or other solid body tissue. The embolic agents 1 may be pushed to their target directly by the hands of the operator outside of the proximal end of the introducer catheter, or by the embolic delivery system, or may be pushed by a pusher element which is in turn pushed by the hands or an embolic delivery system.

An embolic agent 1 may be composed of any biocompatible substance that is capable of becoming filamentous in structure. Possibilities include, but are not limited to:

Polytetrafluoroethylene (PTFE)
Expanded Polytetrafluoroethylene (ePTFE)
Polyester (PET)
Polypropylene (PP)
Polyamind (Nylon)
A fluoropolymer
A polyurethane
Biocompatible Thermoplastic Metallic wire or thread, such as platinum, stainless steel, gold, nickel-titanium alloy (e.g. "Nitinol"), alloy mixture, or any metal or combination of metal that provides the column strength necessary to be pushed through the catheter. It may have an attached agent such as woven polyester fibers, or any other fiber or fabric that can be attached to the wire to provide extra bulk and thrombogenicity (help clot the blood). It could be structured as a helical wire or coil, such as the conventional construction of common 0.035 inch diameter angiographic guide wires widely available. This may contain a solid mandrel wire for extra stiffness, or may occur without the mandrel, thus providing a very soft and flexible, bendable, and nestable wire. An example of such a wire could be a wire similar to the common Bentsen 0.035 inch guide wire with its mandrel removed.

The embolic agent 1 could be constructed from a biodegradable substance such as a polyglycolide, a poly L-lactide, a poly DL-lactide, a poly-caprolactone, a copolymer, or others. Embolic agent 1 may comprise monofilament or multifilament in structure, e.g., braided, woven, or yarn. Its diameter would permit it to fit through a hypo-tube or catheter capable of being inserted into an artery or cavity, usually, but not exclusively, a diameter in the range of 0.008" to 0.1."

Important properties of the embolic agent 1 include the coefficient of friction when dry and in aqueous environment, flexibility, pushability, elastic modulus, stiffness, diameter, tensile strength, and surface irregularity, as relates to friction as well as area of thrombogenic surface exposed to the blood. Also important in some instances is shape memory. The embolic agent 1 may be straight in its resting state, or it may be coiled or have any type of complexity of multiple curves to form a complicated nest or compact structure. It may be introduced in a straightened form as it is constrained it its packaging or the catheters, and then assume its resting shape when placed in the target area. It may also exhibit thermal memory, meaning that it takes on different shapes when at different temperatures. This could allow it to be introduced in a relatively straight form, and then more readily compact into a multiple curved configuration at body temperature once deployed at target.

The embolic agent 1 will need to be stiff enough to allow pushing into and through the catheter without buckling outside of the proximal end of the catheter. Once inside the catheter, the embolic agent 1 will occupy most of the lumen diameter, and will therefore be much less prone to buckling. However it must have enough flexibility to permit nesting and folding into the aneurysm sac with extensive redundancy, so that a great length of it can be deployed and provide replacement of a substantial volume of the aneurysm, thus providing vast total surface area to promote thrombosis of blood. A braided material may provide an even greater surface area on a microscopic level. A hydrophilic compound may be used to keep the wet friction very low.

The embolic agent 1 may be rendered visible on X-ray imaging using techniques that are commonly used in the art. If the embolic agent 1 is metallic, it may be adequately radio-opaque. If it is not, a metallic wire core or stripe may be applied or contained within the embolic agent 1 to provide opacity, or opaque markers, such as dense metals such as gold or platinum, may be placed along the embolic agent 1, either on its surface or imbedded within. The embolic agent 1 may be diffusely or discontinuously impregnated with a radio-opaque substance mixed into its composition or applied like a film, or layered within, to provide visibility under X-ray. Such substances may include barium or bismuth. The various shapes of embolic agent 1 are further described below. To enhance the hydraulic and/or mechanical propulsion of the embolic agent 1, the shape can be altered in numerous ways, some of which are depicted herein.

Figure 2A:
FIGS. 2A-S illustrate different types of novel embolic agents in various embodiments of the disclosed invention.
Figures 1, 2B:
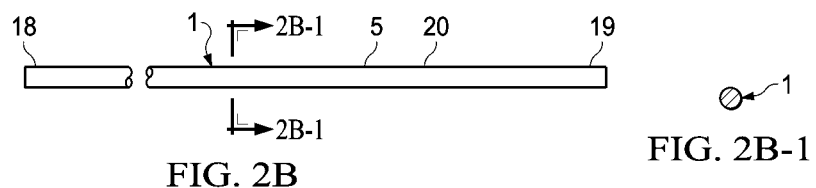
Figure 2C:
Figure 2D:
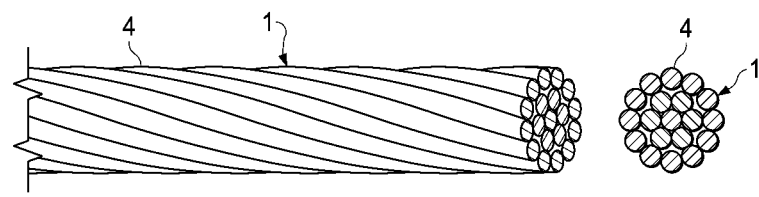

FIG. 2A is a perspective view and FIG. 2B is a longitudinal section view and FIG. 2B-1 is a cross-section view that depicts a simple shape of embolic agent 1. The embolic agent 1 is a simple elongated cylindrical shape, round in cross section, with a proximal end 18, middle portion 20, and distal end 19. Non-depicted variations could include rounded ends. In the depicted embodiment, it is a solid and flexible monofilament 5, with enough column strength to allow pushing through a catheter, but enough flexibility to bend or coil and fit into spaces much smaller than its full length. It may be composed of any of the substances listed herein including polymers or metal, or other biocompatible substances which provide the above characteristics as described herein. The surface of the embolic agent 1 is substantially smooth to reduce friction resistance as it is delivered to the aneurysm or cavity site. FIG. 2C depicts an embolic agent 1 similar to FIG. 2A except its surface is much rougher, imparting different properties which may be desirable for handling during the procedure or for biologic effects once implanted. FIG. 2D shows an embolic agent 1 which is composed of many strands 4 grouped together much as a string or rope may be made from many finer strands 4. Here, the strands 4 are composed of even smaller strands which are too small to be visible in the figure, and are grouped into the larger strands 4 that are depicted. Various contemplated embodiments would include different types of grouping configurations including simple bundling, weaving, braiding, yarn configuration, or any other type of pattern that may yield a filamentous embolic agent 1. This embolic agent 1 may have different surface, biological, thrombogenic and physical properties than the simpler mono-structure depicted in FIGS. 2A-B.

Figures 1, 2E:
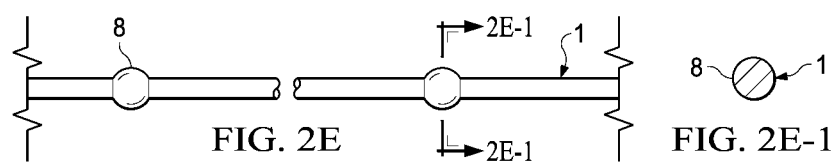
Figures 1, 2F:
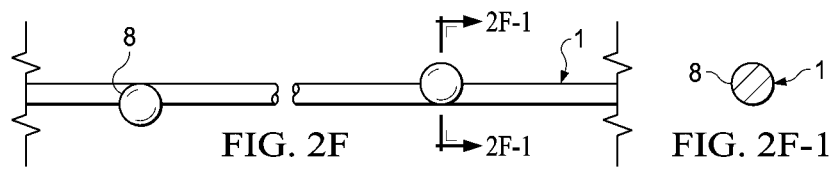

FIG. 2E is a longitudinal section view and FIG. 2E-1 is a cross-section view that shows an embodiment of embolic agent 1 with shapes and composition similar to FIG. 2A, however with the addition of nodes 8 that are roughly spherical, and have a greater diameter than the rest of the embolic agent 1, which is elsewhere constant in diameter with a circular cross section as shown. The nodes 8 can appear at any interval along the length of embolic agent 1 and in one example will occur every X length, where X is shorter than the length of the introducer catheter. Node 8 may act as a piston in a cylinder (for example, the inside lumen of the catheter) where it fits snugly so as to allow hydraulic propulsion of the embolic agent 1, while allowing fluid to flow around the smaller diameter embolic agent 1 to reach the bead. Node 8 could be manufactured from any of the materials described in this invention including polymer, plastic, hydrophilic material, metal, or any other rigid or semi-rigid compound. It may contain dense material, such as platinum or gold, to provide opacity under X-ray. In another contemplated embodiment, the node 8 may not encase the proximal end 18 of the monofilament 5 or its variant material, and instead it may be welded or adherent to the tip of the end of the monofilament 5 or variant material. The nodes 8 are concentrically located along the embolic agent 1, whereas in the embodiment depicted in frontal view in FIG. 2F and in cross section in FIG. 2F-1, the nodes 8 are eccentrically located along the embolic agent 1 in a variation, but with similar function. Nodes 8 depicted are roughly spherical, but variations may be cylindrical, globular, or slightly amorphous, so long as it's greatest diameter is similar to the lumen of the introducer catheter, and still have the desired hydraulic effect, functioning similarly to a piston that results in a substantial seal with the walls of the introducer catheter while still allowing motion through the catheter when hydraulic pressure, or pusher wire, is applied behind it.

Figure 2G:
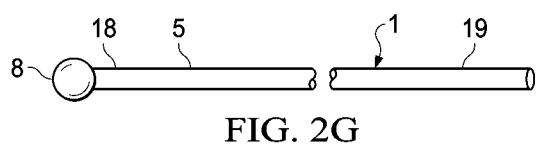
Figure 2H:
Figures 1, 2I:
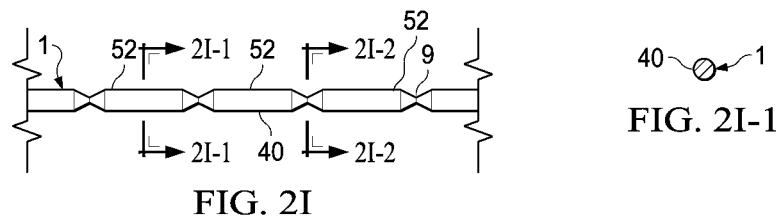
Figures 2, 2I, 2J:
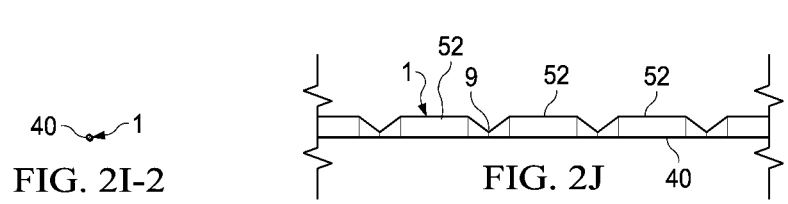

FIG. 2G depicts an embodiment of an embolic agent 1 that is suitable for hydraulic injection. It consists of a monofilament 5, which is round in cross section, has a proximal end 18, and a distal end 19. Attached to the proximal end 18 is a node 8, which consists of PTFE in this example. Node 8 is roughly spherical, and in this example surrounds the proximal end 18 of the monofilament 5. Node 8 is the same, or very slightly smaller, diameter as the introducer catheter 200 (not shown) to be used with it, so that the node 8 will function as a piston that is easily moved by a hydraulic force behind it, as well as by a pusher element such as a wire (not shown) as described elsewhere in this invention. The point of contact between node 8 with the wall of the catheter will be very short, keeping the friction between them to a minimum. The monofilament 5 is narrower in diameter than node 8, and hence also narrower than the catheter lumen, so it will also slide easily through the catheter when hydraulic force is applied to the node. In one embodiment instead of a monofilament 5, any other type of long and narrow material for embolic agent 1 described in this invention, including braided filament, wire (mandrel, braided, or wound), with or without fiber attachments may be utilized. FIG. 2H is a frontal view of a variation of FIG. 2G where the node 8 is attached to a helical wire 33 similar to that described elsewhere in this invention. In other respects, FIG. 2H is similar to FIG. 2G. FIG. 2I is a longitudinal section view and FIG. 2I-1 and FIG. 2I-2 are cross-section views that depict another embodiment of embolic agent 1. Embolic agent 1 is also circular in cross-section but has variable diameters throughout its length as shown. The narrower segments will be referred to as notches 9, between repeating segments 52 of main body 40. In this embodiment, the notches 9 are simply variations in the diameter of the embolic agent 1 and are concentric. This serves a similar function as the nodes described herein. In this embodiment, the larger caliber of the embolic agent 1 may fit snugly into the lumen 209 of the introducer catheter 200 (as shown in the different figures herein), to allow hydraulic propulsion of the embolic agent 1 as fluid pressure is transmitted at the smaller caliber portions of the notches 9. The notches 9 may also serve to make the embolic agent 1 more flexible and compactable. The length and diameter of the variable segments 52 and notches 9 could include many variations. This shape might offer advantages in manufacture, especially if it could be formed from the stretching and/or biaxial orientation of segments 52 of an embolic agent 1 to produce the narrower segments 52. FIG. 2J depicts another embodiment of embolic agent 1 which is circular in cross section in its repeating segments 52 of main body 40 between notches 9, where the notches 9 are eccentrically positioned.

FIG. 2K includes two perspective views of an embolic agent 1 with different types of notches 9 than shown above. The top view is a surface view and the bottom view shows the same embolic agent 1, depicting the internal configuration with dashed lines. In this embodiment, embolic agent 1 is a monofilament 5, round in cross-section as seen in FIG. 2K-1, with many notches 9, one of which is depicted, between repeating segments 52 of monofilament 5. These notches 9 form a circumferential hood-like protuberance which can be used for hydraulic effect, acting like pistons within the lumen of the introducer catheter, to help move the embolic agent 1 through the catheter upon injection of fluid, with the direction of motion as shown by dotted arrow. This embolic agent 1 may be manufactured by cutting a circumferential notch into the filament by applying the cutting device along the longitudinal axis of the embolic agent 1, thus splitting away the hooded portion from the underlying portion of the notch 9. A variation could be made by applying a hooded portion to a filament without cutting into it. FIG. 2L is a longitudinal surface view and FIG. 2L-1 is a cross section view depicting a similar embolic agent 1 with non-circumferential notches 9 that are cut into the embolic agent 1, perhaps by a blade, between repeating segments 52 of main body 40. These non-circumferential notches 9 would not act as sealed pistons, since the cross-sectional shape is not a circle, however they will create drag that could help propel the embolic agent 1 hydraulically within the catheter lumen when fluid is flowing through it. Various contemplated embodiments of embolic agent 1 may include different compositions of material and different configurations of notch 9.

FIGS. 2M-N depict two different embodiments of conventional embolic agents 1 composed of helically wound metal wire 33. FIG. 2M includes a surface view and a cut-away view showing the helically wound wire 33 to be round in cross section, and with hollow space inside 34. In this example, the wire 33 is comprised of wire loops that are not welded or joined together in any way, imparting a great deal of lateral flexibility if desired. The degrees of flexibility, column strength, tensile strength tendency to unravel, and electrolytic properties may be adjusted by use of various metals as known in the art, diameter of the wire 33 that is wound into the helical shape, and the diameter of the overall helical shape. In variation, welds or bonds between some of the loops of wire 33 may be created to change its physical properties, generally imparting more stiffness, column strength, and tensile strength. It may optionally have a mono-filament smaller wire or non-metallic fiber running through its core, tethered at the ends or other various points by welds (not shown) to change the properties to provide more stiffness, or to prevent unraveling or stretching. The embolic agent 1 is depicted as straight, however it may have memory shape to assume other configurations as described below. Helical wire embolic agents are conventionally available, however are limited in length to always be shorter than the introducer catheters, usually substantially shorter, in order to be manually pushed with a simple pusher element similar to a conventional guide wire as explained in FIG. 1M-N. In this novel invention, the helical wire embolic agent 1 may be vastly longer, many times longer than the introducer catheter, because its precise flexibility and handling characteristics, combined with the novel embolic delivery systems and novel detachment systems described herein permit feeding of the novel very long embolic agents described herein. FIG. 2N includes two surface views depicting a conventional embolic agent 1 containing a helically wound wire 33, seen in restrained and unrestrained shapes. It has fiber attachments 3 at various intervals, composed of tufts of very fine strands of woven polyester or other similar fine flexible filament. The top view depicts it straightened, as when constrained within a catheter (not shown). The bottom view shows it unconstrained, as when implanted in a cavity. Embolic agent 1 has shape memory, and when unconstrained, it will assume its pre-determined shape such as the helix depicted, although it could assume any of many shapes, including linear, or simply conforming to the space it occupies, since it is flexible. The fiber attachments 3 serve to occupy space within the target tissue or aneurysm, and promote blood clotting or favorable tissue reaction. Many variations are possible which utilize different shapes or different compositions to similar effect. Any embolic agent described in this invention disclosure may similarly have a memory shape other than the depicted shapes that are used to illustrate the important characteristics of each embolic agent. Variations could include many different types of composition of the embolic agent 1 or its fiber attachments 3, and many different sizes and configurations.

FIG. 2O is a schematic diagram of several varieties of three dimensional memory shapes of embolic agent 1 when unconstrained within a hypo-tube or catheter. From left to right, the shapes depicted comprise a simple spiral, multiple loops, three-dimensional cage, chaotic nest, and random curves. These shapes may apply to many compositions and sizes of embolic agent 1. It is contemplated that a vast variety of different shapes and configurations of embolic agent 1 are possible and in keeping with this invention.

FIGS. 2P-S are frontal views that depict various embodiments of embolic agent 1. These are departures from the long filamentous shapes described thus far. These are shorter in length, usually only a few centimeters, and therefore will require serial administration in greater quantities to fill abnormal cavities. FIG. 2P depicts an embolic agent 1 with a cylindrical shape, solid, having a proximal end 18, a middle 20, and a distal end 19. This is flexible or semi-rigid, and may pass through the lumen of an introducer catheter as described herein. It may be pushed to the target tissues using mechanical means or hydraulic means described herein. In this depiction, embolic agent 1 comprises a polymer monofilament, however in many variations it can be composed of any material listed elsewhere herein. As with all embolic agents described in this invention, variations could also include rounded ends, notches, nodes, hollow lumen, threads, locking mechanism, fiber attachments, memory shape, or a longitudinal slit, as depicted and described in detail elsewhere herein. FIG. 2Q, depicts an agent 1 similar to that in FIG. 2P, but even shorter in length, such that its length is actually less than its diameter. It is otherwise similar in composition and function to that in FIG. 2P. FIG. 2R depicts a spherical embolic agent 1 that is otherwise similar in composition and function to that in FIGS. 2P-2Q. FIG. 2S is a sequence view that depicts an embolic agent 1 with fiber attachments 3 of polyester or similar fine biocompatible thread, attached to a solid rigid core 12, intended for use through relatively large diameter introducer catheters 200 as conventionally available in the field. When unconstrained, this embolic agent 1 has roughly the shape of a sphere. When constrained inside the lumen 209 of the introducer catheter 200, it may elongate slightly, as it compacts overall in size. Once it is pushed out of the introducer catheter 200 into the target tissues, it will expand due to the natural tendency of the tuft of curly fiber attachments 3 to expand. This embolic agent 1 may be pushed by mechanical or hydraulic forces described herein. In variation, the core may be more cylindrical, or it may be absent, and instead the tuft of woven fibers may have integrity of its own, much like a conventional cotton ball.

FIG. 3A shows another embolic agent 1 in longitudinal and cross section view 3A-1. The embolic agent 1 is little different from the embolic agent shown in FIG. 2O, except that the ends are rounded. Three individual embolic agents 1 are shown end-to-end as could occur during use inside an introducer catheter 200 (not shown) or other system element. The embolic agent 1 has a proximal end 18, a middle 20, and a distal end 19. It is round at all levels in cross-section FIG. 3A-1. The proximal end 18 is seen abutted against the distal end 19 of the identical embolic agent 1 below it, and likewise for the third agent on the bottom. It can be seen that pushing on the bottom embolic agent 1 would result in forward motion of the other two if all were contained inside the lumen of an introducer catheter as described herein. It is also evident that pulling backward, or retracting, the bottom embolic agent 1 would not necessarily pull the other two embolic agents, since they are not attached or connected together. This represents a simple system for administering many relatively short embolic agents 1 into the target tissues through an introducer catheter by loading them into the introducer catheter 200 and pushing them forward using hydraulic or mechanical means as described herein.

FIG. 3B shows a similar embolic agent 1; however the shape is slightly more complex. It is also round in cross-section as seen in FIGS. 3B-1 and 3B-2 at all levels, but there are different diameters at different levels. The proximal end 18 and distal end 19 are larger in diameter than the middle section 20, and are equal in diameter to each other. In variation, the transition between different diameters may be more gradual.

FIGS. 3C-D, 3C-1 and 3D-1 are longitudinal and cross sectional sequential views of more complex embodiments of the embolic agent 1 of FIG. 3B where interlocking elements are included to provide additional stability during deployment. Although the specific shapes of the elements in FIGS. 3C-3D are different, the major characteristics are similar and will be described together here for both figures. The embolic agent 1 has a male locking element 24 on its distal end 19, and a corresponding female locking element 25 on its proximal end 18. The middle section 20 is solid, and most of the embolic agent 1 is solid, depicted as the solid portion 23, except for the proximal end 18 containing the female locking element 25, which is basically a hollow portion 22 that is surrounded by the solid portion that is round in cross section on its inner and outer surfaces. The inside and outside surfaces of the entire embolic agent 1 at any level are round. On the left view, two such embolic agents 1 are shown separately, and will come together as shown by dashed line where the male locking element 24 is mated with the female locking element 25, comprising the locking mechanism 10. The locking mechanism 10 will typically be intended to fit snugly, but not tightly, so that pulling the proximal embolic agent 1 downward will not necessarily pull the distal embolic agent with it. Likewise, advancement of the distal embolic agent 1 will not necessarily advance the lower one, which could be left behind. The locking mechanism 10 may facilitate the passage of a series of multiple embolic agents 1, which can be very numerous in number, in a smooth manner, through various elements of the system including the introducer catheter (not shown), embolic delivery system (not shown), their connections, and any others. They will tend to stay lined up as desired when passing through areas where they are not circumferentially constrained. At any time, they may be easily disengaged by being pulled apart.

FIGS. 3E-I depict embodiments of embolic agent 1 which is hollow, and therefore has a tube-like general configuration. As with other embolic agents described herein, this embolic agent 1 has a configuration and composition that permits its introduction into target tissues using embolic delivery systems 324 described herein. Instead of a solid core, it includes a hollow lumen 7. Its composition could be of any of the substances described elsewhere herein for embolic agents. Similar hollow tubes exist in the art for purposes such as micro-catheters that are designed to allow delivery of fluids or small particles to target tissues. In this invention, the tube is adapted in novel ways to serve as an embolic agent 1. FIG. 3E is a perspective view depicting a simple example of a hollow embolic agent 1. It is round in cross-section, has a hollow lumen 7, and a thin wall 2. It has a proximal end 18, middle 20 section, and a distal end 19. As described for other embolic agents herein, the distal end 19 is passed into the target tissues first. The purposes of this embolic agent 1 are the same as described elsewhere herein, but its function may be different. The thin wall 2 and hollow lumen 7, combined with the use of a flexible substance of composition, will enable this agent to fold and kink and nest very well inside the target tissue, as seen in FIG. 3H where a small segment of a hollow embolic agent 1 is easily kinked and folded by minimal external forces. Such kinking could occur at innumerable points along the length of the embolic agent 1. Another quality of the hollow embolic agent 1 is that it will occupy a greater volume of space using less material compared to an otherwise similar solid filament or wire. Its lumen 7 will have potential for flow of fluid, or creation of hydraulic pressure, or be capable of permitting insertion of a guide wire, as described here and in the detailed description of the embolic delivery system. It may also permit novel detachment or fragmentation mechanisms as described elsewhere herein, notably in the detailed description of detachment mechanisms. As will be described in more detail in the description of traction elements 270 hereafter, traction elements 270 may be applied inside or outside of the hollow embolic agent 1 with structure and function described therein.

FIG. 3F depicts is an upper perspective exploded view showing a hollow embolic agent 1, containing a lumen 7, a wall 2, a proximal end 18, a middle section 20, and a distal end 19 similar to seen in FIG. 3E. However, there is the addition of baffles 11, which are fluid-tight plates or membranes that seal off parts of the lumen 7 from other parts. The baffles 11 connect to the wall 2 circumferentially with a fluid-tight seal. A baffle 11 is shown on the distal end 19, which is shown in FIG. 3G, where it provides a seal of the distal end 19. Referring back to FIG. 3F, fluid flowing into the lumen 7 on an end of the embolic agent 1 would meet an obstruction upon reaching a baffle 11, and could lead to an increase in hydraulic pressure or propulsion of embolic agent 1 forward, depending on whether it was allowed to move by external forces. Variations of the hollow embolic agents 1 could include various compositions, wall thickness, lumen sizes, and lengths. The baffles could have different configurations and still be in keeping with their intended function in this invention of creating fluid-tight seals in the lumen 7. The baffles 11 could be of any number and spacing along the embolic agent 1. In other variations, the baffles could be non-fluid tight. Instead, they might contain holes or porosity or configurations that provide partial obstruction to flow of fluids, but not complete obstruction. In this manner drag could be produced without complete blockage of flow. The hollow embolic agent 1 may be open on both ends, closed on both ends, or open and closed on alternate ends. When closed on both ends, it may have porous seals or fluid-tight seals, which would or would not permit inflow of fluid into the lumen 7, respectively. The hollow embolic agent 1 may be radio-opaque, or radio lucent, or may utilize markers as described for other embolic agents herein. FIG. 3I depicts a hollow embolic agent 1 containing a wall 2 and lumen 7 with a baffle 11 closing the distal end 19. It would have a different propulsion characteristic inside an introducer catheter compared to a solid embolic agent 1 or a hollow embolic agent 1 with a baffle 11 on its proximal end 18. The hydraulic pressure would be directed more towards the distal end 19, thus the embolic agent 1 could be less prone to buckling inside the introducer catheter 200 or embolic delivery system 324. In effect, it would behave somewhat as if it was pulled through the introducer catheter than as if it was pushed from its proximal end 18. Much like a windsock, it would be kept fully expanded during this phase of deployment. Once in position in the target tissues, the loss of internal pressure could result in easy kinking and folding as desired.

FIG. 3J introduces two more contemplated embodiments that may be used alone or in combination with other embolic agents 1 as depicted elsewhere herein. The embolic agent 1 example in this figure is hollow having a lumen 7 and a wall 2, round in cross section, semi-rigid, and composed of polymer. It also has ridges 15 along its outer wall. These ridges may be cut or formed into the wall 2 of the embolic agent 1, having many different possible shapes depending on ease of manufacture, but here depicted as small triangular protuberances that are circumferential around the embolic agent 1. These provide extra traction with an embolic delivery system 324, as in this example where feeder rollers 325 are being used to drive the embolic agent 1. The feeder rollers 325 also have small corresponding ridges which will be called roller grooves 326, to provide extra traction, although in variation the roller grooves 326 may be absent. In other contemplated embodiments, any other type of embolic delivery system 324 described in this invention herein may be used alternatively, and the ridges 15 may still serve to provide extra traction or desirable handling characteristics when manipulated by the operator's hands. Other variations also include elements other than ridges as depicted to provide this extra traction. All of the surface characteristics depicted elsewhere herein in the detailed description of traction elements 270 could alternatively be used. Another embodiment is the ridges 15 may not be circumferential around embolic agent 1. Ease of manufacture might lead to use of scoring or ridges that extend only partially around the circumference of the embolic agent 1, or that extend circumferentially with interruptions. Also shown in FIG. 3J is a longitudinal slit 17 along the long axis of the embolic agent 1. This is a cut through the entire wall 2 thickness on one side (not involving the diametrically opposite wall), which permits the semi-rigid embolic agent 1 to be opened up along the longitudinal slit 17 to expose the inner lumen 7, which is now not a continuous circle. In this figure, the longitudinal slit 17 does not extend entire length of the embolic agent 1, but is incomplete at its distal end 19. In different embodiments, it may involve the entire length or a lesser length than shown. The longitudinal slit 17 permits opening of the embolic agent 1, which may then be fed onto a guide wire or other similar object using methods as described in the more detailed descriptions of embolic delivery systems herein.

FIGS. 4A-C depict various embodiments of embolic agent 1 with screw-like threads 16 to facilitate delivery. FIG. 4A is a surface view of a solid embolic agent 1 which is composed of metal or non-metallic materials described herein and has threads 16 circumferentially around its surface much like the threads of a screw in appearance and function. Embolic agent 1 is circular in cross-section as seen in FIG. 4A-1. It is flexible as a result of its flexible composition, or if metallic, due to its very small diameter, similar to a wire strand. This embolic agent 1 may be driven by a rotating threaded driver which functions like a nut on a screw, which when rotated and not allowed to move longitudinally, will drive the embolic agent 1 forward or backward, depending on direction of rotation of driver. Alternatively, threads 16 may engage the ridges 15 or threads 16 on feeder rollers 325 as seen in FIG. 3J. The embolic agent 1 may have a shape memory as described elsewhere herein, although shown here in its straight form as it would be when constrained. FIG. 4B shows a similar threaded embolic agent 1 as seen in FIG. 4A, with the addition of notches 9 at intervals along its length. It is solid and circular in cross section as seen in FIG. 4B-1. Notches 9 may facilitate folding or kinking of the embolic agent 1 once deposited in the target tissues, and are more likely to be added for embolic agents 1 with relatively larger diameters in their main segments 38. FIG. 4C shows another variation where the embolic agent 1 is not solid. As seen in FIG. 4C-1, but is instead small wire that is wound in a manner to create an outer surface similar to the threads 16 of FIGS. 4A-B. This may provide much flexibility while still permitting the mechanical functions of the threads. Optionally, there may be several weld points 21 along its length (see FIG. 4C) where adjacent coils of the wire are welded together. These change the characteristics of the embolic agent 1 by reducing its lateral flexibility, and decreasing its tendency to unravel when the ends are pulled in opposite directions. The frequency of weld points 21 serves to adjust the flexibility to desired characteristics. In other variation, longitudinal stretch resistance is instead provided by a small straight wire or fiber thread in the core that is tethered at both proximal and distal ends of the embolic agent 1, as seen in FIG. 9D.

FIGS. 5A-F are surface and cross-sectional depictions of flexible, predominantly non-metallic embolic agents 1 with radio-opaque markers 13 (FIGS. 5A-E) or radio-opaque substance 14 (FIG. 5F) that will improve visualization during fluoroscopic guidance and diagnostic imaging. Markers 13 made of dense radio-opaque metal, such as platinum, gold, tantalum, bismuth, barium, stainless steel, nickel-titanium alloy, or others are integrated with the embolic agent 1, and as shown in FIG. 5F, radio-opaque substance 14 is diffusely impregnated in the embolic agent 1 during manufacture as is sometimes utilized with angiographic or venous access catheters in common practice. Also, elements with functions related to electrolytic detachment, or fragmentation of the embolic agent 1 into at least 2 fragments through use of electrolytic corrosion, are outlined in some of the figures. The elements coating 31 and capsule 43 are discussed, both describing an electrically insulating layer of non-metallic material surrounding a substantial portion of an electrolytically corrodible wire to provide electrical insulation and prevent corrosion of the wire portion that it covers. In general, the term coating 31 is used for a thin layer, and capsule 43 for a bulkier layer, however these distinctions are relative and their characteristics can be so similar in some embodiments that they may be nearly interchangeable in meaning. The need to distinguish them arises mostly when both layers are present in the same embolic agent 1, where the capsule 43 is usually surrounding the coating 31.

In FIG. 5A, a long metallic wire 6 is surrounded mostly, except on its proximal end 18, by a capsule 43, which is flexible, non-metallic, solid, and may be substantially dielectric. The wire 6 may be electrolytically corrodible in variations where this function is desired. It may also serve as a marker 13. In this figure, it is centrally located in the core of the embolic agent 1 as seen in FIG. 5A-1. Other variations could include a plurality of wires 6, or different lengths or extent on the embolic agent 1, or located elsewhere than centrally, either within the perimeter of the cross section of the embolic agent 1, or on its outside surface. A method of manufacture could include co-extrusion of marker(s) 13 with embolic agent 1. In addition to serving as a marker 13 or instead of serving as a marker 13, the wire 6 may be used to impart the desired balance of flexibility and columnar strength. The wire 6 may also be used to facilitate electrolytic detachment as described herein using novel tools and methods to expose a portion or portions of the wire 6 to make them susceptible to electrolytic corrosion. In various embodiments, the wire 6 in the proximal end 18 of the embolic agent 1 may be surrounded by the capsule 43 as is the rest of the wire 6. In FIG. 5B, the wire 6 or wire marker 13 is eccentric (i.e. it extends most or all of the body 40 of the embolic agent 1), however is not located at the center on the cross-section views of FIGS. 5B-1 and 5B-2. Two types of embolic agents 1 are depicted which have two different methods of manufacture. FIG. 5B-1 shows a monofilament containing the wire 6 or wire marker 13, such as might occur if the monofilament were extruded over the wire as a capsule 43. FIG. 5B-2 shows the wire marker 13 or wire 6 is sandwiched between a core 12 and an outer layer 32 of the capsule 43, such as might occur with a co-extrusion of the 2 layers with the wire 6 in between. As in FIG. 5A, this wire 6 may also be used to provide the desired physical and/or electrolytic properties described herein. The wire 6 is completely encapsulated in this depiction, but in variation various areas may be exposed as described herein.

Figures 1, 5M:
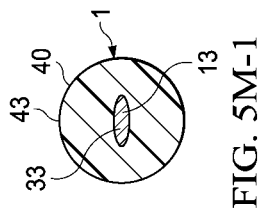
FIGS. 5A-M depict various embodiments of the novel embolic agents with radiomarkers as disclosed herein and which may be sized and detached intra-corporeally as disclosed herein.
Figure 5M:
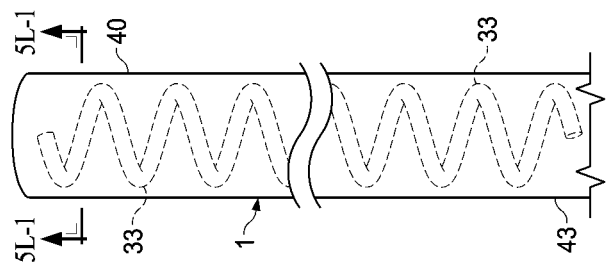
Figures 1, 5L:
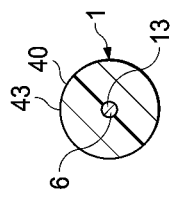
Figures 2, 5L:
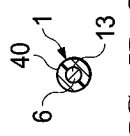
Figure 5L:
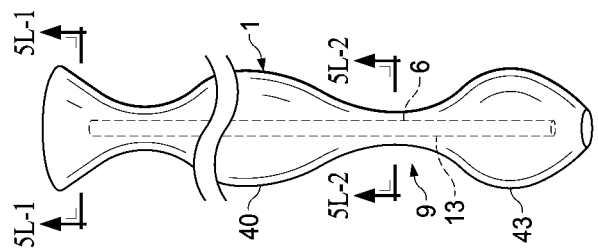

In FIG. 5C, the markers 13 are small spherical shaped beads spaced apart at various intervals along the body 40 of the embolic agent 1 which is a non-metallic monofilament 5. FIG. 5C-1 shows that markers 13 are centrally located in the cross-section of embolic agent 1, however in various embodiments they may be positioned at various locations within or on the surface of embolic agent 1. In FIGS. 5D and 5D-1, markers 13 are bands around the perimeter of the embolic agent 1, which are swaged onto the body 40 keeping the outer diameter substantially identical to non-banded portions of the embolic agent 1. Alternatively, these band markers 13 could be sandwiched between layers 32 of the embolic agent 1 (not shown). In FIG. 5E, an embolic agent 1 that is hollow (as in FIG. 3E), with markers 13 which may be in the lumen 7 held in place with adhesive or by deformation of the inner wall 2 as in FIG. 5E-1 or with markers 13 located eccentrically in the wall 2 as in FIG. 5E-2 where it is imbedded in the substance of the wall 2 using manufacturing methods described herein or conventionally available. FIG. 5E-3 depicts a portion devoid of markers 13. Other embodiments could include various shapes and sizes of marker 13. In FIG. 5F and FIG. 5F-1, there is diffuse impregnation of a radio-opaque substance 14 within the composition of the body 40 of the embolic agent 1. FIG. 5G is a frontal view and FIG. 5G-1 is a magnified cross section view of a hollow embolic agent 1 with a lumen 7 and a wall 2, and two different types of markers 13. The upper marker 13 is swaged onto the body 40 over a mandrel (inside the lumen to prevent collapse) similarly to FIG. 5D, and the lower marker 13 is sandwiched between layers 32 in the wall 2. This embolic agent 1 also has a fine, loosely wound helical wire 33 within its wall 2 to prevent crushing of the embolic agent 1 upon handling or feeding into a catheter, while still allowing flexibility and folding or buckling. FIG. 5H is a perspective view and FIG. 5H-1 is a magnified cross section view of a hollow, tubular-shaped embolic agent 1 with a wall 2 and a lumen 7. There is a metallic wire 6, which may be electrolytically corrodible, running throughout most or all of the body 40 within the wall 2, which is encapsulated and not exposed to the environment or lumen 7, similar to other variations shown or described in FIGS. 5A-B, 5J-M, 6A, 6C-E, and 6G-K, but not limited to these variations. In the embodiment of any encapsulated wire variations just named or described elsewhere herein, encapsulation may be incomplete as exposed wire may be present to allow application of electrical current as described herein. Wire 6 may also serve as a marker 13. It may provide the desired physical characteristics and/or electrolytic effects described herein. Embolic agent 1 may also utilize a coiled wire, or other wire configuration separate from wire 6, within its wall 2 for radial support, as described in FIG. 5G.

FIG. 5I is a frontal view and FIG. 5I-1 is a magnified cross sectional view of an embolic agent 1 composed of non-metallic flexible capsule 43, which may be dielectric, substantially encapsulating several wires 6 running longitudinally, oriented end-to-end, differing from FIG. 5A in that the wires are not one continuous wire, but are separated by gaps 41. This may serve purposes of creating the desired physical characteristics such as more flexibility in the gaps 41, possibly also aided by the placement of notches 9 as in FIG. 2I, as well as electrolytic properties serving to direct corrosion and detachment to a location proximal to a gap. Electrical current will not pass from one wire 6 segment to the others even if within ionic solution, so if electrolytic detachment is performed in the manner described herein, it will only occur along the wire 6 segment that is included in the circuit, which may occur at any location where the manufacturer or the operator exposes the wire 6 to the electrolytic environment such as blood or ionic fluids. The segments of wire 6 distal to the gap will not be electrified, hastening the speed of electrolytic corrosion to the desired point of exposure. The distance between gaps 41 in the wire 6 will usually be greater than the length of the introducer catheter (not shown) so that detachment can occur at or beyond the catheter tip while current is applied to the proximal embolic agent 1 outside the body of the patient in the manner described herein, to a portion where the wire 6 is exposed. This use of gaps 41 in the wire 6 may be applied to other variations containing a long wire insulated by a non-metallic coating or capsule, for example in FIGS. 5A-B and 5G-H.

FIG. 5J is a frontal view and FIG. 5J-1 is a magnified cross section depicting an embolic agent 1 which includes an encapsulated wire 33 where wire 33 is helically wound within the capsule 43. As in other variations depicted herein, the body 40 is substantially dielectric and hence insulates the wire. As in other examples described herein, the metallic wire 33 may also serve as a marker 13. The use of the helically wound wire 33 may serve to provide the desired physical handling characteristics, as well as possibly serve for electrolytic detachment as described herein. FIGS. 5K-M are each frontal views and FIGS. 5K-1-5M-1 are cross section views depicting solid embolic agents 1 that contain a wire 6 or helical wire 33 encapsulated in the body 40 of capsule 43 which is non-metallic and substantially dielectric. FIG. 5K and cross sections FIGS. 5K-1 and 5K-2 depict notches 9 in the body 40. FIG. 5L and cross sections FIGS. 5L-1 and 5L-2 depict notches 9 which are undulating and smooth as shown. FIG. 5M and cross section FIG. 5M-1 depict an encapsulated helical wire 33, which differs from FIG. 5J in that the diameter of the helical wire 33 is closer to the diameter of the capsule 43, imparting different handling characteristics. In each of these depictions, the wire 33 may also serve as a marker 13. Various contemplated embodiments may include combinations of the features described herein including notches 9 for FIG. 5M, gaps 41 in the wires, or other variations as described herein.

FIGS. 6A-6F are longitudinal frontal views and FIGS. 6A-1-FIG. 6B-1 are cross-section views for FIGS. 6A-B, of different embolic agents 1 that are made of flexible, electrically corrodible wire 6 (e.g. stainless steel) or helically wound wire 33, with a thin coating 31 of substantially dielectric flexible material (e.g. PTFE) or another polymer of necessary thickness and lack of small holes that provides substantial low-voltage electrical insulation. Coating 31 may not provide substantial bulk to the overall volume of the embolic agent 1, but it may affect the handling characteristics of the wire such as lateral flexibility, and may also serve to provide lubricity or reduced coefficient of friction as may be desired for the invention. The coating 33 and its use with regard to electrolytic corrosion and detachment are very different from conventional surface coatings of helical wires which are intended mainly to alter handling characteristics and not for electrical insulation. The presence of very small holes, thin areas, and flaky disruption did not completely prevent electrolytic corrosion at undesired locations as demonstrated in our tests, resulting in slower corrosion at desired locations and undesired physical changes in the deployed embolic agent 1. In FIGS. 6A-F, as in other embodiments of electrolytic embolic agents in this invention, the entire portion of wire composed of corrodible metal that may be in the proximity of the ionic medium promoting electrolytic corrosion is coated and therefore resistant to corrosion except in any described areas where coating is removed or intentionally not applied in order to serve as a contact for electrification or as a site for intentional corrosion and detachment. FIG. 6A and cross section FIG. 6A-1 depicts an embodiment with complete or nearly complete coating 31 over the entire body 40 of the wire 6. Exposed wire 6 without coating 31 may be present on the proximal end (not shown) to provide contact with electrical source as described herein. Electrolytic corrosion and detachment could only occur where a second portion of coating is removed by operator to expose the wire 6 as described herein. FIGS. 6B and 6B-1 is a variation of FIG. 6A which includes two or more bare portions 39 of wire 6 that are not covered by coating 31, and are thereby available for electrical conductivity with another wire or electrolytic fluid as described herein. The bare portions 39 may also serve as detachment points 28 where electrolytic corrosion of the wire 6 may occur, permitting separation of the embolic agent 1 into two fragments at that location as described herein. The bare portions 39 may occur at various locations along the body 40 of the wire 6, including areas that have been deposited within the aneurysm or cavity. FIG. 6C-F relate to variations that include helically wound wire 33 with different configurations of coatings 31, each of which may have different ease of manufacture, and different physical properties such as column strength and lateral flexibility. However, all serve to provide an electrical insulation from an ionic environment in which they might be positioned, such as during deployment in the tissues, whereby points of contact and detachment may be controlled by the placement of bare areas 39 where desired. In FIG. 6C, the insulating coating 31 is applied to the helical wire 33 after it has been wound, with application of a continuous layer to the internal surface 54 facing the space inside 34, and to the external surface 42. This may decrease flexibility of the embolic agent 1 due to a binding effect of the wire coils to each other, and for this reason a very pliable and stretchable coating 31 material might be most suitable. In FIG. 6D, the coating 31 surrounds the entire surface of the wire 33 strand that was wound into the helix. One method of manufacture could involve coating the wire 33 strand prior to winding the helix, while another method could involve winding, followed by partial stretching to slightly separate loops, followed by coating, followed by resumption of more compact depicted configuration by memory effect of the wire or by reshaping methods. This helical wire 33 may retain a great flexibility since the individual coils are not bound together, permitting use of a coating 31 with minimal pliability as could be advantageous for other reasons of manufacture or biocompatibility. In FIG. 6E, the coating 31 surrounds the external surface 42 and distal end 19 of the helical wire 31 but not the internal surface 54 facing the void 34 inside. This may be relatively simple to manufacture, however may have similar implications for lateral flexibility as described for FIG. 6C and may benefit from a pliable and stretchable coating 31 material. FIG. 6F depicts a variation of helical wire 33 with coating 31 most notable for its presence of non-coated bare portions 39, which may serve as detachment points 28, at various possible locations along the body 40 of the helical wire 33, similar to that depicted for the non-helical wire in FIG. 6B. These bare areas may be placed by the manufacturer or the operator using tools as described herein, and may occur in all embodiments of helical wires 33 in FIGS. 6C-F. Various embodiments may include all coating 31 types depicted in FIGS. 6C-E. FIG. 6F also depicts the presence of radio-opaque markers 13, showing how they may be positioned internally within the void 34 in the interior of helical wire 33, as may occur with any type of helical wire in this invention. In a common embodiment the markers 13 would be slightly proximal to the bare portions 39 so that the proximal end of the embolic agent 1 is easily identified after detachment occurs at the detachment point 28. As in other helical embolic agents in this invention, those in FIGS. 6C-6F may contain a longitudinal straight wire or fiber which is tethered at the ends or two or more other points along the embolic agent 1 within its core to impart handling characteristics or resist stretching or unraveling.

FIGS. 6G-I are frontal views and FIGS. 6G-1, 6H-1, and 6I-2 are cross section views of embolic agents 1 with complex coatings and encapsulations which may be used for electrolytic detachment as described in the simpler embodiments above. In FIG. 6G, an electrolytically corrodible wire 6 has a thin coating 31 of dielectric flexible material as described in FIG. 6A, and this coated wire 6 is surrounded by a helical winding of a flexible, non-metallic monofilament 5. This may provide desired bulk and thrombogenicity and desired radio-density properties (such as to prevent excessive accumulation of radio-dense metal in the aneurysm or cavity by occupying space with non-radio-dense material). The helical winding of the filament 5 may facilitate lateral flexibility of the embolic agent 1 compared to a bulky solid encapsulation. The inner coating 31 provides electrical insulation even though the wound monofilament 5 may be porous to liquid and therefore not completely insulating. The wound monofilament 5 may be prevented from unraveling or separating from wire 6 by use of adhesive or heat treatment to create enough bonding between the coils, without inducing excessive overall stiffness of the embolic agent 1. In variation, the mono-filament 5 could be substituted with a single multi-stranded filament 4 that is braided, yarn, bundled, or woven for slightly different handling properties. FIG. 6H also includes an electrolytically corrodible wire 6 with a thin dielectric coating 31. However, it is surrounded by multiple small diameter monofilaments 5 which are bundled and helically wound around the wire 6. This may provide desired bulk, thrombogenicity, radio-opacity characteristics, and flexibility, with preservation of electrical insulation by the coating 31 where desired. In variation, each monofilament 5 may be substituted with non-metallic multi-stranded filament 4. The filaments in FIGS. 6G-H may be amenable to heat melting such that a bare portion of the wire could be created using a hot wire or readily available cautery pen or other source of heat to cut and melt the strands without fraying at the modified area.

FIGS. 6I, 6I-1, and 6I-2 depict an embolic agent 1 which includes an electrolytically corrodible wire 6 with a dielectric coating 31, which is mostly encapsulated in a capsule 43 of relatively bulky, flexible, non-metallic solid material roughly similar to FIGS. 5K-M, however different in that in FIG. 6I the notches 9 in body 40 are deep enough to completely expose the coating 31 on the wire 6. The notches 9 help to provide lateral flexibility, as well as facilitating complete exposure of the wire 6 by the operator, by removing a short segment of coating 31 where exposed in the notch 9 through means described herein, and resulting in creation of a potential electrolytic detachment point 28 of the operator's choosing. In variation, the wire 6 may be completely exposed in the notch 9, (i.e., the coating 31 may be absent in a small bare area in the notch 9), preventing need for the operator to remove the coating 31 in this location to expose the wire 6, however potentially resulting in multiple sites of potential electrolytic corrosion or detachment. Variations in FIGS. 6G-I may include use of helical wire instead of straight wire, application of radio-opaque markers, exposure of the wire on the proximal end of the embolic agent which will not be deployed within the aneurysm or cavity, gaps in the wire, and other variations as described herein.

Figure 6J:
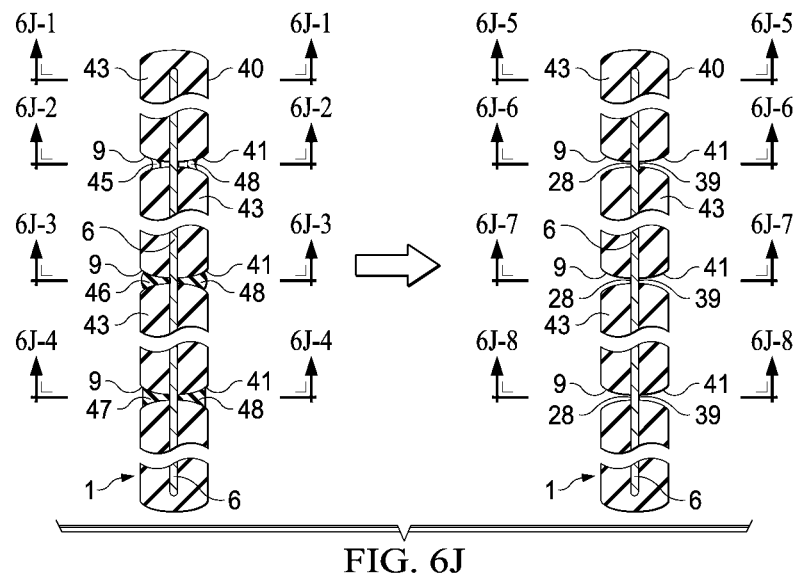
FIGS. 6A-Y show further embodiments of the novel embolic agents which may be sized and detached intra-corporeally using electrolytic means as disclosed herein.
Figures 1, 6J:
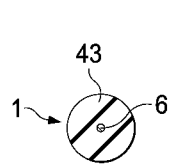
Figures 2, 6J:
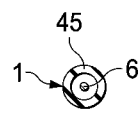
Figures 3, 6J:
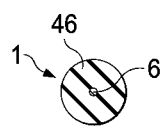
FIGS. 3A-J depict various connection and delivery configurations of the embolic agents and catheter embodiments of the disclosed invention.
Figures 4, 6J:
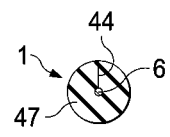
FIGS. 4A-C show threaded embodiments of the novel embolic agents disclosed herein.

FIG. 6J includes sequential views of a variation of embolic agent 1 with encapsulation of an electrolytically corrodible wire 6, which also has easily removable seals 48 that provide electrical insulation of the wire 6 while allowing the operator to expose the wire 6 in the desired location(s) to permit electrolytic detachment in keeping with the objectives of this invention. On the left is a longitudinal section with cross section views depicted in FIGS. 6J-1, 6J-2, 6J-3 and 6J-4. Arrow indicates transformation by operator to configuration on right, where a longitudinal section is depicted and includes cross section views FIGS. 6J-5, 6J-6, 6J-7 and 6J-8. Referring to the figure on left, the embolic agent 1 has a capsule 43 that surrounds a majority of the wire 6, providing electrical insulation. It has no inner coating. There are gaps 41 in the capsule 43, which are a type of notch 9 where adjacent segments of capsule 43 are completely separate from each other. Easily removable seals 48 are dielectric, used to insulate the wire 6 at the gaps 41 by providing a fluid-tight seal with the adjacent segments of capsule 43, effectively maintaining insulation of the wire 6. The easily removable seals 48 are very flexible, allowing bending of the embolic agent 1 at the notches 9 where the capsule 43 provides less restriction to motion than elsewhere in the body 40. The easily removable seals 48 may be easily removed by the operator when desired, exposing the underlying wire 6 at the bare portion 39, making it susceptible to electrolysis at the potential electrolytic detachment point 28. Three different types of easily removable seals 48 are depicted in this figure, although actual device may only incorporate one type in one or more locations. The gap 41 depicted on top is sealed with the easily removable seal 48 called tape 45. The tape 45 is a thin strip of flexible, fluid-tight, non-metallic dielectric material with adhesive on one surface that can be applied to the embolic agent 1 at manufacture circumferentially around the gap 41, adhering tightly to the adjacent segments of capsule 43 and providing a fluid-tight seal under the conditions of use of the device. The operator may easily peel off the tape 45, exposing the bare area 39 or the wire 6, and establishing a potential electrolytic detachment point 28. The middle gap 41 depicts an easily removable seal 48 provided by sealant 46. Sealant 46 is a compound which may be applied at manufacture in liquid or semi-solid form, and curing to a pliable, flexible solid or semi-solid that surrounds the wire 6 and conforms to the edges of the capsule 43. The operator may easily peel or rub this sealant 46 off when desired. In variation, the sealant 46 may be dissolved by a solvent that is applied to it. Choice of compositions of sealant 46, solvent, and capsule 43 will intentionally permit dissolution of sealant 46 but not of capsule 43 or wire 6, so that capsule 43 remains intact, but wire 6 bare area 39 is exposed, creating potential electrolytic detachment point 28. An example of a possible solvent is Dimethyl Sulfoxide (DMSO). Other variant sealants 46 have a melting point higher than the capsule 43 but much lower than wire 6. Application of heat slightly greater than melting point of sealant 46 using tools described herein will result in liquefaction of sealant 46, exposing bare area 39. The bottom gap 41 depicts an easily removable seal 48 comprised of a sealant plug 47, which is firm but flexible, pliable, and solid or semi-solid. It is roughly shaped like a disk but with upper and lower surfaces which mate with the adjacent segments of capsule 43 to provide a seal, and closely surrounds the wire 6, with intention to provide watertight electrical insulation of the underlying wire 6. The sealant plug 47 also has a radial slit 44 as seen if FIG. 6J-4, which due to the plug's 47 pliable nature, may be widened to permit application of the plug 47 to the embolic agent 1 as shown on the left, as well as easy removal by the operator, creating the bare area 39 and potential electrolytic detachment point 28 as seen on the right.

Figures 5, 6J:
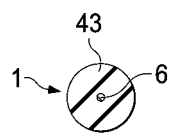
Figures 6, 6J:
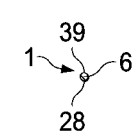
Figures 6, 6J, 7:
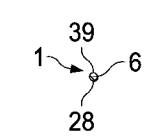
FIGS. 7A-8R depict various embodiments of novel embolic agents and apparatus and means for detaching embolic agents using predominantly mechanical or hydraulic means.
Figures 6, 6J, 7, 8:
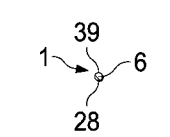
Figure 6K:
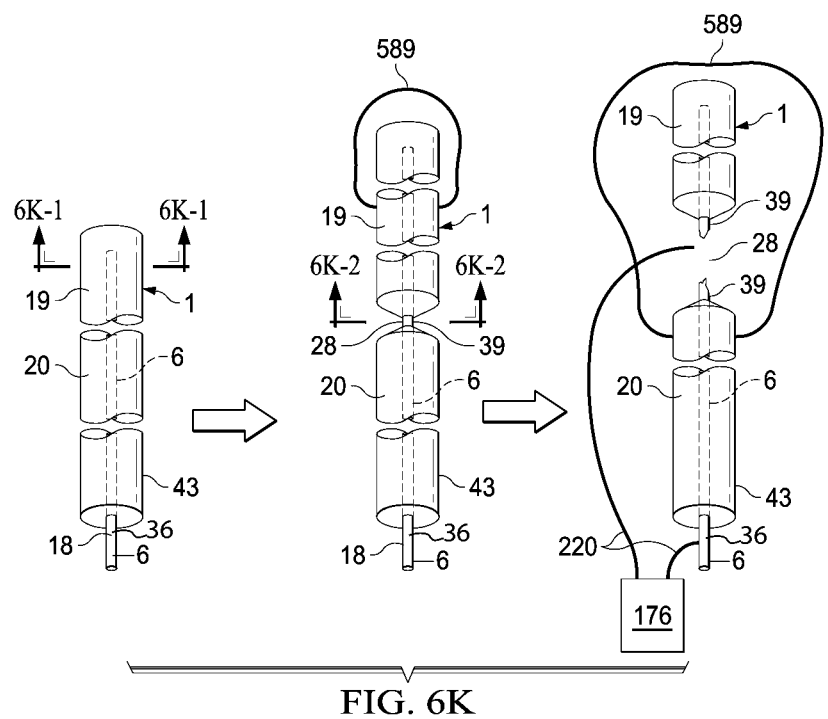
Figures 1, 6K:
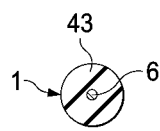
Figures 2, 6K:
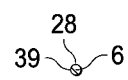

FIG. 6K includes sequential dimensional frontal views and FIGS. 6K-1 and 6K-2 include cross section views teaching the concept of electrolytic detachment in a very simple form. On the left, the embolic agent 1 is shown intact, with an electrolytically corrodible wire 6 encapsulated within a capsule 43, except for its proximal end 18 where the wire 6 is exposed to serve as an electrical contact 36. This exposure may be during manufacture, or may be created by the operator using methods described herein, and may involve proximal areas other than the most proximal end of the embolic agent 1 depicted. After near complete advancement of the embolic agent 1 into the target tissues 589, a small focal portion of the capsule 43 is removed using a tool or any of the various methods described herein, said removal occurring at the mid-portion 20 of the embolic agent 1 which is still outside the body in the operating field, creating the depiction in the middle 20, where the bare portion 39 of the wire 6 is now seen, constituting a potential detachment point 28, as seen in the middle drawing. The embolic agent 1 is advanced further through the introducer catheter (not shown), placing the distal end 19 and bare portion 39 into or near the target tissues 589 in the body where desired as seen in the third drawing on the right. Electrical energy is applied. The electrical source 176 outside of the body is connected to electrical wires 220, one connected to the bare area 39 at the proximal end 18 of the embolic agent 1 which is outside of the body and not in electrical continuity or contact with the body or body fluid in the target tissues 589, and the other in contact with the body or more directly to the ionic body fluid, such as blood, in the target tissues 589 bathing the mid portion 20 and distal portion 19 of the embolic agent 1, including the bare portion 39 of the wire 6 at the detachment point 28 as discussed elsewhere herein. As shown, electrolytic corrosion occurs at the detachment point 28, and the distal portion 19 of the embolic agent 1 is now physically separated from the remainder, which may then be withdrawn from the body from the operator, leaving only the distal portion 19 within the body at the precise desired location. Many different types of embolic agents and configurations, different mechanisms of energy application, and other specific novel devices to facilitate and improve this process are described in this invention and this simple example serves to introduce the concept in a simple form.

Figure 6L:
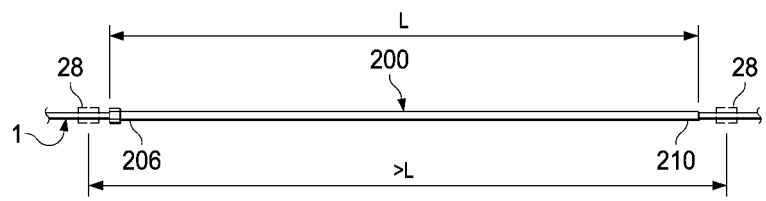

FIG. 6L is a schematic representation to teach a concept that may be mentioned in this invention relating to distances between potential detachment sites 28 of an embolic agent 1, especially when such sites are placed by the manufacturer instead of the operator. As shown, L is the length of the introducer catheter 200 from proximal end 206 to distal end 210 which may be any length but will generally be between 10 cm and 110 cm. In general, the distance between potential detachment sites 28 of the embolic agent 1 will be at least greater than L, so that when it is passed through the introducer catheter 200, the distal detachment site 28 may be beyond and outside the distal end 210 of the introducer catheter 200 while the proximal detachment site 28 is outside of the proximal end 206 of the introducer catheter 200 where it is accessible to the operator outside of the patient's body. Although this description may help to understand a typical embodiment of the invention disclosed herein, exceptions occur and are described herein, and other variations may occur in keeping with the spirit of the invention.

Figure 6M:
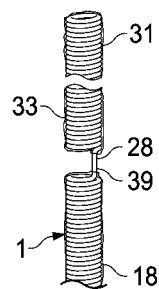

FIG. 6M is a frontal view of an embolic agent 1 composed of a conductive corrodible helical wire 33 with a coating 31 over most of its surface as described herein (FIGS. 6C-E) where at least one potential detachment area 28 is produced at the time of manufacture or by the operator by stretching or shaping the coiled wire 33 in a controlled manner to straighten the wire while separating the coiled segments from each other, and stripping the coating from the small area, as shown. This straight segment has no coating 31, resulting in a bare portion 39, and therefore susceptible to electrolytic corrosion using principles and methods described in this invention. In keeping with descriptions in this invention, the bare portion(s) 39 may be created by the manufacturer or the operator to direct detachment 28 of the embolic agent 1 as desired. In variation, the helical wire 33 may have a short bare portion 39 without having a straight portion, (i.e., there may not necessarily be any alteration of the helical wire's 33 shape associated with the presence of the bare portion 39).

Figure 6N:
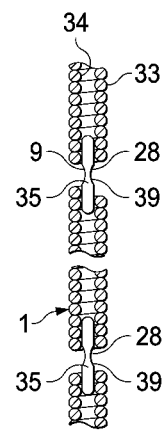
Figure 6O:
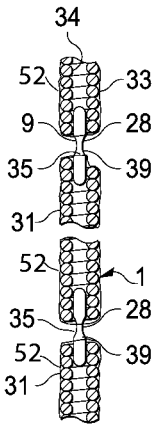

FIGS. 6N-O are longitudinal sections of two types of embolic agents 1 using electrolytically corrodible connectors 35. FIG. 6N includes two or more segments of electrically conductive, non-electrolytically corrodible helically wound wire 33 (e.g. platinum) with one or more potential detachment points 28 at the site of several connectors 35. The connectors 35 are straight, substantially cylindrical, pin-like sold metallic structures made of conductive, electrolytically corrodible material which are non-detachably attached to the internal surface of the helical wire 33, partially occupying the space inside 34, leaving a bare portion 39 between the segments 52 of helical wire 33. They are attached by mechanical, frictional, welding, or chemical bond. Electrolytic corrosion may be directed to the detachment points 28 because electrical current may be conducted to them through the conductive, non-electrolytically corrodible helical wire 33 segments from a source remote from the detachment point 28. Notches 9 may be optionally present, consisting of narrowing of the connectors 35 at the intended detachment points 28, to facilitate and direct corrosion of the thinner portions. The notches 9 may be from machining, stretching, or pre-corrosion of the connectors 35 at manufacture. FIG. 6O is similar to FIG. 6N but has further addition of a non-conductive insulated coating 31 to the helical wire 33 in possible manners shown in FIGS. 6C-E which does not cover the detachment points 28 on the center of the connectors 35, thus directing corrosion to detachment points 28. This may permit the use electrolytically corrodible metals such as stainless steel for the helical wire 33 since corrosion will not occur due to insulation. The points of contact between connectors 35 and helical wire 33 will however not be coated so that electricity may be conducted along the embolic agent 1 from segment 52 to segment 52. In variation of FIGS. 6N-O, variations of tape, sealants, or plugs as described in FIG. 6J may be easily adapted for similar function, to provide easily removable seals which could insulate the connectors 35 from electrolytic corrosion until precise choice of detachment point 28 is chosen by operator for detachment. As with all embolic agents in this invention, radio-opaque markers 13 may be added as described.

Figure 6P:
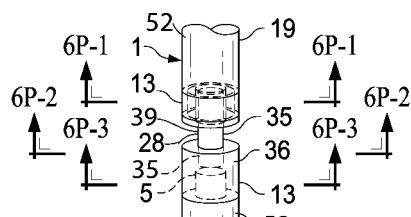
Figures 1, 6P:
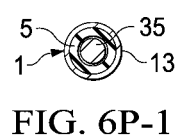
Figures 2, 6P:
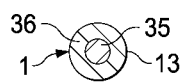
Figures 3, 6P:
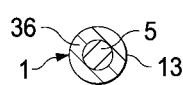

FIGS. 6P-T depict novel embolic agents 1 that permit variable, operator-determined length of detached embolized segment(s) 52 utilizing electrolytic detachment without the need for modification of the embolic agent 1 by operator prior to detachment. FIGS. 6P-T all depict embolic agents 1 that have a repeating cycle of a segment 52 of non-conducting material such as non-metallic monofilament 5 or coated wire, then an electrical contact 36 which conducts electricity to a bare portion 39 of corrodible connector 35 which is a potential detachment site 28, to another segment 52 of non-conducting material such as monofilament 5, and then repeat. Such embolic agents 1 may function in combination with introducer catheters that have electrical contacts near their distal ends, to conduct electricity to the contacts 36 on the embolic agent 1, as described later in this invention, for example in FIGS. 12F, 12G, 12H, and 14B. FIG. 6P is a frontal view from a slightly elevated perspective and FIGS. 6P-1, 6P-2 and 6P-3 are three cross sectional views depicting an embolic agent 1 whose main body 40 is composed mainly of a non-conductive material in the shape of a monofilament 5 as described herein. Rigidly attached is at least one area of a substantially noble or non electrolytically corrodible conductive material such as platinum that provides an electrical contact 36 that is roughly disc shaped and is seen in FIG. 6P-1 to have a hollow center through which a metallic corrodible and conductive connector 35 may pass and to which said contact 36 is connected. During manufacture, this contact 36 may be swaged onto the monofilament 5 and connector 35 simultaneously while they are held end-to-end as shown, and/or could be attached using adhesive, bonding the segments 52 of monofilament 5 into a long embolic agent 1 with adequate tensile strength. The contact may also serve as a marker 13 especially since minimally corrodible metals such as platinum serve well as markers 13. The upper portion of the connector 35 is shown non-detachably attached to the distal end 19 of the next segment 52 using a different method; the connector 35 is inserted into a hollowed space in the monofilament 5, and a marker 13 is swaged around the monofilament 5, providing a strong connection between connector 35 and monofilament 5. Adhesive could also be used. The segments 52 of monofilament 5 are therefore connected into a continuous embolic agent 1 with adequate tensile strength. These 2 methods of bonding the elements may be interchangeable, using one or the other on both sides of the connector 35, or substituting with other conventional method providing the same function. There may be a plurality of segment 52 connections along the embolic agent 1. Such a novel configuration provides for novel function, in that electrical current passing to the contact 36 via a wire in the electrolytic introducer catheter that contacts it (not shown) as will be described later, will then conduct into the corrodible connector 35, and said connector 35 may thus undergo electrolytic corrosion and detachment at detachment point 28. The substantially non-corroding contact 36 serves to provide constant contact with the mating contact of introducer catheters during electrolysis when corrosion is occurring in the corrodible segment 52 of the connector 35, and is likely to occur at the indicated detachment point 28 instead of point of contact with the contact 36 since it is not in contact with the ionic fluid at the latter location. In this example, a second marker 13 is present as a band around a narrowing of the monofilament 5 as is often used conventionally. This second marker 13 may be useful for determining that proper separation of the segments 52 has taken place, and that the proximal end 18 has separated from the distal end 19 so that the distal end 19 may serve as embolic agent 1 in the tissues while the proximal end 18 may be removed from the body. Other contemplated embodiments that could provide similar novel function include the use of a multi-strand non-metallic filament instead of the monofilament 5, presence of other markers or a wire inside the filament to provide structural support, use of a non-corrodible helical wire 33 or straight wire, or a coated corrodible helical wire or coated straight wire instead of the monofilament 5, so long as said wires were not in electrical continuity with the connector(s) 35. In variation this detachment mechanism does not need to be in series, and may only be present in one location, providing novel detachment function in conjunction with a conductive electrolytic catheter described in this invention.

Figure 6Q:
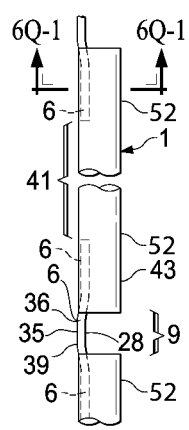

FIG. 6Q is a longitudinal section view and FIG. 6Q-1 is a cross section view depicting an embolic agent 1 which may function roughly similarly to the embodiment shown in FIG. 6P but whose structure permits use of fewer sub-elements with possible simplification of manufacture and decreased cost. It has segments 52 of non-metallic monofilament 5 separated by notches 9, said segments 52 acting as insulating capsules 43 for segments of electrolytically corrodible wire 6 which are separated by dielectric gaps 41 to prevent continuous conduction of electricity along the entire length of the embolic agent 1. In the notches 9, the corrodible wire 6 is not coated or encapsulated as is a bare portion 39 which may be a detachment point 28 with electrolysis. Although the precise position of the wire 6 within the capsule 43 is not limiting and could vary in different embodiments, in the notches 9 the wire 6 is positioned eccentrically as shown, in order to touch the sides of an introducer catheter through which it will be advanced. Said introducer catheter would have a contact point within its distal lumen as seen in some varieties described herein, which would come into electrical contact with the contact 36 of embolic agent 1. When provided with the opposite polarity contact within the surrounding tissues and fluids, corrosion at the detachment point 28 will separate the desired segments 52 of embolic agent 1. The operator may direct the detachment to the specific desired site by aligning the desired contact 36 with the contact on the introducer catheter. The dielectric gaps 41 between segments 52 of wire 6 will prevent corrosion of any other of the many possible bare portions 39 along the embolic agent 1.

Figure 6R:
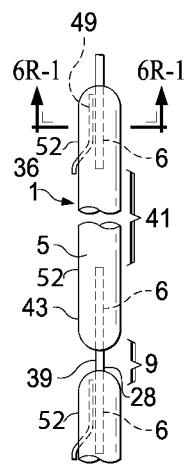
Figures 1, 6Q:
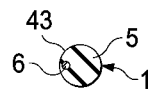
Figures 1, 6R:
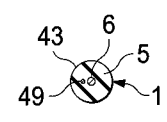

FIG. 6R is a longitudinal section and FIG. 6R-1 is a cross section view depicting another embolic agent 1 which may be used similarly as described for FIG. 6Q but has different structure, mainly due to the addition of a non-corrodible wire 49 to serve as an electrical contact 36. In FIG. 6R, and as shown in FIG. 6Q, the discontinuous corrodible wire 6 is contained in a capsule 43 except the bare portions 39 which may serve as detachment points 28 in the notches 9, and has dielectric gaps 41 between wire segments 52. In FIG. 6R, the corrodible wire 6 does not serve as a contact 36, but instead electricity is conducted to the corrodible wire 6 via a contact 36 comprised of a non-corrodible wire 49 that extends both inside and outside the capsule 43 as shown. Inside the capsule 43, the non-corrodible wire 49 is in direct contact with the corrodible wire 6. As with FIG. 6Q, the contact 36 may contact the contact within the introducer catheter as described herein. FIGS. 6P-R have different manufacturing implications but may provide roughly similar functionality.

FIG. 6S is a longitudinal section and FIG. 6S-1 is a cross section of an embolic agent 1 which will also have similar functionality as described in FIGS. 6P-R, however depicts an embodiment that utilizes a helical wire 33 throughout most of its length instead of materials described for the other embodiments. Embolic agent 1 has segments 52 of electrolytically corrodible helical wire 33 which are protected from electrolytic corrosion by a coating 31 as shown. In variation, non-electrolytically corrodible helical wire could be used without a coating. A connector 35 composed of an electrolytically corrodible metal is non-detachably secured to adjacent segments 52 of helical wire 33 which are separated by a notch 9, connecting them with adequate tensile strength for purposes described herein. Electrical contacts 36 composed of a non-corrodible conductive metal are swaged or soldered or adhered non-detachably to the connector 35, providing a means for electricity to be conducted from a contact in the introducer catheter (not shown) to contact 36, then to the connector 35 which has a bare portion 39 where corrosion may occur and is therefore a detachment point 28. The contact 36 may also serve as a marker 13. Non-conducting adhesive 50 binds and insulates portions of the components helical wire 33, connector 35, and contact 36 as shown, preventing conduction from the connector 35 or contact 36 to the helical wire 33 segments 52. Alternatively, a non-conductive coating 31 may be applied to the portions the connector 35 and contacts 36 that contact the helical wire 33. A plurality of these connections, at many possible distances apart, may be present. Current applied to a contact 36 will only energize the corresponding connector 35 and no others since current cannot pass through the coating 31 to the helical wire 33 and hence to adjacent segments 52, so precise point of detachment 28 can be directed by the operator by positioning relative to the introducer catheter without previous modification of the embolic agent 1 as described herein. In variation, one of the contacts 36 or markers 13 may be omitted and the remaining functions still provided.

FIG. 6T is a longitudinal section and FIG. 6T-1 is a cross section of a variation of FIG. 6S where a different structure to the connector 35, marker 13, bare portion 39, and detachment point 28 are present, although operator usage is roughly similar. The corrodible helical wire 33 segments each contain a detachment point 28 where a bare portion 39 is present as shown, involving as few as one coil or even a tiny portion of one coil, while the remainder of the helical wire 33 segment is rendered non-corrodible by coating 31. Current from a contact in an electrolytically-adapted introducer catheter is conducted to the helical wire 33 in the lower segment 52 at the intrinsic electrical contacts 51 with the connector 35 where it touches the internal surface 54 of the helical wire 33 adjacent to the space inside 34, where there is no coating. Only the external surface 42 is covered and insulated by non-conductive adhesive 50. Therefore the only electrified bare portion 39 of corrodible metal is at the detachment point 28 shown so is the only area where corrosion will occur. The proximal portion of the upper segment 52 of helical wire 33 has circumferential coating 31 and will not be energized when the electrical current is activated and directed by the operator to the depicted contact 36. A plurality of these connections 35 will permit choice of location for detachment without operator modification of the embolic agent 1 by positioning of selected contact 36 with the corresponding contact in the introducer catheter.

FIGS. 6U-6Y-1 are longitudinal section and cross section views depicting novel embolic agents 1 that permit variable, operator-determined length of detached embolized segment(s) 52 utilizing electrolytic detachment 28 after extracorporeal modification of the embolic agent 1 by operator to direct detachment 28 to the desired site. The embolic agent 1 becomes one electrode, and the opposite electrode is supplied by contact at the skin or on a novel electrolytic catheter as part of this invention. Operator modification of embolic agent 1 is not at detachment point 28 and remains extracorporeal for FIGS. 6U-W, and is at detachment point 28 for FIGS. 6W-Y. FIGS. 6U, 6U-1 and 6U-2 depicts an embolic agent 1 which includes a plurality of repeating segments 52, each including a capsule 43 encapsulating the majority of a segment 52 of electrolytically corrodible wire 6, said wire 6 bridging adjacent capsules 43, thereby serving as a connector 35, which has at least one bare portion 39 or is entirely bare, thereby serving as an electrolytic detachment point 28 in the notch 9 between capsule segments 52. A dielectric gap 41 exists between adjacent wires 6 to prevent conduction from one wire 6 to the next. To detach the embolic agent 1 at the desired location, the operator will first use a tool extra-corporeally as described herein to remove a focal portion of capsule 43, at a location such as example modification site 53, to expose the wire 6 creating an electrical contact proximal to the intended detachment site 28, and then apply current to the newly created bare portion (not shown) contact which will energize the single desired intra-corporeal detachment site 28 without energizing potential detachment sites 28 more distally since the dielectric gaps 41 exclude them from the electrolytic circuit. The distance from extracorporeal modification site 53 to nearest distal detachment site 28 will usually be greater than the length of the introducer catheter with this variation. Possible methods of manufacture could include extrusion of capsule 43 over wire segments, or extrusion of capsule 43 over a long continuous wire followed by laser disruption of wire through capsule 43 to create dielectric gaps 41. Capsule 43 may be burned or cut away to create notches 9.

FIG. 6V with cross section FIG. 6V-1 depicts an embolic agent 1 with repeating segments 52 of helical wire 33, which may be composed of electrolytically corrodible metal with a coating 31 as depicted, or with a non-corrodible metal in variation. The segments 52 are connected by connectors 35 composed of electrolytically corrodible metal which is non-detachably bonded to the internal surface 54 of the helical wire 33. The coating is absent for enough helical wire 33 to create an intrinsic electrical contact 51 with the connector 35, and external surface 42 of helical wire 33 has coating or non-conductive adhesive 50 so that the only exposed surface of connector 35 is the bare portion 39 between segments 52 of helical wire 33. The bond between the connector 35 and more distal segment 52 of helical wire 33 includes insulating coating 31 on helical wire 33 to prevent electrical contact 51 with the connector 35, which may further be prevented by a coating 31 around the surface of the involved portion of the connector 35. Said bond may be created by non-conductive adhesive 50 or other conventional means. The operator may remove a portion of coating 31 from the proximal segment 52 of helical wire 33 to apply current, which will be conducted to the bare portion 39 of the connector 35 serving as the detachment point 28. Conduction may not occur to more distal connectors 35 which will not undergo electrolytic corrosion.

FIG. 6W with cross section view FIG. 6W-1 depicts an embolic agent 1 with repeating segments 52 of helical wire 33 composed of electrolytically corrodible metal with a coating 31. The segments 52 are connected by connectors 35 composed of dielectric material which is non-detachably bonded to the internal surface 54 of the helical wire 33, in this example by non-conductive adhesive 50 although other conventional means could be used. The coating is absent on a bare portion 39 of the helical wire 33 slightly proximal to the connector 35. The operator may remove a portion of coating from the extracorporeal proximal segment 52 of helical wire 33 to apply current, which will be conducted to the bare portion 39 of the helical wire 33 serving as the detachment point 28. Conduction may not occur to more distal segments 52 which will not undergo electrolytic corrosion.

FIG. 6X and cross sections views FIGS. 6X-1 and 6X-2 depicts an embolic agent 1 with a continuous electrolytically corrodible wire 6 covered on most of its length by a coating 31 except for a bare portion 39 which serves as an electrical contact 36 near the proximal end 18. Segments 52 of tubing 55 with a wall 2 and a hollow portion 22 surround the wire, with alternating repetition of attached versus non-attached segments 52. Approaching the distal end 19, a metallic marker 13 is swaged onto the tubing 55, thereby gripping the wire 6, creating a fixation point 29 between wire and tubing 55 to prevent sliding motion between them. In the middle portion 20, the segment 52 of tubing 55 is not fixed to the wire 6 and may slide, constrained only by butting against adjacent fixed segments 52. These segments 52 of tubing 55 add bulk and body to the embolic agent 1. Near the proximal end 18, attachment at fixation point 29 is achieved without swaging, and instead may be bonded by adhesive, heat shrinking, heat melting, or other conventional means. Two different types of fixation 29 are shown only for demonstration means and it is likely that only one type of fixation means would be employed for all fixation points 29. Current may be applied to extracorporeal contact 36, and detachment 28 will occur at one of potential detachment points 28 which was stripped of coating 31 by operator as described herein.

FIG. 6Y and cross section 6Y-1 depicts an embolic agent 1 with similarities to that depicted FIG. 6X but utilizing segments 52 of helical wire 33 instead of tubing 55. The segments 52 of helical wire 33 are protected from electrification and hence electrolytic corrosion by a coating 31 on the straight wire 6 and detents 56 that are roughly disc-shaped in this depiction and, in variation may be other shapes, said detents 56 being non-detachably and non-slidably attached to the wire 6 using solder, adhesive, compression, or other conventional means. Said segments 52 surround the straight wire 6 which occupies the space inside 34, but said segments 52 are not attached and may slide on the wire, being detained only at the detents 56, providing flexibility to the embolic agent 1. Corrodible wire 6 is covered on most of its length by a coating 31 except for a bare portion 39 which serves as an electrical contact 36 near the proximal end 18. Current may be applied to extracorporeal contact 36, and detachment 28 will occur at one of potential detachment points 28 between detents 56 which was stripped of coating 31 by operator as described herein (shown here before stripping). In variation, easily removable seal 46 as described in FIG. 6J may be utilized in the space between the paired detents 56 to facilitate operator modification.

Figure 7A:
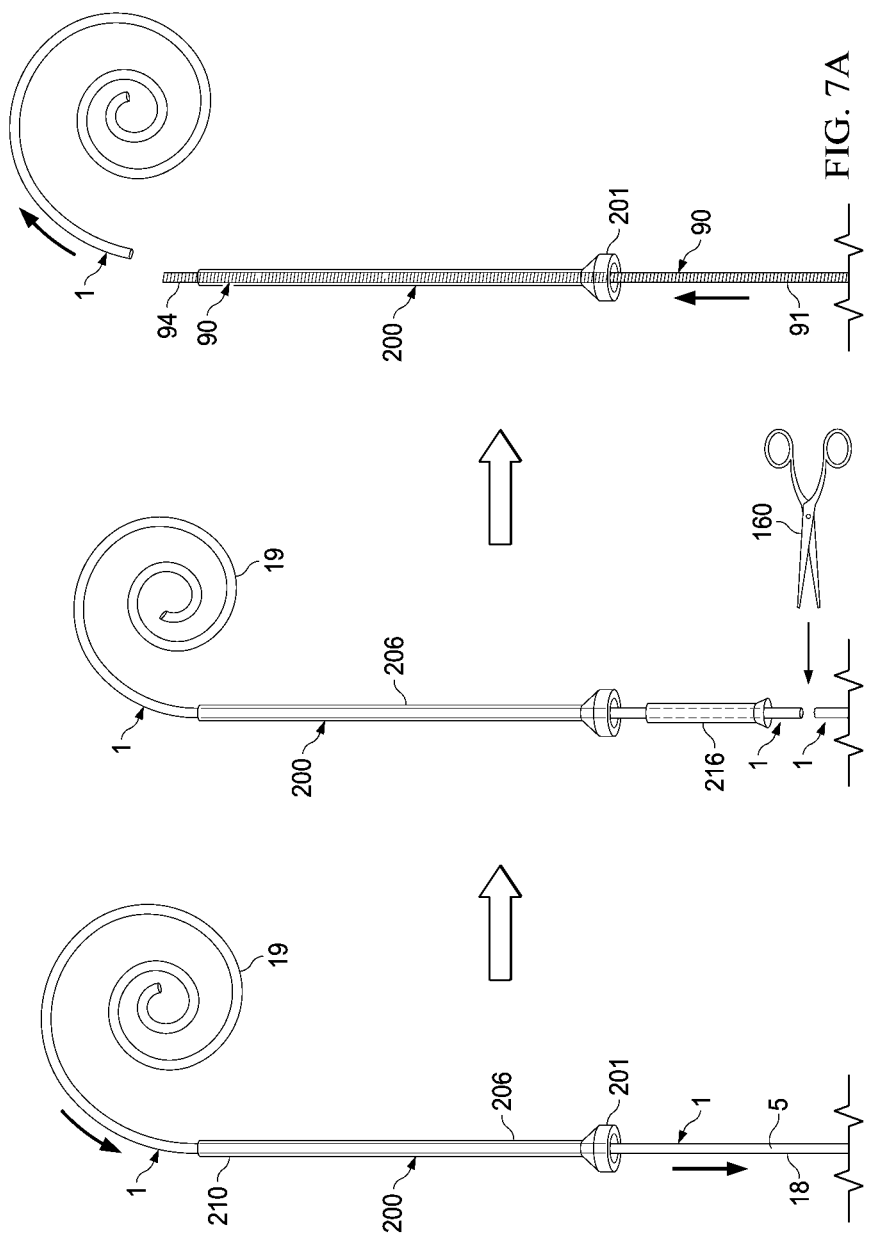
Figure 7C:
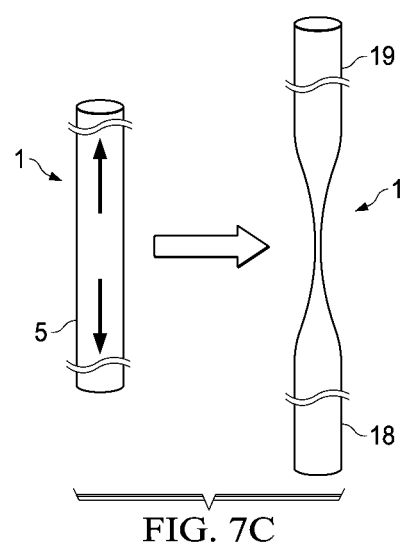

FIGS. 7A-C are each sequential frontal views depicting embolic agents 1 and very simple mechanical methods of detachment using extra-corporeal modification by the operator. In FIG. 7A, an embolic agent 1 comprised of a simple long monofilament 5 undergoes the "cut and retract" method. On the left, embolic agent 1 is seen extending throughout the introducer catheter 200 from the proximal end 206 to the target tissues (not shown) beyond the distal end 210 of the introducer catheter 200, where the distal end 19 of the embolic agent 1 is coiled in a helix. In this figure, it is now being retracted by pulling on the proximal end 18, as shown by the arrow, thus removing some a portion of the embolic agent 1 from the target tissues, back into the extracorporeal operating field proximal to the proximal end 206 of the introducer catheter 200. In the middle figure, the embolic agent 1 is being cut by an embolic detachment tool 160, which is a pair of scissors. In the same figure, an introducer sleeve 216 with a flared end is slipped over the severed end of the embolic agent 1 as shown. The introducer sleeve 216 is then pulled down so that the severed end of the embolic agent 1 is inside it (not shown). Then, a pusher element 90 may be brought into the flared end of the introducer sleeve 216, where its tip 94 will abut the embolic agent 1. The embolic agent 1, pusher element 90 (not shown until third drawing in sequence), and introducer sleeve 216 may all now be pushed in unison until the introducer sleeve 216 abuts the hub 201 of the proximal end 206 of the introducer catheter 200. Then, the introducer sleeve 216 will remain stationary as the severed end of the embolic agent 1 is pushed inside the introducer catheter 200, and the introducer sleeve 216 may now be slipped off the proximal end 91 of the pusher element 90 and discarded. Now, as seen on the right, the tip 94 of the pusher element 90 pushes the embolic agent 1 through the introducer catheter 200 to the target tissues as indicated by curved arrow. The pusher element 90 is now easily removed by retraction. This technique will leave the desired amount of embolic agent 1 within the tissues as determined before retraction and severing. This permits deployment of desired amount of embolic agent 1 while utilizing severing or detachment techniques outside of the body rather than close to the target tissues, as described elsewhere herein, and serves as simple and economical way to use the described embolic delivery systems to administer embolic agents that are much longer than conventional agents.

FIG. 7B shows a method of detachment of the embolic agent 1 that permits repositioning of the embolic agent 1 after modification by operator, but prior to detachment, with option to detach when detachment point 28 is positioned in the target tissues beyond the tip 211 of the introducer catheter 200. On the left, the distal end 19 of the embolic agent 1, which is a non-metallic monofilament 5 in this example, is partially deployed in the abnormal tissues, while the proximal end 18 is seen proximal to the introducer catheter 200, which also has proximal 206 and distal 210 ends. In the figure on the left, it is determined that the amount of embolic agent 1 that is deployed in the tissues is the ideal amount. To detach it with this extent of embolic agent 1 in the tissues, the embolic agent 1 is first retracted by pulling down on the proximal end 18 as indicated by the arrow, which results in the partial retraction of the distal end 19 as shown by the curved arrow. Once the embolic agent 1 has been retracted a distance approximately equal to the length of the introducer catheter 200 (middle drawing), then it is scored with the scoring tool 163, which cuts a fine score around the circumference of the embolic agent 1 but does not cut through its entire diameter. The embolic agent 1 is now weakened, but intact at the detachment point 28. It may now be pushed by the operator into the introducer catheter 200 as indicated by the arrow, which pushes the distal end 19 back into the tissues as they were before retraction and scoring. Once the scored portion has exited the introducer catheter 200 (drawing on right), the proximal end 18 of the embolic agent 1 is rotated by the operator or equipment controlled by the operator. Since the distal end 19 will not easily rotate due to extensive deployment and nesting, there will be twisting forces on the weakened score zone, resulting in complete detachment. Now, the proximal portion 18 of the embolic agent 1 may be removed and embolization is complete. Alternatively, the embolic agent 1 may not need to be retracted prior to scoring. The final length may be estimated, and the score may be applied, then the embolic agent 1 may be pushed in and twisted off.

FIG. 7C shows a method of detachment that permits repositioning of the embolic agent 1 after extracorporeal modification, consisting of weakening by stretching, by operator prior to detachment, with option to detach when detachment point 28 is positioned in the target tissues beyond the distal tip 211 of the introducer catheter 200 as seen in FIG. 7B. The embolic agent 1 is a monofilament 5, which can be stretched when grasped and pulled apart, as shown by the arrows. This results in a weakened, narrow portion as seen on right. This permits pushing and retraction of the distal portion 19 when the proximal end 18 is manipulated by the operator. As in FIG. 7B, it is detached by twisting the proximal portion 18 until it breaks at the detachment point 28. This weakening may be enhanced by scoring as seen in FIG. 7B. In variation, there are transitions at regularly spaced locations along the embolic agent 1 where the material is more susceptible to stretching and weakening. These areas may also serve as extra flexible areas for nesting.

Figure 8A:
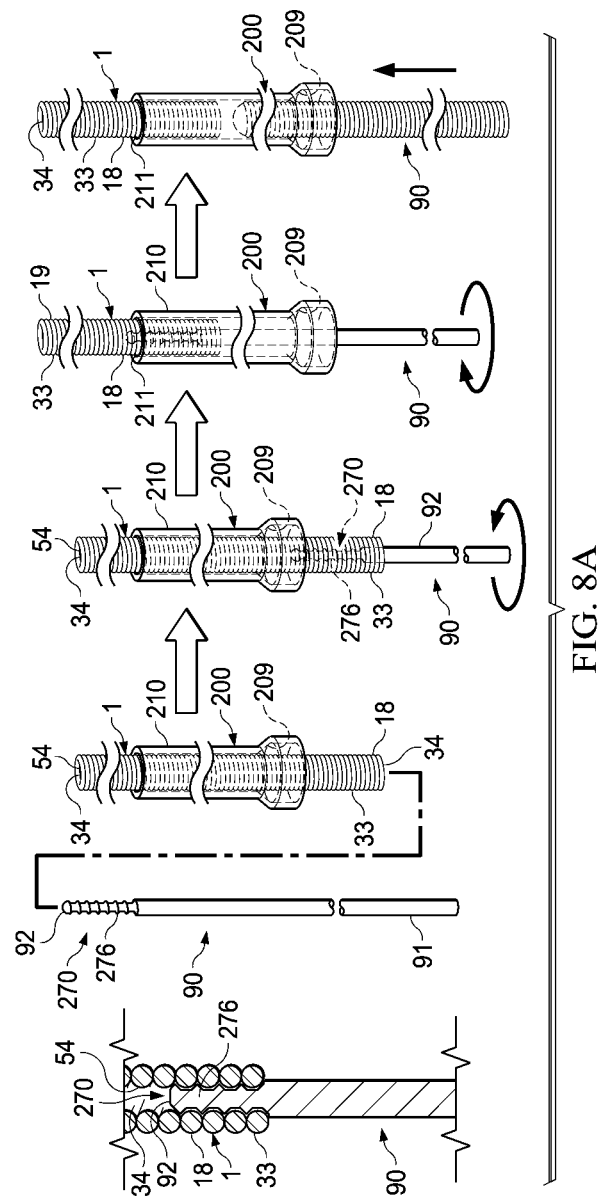

FIG. 8A-11C depict detachment systems for embolic agents which do not rely mainly on electrolytic means and are predominantly mechanical, although may additionally include electrolytic means. FIG. 8A is a longitudinal section view (left) and a 4 part sequential perspective view (right) teaching basic concepts of mechanical detachment and depicting a specific embolic agent 1 and pusher element 90 with a screw-type detachment permitting a controlled advancement or retraction of the embolic agent 1 via the pusher element 90 under operator control. The left drawing shows a longitudinal section of the distal end 92 of the pusher element 90, containing traction elements 270 in form of threads 276, which are specially designed to interface as shown with the inner hollow space inside 34 at the proximal end 18 of the embolic agent 1, which is a helically wound wire 33. In the sequential drawings beginning with the first drawing, a pusher element 90, introducer catheter 200, and embolic agent 1 are shown, where the dotted arrow indicates that the distal end 92 of the pusher element 90 is inserted into the space inside 34 of the helical wire 33, which may have been severed as described herein to the appropriate length by the operator. The distal end 92 of the pusher element 90 has traction elements 270 consisting of threads 276, similar to threads on a screw or bolt, which mate with the pattern on the internal surface 54 of the embolic agent 1. Progressing to sequence on the right, the pusher element 90 is rotated and screwed into the embolic agent 1 which is not rotated, thus resulting in the pusher element 90 advancing into and becoming rigidly attached to the embolic agent 1. The operator may now advance the pusher element 90 and therefore the embolic agent 1 into the lumen 209 of the introducer catheter 200, thereby providing a firmer attachment of pusher element 90 to embolic agent 1 by constraining the helical wire 33 from expanding or spreading apart, since the internal diameter of the lumen 209 is very slightly larger than the outer diameter of the embolic agent 1. Now, the embolic agent 1 may be advanced or retracted by manipulation of the pusher element 90 by the operator directly or indirectly. In this example, the control over the embolic agent 1 persists even after the embolic agent 1 has been extruded completely past the distal end 210 of the introducer catheter 200 into the target tissues, and is no longer constrained within the lumen 209 of the introducer catheter 200. The third sequential drawing shows the pusher element 90 being unscrewed from the embolic agent 1 with a counterclockwise rotation about its long axis (depicted by arrow). The pusher element 90 may then be removed. Prevention of corresponding rotation of the embolic agent 1 which might prevent unscrewing would usually be accomplished due to the substantial extent of the length of embolic agent 1 deployed in the target, usually in a bent, kinked, or curved manner, providing for some degree of resistance to rotation of the embolic agent 1 about its long axis. Partial rotation of the embolic agent 1 could still result in dissociation since the pusher element 90 could be rotated freely, so rotations could be continued until dissociation occurred. In the final drawing of the upper sequence, the pusher element 90 has been removed, and a different pusher element 90, in this example a conventional helical wire 33 is passed into the introducer catheter 200 to push the embolic agent 1 beyond the distal tip 211 of the introducer catheter 200 to the target tissues, moving in the direction shown by the dashed arrow. In variation of method where the threaded pusher element 90 was used to push the embolic agent 1 all the way to the target tissues before dissociation took place, this final step would not have been necessary.

Figure 8C:
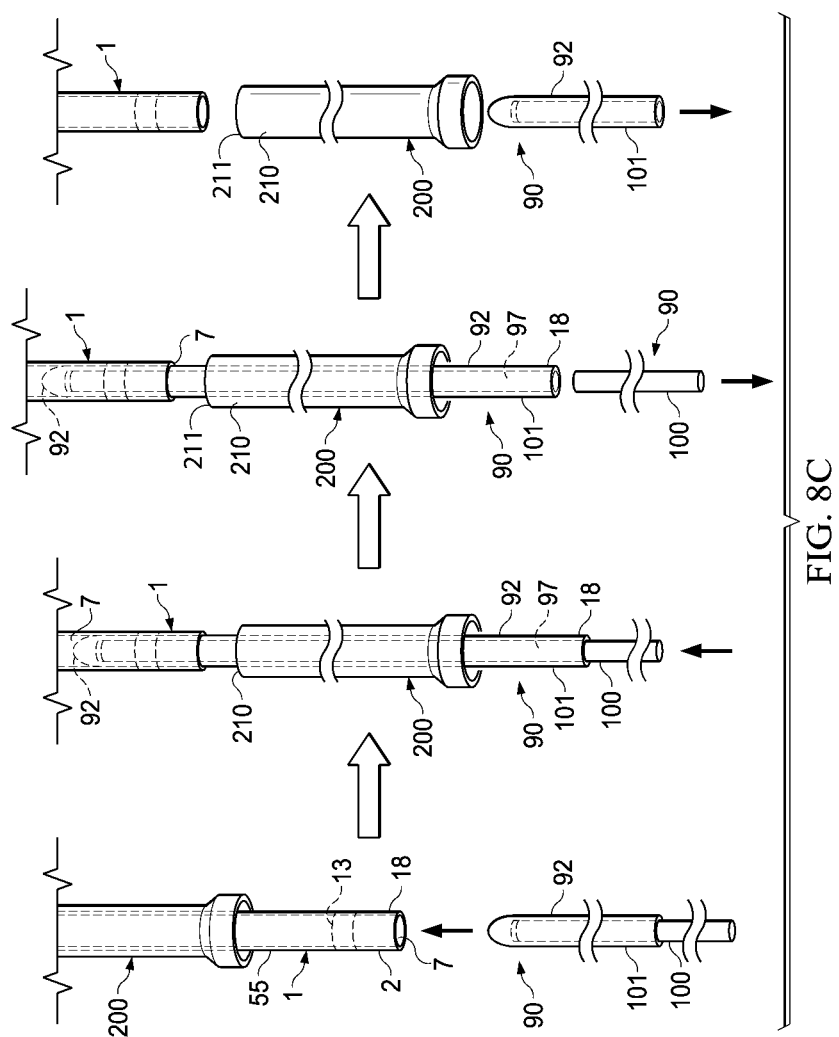

FIGS. 8B-C depict embolic agents permitting operator to determine the length of detached embolized segment with precise operator-determined placement near the tip 211 of the introducer catheter 200 without requirement for operator modification, and have mechanical, lockable components. FIG. 8B is a sequential series depicting a locking detachable embolic agent 1 using a conventional type of locking mechanism 10 in a novel series of repeating segments 52. This embolic agent 1 is shaped roughly similarly to most described herein; round in cross section and long and narrow. Its body 40 is depicted as a monofilament 5 but in variation it could be a helical wire 33. It has repeating segments 52 with locking mechanisms 10. This causes locking of the segments together when constrained inside an introducer catheter 200 or an introducer sleeve 216. As seen on the left, a two dimensional frontal view with a magnified portion shown in exploded view, the embolic agent 1 is constrained within an introducer sleeve 216, and the locking mechanism 10 locks the repeating segments 52 together. In the second figure, a lower perspective view, the embolic agent 1 is seen being driven into the introducer catheter 200 by feeder rollers 325 of the embolic delivery system 324. Before entering the feeder rollers 325, the embolic agent 1 is restrained in the introducer sleeve 216, in which it can easily slide forward or backward, but cannot unlock because the components of the locking mechanism 10 are constrained by the walls of the introducer sleeve 216. In the third drawing, one segment 52 is nearly deployed in the tissues beyond the distal end 210 of the introducer catheter 200, but is still locked. The final drawing depicts the disconnection of the locked elements of the locking mechanism 10 of the embolic agent 1 once pushed into the target tissue, where it is no longer constrained in the introducer catheter 200. Variations of the locking embolic agent 1 are many, and include a different configuration of locking mechanism 10 that would serve the same purpose, and use of many different types of composition materials. As with other embolic agents, the shape and proportions of the system may vary.

FIG. 8C is a sequential view of a lockable detachable embolic agent 1 which does not have repeating segments and is modified by the operator prior to detachment. It permits detachment at any location of the embolic agent chosen by the operator. On the left, an embolic agent 1 has already been cut from a very long continuous embolic agent provided by manufacturer, consisting of a flexible tube 55 with a hollow lumen 7, a wall 2, and periodic markers 13, one of which is seen at the proximal end 18. In variation, it could have a reinforced wall as described herein. In the second drawing, a pusher element 90 has been inserted into the lumen 7 of the proximal end 18 of the embolic agent 1, creating a friction lock, and then embolic agent 1 and pusher element 90 have been advanced in unison beyond the distal end 210 of the introducer catheter 200. The pusher element 90 consists of a relatively stiff wire 100 which may be removably inserted into a long hollow tube 101 whose lumen 97 snugly accommodates the wire 100 as shown, tapers at the distal end 92 so that insertion of the wire 100 to the distal end 92 will result in very slight increase in outside diameter of the tube 101 to create a friction attachment to the lumen 7 of the embolic agent 1, permitting control over the embolic agent by the operator while it is intra-corporeal. The tube 101 of the pusher element 90 has a blunt, closed distal end 92, and is relative stiff, but flexible enough to pass around curves. In the third drawing, the wire 100 has been withdrawn from the tubing 101 of the pusher element 90 by the operator extra-corporeally. Relative stiffness and reinforcement of the tubing 101 helps facilitate this maneuver. With the wire 100 removed, the distal end 92 of the tubing 101 is now more flaccid and is easily removed from the lumen 7 of the embolic agent 1, leaving the embolic agent 1 in the desired tissues in the body, while all other components may be retrieved extra-corporeally by the operator as seen in the fourth drawing.

Figure 8D:
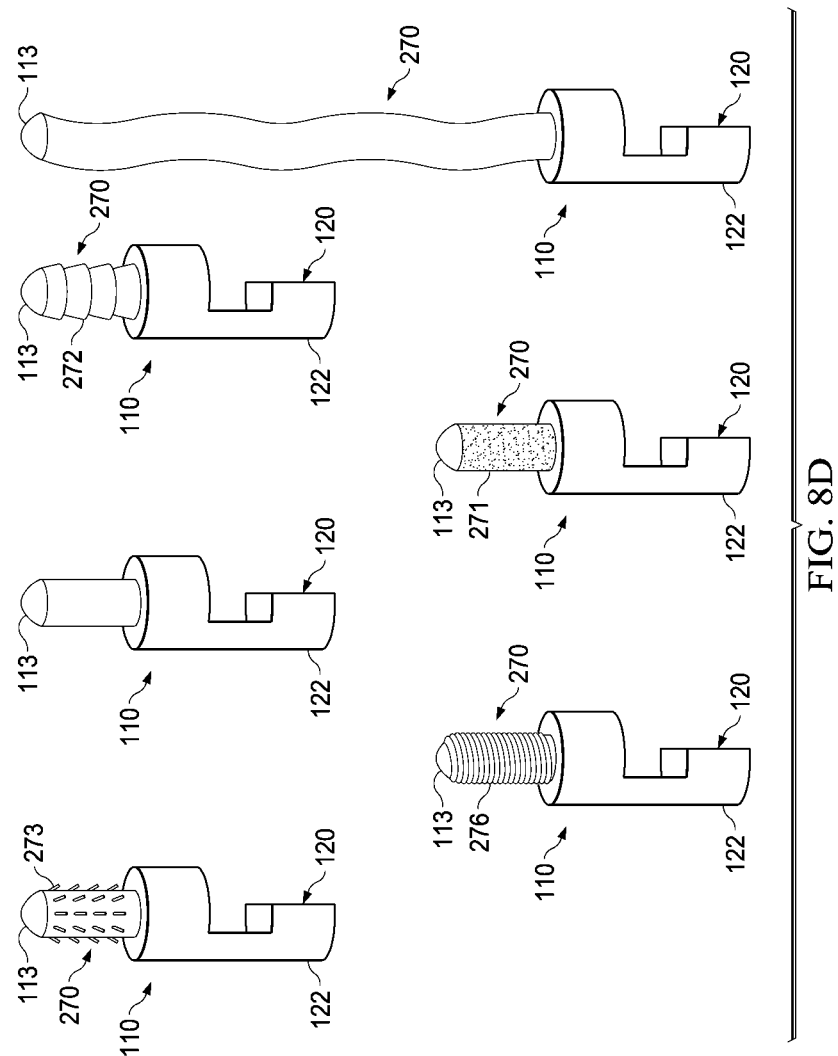

FIGS. 8D-G introduce a novel linking element 110 which is integrated with a detachment element 120 containing traction elements 270 for attachment of an embolic agent to a pusher element, which may be installed onto the embolic agent by the operator, permitting customization of its length and permitting precise detachment near or beyond the distal end of the introducer catheter. FIG. 8D is a perspective view showing 6 examples of linking element 110 which is integrated with a detachment element 120 which are bi-directional locking elements 122, made of a solid, rigid material such as metal or hard plastic, which may be attached to an embolic agent 1 and a pusher element 90 by the operator, so that the two may be locked together or detached as desired, functioning similarly as seen in FIG. 8B. These differ from conventional bi-directional locking elements which are not modifiable by the operator and therefore not allowing operator-determined length of embolic agent 1 as described for this invention. In FIG. 8D, the bi-directional locking elements 122 have an attachment pin 113 which is used to detachably attach to a pusher element 90 and/or embolic agent 1 as shown in FIGS. 8E-F. Secure attachment is aided by the following traction elements 270 depicted in clockwise direction in FIG. 8D: barbs 273, no traction elements, ridges 272, curved attachment pin 113, roughness 271, and threads 276. Rapid curing adhesive may also be applied by the operator to attachment pin 113. FIG. 8E is a longitudinal section view and FIG. 8E-1 is a cross section view of a linking element 110 which is integrated with a detachment element 120, depicted after attachment to the hollowed out end of the pusher element 90 by the operator extra-corporeally, so that the linking element 110 with attachment pin 113, bi-directional locking element 122 with pin 113, and the embolic agent 1 may now function as one unit. The linking element 110 is linked to another bi-directional locking element which is rigidly attached to a pusher element 90, so that all elements may now act in unison with control by the operator while the linking elements 120 are constrained inside an introducer catheter and thereby locked together similar to depicted in FIG. 8B. The embolic agent 1, linking element 110, and one of the detachment elements 120 are detached from the other detachment element 120 and pusher element once pushed beyond the end of the introducer catheter. In the longitudinal view of FIG. 8F and the cross section view of FIG. 8F-1, the bidirectional locking element 122 with pin 113 of the linking element 110 is similarly attached to the lumen 7 of a tubular embolic agent 1. Since it is tubular, it does not need to be hollowed out by operator prior to attachment of its function is otherwise similar to FIG. 8E. The devices in FIG. 8E-F function similarly to the schematic representation in FIG.

Figure 8G:
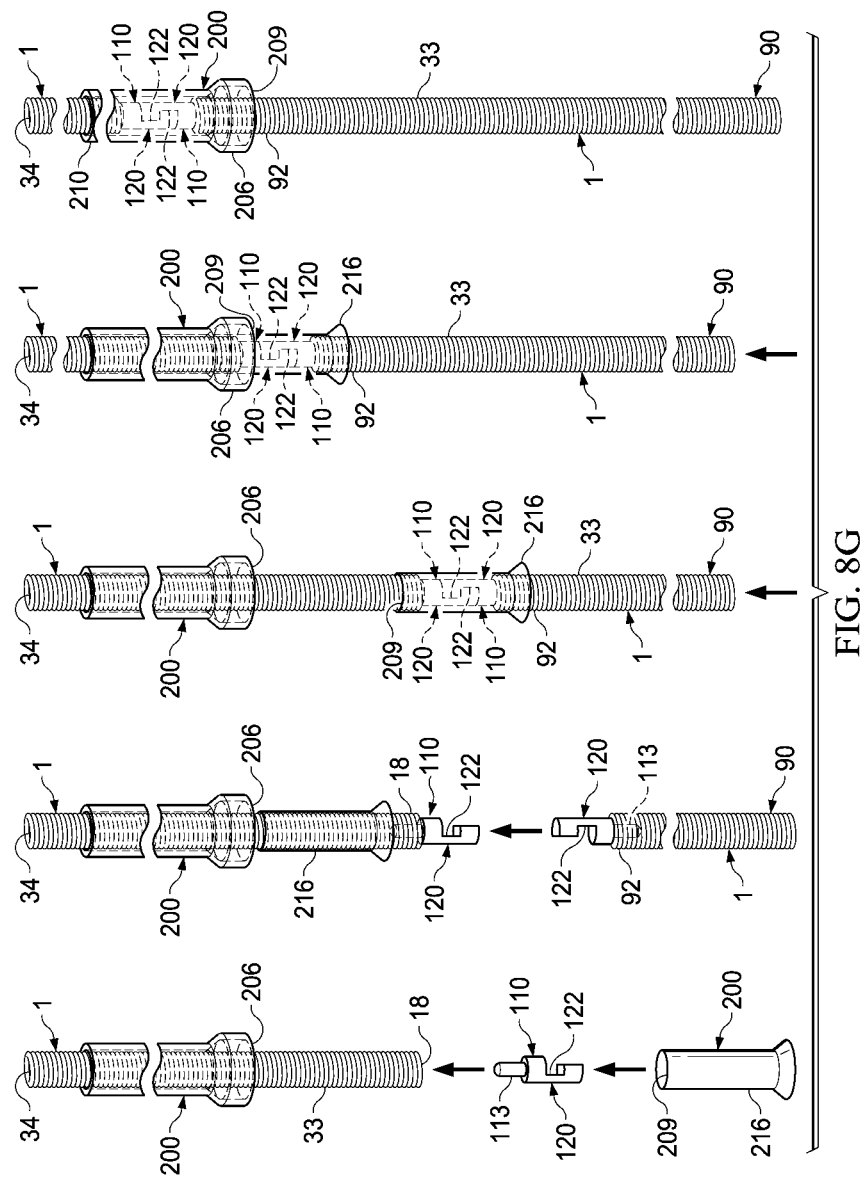

FIG. 8G is a sequential perspective views that depict the use of the linking element 110 which integrates with detachment element 120 of FIGS. 8D-F in conjunction with an embolic agent 1 consisting of a helical wire 33, and a pusher element 90 also consisting of a helical wire 33, and method of use for advancement or retraction and controlled detachment in conjunction with an introducer catheter 200 and an introducer sleeve 216. A helical wire embolic agent 1 is seen extending through the entire length of the lumen 209 of an introducer catheter 200. This has a hollow space inside 34, although in variations may have a mandrel wire or other agent in its space inside 34. The proximal end 18 of the embolic agent 1 is seen, having been severed by the operator using cutting tools described herein or being the natural end of the manufactured embolic agent 1. The attachment pin 113 is inserted into the space inside 34 of the embolic agent 1 and secured using any of the means described herein. The introducer sleeve 216, which is a rigid or minimally flexible tube with a flared end is advanced over the embolic agent 1 yielding the configuration seen in the second figure in the sequence. Now the pusher element 90 is introduced, with the bi-directional locking element 122 of the linking element 110 secured in its distal end 92, either by the operator, or by the manufacturer. As shown by the arrow, it is mated with the bi-directional locking element 122 attached to the embolic agent 1, as seen in the third figure of the sequence, where it can also be seen that the flared end of the introducer sleeve 216 has been slid down over the mated elements so as to constrain them in its lumen 209 so they will stay locked together. Now, as indicated by the arrow, the operator may push the pusher element 90 forward, while simultaneously advancing the mated embolic agent 1, and the introducer sleeve 216 until the introducer sleeve 216 abuts the hub of the proximal end 206 of the introducer catheter 200. As seen by the arrow, the pusher element 90 is advanced forward, and as indicated by the other arrow, the introducer sleeve 216 is now slid down the pusher element 90, out of the figure thus yielding the final drawing where the embolic agent 1 is seen inside the introducer catheter 200, where the bi-directional locking elements 122 remain constrained and locked together. Further advancement (not depicted) will result in deployment of the embolic agent 1 in the target tissues, where now unconstrained, the locking elements 122 may dissociate and the pusher element 90 may be retracted and retrieved as described elsewhere herein.

FIG. 8H is a sequential longitudinal section depiction, with exploded view, of another embodiment of a linking element 110 which is integrated with a detachment element 120 having traction elements 270 which are screw threads 276. The attachment pin 113 in this example has screw threads 276 to help it attach to the embolic device 1 which also has corresponding traction elements 270 of screw threads 276, although any of the variations of attachment pin shown in FIG. 8D are possible here as well including rapid curing adhesive, permitting the use of an embolic agent 1 which does not have screw threads. If screw threads 276 are used on the attachment pin 113, then they may be oriented in the usual manner, or in the opposite direction as shown, such that it would be tightened using counter-clockwise rotation. This might be done so that counterclockwise rotation of the pusher element 90, performed with intention to detach it with detachment element 120, will not result in inadvertent loosening of the linking element 110 from the proximal end 18 of the embolic agent 1. Extra-corporeally, the operator may first screw the linking element 110 into the proximal end 18 of the embolic agent 1, and then screw the distal end 92 of the pusher element 90 into the detachment element, which has traction elements 270 of screw threads 276 to mate with the corresponding screw threads 276 of the detachment element 120. When release of the embolic agent 1 into the target tissues is desired, the pusher element 90 may be rotated counter-clockwise, thus disengaging it from the detachment element 120 and the linking element 110, which stay attached to the embolic agent 1 as it remains in the target tissues.

FIG. 8I is a longitudinal section view of another variation of a detachment element 120 and a linking element 110 that offers an overall shape different from a simple straight-line configuration in order to facilitate nesting into tissues or prevent tissue perforation. The attachment pin 113 is curved, in this example into a gentle right angle, near its junction with the wider portion that uses screw threads 276 for attachment, although any other traction element 270 described herein may be used. The attachment pin 113 is flexible and elastic, allowing it to be straightened when constrained inside the lumen of an introducer catheter (not shown). It will resume its memory shape of the depicted curve once deployed in the tissues. It may be composed of heat sensitive Nitinol which becomes more rigid after warming to body temperature. The rounded shape minimizes risk of trauma or perforation to tissues.

FIG. 8J is a sequential longitudinal section view depicting a variation of a linking element 110 that is intended to reduce possible trauma to the wall of a vessel or other body part. On the left, a detachment element 120 with the traction elements 270 screw threads 276 one end, integrates with a linking element 110 having an attachment pin 113 with traction elements screw threads 276. The linking element 110 is shown in exploded view to be inserted by the operator into the proximal end 18 of an embolic agent 1 that has a wall 2 around a round space inside 34. On the right, the assembly is depicted. The curved attachment pin 113 imparts a gentle curve to the proximal end 18 of the embolic agent 1 when in the resting state with no external forces applied. This may have positive implications when resting in tissues, where the gentle "J" shaped end is less likely to jut against the tissues and cause perforation. The curved attachment pin 113 is composed of a highly flexible and elastic compound, such as types of stainless steel or Nitinol; however, so that when the depicted assembly is inserted into the lumen 209 of an introducer catheter 200 (not shown here) as described elsewhere herein, it will straighten out to allow passage through the lumen 209. Once deployed beyond the tip of the introducer catheter 200, it will resume its memory shape of a curve as shown. Although the "J" shape is depicted, there are many other shapes consistent with this invention that will also serve the function of preventing a straight-line configuration, and thereby reduce the likelihood of tissue perforation.

Figure 8K:
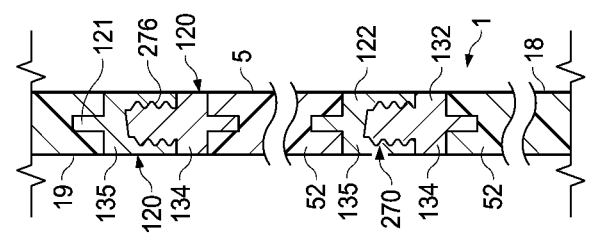
Figure 8L:
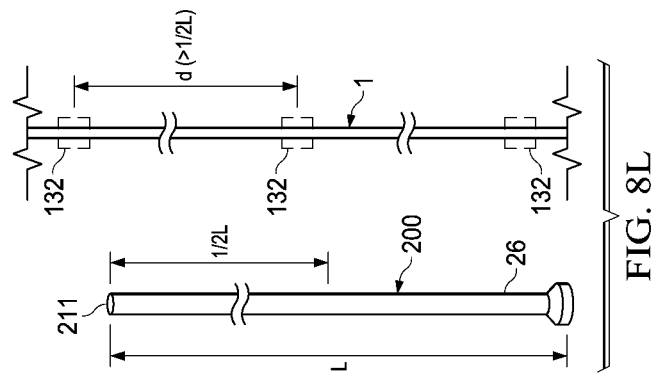
Figure 8M:
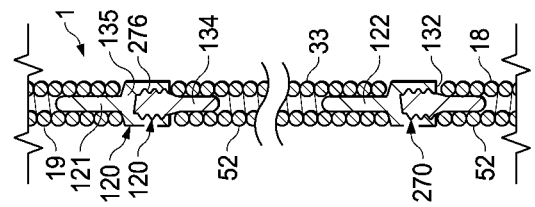
Figure 8N:
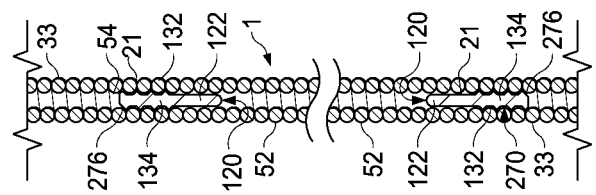

FIGS. 8K, M and N are longitudinal sectional depictions pertaining to embolic agents 1 using threaded detachment elements 120 where the traction element 270 threads 276 of adjacent detachment elements 120 have reversed orientations relative to each other, decreasing ideal distance between detachment points 132, and not requiring modification by operator prior to detachment. In FIG. 8K, the embolic agent 1 is a flexible monofilament 5 with many interlocking repeating segments 52 having the following pattern, from proximal 18 to distal 19: metallic female component 135 of detachment element 120 non-detachably attached to non-metallic monofilament 5 by an attachment pin 121, said monofilament 5 then non-detachably attached to the final component of the repeating segment 52 which is a metallic male component 134 of detachment element 120. Detachment elements 120 utilize the traction elements 270 of threads 276 for locking of male component 134 and female component 135 together. Although segments 52 repeat, each adjacent segment 52 has opposite orientation of the screw threads 276 of the detachment element 120, and will therefore detach using opposite rotational directions. Therefore, when the operator controls the proximal portion 18 of the embolic agent 1 extra-corporeally, they may choose which of the next two detachment sites 132 will detach based on which direction of rotation is used. FIG. 8L demonstrates that the novel design described in FIG. 8K permits the spacing of the distance (labeled as "d") between detachment sites 132 to be less than the length (marked as L) of the of the introducer catheter 200 when operator intends for detachment site 132 to be beyond the distal tip 211 of the introducer catheter 200, so long as d is greater than ½ L. Shorter segment lengths may enable more precise control of embolization. In variation metallic locking mechanisms would not be present and instead the threads would be manufactured into the monofilament segments themselves if using a substance providing sufficient hardness for effective attachment. FIG. 8M depicts an embolic agent 1 of similar description as FIG. 8K except using helical wire 33 in FIG. 8M instead of monofilament 5 as in FIG. 8K. Like FIG. 8K, the detachment elements 120 on adjacent segments 52 have opposite orientation of threads 276 and permit the functionality described in FIG. 8L. FIG. 8N depicts further variation of FIG. 8M in that the non-detachably attached female component 135 of FIG. 8N is not present, and instead in FIG. 8N the internal surface 54 of the helical wire 33 function as the female component of the detachment element 120, with similar function as in FIGS. 8K and 8M. Also in FIG. 8N, there may be weld points 21 in the helical wire 33 at the site of mating with the male component 134 of the detachment element 120 of the adjacent segment 52, in order to prevent spreading of the wire coils which might decrease the strength of the lock. Because the embolic agent 1 will not typically be rotated during phase of its advancement through the introducer catheter 200 (not shown), the locking mechanisms 122 may all be secured rather loosely at the time of manufacture, so that little rotational force will be required at the time of desired detachment 132.

FIG. 8O is a sequential representation of a detachment mechanism using a detachment element 120 which includes a tube 124, and is used in conjunction with a pusher element 90. The embolic agent 1 has operator-determined variable length and infinite choices of detachment sites 132. The long embolic agent 1 is severed and further modified by the operator using an embolic detachment tool 160 which narrows the proximal end 18, so that it will fit snugly into the distal end 92 of the tube 124 of the detachment element 120. Cutting and modification are not shown in this figure but are described herein. The first drawing on the left depicts an optional stabilizer 169 which is an embolic detachment tool 160 element consisting of 2 flat solid plates with a stabilizer groove 170 having friction surfaces, and extending longitudinally along the surface of each plate and forming a round channel when the plates are pressed together (horizontal arrows) and merged as shown, to stabilize the pusher element 90 and the embolic agent 1 so that the former can be inserted into the latter (direction of vertical arrows) without bending or difficulty. Alternatively the operator will simply use their fingers. Once inserted as seen in the middle figure, the pusher element 90 can now be used to advance or retract the embolic agent 1 within the introducer catheter (not shown). Detachment 132 is seen in the third drawing on the right. The pusher element 90, which may be a conventional wire 100 is inserted by the operator into the lumen 97 of the proximal end 91 pusher element 90 and advanced until its tip 94 abuts the embolic agent 1. This may provide more stiffness in advancing the embolic agent 1. Once detachment 132 is desired, the pusher element 90 is advanced while holding the tubing 124 static, pushing the embolic agent 1 out of the tip 94 of the pusher element 90 as shown, showing a wire 100 could be advanced with some force when it abuts the proximal end 18 of the embolic agent 1, thus pushing the embolic agent 1 out of the tip 125 of the tube 124 and the embolic agent 1 out of the tube 124 thereby detaching it from the detachment element 120. FIG. 8P is a frontal view depicting an embolic agent 1 that has operator-determined variable length and infinite choices of detachment points 132 using hydraulic pressure. It is shown with a pressure generator 172, in this case a syringe 653. The description of device and use is the same as FIG. 8O until the third drawing in the sequence, when detachment differs in that hydraulic pressure is used to force the embolic agent 1 out of the tip 125 of the tube 124 thereby detaching it from the detachment element 120.

Figures 1, 2, 8Q:
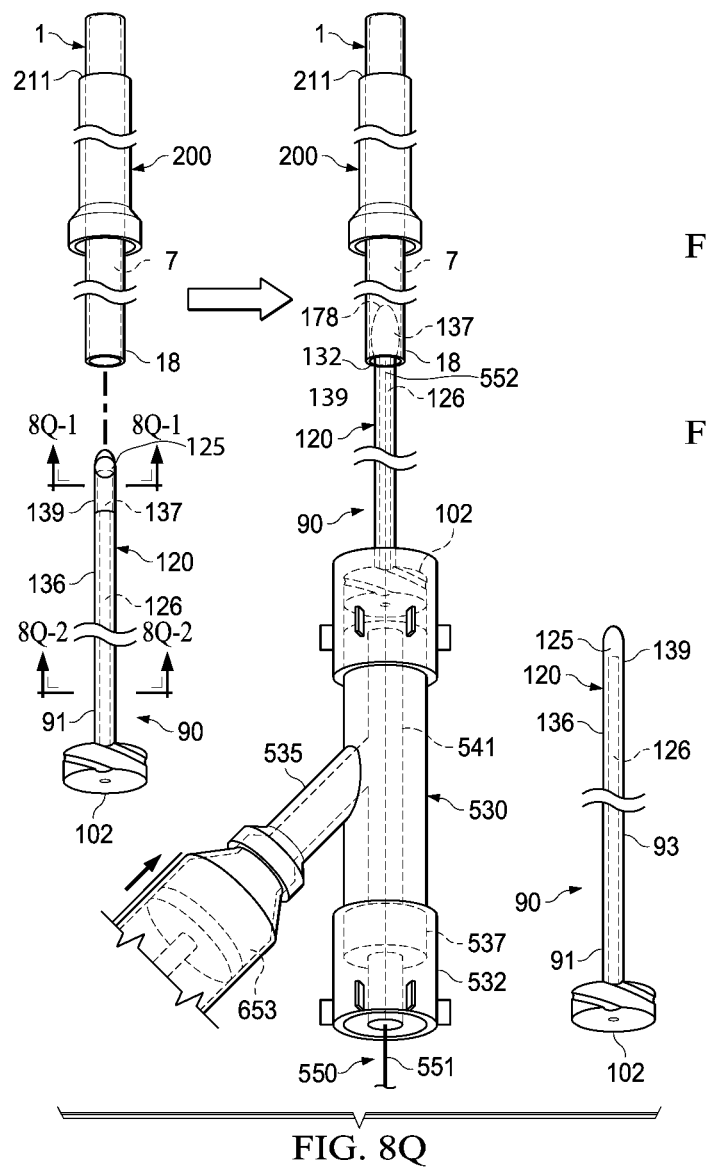

FIG. 8Q is a 2 part sequential series with 3 dimensional frontal views and cross sectional views FIG. 8Q-1 and FIG. 8Q-2 of a detachable embolic system 1, plus a single 3 dimensional view of a variation of the detachment element 120. It depicts an embolic agent 1 that has operator-determined variable length and infinite choices of detachment points 132 when combined with a detachment element 120 using hydraulic pressure differently than FIG. 8P. FIG. 8Q shows, beginning on the left, an embolic detachment element 120 which is a smooth flexible tube composed of a polymer, possibly with very fine metal wires reinforcing its wall 136 in a conventional manner, containing a central hollow lumen 126 and integrated with a pusher element 90, with a hub 102 on its proximal end 91. The detachment element 120 has a closed, solid tip 125. The lumen 126 passing through the integrated pusher element 90-detachment element 120 is fluid-tight except for the opening at the hub 102 of the proximal end 91, which may be connected to syringe 653 for injecting fluid to create increased pressure within the lumen 126. On the distal end 139 a balloon 137 is located, that is in continuity with the lumen 126 and may therefore be filled with fluid or saline under pressure, thus expanding its diameter. In an example of a variation seen on the bottom right view a detachment element 120, instead of a balloon, the distal end 139 may simply have a wall 136 that is composed of a compliant material, while the middle 93 and proximal end 91 of the pusher element 90 are composed of a non-compliant material. In this variation, compliant distal end 139 of the detachment element 120 would swell in diameter upon application of hydraulic pressure into the lumen 126, and thus serve a similar purpose as a balloon. The detachment element 120/pusher element 90 may have a combination of rigidity and flexibility that allows pushing around bends, and which may have a transition between more rigidity in its proximal end 91 relative to a more flexible distal end 139. In variations, it could have a variety of compositions. The figure in the middle shows the detachment element 120 inserted into the hollow lumen 7 of the embolic agent 1 at its proximal end 18, which has been severed using means described herein, or is the natural proximal end 18 of the embolic agent 1 as manufactured. Then, progressing through the sequence as indicated by the solid arrow, the hub of the syringe 653 is connected to the side port 535 of the side-port adaptor 530, and the hub 532 of the side port adaptor 530 is attached to the hub 102 of the proximal end 91 of the pusher element 90. A conventional pressure manometer may be included to provide predictable inflation pressures. In this figure, a small diameter guide wire 550 is shown extending through the entire length of the lumen 126 of the pusher element 90 and detachment element 120, with its distal tip 552 as shown, and then extending proximally out through the lumen 541 of the side port adaptor 530, through its O-ring 537, and further proximally into the environment where its proximal end 551 is located and available for manipulation by the operator. This guide wire 550 represents an optional element that the operator may or may not choose to advance into position as shown, in order to provide additional stiffness to the detachment element 120 in order to facilitate its function as a pusher 90 or retractor of the embolic agent 1. Because the O-ring 537 of the side port adaptor 530 may be tightened around the guide wire 550, the seal is fluid-tight and pressure may still be transmitted from the syringe 653 to the balloon 137 or the distensible distal end 139 of the detachment element 120. Now that all the connections are secured, fluid or gas is injected by the syringe 653 as indicated by the solid arrow, or by other conventional means, to generate hydraulic pressure in the lumen 126 and the balloon 137. The balloon 137 [or compliant distal end 139 of detachment element 120 if described variation is used], is seen to swell in diameter, thus pressing outwardly against the inside of the hollow embolic agent 1, which does not itself stretch substantially radially due to the tensile strength of its wall 136 reinforcement, providing friction grip. This makes the detachment element 120 essentially function also as a pusher element 90, allowing operator to deposit the embolic agent in the target tissues beyond the tip 211 of the introducer catheter 200, at which time the pressure can be released from the syringe, or made negative by retraction of the plunger of the syringe, to deflate the balloon 137 or the distended wall 136 of the distal end 139 of the detachment element 120 (depending on whether first embodiment or described variation is used). Detachment element 120 may now be removed. In variation, a helical wire 33 with a hollow space 34 inside as described herein may be used instead of a tubular embolic agent 1 with same overall effect as described in FIG. 8Q.

Figure 8R:
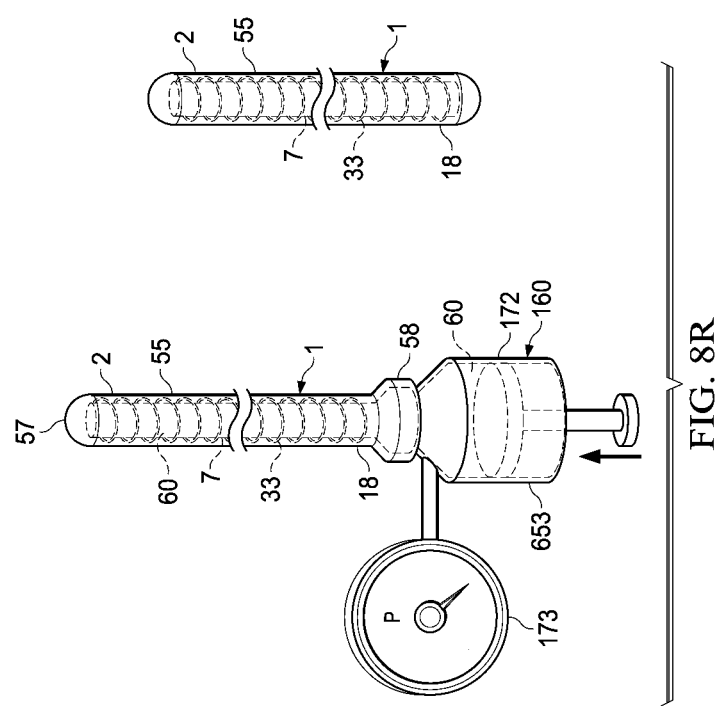

FIG. 8R depicts two variations of an embolic agent 1 that has operator-determined variable length and infinite choices of possible detachment sites, using hydraulic pressure to provide turgidity, while permitting a hollow lumen 7 throughout most of the embolic agent 1 to be used as part of a variety of detachment mechanisms described in this invention. On the left, the embolic agent 1 is a very long tube 55 with a hollow lumen 7, in this case reinforced by conventional helical wire 33 imbedded within its wall 2, although other conventional reinforcement structures used in catheters may be used in this embolic agent 1, where the use of a reinforced tubular structure is novel. The great flexibility of this hollow tube is an advantage for nesting in abnormal tissues, but it benefits from extra stiffness gained from hydraulic pressure during advancement by the embolic delivery system. The tip 57 is closed, and the only opening is via the proximal hub 58. It is shown with a pressure generator 172, in this case a syringe, attached to its proximal hub 58 with a pressure meter 173 interposed, indicating the pressure in the lumen 7 of the embolic agent 1 created by the fluid 60 in the pressure generator 172 and lumen 7. The pressure generator 172 may have been applied by the operator at the time of the procedure. In variation, as seen on the right, there would be no pressure generator 172 or pressure meter 173, and instead the proximal end 18, and thereby the entire embolic agent 1, would be packaged by manufacturer with a fluid-tight seal throughout, with pressurized fluid 60 filling the lumen 7 and providing the optimal pressure for purposes herein. The pressurization provides turgidity and increased stiffness of the embolic agent 1 so that it may have the desired properties for advancement by the embolic delivery system (not shown) as described herein. Once the desired length of embolic agent 1 has been deployed within the body, the embolic agent 1 may be severed extra corporeally creating a new proximal portion with an accessible lumen 7 as described in this invention. Pressure will be lost within the embolic agent 1, however it is no longer necessary since the last portion will not be advanced using the embolic delivery system 1 but instead will be advanced manually, after attachment of any of the many detachment elements and pusher elements described herein. The entire embolic agent 1 is advanced into the tissues, detached, and other elements removed as described in this invention.

Figure 9A:
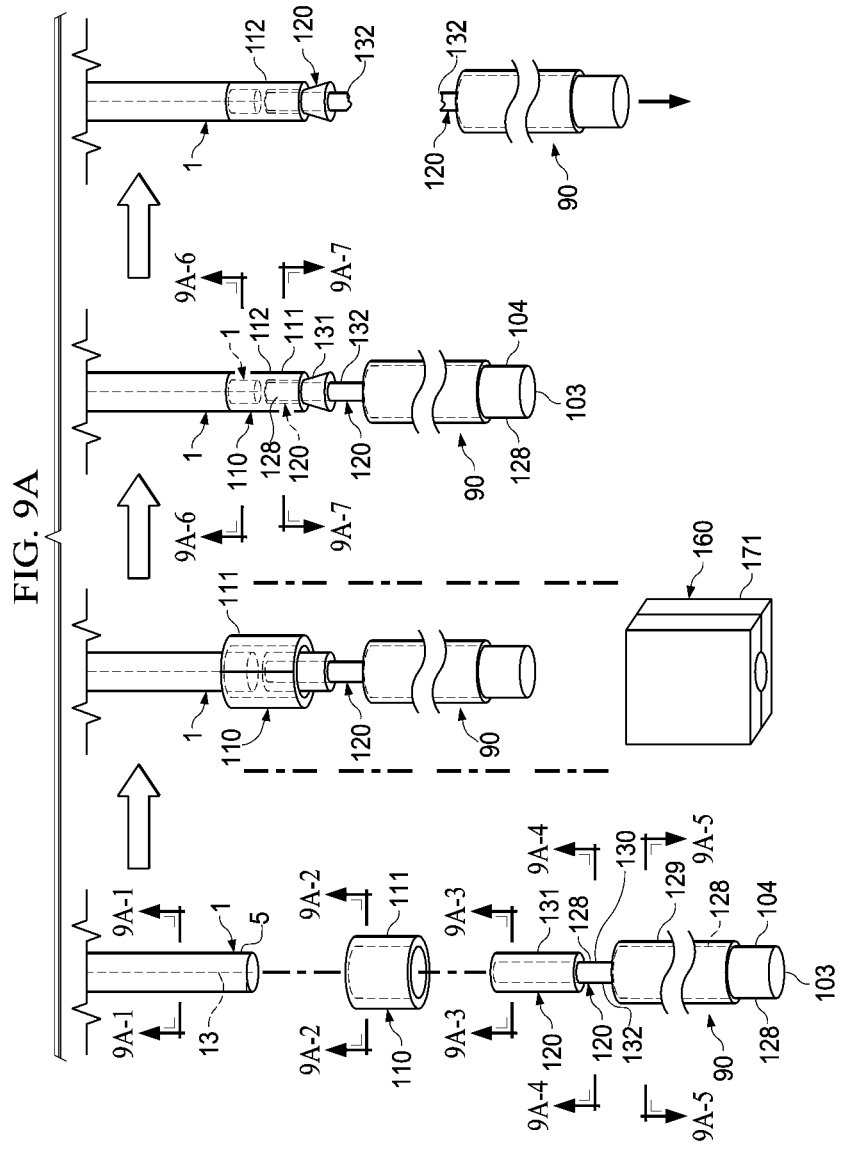
Figure 9D:
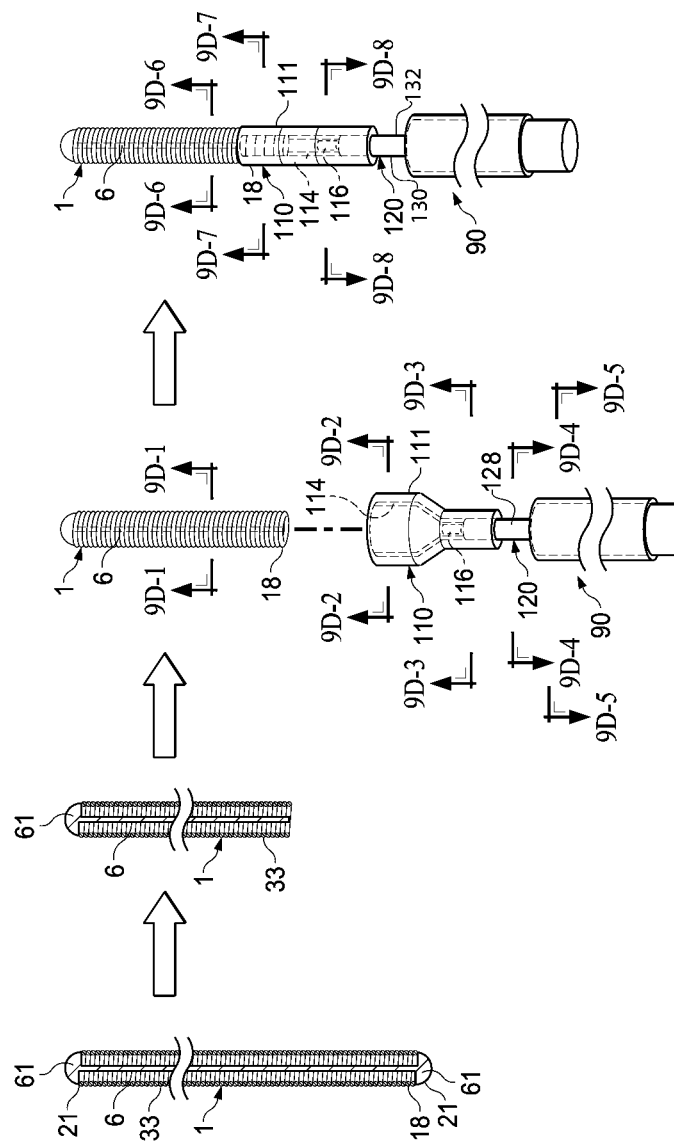

FIG. 9A includes four frontal sequential views, and many cross section views FIGS. 9A-1 to 9A-4 and 9B-1 to 9B-4 depicting an operator-controlled linking element 110 that may be used to link a wide variety of embolic agents to a wide variety of types of detachment elements, providing versatility and broadening of applications for many elements. On the left, several elements are shown and are included in cross section FIGS. 9A-1 to 9A4 before linking as they might be experienced by the operator in the extra-corporeal operating field. Included is a portion of the embolic agent 1 consisting of a non-metallic monofilament 5 containing a marker wire 13, the linking element 110, which in this case is a swage ring 111, a detachment element 120, which is electrolytic, and a pusher element 90 which transitions imperceptibly with the detachment element 120. The swage ring 111 is a metallic hollow ring which is amenable to concentric compression and deformation, thereby bonding and linking other elements in its center. At the core of the pusher element 90 and the detachment element 120 is an electrolytically corrodible wire 128 which is continuous throughout the detachment 120 and pusher 90 elements and available for electrical contact proximally in the operating field extracorporeally at the contact point 103. In the detachment element 120, the wire 128 is surrounded and electrically insulated by a dielectric semi-rigid capsule 131. Progressing more proximally, the wire 128 is not insulated at the short bare portion 130, which serves as the detachment point 132. Proximal to the bare portion 130, in its non-tapered long portion, the wire 128 is coated with an electrically insulating coating 129. Progressing more proximally into the pusher element 90, the continuous wire 128 remains coated as seen in FIG. 9A-5 until its proximal end where there is another bare portion 104 which serves as an electrical contact 103 to connect to energy source as described in this invention. In the second drawing, the embolic agent 1 and the detachment element 120 have both been inserted into opposite ends of the hollow swage ring 111 by the operator in the operating field extracorporeally. An embolic detachment tool 160, in this case a swaging tool 171, is then applied providing concentric compression. In the third drawing, the swaging tool has been removed, and the swaged elements are seen linked together securely, with compression of the swaging ring 111, the embolic agent 1, and the capsule 131. This is also depicted in cross section FIGS. 9A-6 and 9A-7. The operator now has complete control of the embolic agent 1 by controlling the pusher element 90, and may advance or retract the embolic agent 1 at will even when it has passed into the target tissues in the body beyond the introducer catheter (not shown). When proper position of embolic agent 1 is achieved, the operator may perform electrolytic detachment. Current may be applied to the wire 128 extra-corporeally at the contact 103, and opposite polarity charge may be conducted to the ionic medium around the detachment point 132 using methods described in this invention. The fourth drawing shows the effects of electrolytic corrosion with detachment 132 of the detachment element 120 into fragments, with the upper fragment remaining non-detachably attached to the embolic agent 1 and the lower fragment remaining non-detachably attached to the pusher element 90. The swage ring 111 may also serve as a marker 112 of the end of the embolic agent 1, especially if a dense metal such as platinum us used.

FIG. 9B is a two part series which includes cross section FIG. 9B-1 depicting a variation of the foregoing using a tube-like embolic agent 1 with a hollow lumen 7. In the first drawing, the wire 128 of the detachment element 120 extends distally beyond the capsule 131 as shown, so that when the detachment element 120 is inserted into the swage ring 111 as seen in the second drawing, the wire 128 extends into the lumen 7 of the embolic agent 1, and serves effectively as a mandrel when swaging compression is performed as described above (not shown). A marker wire 13 is present in the wall of the embolic agent 1.

FIG. 9C is a two part 3 dimensional sequential series with cross sections FIGS. 9C-1 to 9C-8 depicting a variation of FIG. 9A with reduced components and simpler operation by operator in the field. The capsule 131 around the corrodible wire 128 in the detachment element 120 has been omitted, and a non-corrodible metal is used for the swage ring 111. Electrolytic corrosion may still only occur at the bare portion 130 detachment point 132. Although other non-corrodible metals could be used for the swage ring 111, platinum is used in this figure, and it also serves as a radio-opaque marker 112 which will remain non-detachably attached to the proximal end of the embolic agent 1 after swaging, and after detachment, thereby allowing the operator to know the position of the entire embolic agent 1 upon detachment. In an embodiment, omission of the capsule 131 may simplify manufacturing. Also seen in the first drawing on the left is another variation including the non-detachable attachment of the proximal portion of the swage ring 111 to the corrodible wire 128. This is shown as having been swaged on, however other conventional means such as welding, brazing, soldering, or adhesive could be used. This pre-attachment presents the operator with fewer separate components and a simpler procedure to perform in the field. The operator will insert the proximal end 18 of the embolic agent 1 with marker 13 into the swage ring 111 and apply the swage tool (not shown) to achieve the result in the second drawing, where, as in FIGS. 9A-B, the pusher element 90 and embolic agent 1 are securely linked by the linking element 110 and detachment element 120 until operator chooses to perform detachment as described in FIG. 9A. In variation of FIG. 9C, a dielectric coating or capsule around the distal end of the wire 128 of the detachment element, similar to the coating 131 in FIG. 9A, may be present to prevent electrical conduction from wire 128 to swage element 111. This would allow use of electrolytically corrodible metal for swage element 111, or if non-corrodible metal were used, the coating would decrease the physical size of the electrode possibly hastening electrolytic corrosion at the intended detachment point 132.

For FIGS. 9A-C, in variation, a non-corrodible wire may be substituted for the coated portion of the corrodible wire 128 to conduct electricity to the bare area 130 of the corrodible wire 128, using conventional metal-metal connection techniques. In FIGS. 9A-C, an electrolytic detachment mechanism was shown simply for demonstration purposes, as nearly any other type of detachment system may be substituted due the versatility provided by this novel linking method. Many other variations are possible using the linking element described, as almost any detachment mechanism, including those of this invention as well as conventional or described elsewhere, may be easily envisioned to be linked with nearly any embolic agent by someone experienced in this field, thereby providing the novel features of this invention including a variable-length embolic agent whose length is determined by the operator during the procedure, and whose overall length may far exceed those of conventional or previously described agents.

FIG. 9D is a four part sequential series. The first two drawings are longitudinal sections, and the last two are frontal views with cross-section views depicted in FIGS. 9D-1 to 9D-8. The first drawing on the left depicts an embolic agent 1 consisting of a helical wire 33, with blunt end pieces 61 on both proximal 18 and distal 19 ends, said end pieces non-detachably connected to the same straight wire 6, and said end pieces also optionally non-detachably connected to the helical wire 33 at its proximal 18 and distal 19 ends at what will be called the weld points 21 although solder or other conventional means may be used. This configuration permits flexibility of the embolic agent 1 while preventing excessive elongation of the embolic agent 1, which may be important if retraction is desired by pulling on the proximal end 18. The embolic agent may be composed of corrodible or non-corrodible metal but will not be subject to electrolytic corrosion due to dielectric lining 114 as will be described. This embolic agent resembles some conventional available agents. In variation, the wire 6 may be substituted with a non-metallic strand. In the second drawing, the embolic agent 1 has been severed by a cutting tool (not shown) by the operator in the operating field extracorporeally, when the desired length has been determined, cutting through the helical wire 33 and the straight wire 6. In the third drawing, the severed embolic agent 1 is about to be inserted into the cup-like opening of the linking element 110, which is a swage ring 111 that has been pre-attached non-detachably to the detachment element 120 as in FIG. 9C. In FIG. 9D, an additional component is shown, which is a lining 114 made of durable, semi-rigid dielectric material that is placed into the proximal portion 18 of the available space within the swage ring 111 at the time of manufacture. Once inserted into the swage ring 111, the proximal end 18 of the embolic agent 1 will abut the plug 116, which is a compressible dielectric material that sits between the embolic agent 1 and the distal tip of the wire 128, thereby preventing current flow from latter to former. The lining will electrically insulate the embolic agent 1 from the swage ring 111 and the corrodible metal wire 128 of the detachment element 120. Therefore the embolic agent 1 is not in electrical continuity with the wire 128. The fourth drawing shows the assembly after swaging by the operator with swage tool (not shown). All elements are now linked and advancement and retraction of embolic agent 1 is achieved by manipulation of pusher element 90, until desired time to detach using means described in FIGS. 9A-C, including electrolytic detachment at the detachment point 132 in the bare portion 130 of the wire 128. In variation, the dielectric lining 114 may extend throughout the entire inside surface of the linking element 110, thereby providing insulation between the electrified wire 128 and the swage ring 111, thereby limiting size of electrode to the bare portion 130 of the wire 128 to possibly hasten its electrolytic corrosion, and permitting use of corrodible metal for the swage ring 111.

FIG. 9E is a series of frontal views of a system and method utilizing a linking element 110 as shown in FIG. 1I. On the left, the distal introducer catheter 200 is within the body cavity and the proximal portion is extracorporeal. Most of the embolic agent 1 is a tube with a wall 2 and a lumen 7 and has been passed into the body cavity, and the proximal portion has been severed using the operator using an embolic detachment tool 160 (not shown). The distal end 92 of a pusher element 90 is attached to a detachment element 120, which in this example is electrolytic and has a bare portion 130 of corrodible wire 6 which will serve as a detachment site 132, and functions as described in this invention. The detachment element 120 is non-detachably connected to the linking element 110, which is this example is a round, blunt-tipped rigid object with a diameter large enough to fit snugly into the lumen 7 of the proximal end 18 of the severed embolic agent 1 without substantially stretching it. The wall 2 of the embolic agent may be reinforced to help prevent stretching. The linking element 110 is attached by the operator to the embolic agent 1, with attachment optionally aided by traction elements 270 or adhesive (not shown). As seen in the second drawing, the embolic agent 1 has now been pushed entirely into the body by the operator by advancing the pusher element 90, with control over advancement and retraction. In the third drawing, detachment has been performed at the detachment point 132, the embolic agent 1 is left in place as the pusher element 90 and part of the detachment element 120 are removed. In variation, nearly any type of detachment element such as mechanical detachment systems described herein, or conventional systems, may be substituted for the electrolytic detachment mechanism in this example.

FIG. 9F and cross-section views 9F-1 to 9F-3 depict a system that uses a linking element 110 and electrolytic detachment in a novel manner to enable the novel utilities of this invention. It also demonstrates a variation for electrolysis where by a second separate smaller electrical wire 143 is used to carry current instead of the structural pusher 90. On the left drawing, the very long embolic agent 1, which is composed of an electrolytically corrodible wire 6 surrounded and insulated by a capsule 43 as described in this invention, has already been severed at the proximal 18 aspect by the operator as described herein. After severing, a small portion of the capsule 43 at the proximal end 18 was stripped or burned off or otherwise removed as described herein using detachment tools described later herein, leaving a short segment of bare 130 wire 128 which constitutes the detachment element 120. The pusher 90 is shown here as a dielectric monofilament, although an insulated wire or non-insulated wire could be used so long as it was not in direct electrical contact with the linking element 110 (e.g. separated by a dielectric material). A second insulated electrical wire 143 of very small diameter passes alongside the pusher element 90 and makes electrical contact with the linking element 110 which is attached to the pusher element 90. The linking element 110 is a non-corrodible metal such as platinum so it will also serve as a radio-opaque marker 13. Alternatively, it may be a corrodible metal so long as it would be coated with insulation everywhere except within the hollow core 115, which is a small round hollow area in the center of at least a portion of the linking element 110 that may receive the wire 128 of the detachment element 120 on the embolic agent 1 and provide electrical contact between the two elements. Coating 129 of the linking element 110 may be applied in variation even when using non-corrodible metal composition in order to prevent inadvertent contact with opposite polarity electrode contact in an electrolytic introducer catheter as described in this invention. In the center drawing, the operator has inserted the wire 128 into the swage ring 111 and swaged it to create a non-detachable attachment, and also leaving a short distance between the linking element 120 and the capsule 131 where a short segment of bare portion 130 of wire is exposed to the surrounding fluids (not shown). In the third drawing, the operator has applied current from an electrical source 176 as described elsewhere in this invention, using a novel electrolytic introducer catheter described herein (not shown), resulting in corrosion and detachment at the detachment point 132. This figure represents a relatively simple yet highly functional detachment system that enables variable length embolic agents under full operator control and detachment at the tip of an introducer catheter. Although the use of the separate insulated electrical wire 143 could be avoided through use of novel aspects of this invention such as electrified introducer catheters, it is shown here to demonstrate that the linking mechanism opens up possibilities for increased detachment functionality of variable length and multiple detachment site options even when using more conventional electrolytic means.

FIG. 9G with cross sections 9G-1 to 9C-4 depict a system similar to that of FIG. 9F however instead of electrolytic means, detachment of the embolic agent 1 may be accomplished with nearly any type of mechanical detachment system in this invention or elsewhere similar to the manner of FIG. 1I. On the left, the embolic agent 1, shown partially within the introducer catheter 200, is the same as FIG. 9F except the wire 6 need not be corrodible, and could be a denser metal serving as a marker 13 as seen in cross section FIG. 9G-1. Cross section view FIG. 9G-2 shows The linking element 110 with hollow core 115 of FIG. 9G which is similar to that in FIG. 9F except in the absence of electrification in this system, this element and all others may have composition and interfaces without regard to electrical concerns. The linking element 110 is non-detachably attached to a detachment element 120. This detachment element is similar to the interlocking bidirectional mechanism described herein but in this embodiment is mainly used to denote nearly any variety of mechanical detachment system. The second part or the detachment element 120 is non-detachably attached to the pusher element 90. The second figure shows the array of elements all now securely linked together while constrained within the lumen 7 of the introducer catheter 200. The third drawing shows detachment 132 when desired by operator when detachment elements 120 are pushed beyond the tip 211 of the introducer catheter 200. Replacement of the depicted mechanical element with many other types of mechanical detachment system could be accomplished by someone skilled in the art using conventional means.

Figure 10A:
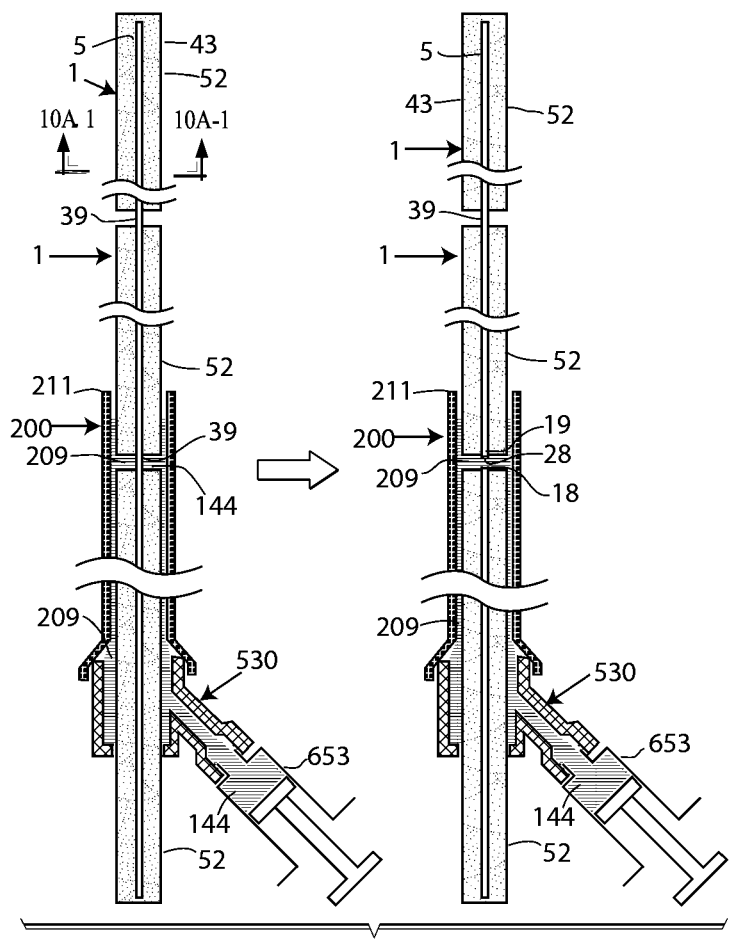
FIG. 10A show an embodiment of a novel chemical embolic agent detachment system as disclosed herein.

FIG. 10A depicts one embodiment of a novel detachment system using chemical means. On the left is a flexible embolic agent 1, round in cross section depicted in FIG. 10A-1, composed of a strand of biocompatible material, in this case a monofilament 5 which is amenable to dissolution in biocompatible solvent such as dimethyl sulfoxide (DMSO). This monofilament 5 is surrounded by a capsule 43 of biocompatible material which is not subject to dissolution in the same solvent. The embolic agent 1 is composed of repeating segments 52 with bare areas 39 of non-encapsulated monofilament 5 exposed to the environment. The tip 211 of the introducer catheter 200 is positioned in the body cavity (not shown) to be treated and the embolic agent 1 is advanced to near completion into the cavity. There is one bare area 39 inside the lumen 209 of the introducer catheter 200. A side port adaptor 530 is connected to the introducer catheter 200 in conventional manner to allow injection of liquid solvent 144 from an attached syringe 653 into the side port adaptor 530, where it may flow into the lumen 209 of the introducer catheter 200. A precisely measured volume of solvent 144 is injected, corresponding to the known void space of the lumen 209 of the introducer catheter 200 and side port adaptor 530, in order to fill the introducer catheter 200 nearly to its tip 211, thus bathing the bare area 39 with solvent. After an adequate dwell time, the figure on the right depicts dissolution of the bare area 39 and subsequent detachment 28 of the embolic agent 1 into distal 19 and proximal 18 fragments. The solvent may be aspirated, and the distal embolic agent 1 fragment may be pushed by the proximal fragment or by a pusher (not shown) to deposit completely within the body cavity. This embolic agent 1 and detachment system offers function similar to shown in FIG. 1G in a system that may be simple to produce at low cost, and simple to use. In variation, instead of a monofilament 5, a polyfilament may be used with similar effect.

Figure 11A:
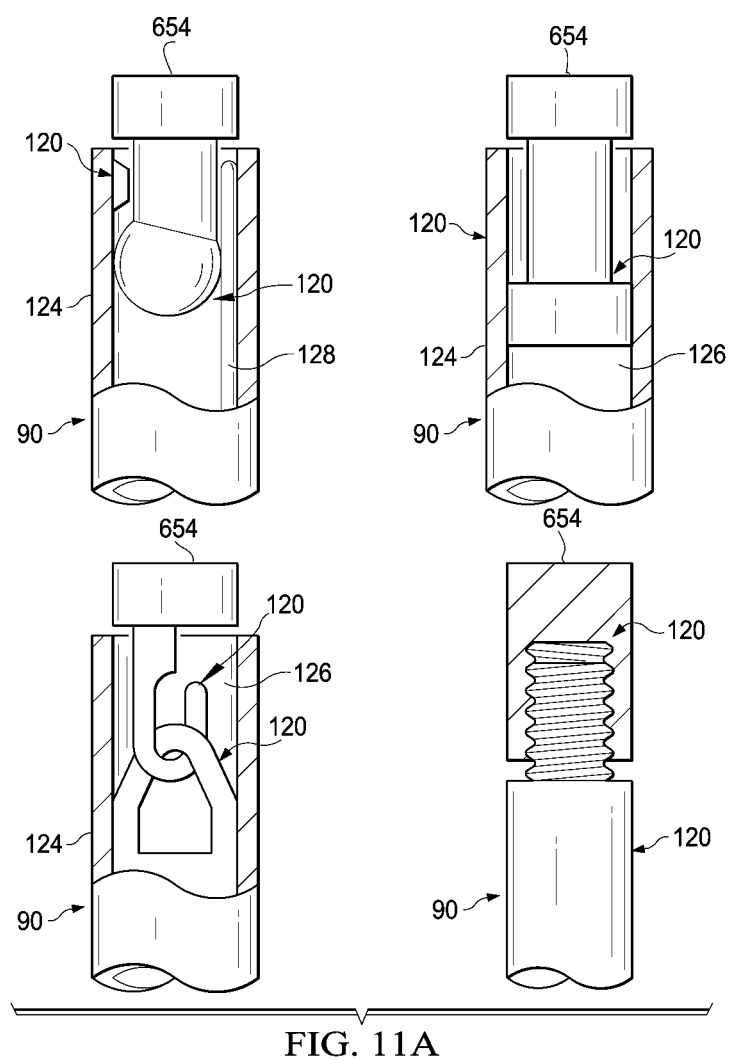
FIG. 11A depicts various embodiments of conventional mechanical detachment elements which may be employed in novel manner using linking elements and detachment mechanisms as described herein.

FIG. 11A is a series of drawings representing general types of detachment mechanisms that have been previously reported. They are reviewed briefly here to illustrate one of the novel concepts of this invention, regarding the use of a linking element to enable the application of conventional detachment mechanisms for use with a variable-length embolic agent, whereas previously conventional agents were confined to manufacturer pre-determined lengths when similar detachment elements were used, as in FIGS. 1E-F. In the invention disclosed herein, variable-length systems as seen in FIGS. 1I-K are made possible when using the conventional mechanical detachment systems of FIG. 11A, or when using novel detachment systems described in this invention. In each example in FIG. 11A-11C, there is a point of non-detachable attachment 654 to an embolic agent (not shown) in a conventional system, or to a linking element (not shown) as in this invention, said linking element being non-detachably attached to a detachment element 120, and said detachment element 120 detachably attaches to a second detachment element 120 which is integrated with a pusher element 90. Referring back to FIG. 11A, detachment of the two detachment elements 120 occurs, from left to right in the examples, when a wire 128 is retracted making room for the detachment element 120 to pass beyond a narrowing in the tube 124 of the detachment element 120, when hydraulic pressure is applied into the lumen 126 of the tube 124 of the detachment element 120, when the two detachment elements 120 are pushed beyond the tip of the tube 124 and unhooked from each other, or when the two detachment elements 120 are unscrewed from each other. Other types of detachment elements are previously reported and not shown here, but are nevertheless amenable to adaptation using this invention as described.

Figures 1, 11B:
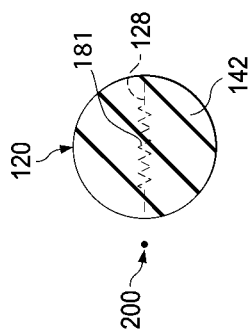
FIGS. 11B-C heat sensitive glue detachment mechanism adapted in novel manner with linking element to provide for ability to shorten embolic agent or choose detachment point.
Figure 11C:
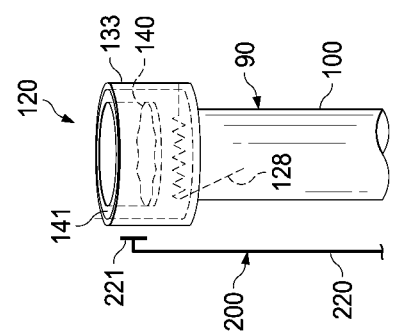
Figure 11B:
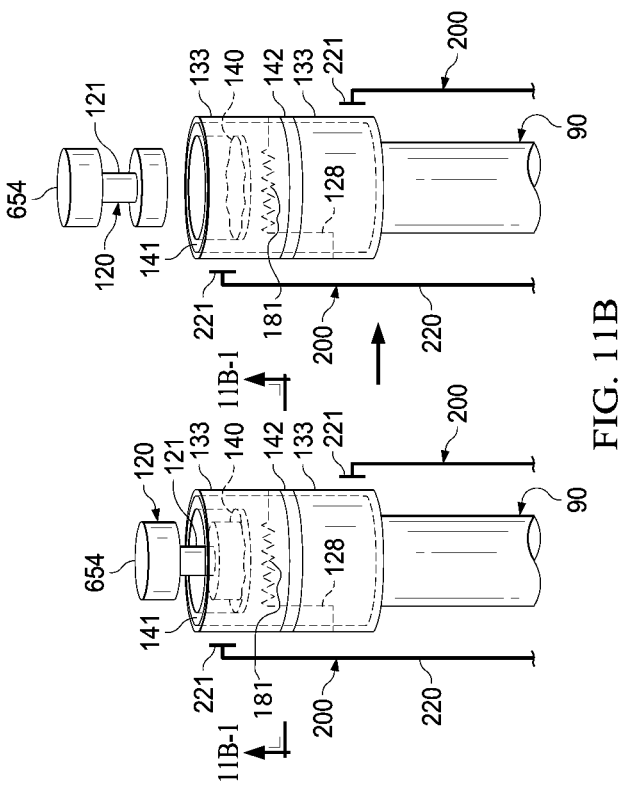
Figure 12B:
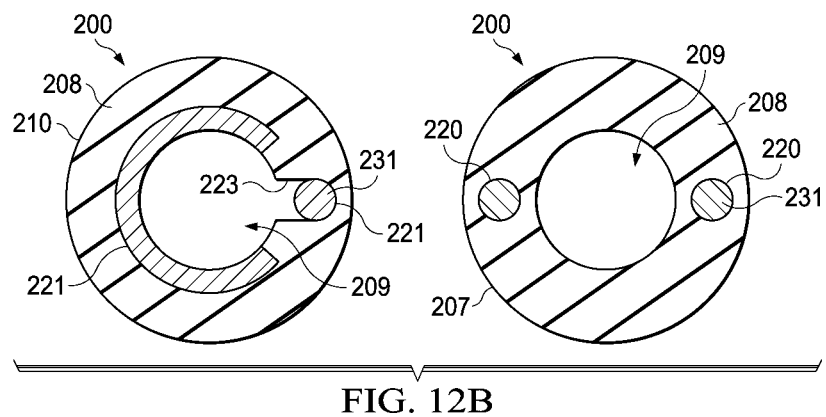
Figure 12C:
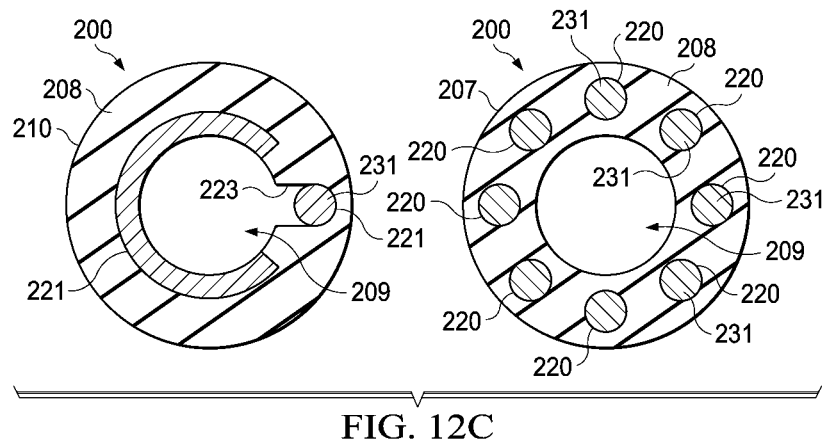
Figure 12D:
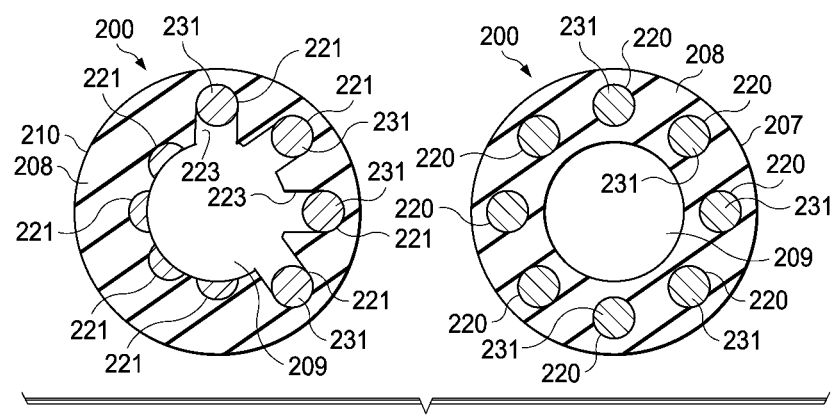
Figure 12E:
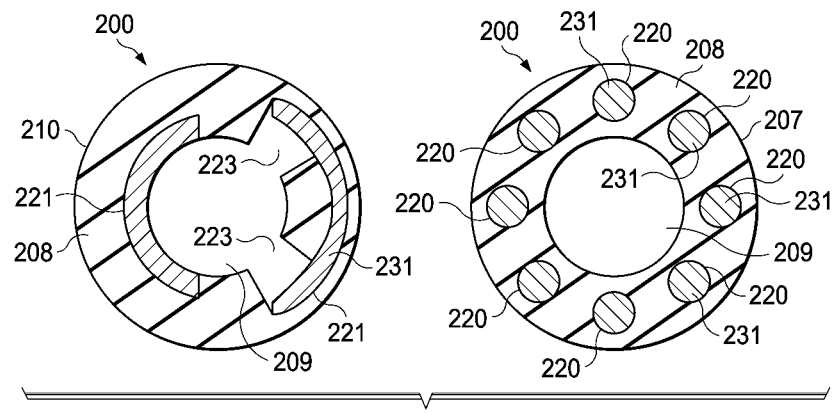
Figures 1, 12G:
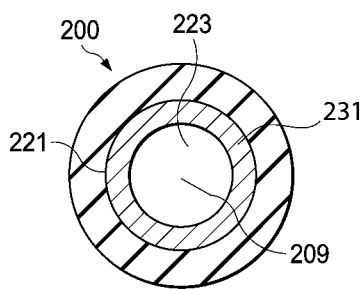
Figures 2, 12G:
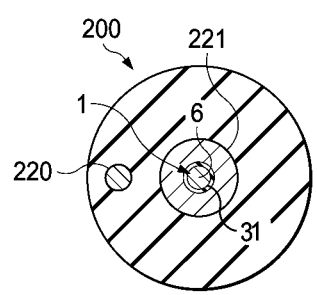
Figures 3, 12G:
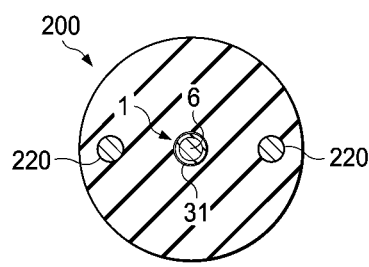
Figure 12G:
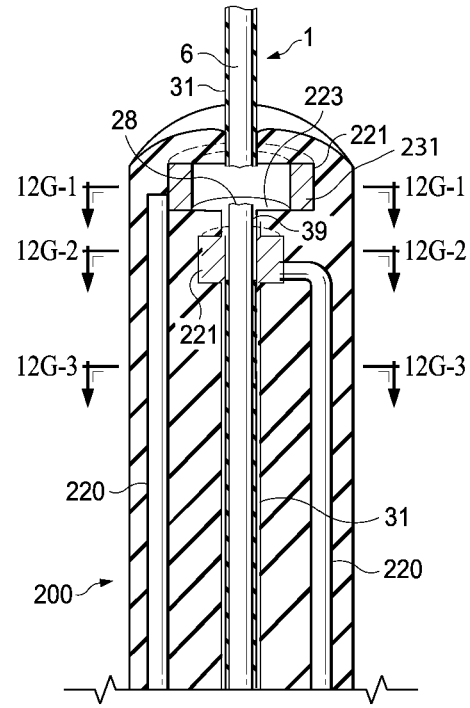
Figure 12I:
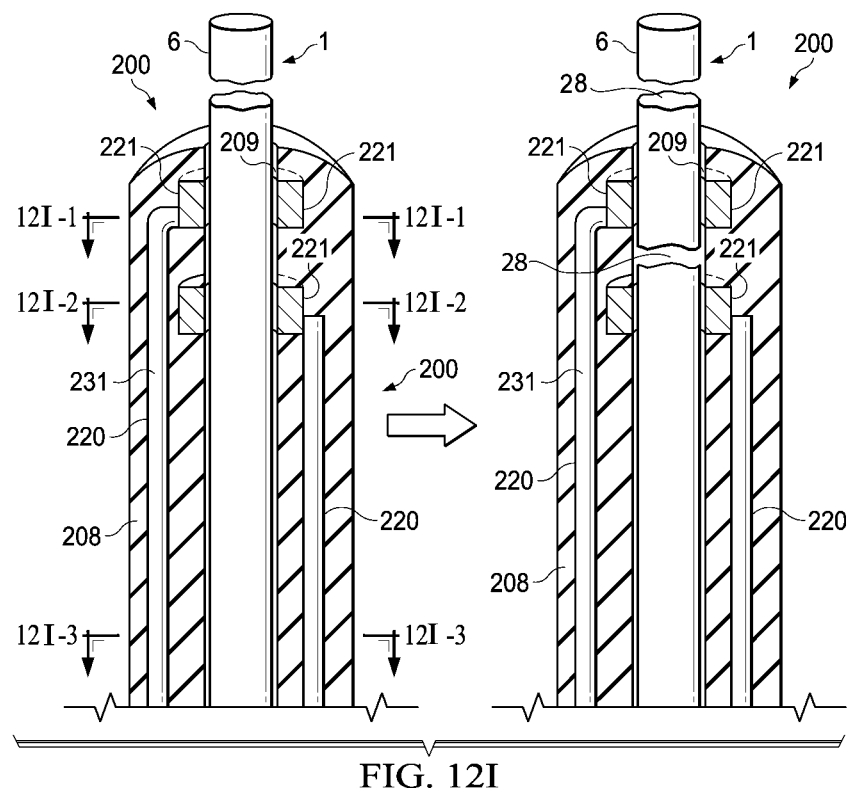
FIG. 12I depicts a novel catheter containing electrical elements comprising two electrodes and embolic agents whereby non-electrolytic electrical means provide detachment of embolic agent.
Figures 1, 12I:
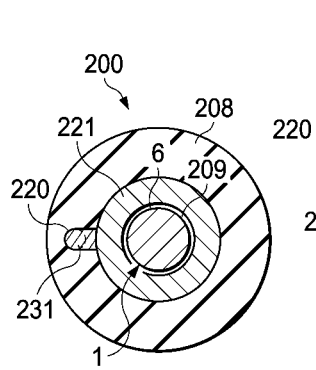
Figures 2, 12I:
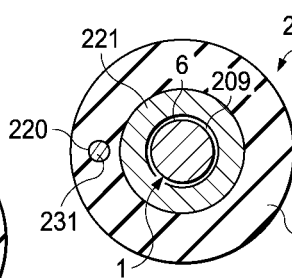
Figures 3, 12I:
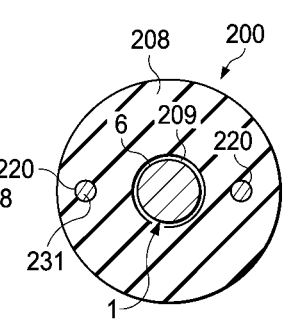

FIG. 11B and cross section 11B-1 are a representation of a detachment system using heat sensitive glue which may be used in a novel manner with this invention by combining with a linking element (not shown), and a novel electrified introducer catheter as shown in FIG. 12I, enabling a variable length embolic agent (not shown). On the left, a pusher element 90 is non-detachably attached to a detachment element 120, containing a cup 141 with heat sensitive glue 140 in its bottom, thereby creating a detachable attachment to the attachment pin 121 of the second part of detachment element 120, which has a point of attachment 654 to the embolic agent (not shown) of a conventional device as in FIGS. 1E-F, or the linking element 110 in this invention with configurations represented by FIGS. 1I-K. The cup 141 is of a dielectric material with a high melting point, and has a heating element 181 in its solid portion with sufficient electrical resistance to become warm enough to melt the glue when charge is applied. The Wire 128 passes to the outer layers which are two conductive metal contacts 133 that that are insulated from each other by a layer of dielectric material 142. These contacts 133 come into contact with the electrical contacts 221 of the introducer catheter, said contact 221 being attached to an electrical wire 220 (catheter not shown, wires schematically represented). This configuration of the introducer catheter 200 is seen in more detail in FIG. 12I. In the figure on the right, applying electrical energy (not shown) to the wires 220 of the introducer catheter 200 will heat the glue 140, melt it, and allow the attachment pin 121 to detach, thereby releasing the embolic agent 1 (not shown). Non-detachable attachment of the detachment element 120 to a linking element 110 (not shown) at the point of attachment 654 as described in this invention, along with the electrically active introducer catheter 200 will enable an operator controlled variable-length embolic agent with full control of embolic agent via control of pusher element 90 extra-corporeally. FIG. 11C depicts a variation where there is only one electric wire 220 and one electrical contact 221 in the introducer catheter 200, and the circuit is completed by having the electric wire 128 of the detachment element 120 complete a circuit with the electric wire 100 of the pusher element 90, so that the proximal end (not shown) of the pusher element 90 in the operating field can become the second point of electrical contact 133 with the energy source. Otherwise the use and effect is similar to FIG. 11B. This system could use a single-electrode introducer catheter such as shown in FIG. 14B, although used differently than depicted there because the second electrode would be connected to the contact 133 of the pusher element 90 instead of to the skin.

FIGS. 12A-H describe various types of introducer catheters 200 containing two electrodes that have novel functionality with regard to electrolytic detachment of embolic agents. Conventional electrolytic detachment mechanisms do not incorporate electrolytic or detachment-related functions into the introducer catheter, which limits the function of the detachment mechanism. For example, the ability to combine controlled detachability with an operator-determined variable length embolic agent is limited. The use of wires 220 and contacts 221 in the introducer catheter 200 will provide functionality that is not possible with conventional systems that incorporate the conductive elements on the body of the embolic agent or its detachably attached pusher element, said conventional systems not having the versatility of this novel disclosed system to use embolic agents that may undergo detachment at a single chosen point from amongst a plurality of possible points along its length, thus enabling the use of very lengthy embolic agents that are disclosed herein and in keeping with the spirit of this invention including the treatment of large abnormal cavities. FIG. 12I describes an introducer catheter 200 also having anode and cathode both incorporated into the catheter body, however not intended for electrolytic detachment, and instead with both electrodes making direct contact with electrical contacts on other elements related to detachment mechanisms that involve electrification.

FIG. 12A with cross section views FIGS. 12A-1 and 12A-2 show an introducer catheter 200 with a hub 201 on its proximal end 206, a middle 207, a distal end 210, a wall 208 and lumen 209, and is flexible, yet remains pushable as described elsewhere herein for all other introducer catheters 200. It may have more complex architecture to provide ideal physical properties in keeping with conventional systems. Novel elements include electrically conductive wires 220 that are exposed to the environment at the hub 201 where they may be connected to external wires 174 that connect to a source of DC current 176 such as a battery. The electrically conductive wire 220 on the left passes, insulated, through the dielectric wall 208 of the catheter to its distal end 210 where it then comes in contact with the lumen 209 at a point called the electrical contact 221, where it will contact the corresponding contact point of an embolic agent as seen in later figures. The contact 221 may be composed of a noble non-corrodible metal so that it does not diminish during electrolysis, thereby maintaining full contact until detachment has occurred at the designated detachment point. The opposite pole of the power source 176 connects the second electrically conductive wire 175 to the electrically conductive wire 220 on the right, of opposite polarity 231, which then passes insulated in the wall 208 of the introducer catheter 200 to reach the second electrical contact 221 of opposite polarity 231 at the distal end 210, which is not directly in contact with the bulk of the lumen 209 or the contact of the embolic agent (not shown). Instead, it contacts the ionic fluid such as blood or saline solution (not shown) in the lumen recess 223 in which ionic fluid or blood will be present. This will support electrolytic corrosion of the corrodible portion of the embolic agent as depicted in many forms in this invention. The embolic agent (not shown) has an outer diameter very slightly smaller than the inner diameter of the introducer catheter 200 so cannot directly contact the recessed contact 221 of opposite polarity 231 on the right, preventing short circuit.

FIGS. 12B-E depict cross sections of variant introducer catheters 200 that provide roughly similar function as described for FIG. 12A. In each figure, the drawing on the left represents a distal location 210 on the introducer catheter 200 and the figure on the right represents a middle location 207. In FIG. 12B, the distal end 210 of the introducer catheter 200 has a contact 221 that occupies a large portion of the lumen 209 within its wall 208 as shown, to provide extensive contact with the contact on the embolic agent (not shown). As in FIG. 12A-1, the second contact 221 of opposite polarity 231 is recessed within the lumen recess 223 within its wall 208. As shown in the figure on the right, in the middle portion 207 of the introducer catheter 200, the corresponding wires 220 for each polarity are seen coursing insulated within the wall 208. FIG. 12C is similar to 12B except that multiple wires 220 are used for each polarity converging onto their respective contacts 221. This may permit the use of smaller sized wires 220 or the wires may be structured so as to also provide stiffness and support properties to the introducer catheter 200 that are desired. In this example, the first 4 wires 220 in the clockwise direction beginning with the 12 o'clock position service the recessed contact 221 of opposite polarity 231 from the other wires 220 which service the contact 221 on left. FIG. 12D shows a variation whereby there are multiple contacts 221 in continuity with the lumen 209, each with its own wire 220, and there are multiple recessed contact 221 of opposite polarity 231 in lumen recesses 223, each contact 221 also being connected to its own wire 220. FIG. 12E depicts a variation whereby there are multiple wires 220 per contact 221, and the contact 221 on the left is in contact with a large portion of the lumen 209, while contact 221 of opposite polarity 231 on the left is crescent shaped and recessed in the lumen recess 223 with a portion of wall 208 in the middle 208 that prevents direct contact between electrified embolic agent 1 and contacts 221, which instead contact the ionic fluid or blood bathing the area.

FIG. 12F with cross section FIGS. 12F-1 to 12F-3 are a sequence view of a different embodiment of a two-electrode introducer catheter 200 showing an example of the detachment process. The introducer catheter 200 has, within its wall 208, a wire 220 for one polarity and another wire 220 of opposite polarity 231 that end in respective contacts 221 near the tip 211 of the catheter as shown. The contact 221 of first polarity 230 is circumferential and protrudes very slightly into the lumen 209, to increase surface contact with contact 36 on the embolic agent. Therefore the second contact 221 of opposite polarity 231 is at a different level within the catheter, closer to the tip 211 of the introducer catheter 200, and is recessed within the circumferential lumen recess 223 containing ionic fluid or blood. Said contact 221 may not directly contact the embolic agent but is in close proximity. The embolic agent 1 is similar to that described in FIG. 6P except the distal marker 13 is located slightly more distally as shown, is one of several novel types described herein that could be used in this system. It has a monofilament 5, and an electrically corrodible wire 6 which also forms a connector 35. The embolic agent 1 has an outer diameter that is very slightly smaller than the inner diameter of the introducer catheter 200. The power source and external wires are not depicted because they are similar to those depicted in FIG. 12A, where wires exit the proximal end 206 of the introducer catheter 200 to contact with wires 175 from the power source 176. When DC power is applied, the circuit is as follows: power source to wire 220 to contact 221 of first polarity 230 to contact on embolic agent 1 (non-corrodible metal) to connector 35 (electrolytically corrodible metal), through ionic solution to contact 221 of opposite polarity 231 to wire 220 of opposite polarity 231 to power source. Electrolytic corrosion occurs at the connector 35 which becomes the detachment point 28. The distal fragment of embolic agent 1 remains in the target tissues (not shown) and the other elements are removed. The proximal fragment of embolic agent 1 may be used as a pusher to push the last few millimeters of embolic agent 1 out of the introducer catheter 200. Since the embolic agent has a series of connectors 35, the operator may choose which site will become the detachment point 28 without any modifications of the embolic agent 1 by simply positioning the chosen site at the level of the contacts 221 in the introducer catheter 200.

FIG. 12G and FIGS. 12G-1 to 12G-3 depicts various views and cross sections of a similar electrolytic introducer catheter 200 seen in FIG. 12F, but with minor modifications and using a smaller diameter embolic agent 1 of a different type. The system is shown after electrolytic corrosion of the embolic agent 1 at the detachment point 28 has already occurred in the manner described in this invention. The embolic agent 1 is an electrolytically corrodible wire 6 with an insulating coating 31 over most of it, except in the bare area 39 which is positioned to be in contact with the proximal contact 221 and in close proximity to the distal contact 221 of opposite polarity 231 in the lumen recess 223 of the introducer catheter 200. The power source and external wires are not depicted as they are similar to those shown in FIGS. 12A-F, where electrical wires 220 exit the proximal end 206 of the introducer catheter 200 to contact with wires 174 from the power source 176.

FIG. 12H and cross section FIGS. 12H-1 and 12H-2 show an embodiment of the introducer catheters 200 with both electrodes incorporated, with one electrode making physical contact with the embolic agent 1 and the other contacting the body fluids or ionic flush solution. Introducer catheter 200 has two electrical wires 220 imbedded in its wall 208, insulated from the environment and the lumen 209. One wire 220 ends in the proximal one of the two contacts 221, and the contact 221 is concentric and protrudes slightly into the lumen 209 to make contact with the corresponding contact 221 on the embolic agent 1. The other wire 220 is of opposite polarity 231, and is helically wound in the wall 208 of the introducer catheter 200 to provide structural functions as well as electrical. The other contact 221 of opposite polarity 231 is located on the outside of the wall 208 of the introducer catheter 200 and will contact body fluids, tissues, or ionic flush solution. The proximal ends of wires 220, which are not shown but are similar to those depicted in FIG. 12A, exiting the introducer catheter 200 proximally and contacting the wires 220 of the power source 176 for both electrodes. The embolic agent 1 in this example is described in detail in FIG. 6S and has a contact 36 which contacts the contact 221 on the introducer catheter 200, said contact 36 also contacting the connector 35 which is electrolytically corrodible and does not conduct to the embolic segment 52 distal to the detachment site 28 at the bare area 39. When DC current is applied, electrolysis will occur at the detachment point 28 of the embolic agent 1 as described herein.

FIG. 12I and cross section FIGS. 12I-1 to 12I-3 depicts an introducer catheter 200 with both electrodes in its structure, but is not structured for electrolytic detachment and instead enables other types of detachment by making direct physical and electrical contact of both of its electrodes with corresponding contacts 221 on the embolic agent 1 or its related detachment 120 or pusher 90 elements (not shown). In this example, it is shown to be used to facilitate the creation of heat in order to cause detachment 28 through melting of metal, solder, heat-sensitive glue, or heat sensitive electrically conductive glue. The depicted introducer catheter 200 has two wires 220 imbedded in its wall 208, one on the left of opposite polarity 231 from the other on the right. Each wire 220 exits the introducer catheter 200 and connects to a power source as described for FIG. 12A and FIG. 12H. Both wires lead to contacts 221 which protrude slightly into the lumen 209 and physically contact the embolic agent 1 which is a wire 6 that is composed of an electrically conductive metal with a relatively low melting point that is above body temperature. When power is applied, current will flow predominantly through the short segment of metal in the wire 220 between the contacts 221 of the introducer catheter 200 at the detachment point 28, resulting in detachment as shown in the second drawing. The wire 6 in this area will have a sufficient electrical resistance that results in generation of adequate heat to quickly melt the metal. This embodiment may also be used with the detachment system depicted in FIGS. 11B and 12J.

Figure 12J:
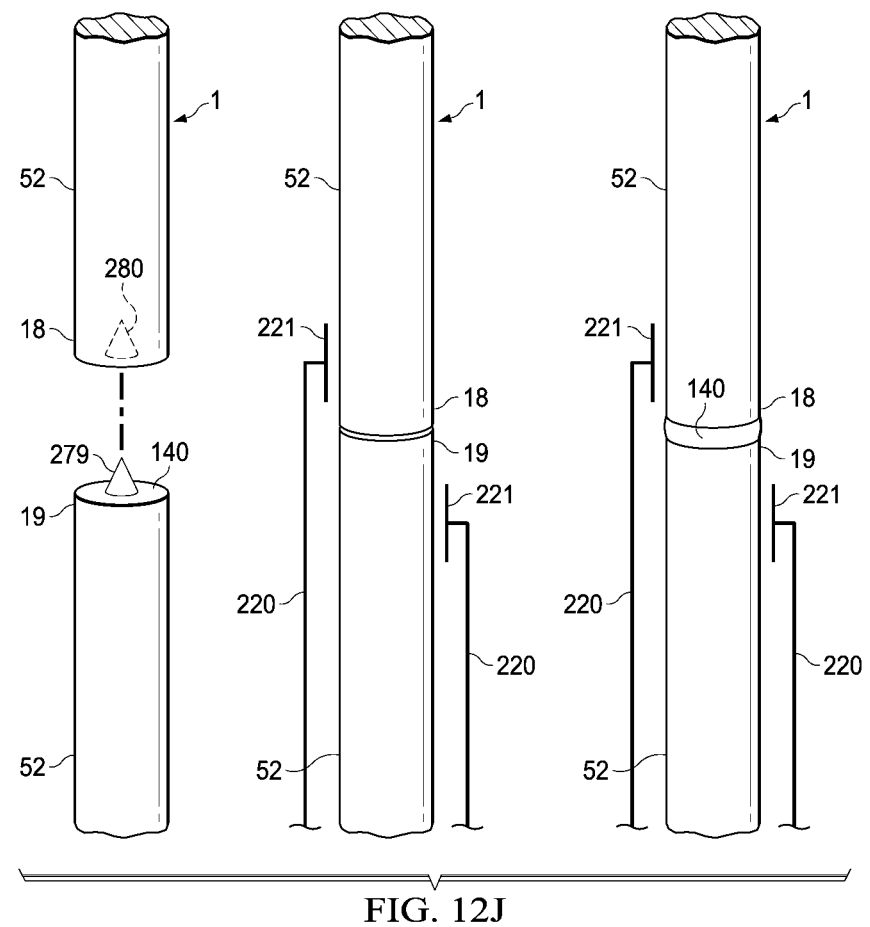
FIG. 12J depicts various embodiments of embolic agents useful to some embodiments of delivery system as described herein.

FIG. 12J shows two embodiments of embolic agents that may be used with the introducer catheter 200 in FIG. 12I. The first two drawings depict the same embolic agent 1, exploded on the left and non-exploded in the middle view. The embolic agent 1 includes a series of repeating segments 52, each with a proximal end 18 and a distal end 19. Composition of the embolic agent 1 is a conducting metal or metalloid. On the distal end 19 of each segment 52 is a protuberance 279, shaped like a cone, which mates with a depression 280 in the proximal end 18 of the abutting segment 52 providing electrical contact between the segments 52. On the flat portion of the mating surfaces, heat sensitive glue 140 or solder is present, which is preferably conductive but not necessarily so. In the middle drawing, the embolic agent 1 is seen intact functioning physically as a unit, and the locations of the contacts 221 and wires 220 of the introducer catheter 200 are shown schematically. When current is applied, it passes through the metal embolic agent 1 between the contacts 221. The composition of the embolic agent 1 in this location provides sufficient electrical resistance to generate heat that melts the bond, allowing the segments 52 to separate. The drawing on the right shows a variation where there is a small gap between the segments 52 filled by a small amount of solder or conductive glue 140 which will melt when current is applied, resulting in separation of the segments 52.

Figures 1, 13A:
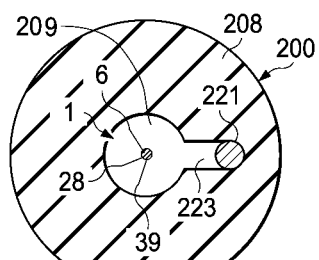
FIGS. 13A-F depict various embodiments of novel introducer catheters containing electrical elements comprising one electrode which are utilized in conjunction with the embolic agents and embolic delivery systems described herein.
Figures 2, 13A:
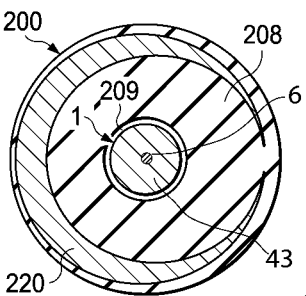
Figure 13A:
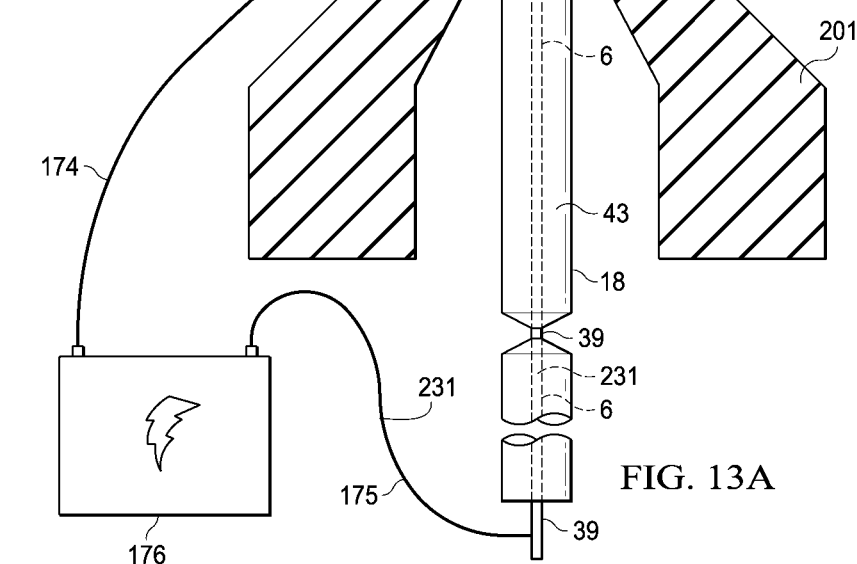

FIGS. 13A-E depict electrolytic introducer catheters 200 that include one electrode within their structure. In some uses, the embolic agent and related elements function as the other electrode for completing the circuit. In other uses, the electrode in the catheter may be used to provide current to an area of the embolic agent or related detachment elements focally near the tip of the catheter without electrifying a long segment of embolic agent, thereby providing the novel functionalities of this invention. In FIG. 13A and cross section FIGS. 13A-1 and 13A-2, one electrode from a power source 176 connects to wire 174 at or near the hub 201 of introducer catheter 200 which connects to the wire 220 helix imbedded in the wall 208 of the introducer catheter 200, said wire 220 coming into contact with the contact 221 near the tip 211 of the introducer catheter 200, where the contact 221 ends in a lumen recess 223 communicating with the lumen 209. There it is in proximity with, but may never physically touch, the embolic agent 1 due to smaller diameter of recess 223. Although many different embolic agents could be used with this introducer catheter 200, the catheter in this embodiment is described in detail in FIG. 6K. The operator positions the embolic agent 1 so that the bare area 39 is near the tip 211 of the introducer catheter 200. The hub 201 of the introducer catheter 200 is located extracorporeal of the patient body while the tip 211 and a substantial portion of the embolic agent 1 are located in or near the target tissues (not shown). The second wire 175 from the power source 176 is connected to the bare portion 39 on the proximal end 18 of the embolic agent 1. In this example, there is another bare area 39 seen proximal to the hub 201 of the introducer catheter 200, however electrolysis will not occur here because it is not in contact with body fluids or ionic flush and is open to the air of the operating field. Therefore, the conductive wire 6 of the embolic agent 1 will be of opposite polarity 231 than for the introducer catheter 200. When current is applied, electrolytic corrosion will occur at the bare area 39 near the tip 211 of the introducer catheter 200, which is in the body (not shown), and detachment will occur at the detachment point 28. This variation of introducer catheter 200 permits the use of many embolic agents 1 for some of the objectives of this invention, for example enabling the use of a very long, operator-determined length of embolic agent 1 with controlled detachment 28 near the tip 211 of the introducer catheter 200.

Figure 13B:
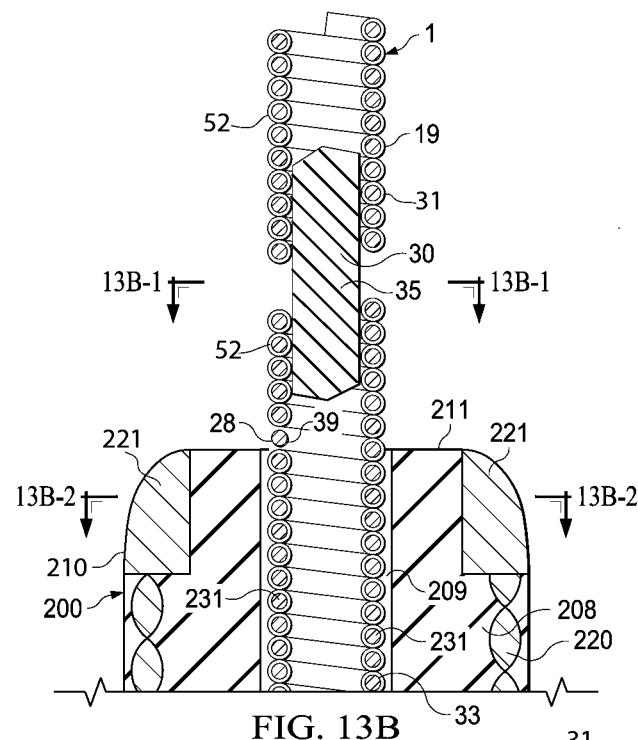
Figures 1, 13B:
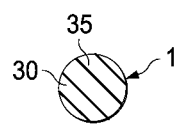
Figures 2, 13B:
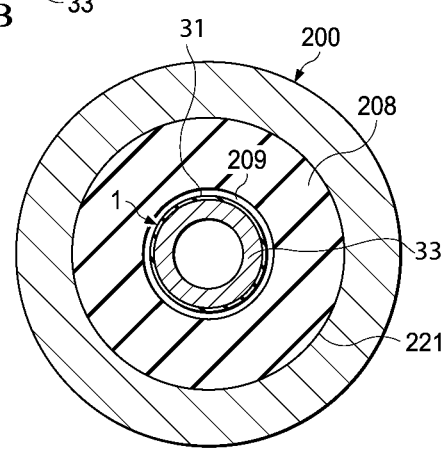
Figure 13C:
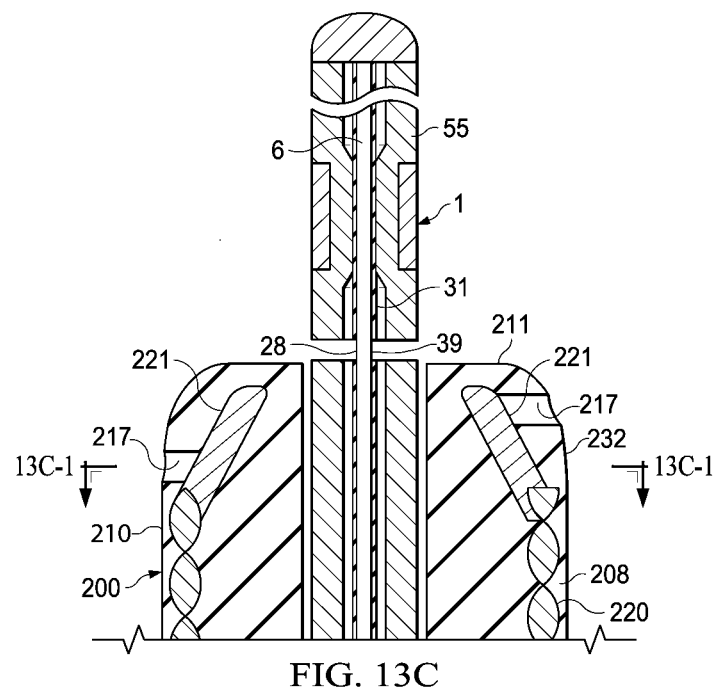
Figures 1, 13C:
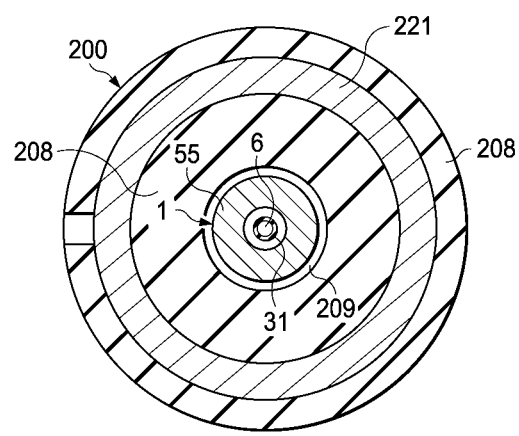

FIGS. 13B-C and cross section FIGS. 13B-1 to 13C-1 show views of variations of electrolytic introducer catheters 200 that include one electrode within its structure. The distal ends 210 of the introducer catheters 200 are depicted. In FIG. 13B, the electrical wire 220, as in FIG. 13A, is helically wound within the wall 208 of the introducer catheter 200 and makes contact with contact 221 at the tip 211 of the introducer catheter 200, which in turn makes contact with the body fluids, tissue, and flush solution inside the body (not shown). The embolic agent 1 in the lumen 209 of the introducer catheter 200 is similar to the one shown in FIG. 6W where it was described in more detail. Briefly, it has a corrodible wire 33 with a coating 31 and is composed of segments 52 that are connected by connectors 35 which are composed of dielectric material. As shown in FIG. 13A, it has a bare area in the operating field extra-corporeally where the opposite pole of the power source may be connected (not shown). When current is applied to the wire near the hub of the introducer catheter (not shown) and to the extracorporeal contact on the embolic agent (not shown), the contact 221 of the introducer catheter 200 serves as an electrode, and the bare area 39 of the embolic agent 1 wire 33 will serve as the electrode of opposite polarity 231. Electrolysis will result in corrosion and detachment at the detachment point 28 as there are no other bare areas more proximally and current will not flow more distally than the visualized connector 35 because it is a dielectric 30. The position of the contact 221 could potentially allow direct contact between the contact 221 and the distal portion 19 of embolic agent 1 that is already deployed into the target tissues, which will often touch the tip 211 of the introducer catheter 200. This could create a short circuit, so only embolic agents which are insulated, non-conductive, or non-electrified distally to the detachment point, such as the depicted embolic agent 1, would be used with this variation. FIG. 13C shows a variation of FIG. 13B where the contacts 221 of the introducer catheter 200 are imbedded in the wall 208, with side holes 217 extending from the contact 221 to the outer surface 232 of the wall 208 of the introducer catheter 200. Other aspects of the description of the introducer catheter 200 are the same as for FIG. 13B. The embolic agent 1 shown in this embodiment is the same as the one described in detail in FIG. 6X, although many embolic agents described herein would also work with this system. When the power source wires (not shown) are connected to the introducer catheter 200 and the embolic agent 1 extracorporeally, electrolysis will occur with corrosion at the intra-corporeal bare area 39 of the conducting corrodible wire 6 which is surrounded by insulating coating 31 everywhere intra-corporeally except the bare area 39 which was created by the operator using detachment tools (not shown and as described elsewhere in this disclosure) and will result in detachment of the embolic agent 1 at detachment point 28. In this example, the side holes 217 are too small to allow embolic agent 1 which is already coiled in the target tissues (not shown) around the tip 211 of the introducer catheter 200 to touch the contact 221. Therefore, a short circuit will not occur even if there are un-insulated conductive portions of embolic agent 1 distal to the detachment point 28, which could be a consideration with other embodiments of embolic agent.

Figure 13D:
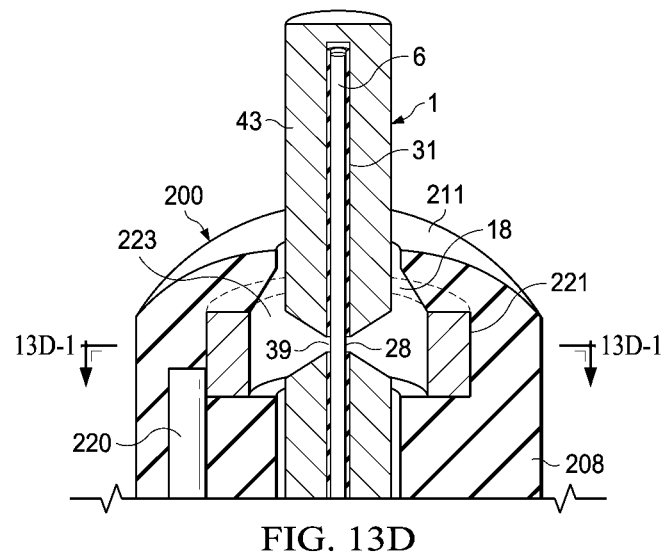
Figures 1, 13D:
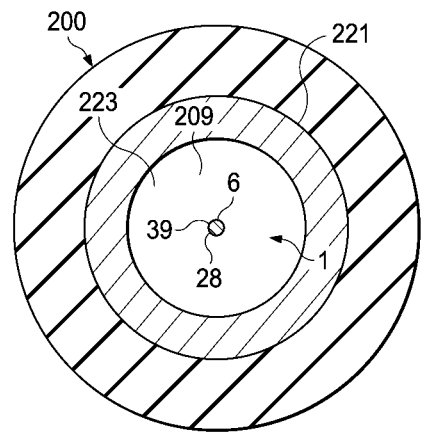

FIG. 13D shows another variation where introducer catheter elements and embolic agent elements serve as both electrodes for electrolytic function. The introducer catheter 200 has one wire 6 serving one contact 221 near the tip 211, said contact recessed away from the lumen 209 in a lumen recess 223, contacting the blood or flush fluid (not shown) present in the lumen 209, which also bathes the embolic agent 1 in this area. The embolic agent 1 is the same as shown in FIG. 6I but is shown in its modified state, whereby a short bare area 39 has been created by removing a short segment of the coating 31 as described herein, causing the detachment point 28 where electrolytic corrosion will occur once power is supplied to the wire 220 of the introducer catheter 200 as described in FIG. 13A, as well as to the wire 6 in the embolic agent 1 at a bare portion in its proximal portion in the operating field, (not shown) similar to as that described in FIG. 13A and elsewhere herein.

Figure 13E:
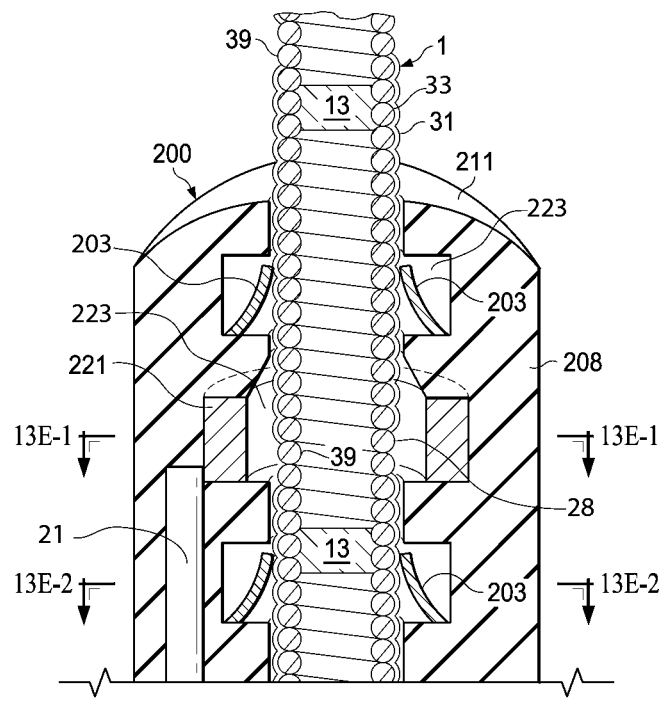
Figures 1, 13E:
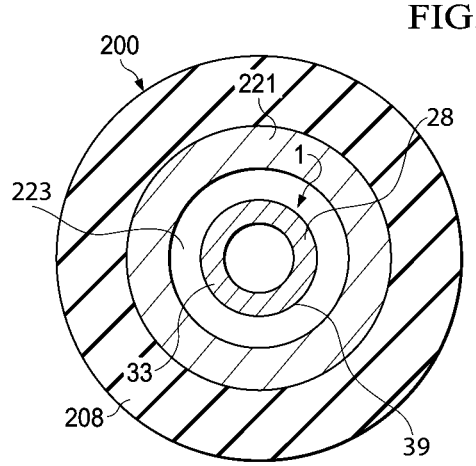
Figures 2, 13E:
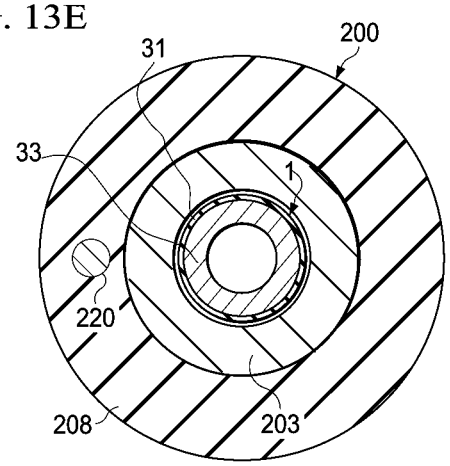

FIG. 13E and cross sections FIGS. 13E-1 and 13E-2 depict an embodiment of introducer catheter 200 similar to that shown in FIG. 13D, except with addition of electrically insulating one-way valves 203 which are used to create a small local environment within the introducer catheter for electrolytic corrosion while dampening the flow of current to surrounding fluids and tissues where secondary corrosion of other bare areas of corrodible metal could otherwise occur. Reference to FIG. 13D should suffice for explanation of other elements of introducer catheter 200 of this variation in FIG. 13E. The embolic agent 1 is described in detail in FIG. 6F, and includes a corrodible helical wire 33 with coating 31, with uncoated bare areas 39 in multiple locations and radio-opaque markers 13. The valve 203 is, in this embodiment, a conventional semi-rigid non-porous elastic compound, such as latex or silicone or other compound with similar characteristics, capable of providing a substantially fluid-tight seal around the embolic agent 1 near the tip 211 of the introducer catheter 200, with said valve 203 located in a recess 223 in the internal wall 208. This valve 203 is a round leaflet shaped to permit flow from proximal to distal but not in the opposite direction. It will permit the passage of the embolic agent 1 in the usual manner. The valve 203 provides sufficient seal without overly obstructing longitudinal motion of the embolic agent 1. There are two valves 203, one proximal and one distal to the recessed contact 221 where electrolysis may take place. The valves are sufficiently electrically insulating to prevent substantial electrolytic effect or corrosion of bare areas 39 of corrodible embolic agent 1 that may exist in the proximal introducer catheter 200 or distal to the tip 211 of the introducer catheter 200 in the target tissues (not shown). This helps to direct electrolysis of the corrodible embolic agent 1 to the desired site indicated for detachment point 28. Effective isolation of the small volume of ionic flush solution which is electrified for electrolysis may improve the results when using very simple varieties such as uncoated corrodible wires or those with multiple bare areas that are all electrified such as in this example.

Figure 13F:
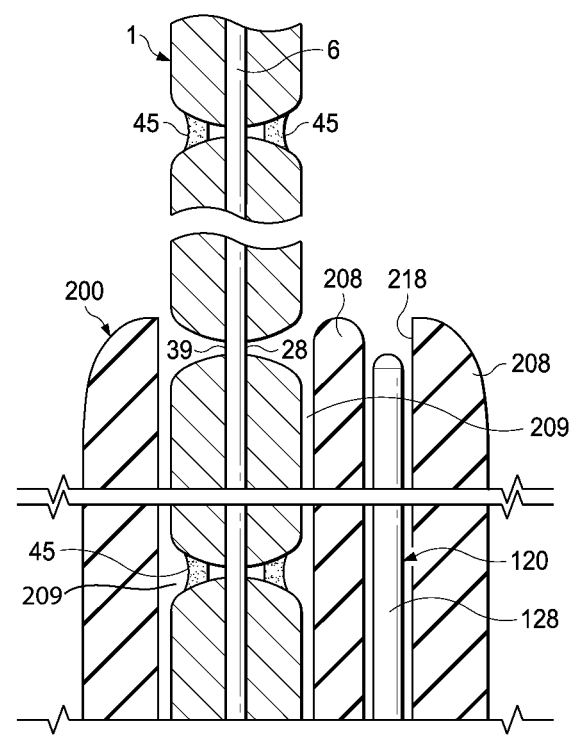

FIG. 13F depicts a section of a dual lumen introducer catheter 200 allowing for insertion of a conductive wire 128, which is a detachment element 120, into the additional lumen 218 similar to the manner in which a guide wire or embolic agent 1 is inserted in conventional catheters. The conductive wire 128 is connected to the power source in the operating field (not shown), and the conductive wire 6 of the embolic agent 1 in the lumen 209 is connected to the opposite electrode as seen in FIG. 13A. The embolic agent 1 was described in detail in FIG. 6J. It has tape 45 sealing the bare areas 39 as manufactured, and has been modified in this example by the operator who has removed the tape in one area, leaving a bare area 39 at the planned site of detachment 28. This introducer catheter 200 has advantage of simplicity of design and manufacture.

The series of embodiments in FIGS. 13A-F provide rapid electrolytic detachment of embolic agent 1 using 1 electrode as an integral part of the introducer catheter 200, or inserted into a second lumen 218 of a modified catheter 200. Many different types of the embolic agents which are not shown in FIGS. 13A-F but are described in this invention are compatible with these systems and can be used in variation. Other possible embodiments could include different configurations of wires or contacts so long as the main electrolytic process remains intact.

Figure 14A:
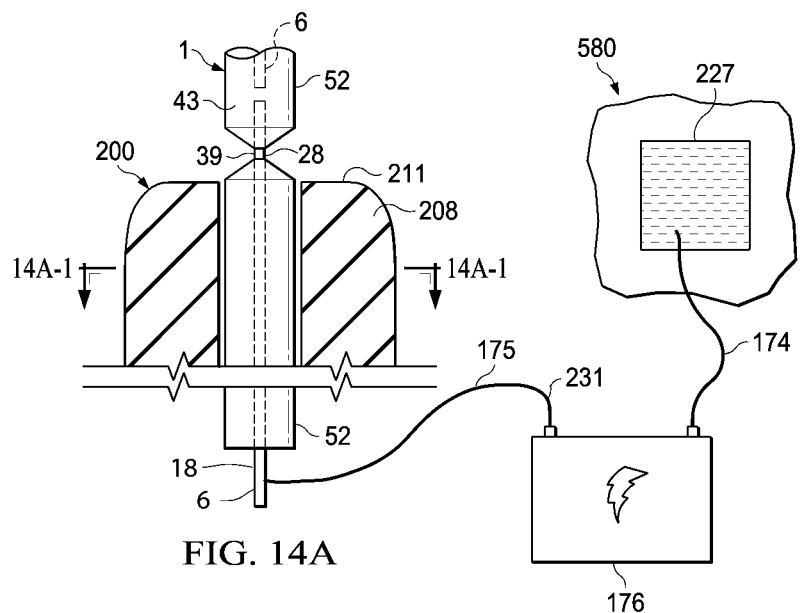
FIGS. 14A-B depict various embodiments of variations of use of electrical systems to provide detachment as described herein.
Figures 1, 14A:
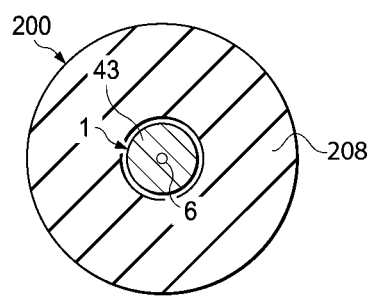
Figure 14B:
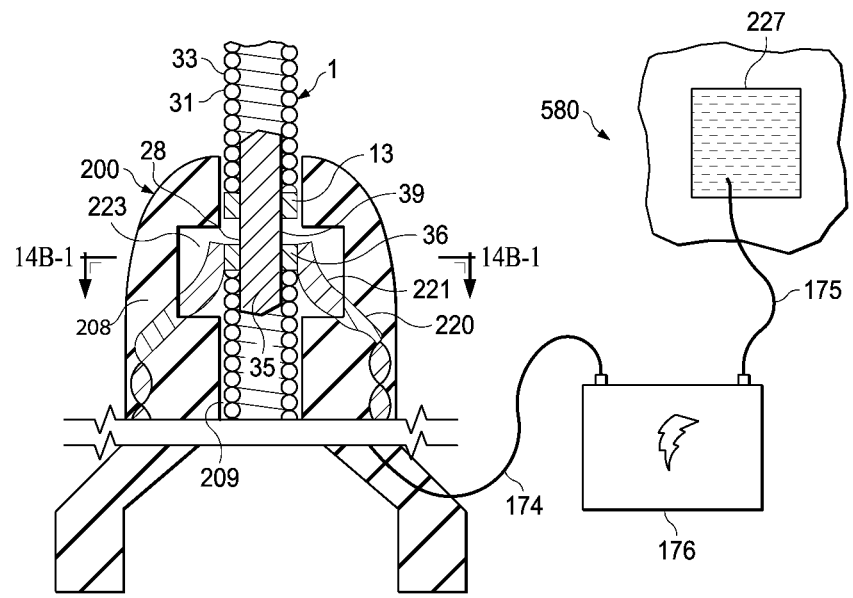
Figures 1, 14B:
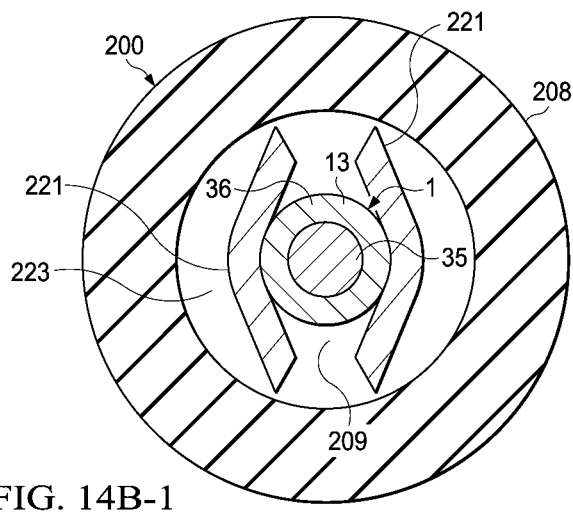

FIGS. 14A-B depict two variations of electrolytic detachment systems that apply one electrode to the skin of the body 580 and the other electrode to the conductive wire in the embolic agent 1. FIG. 14A is a longitudinal section and with FIG. 14A-1 cross section view of an introducer catheter 200 and embolic agent 1, with a schematic drawing of power source 176 and skin pad 227. This introducer catheter 200 does not have electrolytic components integrated within it and is essentially a conventional introducer catheter. The embolic agent 1 is described in detail in FIG. 6U. Other embolic agents in this invention would work well with this system as well. The wire 174 from the power source 176 is connected to a conductive skin pad 227 which is applied to the skin on the body 580. The second wire 175 of opposite polarity 231 from the power source 176 is connected to the wire 6 of the embolic agent 1 at the proximal end 18 in the operating field as described herein. The bare area 39 of the embolic agent 1 where there is no capsule 43 or coating is positioned at the tip 211 of the introducer catheter 200 that is within the target tissues (not shown). Not visualized here are bare areas beyond the tip 211 of the introducer catheter 200, already deployed in the target tissues which will not undergo electrolytic corrosion because the wire 6 in the embolic agent 1 is not continuous from segment 52 to segment 52, and are insulated by the dielectric capsule 43. This configuration of electrolytic wiring and its use in combination with the novel embolic agent 1 shown, as well as many other novel agents described herein, provide novel functionality including the potential for use with very long embolic agent 1 whose length is variable and determined by the operator intra-procedurally with detachment at an operator-determined location such as the tip 211 of the introducer catheter 200.

FIG. 14B and cross section view FIG. 14B-1 show an embodiment of electrolytic introducer catheter 200 with a different type of electrical contacts 221, which are pliable and flexible and have a bias towards the center of the lumen 209 which keeps them in constant contact with the embolic agent 1 even if its diameter is smaller than the lumen 209, or if its diameter shrinks due to corrosion as could occur in the event of a corrodible contact 36 on some variations of embolic agent 1. The contacts 221 are positioned in a circumferential lumen recess 223 may be leaflet-like, as depicted, or may be similar to very fine wire brushings. This depiction includes the embolic agent 1 described in FIG. 6S, which has non-corrodible contact 36 which also serves as a radio-opaque marker 13, and the helical wire 33 is has a coating 31. The connector 35 of the embolic agent 1 is corrodible and electrified via the contacts 36 of the embolic agent 1. Current flows through the wires 174 of the power source 176 to the introducer catheter 200 wires 220 which pass current to the contacts 221, passing current to the contact 36 of the embolic agent 1, then to the connector 35 which corrodes and detaches at the detachment point 28. The other electrode of the power source is connected by wire 175 to the skin pad 227 on the skin of the patient body 580. In variation, a needle may be used instead of a skin pad 227. These brushing type or leaflet type contacts 221 of the introducer catheter 200 could be used in any of the variations of introducer catheters 200 described in this invention that have contacts that directly contact the embolic agents. In one embodiment, the lumen recess 223 may not be circumferential, or may be unilateral, so long as constant contact with embolic agent 1 is maintained.

FIGS. 15A-B are depictions of two embodiments of venting catheters which may be helpful to prevent over-pressurization of an aneurysm cavity (also referred to as a "sac") when inserting a volume of material into it as occurs with this invention. If there are no pathways for egress of blood from the sac during embolization, pressure could build up unless venting occurs through the catheter, thereby preventing complications such as rupture during the procedure. The other benefit of the venting lumen is to allow injection of fluids such as flush or contrast material, and in some examples to allow passage of small transducer probes to measure pressures directly in the cavity. FIG. 15A shows an introducer catheter 200, which is a venting catheter because it has an additional lumen 218 as well as the lumen 209 used for other purposes described herein. Catheters with multiple lumens are already conventionally available, and in this example we describe a novel configuration and combination with other elements that are well suited for the objectives of this invention. The additional lumen 218 may be small because its purpose of venting fluid may still be served, and its shape in cross section may be irregular as shown in order to keep the outer diameter of the introducer catheter 200 as small as possible. This lumen 218 communicates with the side port 212, which will accept a syringe, tubing, or other conventional elements. This example embodiment also shows a pressure transducer 655 integrated within the introducer catheter 200 at its tip 211, to sense the pressure within the aneurysm 582 and provide feedback to prevent over-pressurization. The transducer 655 connects to a wire 220 in the wall 208 of the introducer catheter 200 which exits near the hub 201 and will connect to a monitor (not shown). FIG. 15B shows a variation whereby a transducer 655 is not integrated into the catheter, but may be inserted into the additional lumen 218 or removed at will. When inserted, it may be near the tip 211 of the introducer catheter 200 to sense the pressure in the aneurysm 582. Alternatively, the hub 201 corresponding to the additional lumen 218 may be connected to conventional tubing (not shown) which may be connected to an extracorporeal pressure transducer 655, whereby pressures may be measured in this other conventional manner. In this example embodiment, the additional lumen 218 is round in cross section to accommodate a transducer 655 on a wire 656, or conventional guide wires or other conventional accessories which are typically round in cross section. Also depicted are multiple side holes 217 in the wall 208 opening the additional lumen 218 to the local environment, in this case the aneurysm 582. These may help maintain communication of the lumen with the local environment since end-holes may sometimes occlude or become covered by tissue. As depicted in FIGS. 15A-B, these venting catheters may be used on combination with a second introducer catheter of smaller diameter (not shown) that may be inserted co-axially through the main lumen 209. This could include micro-catheters, which a name often is given to small diameter catheters that pass co-axially through other catheters. Alternatively, minor conventional modification of these venting catheters with a hemostatic valve (not shown) on the hub 201 corresponding to the main lumen 209 could convert them to an introducer sheath which could be used in a similar manner of permitting co-axial introduction of an additional introducer catheter (not shown).

FIG. 16A is an overhead view, with a side view of select elements, of an embolic delivery system 324 that pushes the embolic agent 1 using feeder rollers 325. The components of this system are all derived from conventionally available mechanical parts, which are arranged in the novel manner shown to provide the novel functions described in this invention. The simple nature of this figure will suffice to teach this system and method since the individual components are well known in the art of non-medical systems such as wire feeders and other automation devices. This embolic delivery system 324 includes a drive pulley 331, a drive shaft 332, a hand crank 335, a timing belt 328, a tensioner pulley 343, two timing pulleys 379, two feeder rollers 325, and pulley shafts 336 for each pulley. The timing belt 328 has teeth that mesh with corresponding teeth on the timing pulleys 379 to provide a more precise synchronization between the 2 feeder rollers 325. These components are affixed to a rigid housing 384 (depicted partially on the side view only) to maintain their proper positions and orientations. Other depicted components of the embolic delivery system 324 include a mounting hole 382, and a shaft sleeve 383. Also shown is an introducer catheter 200 and embolic agent 1, shown being advanced into an aneurysm 582.

The operator (not shown) may manually turn the hand crank 335, which is rigidly and non-movably attached to the drive shaft 332, which is also rigidly and non-movably attached to the drive pulley 331. The drive shaft 332 is attached to the housing (not shown) to allow rotational motion without substantial motion in any other dimension. Rotation of the hand crank 335 thus imparts rotational motion to the drive pulley 331 as shown by the dashed arrow, which then drives the timing belt 328 as shown by solid arrows. The timing belt 328 then drives the timing pulleys 379 in rotational motion (depicted by solid arrows). The timing pulleys 379 are rigidly and non-movably attached to their pulley shafts 336 and thus cause the pulley shafts 336 to rotate. They do not move in any other dimension because they are mounted to the wall 372 of the housing 384 as described above for the drive shaft 332. The feeder rollers 325 are rigidly and non-movably attached to the pulley shafts 336, so they will rotate along with the timing pulleys 379.

The feeder rollers 325 roughly resemble rigid discs of hard plastic or metal, however the outer rims may be composed of a softer material with a high coefficient of friction such as a synthetic rubber or urethane to provide traction against the embolic agent 1 which is sandwiched between the two of them. When pressed against the embolic agent 1 in the manner shown, their rotations will project the embolic agent 1 forward into the introducer catheter 200 as indicated by the straight solid arrow. Reversal of direction of drive shaft 332 rotation will cause the opposite motion of the embolic agent 1, withdrawing it from the introducer catheter 200.

The tensioner pulley 343 is also part of the drive train, however it is mounted differently to the housing in order to serve its functions of providing proper tension to the timing belt, as well as to re-direct the course of the timing belt 328 to perform needed functions such as to provide to more surface contact area of the timing belt 328 with the timing pulley 379 seen on the right. A shaft sleeve 383 is mounted slidably in the long mounting hole 382 in the housing (not shown), which in this example has a simple rectangular shape. When conventional means of fastening the shaft sleeve 383 to the housing (not shown) are freed, the shaft sleeve 383 may slide up or down within this mounting hole 382. When conventional fastening means are tightened, rigidly securing the shaft sleeve 383 to a specific location in the mounting hole 382, then it may not move in any dimension relative to the housing. The pulley shaft 336 may rotate freely within the shaft sleeve 383, but not move in any other dimension once the shaft sleeve 383 is rigidly secured within the mounting hole 382. The tensioner pulley 343 may be mounted on the pulley shaft 336 either rigidly and non-movably, or in a manner that allows rotational or translational motion on the pulley shaft 336, since tensioner pulley 343 is idle and passive and need only rotate freely in a spatial position that permits the application of appropriate tension on the timing belt 328 for smooth function and proper orientation.

An introducer catheter 200 is shown receiving the embolic agent 1 from the feeders in this example. In one embodiment, the embolic agent 1 could be fed directly into a specialized element that subsequently leads it to an introducer catheter 200, or it could be fed into a side port adaptor and/or introducer element 337, as described in FIGS. 16D-G before passing on to an introducer catheter 200. Also in variation, the feeder rollers 325, and part or all of the remaining elements of the embolic delivery system 324 in FIG. 16A could be enclosed in a housing that is fluid-tight and capable of being continuously flushed with an irrigant fluid as described elsewhere herein. In one embodiment, instead of the operator's hand, a conventional power motor, such as a small electrical motor, with gearing to produce desired rotational speed could be used to power the embolic delivery system 324. In variation, the tensioner pulley 343 mounting apparatus may be less rigidly secured within the mounting hole 382 during use, utilizing a spring mechanism or other conventional system that will provide the appropriate tension to the timing belt 328. The two feeder rollers 325 in FIG. 16A, and associated timing pulleys 379, are depicted as having their pulley shafts 336 mounted to the housing 384 with a fixed distance between them. In a variation, at least one of them would be slidably adjustable from side to side to give control over the force with which they compress the embolic agent 1 to provide the optimize the task of pushing it as described herein. A grooved variation of feeder roller 325 is seen in FIG. 16G.

FIG. 16B is a depiction of an embodiment of an embolic delivery system 324 similar to FIG. 16A, but with an increase of the surface contact between the embolic agent 1 and the elements that push it, through the use of 2 additional continuous timing belts which also function to frictionally push the embolic agent 1 and are called feeder belts 378. Many of its components are the same as in FIG. 16A, so for brevity they are not described here again. In this embodiment, there are six feeder pulleys 380 and two timing pulleys 379, which are attached to shafts 336 and a housing as described for the feeder rollers 325 and timing pulleys 379 in FIG. 16A. A first and second feeder belt 378 pass around the feeder pulleys 380 in each column. The feeder belts 378 are toothed on the inside to mesh with the toothed pulleys, but not on the outside where they interface with the embolic agent 1. As the bottom two timing pulleys 379 and associated feeder pulleys 380 are driven by the drive train as described in FIG. 16A, they in turn drive first and second feeder belts 378, which cause rotation of each feeder pulley 380. The outside of these first and second feeder belts 378 is a high friction material that contacts the embolic agent 1 over substantial length, and its friction against the embolic agent 1 is also aided by the tension of the feeder pulleys 380 at each point of pairing of the columns, where tension may be adjusted to provide optimum propulsion of the embolic agent 1 and smooth function of the system. Embolic agent is shown being advanced into introducer catheter 200.

All of the various embodiments described for FIG. 16A could likewise be applied to those shown in FIG. 16B. Additional embodiments for that shown in FIG. 16B could include alterations in the outside surface of the first and second feeder belts 378. The outside surface of these feeder belts 378 could have traction elements of many different types as described elsewhere in this invention, to provide traction against the embolic agent 1 that they contact. Likewise, the embolic agent 1 could employ the proper corresponding traction elements as described in this invention. The feeder belt 378 could also have a groove running longitudinally along the mid portion of its outer surface, somewhat like the groove 387 described on the feeder roller 325 in FIG. 16G.

FIG. 16C describes another variation of embolic delivery system 324 with a modification that may make it slightly simpler to manufacture, as well as to reduce the critical distance between the friction surface between embolic delivery system 324 elements and the embolic agent 1, which will be called the free distance 386. The free distance 386 is so named because the embolic agent 1 is "free" from constraint within the feeder elements, or the introducer catheter 200 or other component that receives the embolic agent 1 from the embolic delivery system 324. The embolic agent 1 within the free distance 386 is prone to buckling and errant feeding elsewhere than the introducer catheter 200, resulting in failure, particularly for the more flexible types of embolic agent 1. Reduction of the free distance 386 will therefore help prevent failures and allow use of more flexible embolic agents 1. In this figure, the free distance 386 is reduced by using very small diameters of the feeder pulleys 380 on their pulley shafts 336 closest to the introducer catheter 200. This allows the proximal end 206 of the introducer catheter 200, which in this example is mildly flared to accept the embolic agent 1, to be very close to the last point of contact with the feeder belt 378 that is pushing it forward.

The two large feeder pulleys 380 are driven by a drive train (not shown) and could be of the same conventional type as already described in FIGS. 16A-B, where a drive pulley drives a timing belt that drives the shaft that holds the two other elements so they rotate in unison. The two feeder pulleys 380 in FIG. 16C will rotate in the directions shown by the curved arrows, thus driving their respective feeder belts 378, which pass around six small feeder pulleys 380 that are mounted to the housing (not shown) by their pulley shafts 336 so as to permit free rotation around their longitudinal center-line without any other motion except possibly for some minimal translational motion to permit adjustment of the degree of pressure that they apply to each opposing shaft 333 and thus to the embolic agent 1 between them. The feeder belts 378 are toothed internally to mesh with the pulleys, but have a smooth outer surface to then push the embolic agent 1 forward into the introducer catheter 200 as shown by the straight arrow. As in other variations, the system may be operated in reverse to retract the embolic agent 1, and it may be powered manually or by a power motor.

FIGS. 16D-G include schematic views showing different embodiments of introducer elements 337 to facilitate the pushing of the embolic agent 1 without buckling or misfeeding in the free distance 386. FIG. 16D shows a hub 354 of the introducer element 337 where the hub 354 is not flared or fashioned with any specialized aspects; it is a simple tube shape with the thinnest possible wall that provides adequate support. Hub 354 may be made of metal or strong hard plastic to provide a thin wall. This may allow a very low free distance 386. FIG. 16E shows a flared or conical hub 354 that is round in cross section. It increases the capture width of embolic agent 1 as described above, but also increases free distance 386. FIG. 16F includes a side view as well as an overhead view showing a more complex hub 354 which includes 2 hoods 446 that extend over the flat planar surfaces of the feeder rollers 325 but do not touch them. These serve to permit both desirable functions of low free distance 386 since the non-hooded portions are narrow and can fit between the upper portions of the feeder rollers 325, and to also help to re-direct embolic agent 1 that has strayed out of the plane parallel to the flat plane of the feeder rollers 325. FIG. 16G shows a grooved feeding roller 325 depicting the groove 387 where the embolic agent 1 could be running. This serves to increase the surface area contact between the feeder roller 325 and the embolic agent 1, to provide better traction, and also to maintain the position of the embolic agent in the precisely desired spatial location in order to facilitate the pushing of it into the receiving lumen of the introducer element with less risk of it buckling or misfeeding due to angulation of its trajectory. Integration of feeding elements of the embolic delivery system and introducer elements 337 with other elements in the chain of delivery of embolic agent to tissue are further outlined in FIGS. 27A-B.

Figure 17:
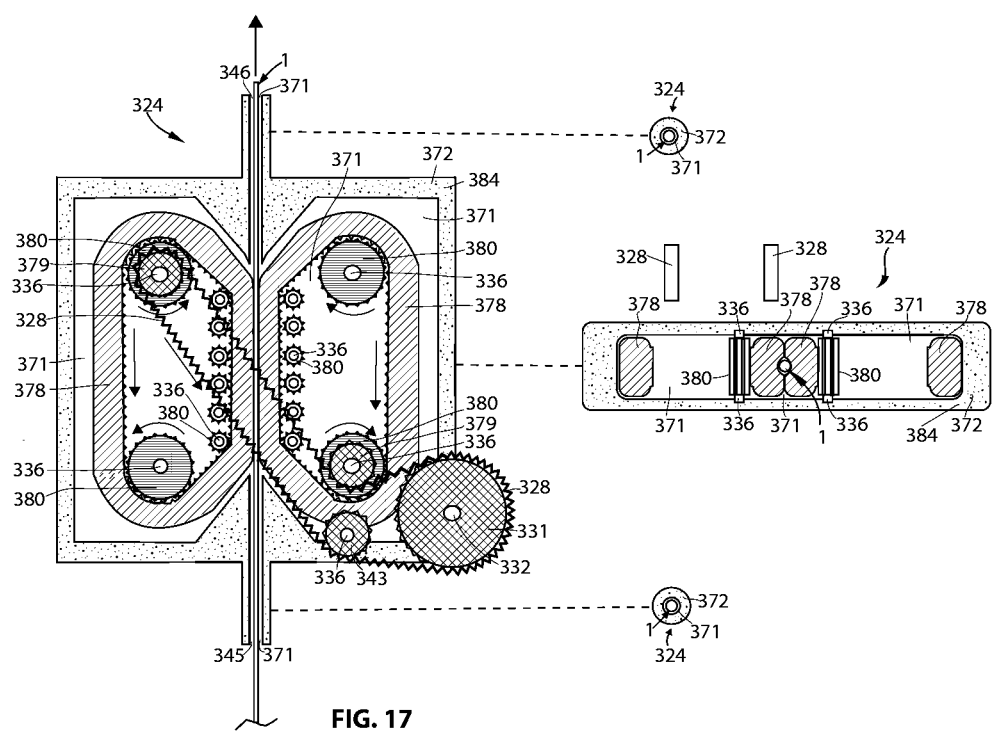

FIG. 17 depicts another novel embolic delivery system 324 for introduction of a wide variety of embolic agents 1 described herein. Some of the prominent features of this system include a long surface area of contact between the driving elements of the embolic delivery system 324 and the embolic agent 1 enabling substantial friction between them to facilitate the purpose, as well as a continually constraining channel for the passage of the embolic agent 1 through the embolic delivery system 324 to prevent buckling or kinking of the embolic agent 1 at any point before it is deployed within the target tissues beyond the tip of the introducer catheter (not shown).

The depicted embolic delivery system 324 includes a housing 384 composed of a rigid wall 372 containing a hollow lumen 371 with a complex architecture as shown. The lumen 371 is continuous throughout the system such that a fluid injected at inlet port 345 would eventually flow out of the outlet port 346, and could bathe the components at any location in the lumen 371. The wall 372 could be any rigid material, most likely plastic or polymer. In this housing are mounted other components that drive the embolic agent 1 upward as indicated by dashed arrow. These include a feeder belt 378 and feeder pulleys 380. Also present, outside the housing 384, are connected drive train components including timing pulleys 379, tensioner pulley 343, timing belt 328, pulley shafts 336, drive pulley 331, and drive shaft 332. These drive and feeder elements are conventionally available. The drive shaft 332 is rotated by an external force, which could be manually driven, such as via a hand crank or motor driven as described herein, using conventional mechanical linkages and gearing as needed. The drive pulley 331 is fixed rigidly to the drive shaft 332, thus rotating with the drive shaft 332, and causing the timing belt 328 to move as shown. The timing belt 328 drives the timing pulleys 379 as shown, with said pulleys rigidly fixed to the pulley shafts 336 which are also rigidly fixed to the feeder pulleys 380, which are thus also driven as shown in the top drawing. The pulley shafts 336 of the timing pulleys 379 pass through substantially water-tight holes in the housing 384 to connect to and drive the internal feeder pulleys 380. The drive shaft 332 and pulley shaft 336 of the tensioner pulley 343 do not need to fully penetrate the wall 372 of the housing 384. The tensioner pulley 343 serves to route the timing belt 328 as desired and to maintain proper tension on the timing belt 328. The feeder pulleys 380 then drive the feeder belt 378, which is pressed against the embolic agent 1 by the array of smaller feeder pulleys 380, and feeds it in the direction as indicated by dashed arrow.

This described embolic delivery system 324 may be connected to an introducer catheter (not shown) directly or indirectly using means described elsewhere herein, with transfer of embolic agent from depicted embolic delivery system 324 to remaining portions of invention as depicted elsewhere herein. The introducer catheter or intermediate element may be attached to the outlet port 346 using conventional attachment means. The embolic agent 1 enters the embolic delivery system 324 through the inlet port 345, where a side port adaptor (not shown) could also be used to allow passage of embolic agent 1 as well as infusion of flush solution. In one embodiment, the device may be more open, such that the wall 372 does not enclose the lumen 371. In this system, fluid flush would not be circulated in the depicted system, although it would usually be used for the side port adaptors and introducer catheters as described elsewhere herein. In another embodiment, many elements of the drive train that are herein depicted outside of the housing 384 could be located inside the housing, with protrusion of only the drive shaft.

FIGS. 18A-H depict different embodiments of traction elements 270 that may be applied along the inside and/or outside walls of embolic agents 1 or modified pusher elements 90, differing from conventional pusher elements as described herein. These traction elements 270 will provide extra friction or mechanical traction when desired for the movement of the embolic agent 1 in the desired direction by another element such as a feeder roller in an embolic delivery system or a pusher element 90. In brief summation, conventional pusher elements typically push an embolic agent through an introducer catheter whose lumen diameter is very similar to the outer diameters of the embolic agent and pusher element, like one piston pushing another through a tube. The devices depicted in FIGS. 18A-F depict novel attributes termed herein as traction elements 270 which may provide at least two novel functions, including the ability to effect a net forward advancement of the embolic agent 1 by imparting a to-and-fro motion on the pusher element 90 (i.e., conversion of bidirectional motion of the pusher element 90 into unidirectional motion of the embolic agent 1 due to a directional bias of the traction elements) and the retraction of the embolic agent 1 effected by retraction of the pusher element 90 without a rigid attachment between the two elements. The quality of directional bias is present in many but not all of the traction elements 270 described herein. Even when partial motion of the embolic agent 1 in the undesired direction occurs, the overall net effect will be of forward motion of embolic agent 1 despite to-and-fro motion of the pusher element 90. In other contemplated embodiments, the pusher element 90 and embolic agent 1 are actually mechanically locked together when constrained within the introducer catheter 200 however using a different mechanism than as previously described for FIGS. 1D-1L and 8A-11C. Another function of the traction elements 270 in some variations may be to simply increase traction between pusher element 90 and embolic agent 1 in systems where they exist side-by-side within the introducer catheter 200 instead of simply end-to-end as described in FIG. 1D.

FIGS. 18A-F depict various embolic agents 1, most with traction elements 270 as shown. Depicted embolic agents 1 are flexible, composed of polymer, but could be composed of any predominantly non-metallic flexible substance such as those listed elsewhere herein. A pusher element 90 of appropriate length and diameter that would be inserted into the lumen of the embolic agent 1 would encounter the traction elements 270, causing traction between the two components so that movement of one component may move the other. Such traction may be preferentially unidirectional, or bidirectional, depending on the nature of the traction elements 270 as described in more detail below. Unidirectional traction could have the effect of net forward motion of the embolic agent 1 despite the pusher element 90 having a back-and-forth motion. FIG. 18A depicts an embolic agent 1, hollow, round in cross section, with a lumen 7, a wall 2, and with a full wall 2 thickness longitudinal slit 17 running the entire length of the embolic agent 1. It has smooth inner and outer surfaces with a proximal end 17, a middle 20, and a distal end 19. FIG. 18B depicts the embolic agent 1, opened up along the longitudinal slit 17 to expose the inner surface, which can be seen to be smooth. Such a splaying open defies the memory of the embolic agent 1, which would appear as FIG. 18A in its resting state, however is opened in FIG. 18B for purposes of description. Traction element 270 in the form of an adhesive compound 50 is applied to the surface. This compound could be of many types of glues or cements, but would preferably be biocompatible, not having harmful effects if small amounts remained on the embolic agent 1 after deployment, and also would provide only a weak bond that is sufficient to provide the necessary traction, but weak enough to permit easy separation of the embolic agent 1 from the pusher element 90 when desired. This would allow for bidirectional traction. Similarly, FIGS. 18C-F are similar views of similar embolic agents 1 except with traction elements 270 integrated along their internal surface. FIG. 18C depicts traction elements 270 of roughness 271 distributed along the entire inner surface. This roughness could result from scoring of the surface with a sharp blade, or special cutting tool that produces a scoring pattern, or from molding of the surface during manufacture. Chemical treatment could also potentially result in a rough texture. Such roughness may cause increased traction in a bidirectional manner upon motion of an appropriate pusher element 90, such as one with smooth outer surface as seen in FIG. 18I. If the pusher element 90 had directional traction elements 270 on its outer surface as described below for FIG. 18M, the traction of the two components when used together could now be preferentially unidirectional.

FIG. 18D depicts an embolic agent 1 with traction elements 270 composed of small ridges 272. These mildly elevated ridges 272 are shown circumferentially around the inner surface, although in variation they could be less than circumferential. They are shown as symmetrical along their long axis, so as to provide bi-directional traction when used in conjunction with a non-directional pusher element 90 such as that seen in FIG. 18I. Preferentially unidirectional traction could occur if used with a pusher element 90 with unidirectional traction elements 270 such as depicted in FIG. 18M. In a variation, these ridges 272 may be asymmetrical along the long axis of the embolic agent 1 so as to provide unidirectional traction even when used with a bidirectional pusher element 90 such as in FIG. 18I. Ridges 272 may be formed by the cutting away of material around them during manufacture, or by the building up of the ridges by application of material that is welded or cemented to the surface.

FIG. 18E depicts an embolic agent 1 with traction elements 270 in the form of barbs 273 directed downward, applied to the inner surface. Barbs 273 may be applied to the surface with cement, or created by extraction of material from the wall of the catheter around them. They provide preferential unidirectional traction when used with any type of pusher element 90. FIG. 18F depicts an embolic agent 1 with the traction elements 270 scales 274, similar to fish scales, directed downward on the surface. These will also exert preferentially unilateral traction. FIG. 18G-H are contemplated embodiments showing variation of scales 274, with a circumferential scale 274 pattern around the lumen 7 in FIG. 18G, and non-circumferential scales 274 around the lumen 7 in FIG. 18H.

FIGS. 18I-M depict variations of surface properties and traction elements 270 on the surfaces of various examples of pusher elements 90. FIG. 18I depicts a smooth surface on a standard pusher element 90 with added traction elements 270 of adhesive 50. It has a proximal end 91, a middle 93, and a distal end 92. FIGS. 18J-M depict pusher elements 90 with added traction elements 270, and a transition 95 between surface with transition elements 270 and surface with no traction elements 270. The traction elements include roughness 271 in FIG. 18J, ridges 272 in FIG. 18K, barbs 273 in FIG. 18L, and scales 274 in FIG. 18M, where they are depicted in two examples of configurations, including circumferential and non-circumferential. The direction of the directional traction elements 270 in FIGS. 18L-M are reversed from the direction of the traction elements 270 on the embolic agents 1 in FIGS. 18E-H because the usual intention in practice would be to advance the embolic agent 1 upon advancement of the pusher element 90.

Any of the pusher elements 90 depicted in FIGS. 18I-M could be used in combination with any of the embolic agents 1 in FIGS. 18A-18F, for different effects. Variations in the devices in FIGS. 18A-M could include many factors including longer or shorter lengths than those shown (in practice the pusher elements 90 would likely be considerably longer), absence of a transition 95 with traction elements 270 along entire length, and other possible types of irregularities or non-smooth textures to provide traction, both in a unidirectional or bi-directional manner. Any of the circumferential traction elements 270 could be non-circumferential. The embolic agents 1 may not contain a longitudinal slit 17 or slit 17 may be incomplete or spiral in configuration. Instead of ridges added to the surface, depressions in the surface could be cut away to provide traction and a similar surface effect. In variations, the described traction elements 270 may occupy only portions of the inner surface. The traction elements 270 may also be applied to the outer surface of the embolic agents 1, alone or in combination with application to inner surface. The method of using embolic agents 1 or pusher elements 90 with traction elements is described in more detail in discussion of embolic delivery systems.

FIGS. 19A-E show other types of traction elements 270, which differ mainly from those in FIGS. 18A-18M in that the pusher element 90 and embolic agent 1 are adjacent within the lumen 209 of the introducer catheter 200 during the method of use to be described. In these figures, the introducer catheter 200 is seen to have a wall 208 and lumen 209 as in other depictions. In the lumen 209 are an embolic agent 1, and a pusher element 90, side by side.

In FIG. 19A, a simple configuration is depicted where the introducer catheter 200 and pusher element 90 are both round in cross-section, as in usual conventional elements known commonly in the art. This provides little traction between them since there is little surface area contact, so movement of one of them may not effect significant motion of the other. FIG. 19B depicts a configuration for embolic agent 1 and pusher element 90 whereby there is an increase in the surface area of contact between the two elements, thus leading to more traction so that motion of the pusher element 90 along its longitudinal axis is more likely to result in similar motion of the embolic agent 1. FIGS. 19C, 19D, and 19E show different configurations of traction elements to increase friction between them while maintaining a round cross sectional shape for the two of them together as shown. The traction between the elements depends on frictional forces since the depicted configurations do not lead to a mechanical locking together of them with respect to motion along the longitudinal axis. The traction elements do not need to deform to prevent sliding of one element against the other while constrained within the introducer 200. The function of the traction elements 270 seen in FIGS. 19A-E can be many fold and will also be described in descriptions of embolic delivery systems herein. One way to make use of these elements could be for the operator to pinch the embolic agent 1 and pusher element 90 together with his fingers outside of the proximal hub of the introducer catheter 200, and then advance them as a unit. This could be useful if the embolic agent 1 were so flexible (to facilitate nesting within the target tissues) that it is difficult to advance through the catheter alone. Once the pusher element 90 reached the target tissues, the embolic agent 1 could be held stationary while the pusher element 90 was withdrawn until the tip was near the proximal hub of the introducer catheter 200, when the cycle could be repeated and the 2 elements could be pinched together and advanced as a unit again. This could result in a rapid administration of a large amount, or great length, of embolic agent 1 as the pusher element 90 could be advanced and withdrawn repeatedly fairly rapidly since it may never completely be retracted out of the catheter. This method could also be automated, whereby a machine performs the same simple manipulations just described for the operator's hands. This is shown in more detail in discussion of an embolic delivery system elsewhere herein.

FIGS. 20A-20H depict traction elements 270 having additional mechanical locking functionality beyond simple friction. These traction elements 270 prevent sliding of the embolic agent 1 along the pusher element 90 while constrained within the catheter, unless there is deformation of one of the elements. Thus prevention of sliding is not due to friction alone as was described for FIGS. 19A-E. There configurations enable 1:1 forward (advancement) or backward (retraction) motion of the embolic agent 1 by manipulation of the pusher element 90 with little or no sliding between them, however they do not permit unidirectional bias of motion, so a bidirectional motion of the pusher element 90 cannot be used to effect a net forward motion of the embolic agent 1, differing from FIGS. 19A-E. FIG. 20A depicts a locking traction element 270. The embolic agent 1 is engaged with the pusher element 90 when inside the lumen of an introducer catheter 200 (not shown). Both embolic agent 1 and pusher element 90 have traction elements 270 with depressions 280 and protuberances 279 that mate together. Both elements are roughly round in cross-section, whereas in FIG. 20B the cross-sectional shape of the embolic agent 1 and pusher element 90 are both closed incomplete circles so that when mated, they are together round in cross section, to better conform to the lumen 209 of the introducer catheter 200. In FIG. 20C, as the elements of FIG. 20B are pushed out of the tip 211 of the introducer catheter 200, as indicated by the arrow, they are no longer constrained, and may separate.

Two other types of locking mechanical traction element 270 configurations are depicted in FIGS. 20D-F and FIG. 20G-H. FIGS. 20D-E depict traction elements 270 comprised of pins 277 on the pusher element 90 and holes 278 on the embolic agent 1 that fit together when they are constrained together inside the catheter lumen. FIGS. 20E-H depict an embolic agent 1 and pusher element 90 that have traction elements 270 comprised of depressions 280 and protuberances 279 that mate as seen in FIG. 20G. In FIG. 20H, it can be seen that the overall cross-sectional shape of the conglomerate is roughly round, thus fitting into a round lumen of an introducer catheter 200. These traction elements 270 may have advantage in manufacturing, as the depressions 280 and protuberances 279 could be created by a rotating round tool or file that is applied to the embolic agent 1 and pusher element 90.

FIG. 21A disclose one embodiment where the pusher element 90 may be of a simpler manufacture than a similar variation shown in FIG. 20D-E. In FIG. 21A, the embolic agent 1 has many traction elements 270 in the form of pins 277 along the otherwise flat face of its length in two columns as shown. As in FIG. 20D, embolic agent 1 cross sectional shape is a closed incomplete circle (where the pins 277 are not located). The pusher element 90, unlike FIG. 20D, does not have corresponding holes, and instead is a deformable member with enough tensile strength to resist substantial stretching or breaking when pulled with enough force to cause motion of the embolic agent 1. It is also semi-rigid as in other described pusher elements 90 described herein. Its traction with the embolic agent 1 is derived from the tendency for the pins 277 of the embolic agent 1 to press into, and deform, the mating surface of the pusher element 90 when both are constrained inside the introducer catheter 200. The cross-sectional view on top right depicts the embolic element 1 and the pusher elements 90 in their natural state outside of an introducer catheter 200. Note that the pusher element 90 in cross section is basically a rectangle with rounded corners as shown, although in variation it may not have rounded corners, or may be a closed incomplete circle as in FIG. 20D. FIG. 21A also shows the deformed configuration of the pusher element 90 in the cross sectional view on the lower right, where it is constrained inside the lumen 209 of the introducer catheter 200 with the embolic agent 1. The depressions 280 in the deformable pusher element 90 caused by the pins 277 of the embolic agent 1 serve to provide traction between the embolic agent 1 and the pusher element 90 so that pushing or pulling the pusher element 90 will cause corresponding motion of the embolic agent 1. In variation, the pins 277 could be on the pusher element 90, while the embolic agent 1 could be the deformable agent without pins 277 or corresponding holes. This may offer advantage in some situations where it is more desirable for purposes of manufacture, or purposes of functional properties, to make the embolic agent 1 more deformable, and place the more rigid traction elements 270 such as the pins 277 on the pusher element 90.

FIG. 21B is a longitudinal and cross sectional view of another variation where the traction elements 270 consist of barbs 273 on the embolic agent 1, and the deformable pusher element 90 has traction against the embolic agent 1 when constrained in the introducer catheter 200 as shown. They are shown being pushed or pulled out of the lumen 209 of the introducer catheter 200. The pusher element 90 could be composed of different materials, including soft plastic or polymer, or a woven strip as will be described FIG. 21C. In variation, the traction elements 270 could be scales 274 or one of the many other traction elements 270 described herein. Also, the traction elements 270 could be on the pusher element 90 instead of the embolic agent 1, and the deformable agent would be the embolic agent 1.

FIG. 21C is a perspective view of a small magnified portion of a woven strip serving as a pusher element 90 as seen more grossly in FIG. 21A or FIG. 21B. The micro filaments 106 are woven, as shown in FIG. 21C, into a strip that can be extremely long (shown here truncated at the top and bottom). The longitudinal fibers give the strip a high tensile strength, and the horizontal weave gives it a definable shape, as well as providing a means for traction elements 270 such as barbs 273 on the embolic agent 1 (not shown) to catch on and provide traction, since they would typically hook over these horizontal fibers because they would be oriented as in FIG. 21B, and the strip would be moving along its longitudinal axis as it is pulled or pushed. This pusher element 90 could be of many different shapes in its cross section, from a simple round shape, to a rounded rectangle, or other shape that suited the purpose of the specific embolic delivery system 324 or introducer catheter 200.

FIG. 21D depicts a system which provides traction of pusher element 90 against embolic agent 1 while permitting a circular cross-sectional shape of embolic agent 1 for ease of manufacture and passage through conventional elements. Pusher element 90 and introducer catheter 200 with an embolic agent 1 seen in perspective view, embolic agent 1 and pusher element 90 outside of a catheter and constrained within the lumen 209 of an introducer catheter 200, which has a wall 208. In the depicted embodiment, the embolic agent 1 is a helical wire 33 with central wire 6 as described herein. The pusher element 90 is a solid member composed of material, such as solid polymer or woven substance, as depicted in FIG. 21C, which is flexible to lateral bending, but has substantial tensile strength like a typical household string. When constrained in the introducer catheter 200, it deforms somewhat to increase surface contact area with the embolic agent 1 and corresponding ridges 272 of the woven wire, which are serving also as traction elements 270. Pushing or pulling the pusher element 90 will therefore move the embolic agent 1 correspondingly. This type of system may be useful in a variation of the embolic delivery system 324 such as seen in FIGS. 22B and 22G. It has the feature of stabilization of the embolic agent 1 to lateral movement while in the embolic delivery system 324, because the diameter of the embolic agent 1 is greater than the width of the lumen 209 containing the pusher element 90, so the non-compressible embolic agent 1 cannot pass into the smaller portion of the lumen 209 once the pusher element 90 has been stripped away, in a system similar to FIG. 22B or 22G where the embolic agent 1 passes into a smaller lumen which is a circle in cross-section and only slightly larger than the diameter of the embolic agent 1.

FIG. 21E is a depiction of another variation of traction elements 270 used with embolic agent 1 and pusher element 90, where both are resistant to axial compression and therefore maintain circular configuration in cross section even when pushed together side-by-side as when constrained within the lumen 209 of an introducer catheter 200 (seen in cross section view only) which has a wall 208 that resists axial stretching or change in shape. Both have scales 274, which are oriented in opposite directions as shown, to provide traction. In variation, many other types of traction elements 270, as described herein, may be used with similar effect.

FIG. 21F depicts a manufacturing element 630 that may assist in the manufacture of the type of embolic agent 1 shown in FIG. 21D. It consists of a very rigid press 631 through which the embolic agent 1 and the pusher element 90 may be positioned as shown. Embolic agent 1 has traction elements 270 consisting of ridges 272. External force in direction indicated by large arrows may be applied, which allows the press to be compacted via the press joints 632 where the two components are slidably connected. This results in compression of the pusher element 90 against the embolic agent 1 with great force, causing them to bond together in a detachable manner that permits their function as described in this invention. If the mechanical attachment caused by the impression and deformity of the deformable pusher element against the ridges 272 on the embolic agent 1 did not provide sufficient bonding force, then it could be aided with addition of a sticky substance of adhesive so long as bonding was not so excessive as to prohibit dissociation during usage.

FIGS. 22A-G depict a system and variations that have a novel method of causing advancement of the embolic agent 1 by pulling a very flexible pusher element 90 which is adjacent to the embolic agent 1 and exerts force on it using traction elements 270, and which is then stripped away from embolic agent 1 which continues to be projected forward. These represent another novel system and method for delivery of embolic agent 1 into abnormal tissues. FIG. 22A is an upper perspective view of examples of pusher element 90, traction elements 270, and embolic agent 1. The traction elements 270 in this example are convex on embolic agent 1 and concave on pusher element 90 versions of the same pattern, where the contour is a series of repeating depressions 280 and protuberances 279 that can nest together without increasing the overall diameter of the larger member, in this case the embolic agent 1. The pusher element 90 is inserted into the concavity of the embolic agent 1, where it nests, with traction elements 270 on both members engaged. When nested, the overall configuration in cross-section is roughly circular, as seen later in FIG. 22B. It is evident in FIG. 22B that a pulling or pushing motion of the pusher element 90 would cause a similar motion of the embolic agent 1, especially if they were both in the restrictive lumen 371 of embolic delivery system 324. FIG. 22B depicts views of the embolic agent 1 and pusher element 90 and traction elements 270 of FIG. 22A, shown being used with an embolic delivery system 324. The embolic delivery system 324 has a lumen 371 allowing the passage of an embolic agent 1 from its proximal end 385, through the middle 388, and exiting the distal end 389, as shown by the arrow. The embolic delivery system 324 has a rigid wall 372 for support and to contain fluids and provide a fluid-tight seal where needed. The pusher element 90 is fed through a bifurcation 375 of the lumen 371 and exits the embolic delivery system 324 through a side port 347 as shown by the dotted arrow. The embolic agent 1 enters the embolic delivery system 324 through the inlet port 345 and exits through its distal end 389, where it may then pass into introducer catheter (not shown) or other intermediate elements as described herein. Many variations of traction elements 270 are possible with similar effects. The driving force for the advancement of the embolic agent 1 comes from the pusher element 90, which may be pulled by the operator's hands, or by more components of the embolic delivery system 324, as shown in this depiction, where the pusher element 90 is being pulled by a spool 364 with a hand crank 335, the latter two elements being depicted in a drawing of different scale in FIG. 22C where the spool 364 and hand crank 335 are shown in overhead and side views, and the pusher element 90 is also seen rolled up on the spool 364. In FIGS. 22B and 22C, the operator turns the hand crank 335, which is attached to the spool 364, and thereby the spool turns, taking up the pusher element 90, and thereby pulling it from the from embolic delivery device 324, thereby causing the described motions of the pusher element 90 and embolic agent 1. The spool 364 permits rapid deployment, and containment of the length of used pusher element 90, which, for treatment of a large abnormal cavity, could possibly be several hundred feet in length. These bulky components such as the spool 364 or operator's hands, providing the driving force for the pusher element 90 would be outside of the body that contains the abnormal cavity to be treated, while the distal end of the introducer catheter (not shown) is inside the body. Thus the small diameter elements are inside the body, while the larger elements do not require insertion through body tissues. Once the desired length of embolic agent 1 has been delivered, or determined, methods for completion including severing of the embolic agent 1, or placement of short segments, or pushing of the last portion with a conventional pusher element 90 that is simply pushed by the operators hand and thrusts the trailing end of the embolic agent 1 forward, may be used, and these techniques are described in more detail elsewhere herein for different embodiments of the invention.

FIG. 22D depicts a minor variation where the side port 347 has an obtuse angle of departure from the embolic delivery system 324. This might serve to reduce friction and binding forces of the pusher element 90 against the lumen 371 of the embolic delivery system 324, facilitating the intended function of the system, and reducing risk of breakage of the pusher element 90, and to enable a reduction in rigidity or thickness of the proximal end 385 of the embolic delivery system 324 since the force of retraction of the pusher element 90 will not be directed proximally, which potentially bend the embolic delivery system 324 if the elements were not rigid enough to prevent it. The force required to pull the pusher element 90 can be provided by similar means as in FIG. 22B. The embodiments depicted in FIGS. 22A-G have another advantage of permitting the pusher element 90 to be highly flexible, without need for columnar strength, since it is being used as a pulling agent. It will therefore need to have adequate flexibility to round bends and tensile strength to withstand pulling forces.

FIG. 22E shows two variations of embolic delivery systems 324 to demonstrate possible differences in proportions of devices described in FIGS. 22B, 22D, and 22G. In the example on bottom, the distance from hub 354 to bifurcation 375 is quite short, so that only the narrower diameter portion of the embolic delivery system 324 would be inserted into the body thereby reducing the diameter of the opening to a minimum, and serving in a manner similar to an introducer catheter as described herein. In the top example, the distance from hub 354 to bifurcation 375 could be much longer, so that traction on the embolic agent 1 occurs close to the distal end 389 of the embolic delivery system 324, ensuring forward motion of even very flexible and soft embolic agents 1. Such an embodiment might be used in conjunction with a small diameter introducer catheter as described elsewhere, or may be used in a manner similar to an introducer catheter, i.e. partially inserted into the body.

In a variation of the foregoing, it is easy to envision the use of many different types of traction elements 270, embolic agents 1, or pusher elements 90 than depicted, with similar effect. By way of some examples, the embolic agent 1 and pusher element 90 may be shaped very differently; they could be square or rectangular in cross section, and they could employ any type of traction element described herein. They could use an adhesive bond or electrostatic attraction instead of the other traction elements. There could be very small microfilament ties or bands connecting the two elements, possibly wrapping around the elements, said bands being easily broken when they are pulled apart. There could be stitching of very fine filament that is bound tightly to the pusher element 90 being stripped away, but is loosely stitched around the embolic agent 1 such that gentle traction when desired will unravel the stitching and dis-associate the two elements, leaving the small fibers attached to the pusher element 90 which is not implanted. The embolic agent 1 could be nested inside the pusher element 90 instead of the opposite as depicted in FIG. 22A. Many other variations are possible that would still be in keeping with the novel aspects of this invention.

FIGS. 22F-G depict an embodiment as described and shown in FIGS. 22A-E. FIG. 22F shows an embolic agent 1 that includes traction elements 270 composed of ridges 272, which could also be described as an alternating series of protuberances 279 and depressions 280 in a pattern often seen in conventional helical wires. The pusher element 90 is seen wrapped around the embolic agent 1 with a longitudinal slit 96 that makes the cross-sectional configuration an incomplete circle (also shown in FIG. 22G.) The outside surface of the pusher element 90 is smooth, but the inner surface has traction elements 270 corresponding to those of the embolic agent 1 to allow a mating of the elements, and also consisting of alternating series of protuberances 279 and depressions 280. Also shown in FIG. 22F, the pusher element 90 is seen being stripped away from the embolic agent 1 by a force directed upward and to the right, depicted by the arrow. When this leading edge of the pusher element 90 is pulled by the operator or other means, it can forcibly unwrap from around the embolic agent 1 that it enveloped, and in doing so, the traction elements 270 will exert an upward force on the embolic agent 1 so long as the embolic agent 1 is forcibly maintained in the same orientation by an external element such as the lumen 371 of the embolic delivery system 324 seen in FIG. 22G.

In FIG. 22G, an embodiment of the embolic delivery system is shown. Embolic delivery system 324 with a wall 372, lumens 371, a bifurcation 375 of the lumens 371, a side port 347, and an inlet port 345 is shown. The embolic agent 1 and pusher element 90 of FIG. 22F are seen passing into the inlet port 345 of the embolic delivery system 324, with the pusher element 90 enveloping the embolic agent 1. In this example embodiment, the embolic agent 1 is composed of a series of shorter segments 52 that have a proximal end 18 that abuts the distal end 19 of the adjacent segment. Before entering the embolic delivery system 324, these segments are maintained in proper position by the continuous enveloping pusher element 90. When these elements reach the bifurcation 375 of the lumen 371 into two lumens 371, one of which continues straight on and provides a channel for the movement of the embolic agent 1 to the target tissues (not shown), and the other lumen 371 bifurcating at an angle and providing passage for the pusher element 90. The embolic agent 1 is maintained within the larger of the two lumens 371 because it is too large to fit into the smaller one, and because its direction of motion in a straight line is maintained by its inability to prolapse into the smaller lumen 371 during normal forces of normal operation, while the pusher element 90 unwraps from around the embolic agent 1, crumples due to its flexibility and poorly formed shape when not containing the cylindrical embolic agent 1, and is pulled by the operator or other instrument out through the side port 347. The pusher element 90 is depicted as a dashed line as it passes around the embolic agent 1 near the bifurcation 375 to indicate that is it out of the plane of the 2-dimensional longitudinal section in this figure. The pusher element 90 will provide an upward force on the embolic agent 1, driving it forward. Each segment 52 of embolic agent 1 will push the previous one forward, since they are all constrained in a lumen 371 that is only slightly larger than the diameter of the embolic agent 1. The use of segmented embolic agent 1 is optional, and instead a very long single element may be used as described elsewhere herein. As depicted, this system performs the novel function of administering numerous short or medium length embolic agents 1 in rapid succession.

Different methods of manufacture of the pusher element 90 are possible. It could be injection molded, made of polymer, to its desired shape. It could be made like a conventional smooth-walled tube, and then the slit 96 added to the side, then the traction elements 270 cut or heat-molded on. It could be made from a heat-shrinkable tubing, possibly reinforced with longitudinal fiber elements of high tensile strength, into which the embolic agent 1 is inserted, then heat applied, and the pusher element conforms to the contour of the embolic agent 1 then the longitudinal slit 96 applied by a cut.

Many variations of the system in FIGS. 22F-G are possible. Almost any type of traction element 270 could be used instead of those depicted. The surfaces of the embolic agent 1 and pusher element 90 could all be smooth, and the necessary traction supplied by frictional forces, or the application of a small amount of weak adhesive that can be overcome when necessary for the elements to separate. Different shapes of embolic could be issued instead of cylindrical; it could be dumbbell shaped, or of many different types of shape.

FIG. 22H depicts another variation of embolic delivery system 324 variation of the previous two figures, employing the use of embolic agent 1 and pusher element 90 that employs traction elements 270 in a manner that causes forward propulsion of the embolic agent 1 by using pulling forces instead of simply pushing forces, thus taking advantage of the advantages of the effects of pulling flexible objects over pushing them. This is novel since current mechanisms for advancing embolic agents in conventional systems use pushing forces only. The embolic delivery system 324 includes a housing 384 with a wall 372 and a hollow lumen 371 that is continuous throughout and allows passage of other elements as well as infusion of fluids. It also has a side-port 347 for conventional delivery of infusion fluids, an inlet port 345 for entrance of the embolic agent 1, and an outlet port 346 for exit of the embolic agent 1. It also has another inlet port 345 for entrance of the pusher element 90, and another outlet port 346 for the exit of the pusher element 90. Embolic agent 1 and pusher element 90 are intended to usually travel in the direction shown by the arrows, although retraction in the opposite direction may occur sometimes for proper position of the embolic in the target tissues (not shown). All of the inlet ports 345, and the outlet port 346 for the pusher element 90 include an O-ring 373 to allow adjustable fluid-tight seal around the elements passing through them. The outlet port 346 for the embolic agent 1 is a conventional rotating male connector that may connect and lock to conventional female connections widely used in the art, and which may be on the proximal end of an introducer catheter (not shown) so that the embolic agent 1 may be smoothly and easily transferred from the depicted embolic delivery system 324 into the introducer catheter or intermediate element that leads to introducer catheter that carries the embolic agent 1 to the target tissues.

The embolic agent 1 may have traction elements 270 as shown, in this example in the form of ridges 272, although many variations are possible. The embolic agent in this example is a helical wire 33 with central wire 6 as described herein, and is flexible to lateral bending but semi-rigid to axial compression. The pusher element 90 shown does not have traction elements, and is instead softer than the embolic agent 1 and will therefore conform to the contour of the ridges 272 as shown in the figure, when the two elements are pressed together by the constraints of the system, and the pressure caused by the feeder pulleys 380. In other embodiments, traction elements 270 may also be on the pusher element 90, or may be only on the pusher element 90 and not on the embolic agent 1. The feeder pulleys 380 rotate around the pulley shafts 336 that are fixed to the wall 372 of the housing 384, so their only allowed motion is rotational. They directly contact the pusher element 90 and embolic agent 1 and are within the lumen 371 of the embolic delivery system 324. The feeder pulleys 380 squeeze the embolic agent 1 and pusher element 90 together to increase the friction and traction between them. In variation, more sets of feeder pulleys 380 may be included for more areas of pressure. The operator (not shown) may pull the pusher element 90 from its upper aspect outside the confines of the embolic delivery system 324, causing forward motion of the embolic agent 1 and pusher element 90 as shown by arrows. In another embodiment, the pusher element 90 may be a continuous loop, like a belt, so that it can be much shorter perform the same function as depicted. This loop may be manually pulled by the operator, or could be connected to a drive system similar to that shown in FIG. 17. The drive system could be outside of the housing 384 of the embolic delivery system 324. This embodiment could also be considered a variation of FIG. 17 where the pusher element 90 essentially becomes very similar to the feeder belt 378 in FIG. 17, and the main difference between them is the fewer drive elements inside the lumen 371 in FIG. 22H. To this effect further variation could include bilateral and symmetric pusher elements 90 and feeder pulleys 380 for the system of FIG. 22H. In other variation, the embolic agent 1 and pusher element 90 may be packaged together by manufacturer, similar to method seen in FIG. 22B, FIG. 22D, and FIG. 22G, and enter together through the main inlet port 345 instead of depicted example in FIG. 22H where pusher element 90 enters separately via second inlet port 345. Another variation could include a second or more set of feeder pulleys 380, particularly near the bifurcation 375 to assist with compression of embolic agent 1 against pusher element 90, and to provide a smoother motion of moving elements.

FIGS. 23A-E depict an embodiment of embolic delivery system 324 that translates a to-and-fro or bidirectional linear motion of the pusher element 90 into incremental linear forward motion of the embolic agent 1. In brief summary of operation, an upward linear motion of the linear trolley 410 effects a predominantly and roughly similar linear motion of the cam 407 and cam block 408, but also causes a very slight clockwise rotation of the cam 407 causing it to tightly grasp the embolic agent 1 and pusher element 90 against the cam block 408, so that linear motion is also imparted to the embolic agent 1 and pusher element 90 in unison. When the direction of linear motion is reversed, the cam 407 rotates counterclockwise slightly, releasing its grip on the embolic agent 1, so that the cam 407 and cam block 408 and connected elements may slide predominantly linearly, without also pulling the embolic agent 1, which may remain stationary at this time. The pusher element 90, being attached to the linear trolley 410 will be retracted. Thus the overall effect is to advance the embolic agent 1 incrementally with each cycle, while there is no net motion of the pusher element 90 with each cycle. The distal end 92 of the pusher element 90 is depicted close to the middle 207 of the introducer catheter, however its position within the introducer catheter 200 is manually adjustable by the operator and could be variable as fits the needs of the situation.

Figure 23A:
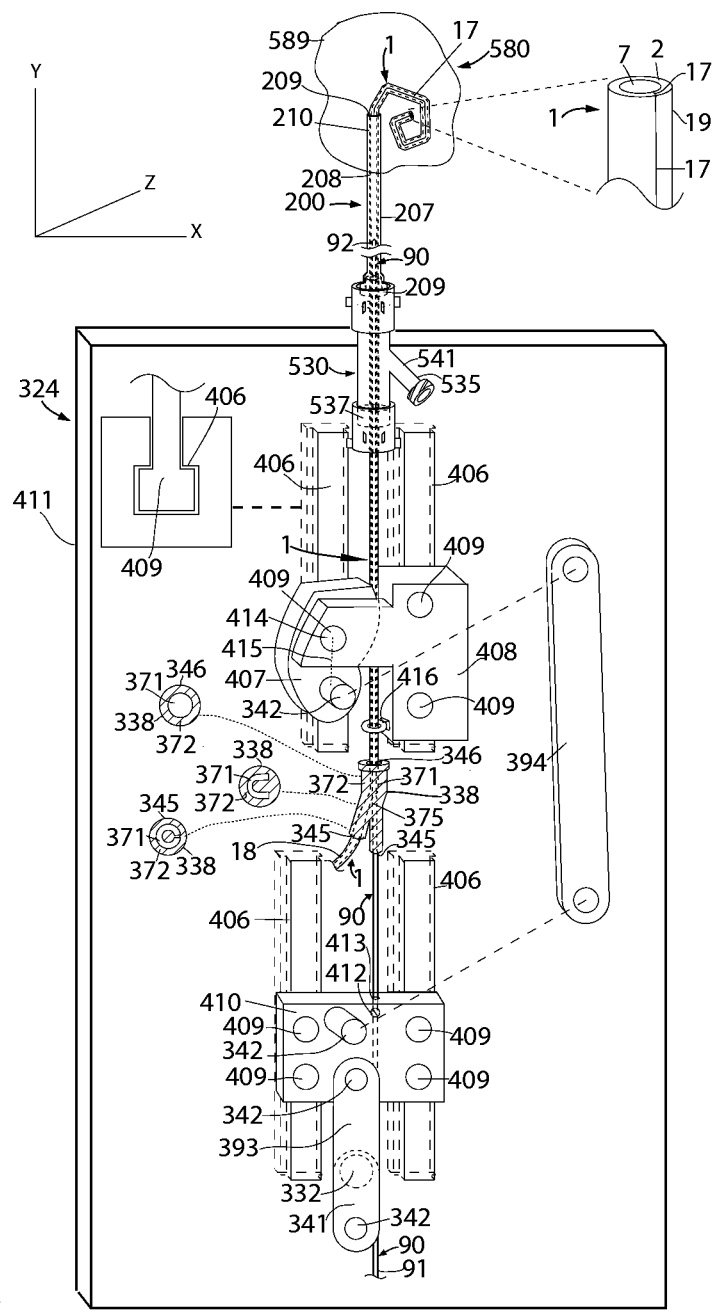

FIG. 23A depicts the track portions 406 of a guider 338, both to be described in detail below. It also depicts a magnified 3 dimensional perspective view of the embolic agent, which is very similar to FIG. 18A. The embolic agent 1 has a wall 2 and a central round lumen 7 similar to a conventional tube, however with a longitudinal slit 17 of full wall 2 thickness, which in this example extends all the way from the distal end 19 to the proximal end 18. FIG. 23A and FIG. 23B both represent the beginning of the motion cycle where all components are stationary for a point in time as one cycle ends and another begins, and direction of linear motion is reversed as described below. FIGS. 23B-E depict the system sequentially during a complete cycle. In FIG. 23A, an embolic delivery system 324 contains a guider 338, a rigid cam 407, a rigid cam block 408, a simple guider 416 attached to the cam block 408, and a rotary-to-linear motion apparatus which includes several rigid components including a first linkage arm 341, and a second linkage arm 393 shown in exploded fashion, a third linkage arm 394, 4 rotational joints 342, and upper rotational joint 414 a drive shaft 332, 4 tracks 406, and 7 track pins 409, and a simple guider 416. One of the track pins 409, located on the cam 407, also serves as the upper rotational joint 414 of the cam 407.

Function and further detail is now provided for FIGS. 23A-E. The drive shaft 332 is rotated by a drive train that is not pictured here but uses a conventional rotary system such as a hand-crank or electric motor and gearing as needed. The rotating drive shaft 332 is connected rigidly to the first linkage arm 341, which is connected to the second linkage arm 393 by a rotating joint 342 that allows only rotary motion, like a pivot point, as is the case for all rotating joints 342 in this figure. The second linkage arm 393 is connected to the linear trolley 410 by a rotational joint 342. The linear trolley 410 is slidably connected to two fixed, stationary tracks 406 via track pins 409 as shown and detailed further in the cross section view. The track pins 409 are rigidly connected to the linear trolley 410, which rests on the tracks 406. The tracks are rigidly incorporated into the rigid board 411 which serves as the stabilizing mount for several elements including the tracks 406, guider 338, and side port adaptor 530, none of which may move in any direction relative to the board 411. The rigid board 411 is generally flat in this depiction, however may have various contours as needed to mount components in a conventional manner in order to achieve the effects described herein. The board 411 may be composed of any rigid material or rigid compound such as hard plastic. It serves an important role in maintaining the proper alignment of various components for their function as being described herein. Components not directly connected to the board 411 may be permitted to move more flexibly according to their specific characteristics, e.g. the introducer catheter 200 which passes from the outside of the body 580 to the inside of the body 580.

The four track pins 409 and the linear trolley 410 may only move in a purely linear fashion along the Y axis by sliding of the track pins 409 in the cam block 408. The shape of the track pins 409 and cam block 408 do not permit detachment of the two elements or substantial motion in the X or Z axes. Thus the rotary motion of the drive shaft 332 is converted to linear motion of the linear trolley 410 by the action of the first linkage arm 341 and second linkage arm 393 as will be shown in FIGS. 23B-E. The pusher element 90 is detachably, rigidly connected to the linear trolley 410 by passing through a hole oriented along the Y axis of the linear trolley 410 as shown, with a set screw 412 that may be tightened to secure the pusher element 90 rigidly, or loosened to allow it to slide in the hole 413 in the linear trolley 410. In FIGS. 23A-E the set screw 412 is always tight so the pusher element 90 is always secured. The operator may choose to loosen it for various functions not described in detail herein such as manual operation of the pusher element 90 for many purposes commonly practiced in the art. The linear trolley 410 and the cam 407 are connected by the third linkage arm 394 by 2 rotating joints 342 so that the linear motion may be substantially transferred to the cam 407 and connected components including the cam block 408, and attached smaller elements to be described. Of important note is that the linear motion of the linear trolley 410 is not entirely transferred to the cam 407 because the mounting system of the cam also permits rotational motion of the cam 407 around the upper rotational joint 414 of the cam, which is also the track pin 409 for the cam, thus keeping a purely linear motion of the center point of the track pin 409 and upper rotational joint 414 while allowing a swivel or rotational motion of the cam 407 in addition to its linear motion. The cam 407 is attached to its cam block 408 solely by this one track pin 409 so that its rotation may occur. Notably, the rotational motion of the cam is very minimal, perhaps only a few degrees, because upon being rotated clockwise, the cam meets the cam block 408 and the interposed embolic agent 1 containing the pusher element 90, and may not rotate further because the cam block 408 is mounted to its cam block 408 by two track pins 409 and therefore may only move linearly in the Y axis without substantial rotation. Also important to this relationship is the connection between the cam 407 and cam block 408 is solely at the upper rotational joint 414, thus permitting rotation motion of the cam but not the cam block. The rotational joint 342 of the cam that connects to the third linkage arm 394 does not engage the track, and may thus rotate around the axis of the upper rotational joint 414 along with the rest of the cam 407.

Prevention of substantial counterclockwise rotation of the cam 407 during an upward linear motion of the system is effected by 2 mechanisms, with a third possible mechanism described but not depicted. First, an imaginary dashed line 415 from the center of the rotational joint 342 and upper rotational joint 414 of the cam 407 is slightly off the pure Y axis as shown. This creates a bias towards clockwise rotation of the cam 407 upon upward thrust of the third linkage arm 394. Second, the third linkage arm 394 is also longitudinally oriented slightly off the Y-axis to create another bias towards clockwise rotation of the cam 407 upon upward motion of the third linkage arm 394. Third, a conventional detent mechanism could be mounted on the cam 407 and cam block 408 or other elements in many possible conventional ways to prevent counterclockwise rotation of cam during upward linear motion of other elements.

Upon downward motion of the linear elements, the reverse rotational cam 407 motion will occur. The downward force upon the rotational joint 342 of the cam will tend to pull the cam in a counterclockwise direction until the described imaginary line 415 is roughly in-line with the long axis of the third linkage arm 394, which is roughly oriented along the Y axis with slight bias as described above. Again, the rotational motion of the cam is very small, but is enough to release pressure between the cam 407 and the cam block 408 and therefore free the embolic agent 1 and pusher element 90 from their grasp. The points along the edge of the cam 407 facing the cam block 408 have an increasingly greater distance from the center of rotation at the upper rotational joint 414 in passing from inferior to superior aspect, in order to provide the gripping function upon clockwise rotation. This gripping function is enhanced by the cam's 407 shape because as commonly occurs with conventional cam gripping mechanisms such as those used in rope climbing gear or other mechanisms, the force in the opposite downward linear direction applied by the embolic agent 1 and pusher element 90 due to some inevitable resistance to being pushed upward, against the gripping surfaces of the cam 407 and cam block 408 will serve to further force the cam's 407 clockwise rotation. In this manner, the more resistance there is to pushing the embolic agent 1, the greater will be the grasping force around the embolic agent 1 to help increase the friction and push it in the desired direction. Also to enhance this friction, the cam 407 and cam block 408 may be enhanced with material(s) with a high coefficient of friction such as urethane, for example, along the surfaces that come into contact with the embolic agent 1.

Now the aspects and motion of the embolic agent 1 and the pusher element 90 are considered here. As described throughout this invention, an object is to dispense a potentially large quantity of the embolic agent 1 to a relatively large body cavity or target tissue 589, passing it from its storage system, through the embolic delivery system 324 and various associated components, and through an introducer catheter 200 which itself passes from outside of the body 580 to the target tissue inside the body 580. In FIG. 23A, the storage of most of the proximal end 18 of the embolic agent 1 is not depicted, and may be similar to one of the variations described elsewhere herein. In this example, embolic agent 1 need not be stored inside a tank or enclosed structure, as it is not necessarily bathed in fluid while in its containment apparatus. Storage in this example could be as simple as a conventional spool or reel, or other method of preventing tangling and providing delivery with low resistance. Storage of most of the proximal end 91 of the pusher element 90 is also not depicted. This would usually be accomplished in a conventional manner used commonly in the art, such as simply laying it out in the workspace, either in a straight or curved path, or with one to three simple coilings performed manually by the operator. The pusher element's 90 length is not as variable or as great as the embolic agent 1 since it is not continuously deployed into the target tissues 589 and is simply a tool of delivery of the embolic agent 1. Therefore it is manageable using commonly used means in the art.

The course of the embolic agent 1 is discussed now. It is pulled into the embolic delivery system 324, first entering the guider 338, whose role it is to prepare the proper position of the embolic agent 1 for feeding into the mechanism of cam 407 and cam block 408. It also serves to provide a novel function of integrating the flexible hollow embolic agent 1 with the solid semi-rigid pusher element 90 such that the pusher element 90 is co-axially positioned within the embolic agent 1. Coaxial positioning of pusher element 90 inside catheters (not embolic agents) is conventional and conventionally accomplished by passing one through the end of the other. However, this is not possible in this invention due to the great length of the embolic agent 1, so novel aspects include the entry of the pusher element 90 into the longitudinal slit 17 of the embolic agent 1, as well as the novel use of a hollow embolic agent 1, and the novel method of passing it over the stiffer pusher element 90 using coaxial technique. Once the embolic agent 1 exits the guider 338 with the pusher element 90 located coaxially inside of it, the embolic agent 1 and pusher element 90 then pass through the simple guider 416 which is rigidly attached to the cam block 408. The simple guider 416 serves to position the embolic agent 1 and pusher element 90 for feeding in between the cam 407 and cam block 408 as described in more detail shortly. When pushed upwards by the cam 407 and cam block 408, the embolic agent 1 and pusher element 90 then pass into the side-port adaptor 530. Although the side port adaptor 530 is optional and could be eliminated, and the elements fed directly into the introducer catheter 200 instead, the side port adaptor 530 may serve to standardize the system somewhat since different introducer catheters 200 may be employed with one standard side port adaptor 530 that could be included with a kit. It also permits the application of flushing fluids at this level, which could be infused into the side port 535 using conventional methods described elsewhere in this invention and standard in the art.

Since its lumen 541 becomes continuous with the lumen 209 of the introducer catheter 200 when they are connected rigidly, the flushing fluids may pass into the target tissue 589 in this manner. Once the embolic agent 1 and contained pusher element 90 pass though the side port adaptor 530 into the introducer catheter 200, and then the embolic agent may continue on into the target tissues 589. The pusher element 90 does not similarly accumulate in the target tissue 589 due to the mechanisms described in detail herein, and the farthest extent of its distal tip could be variable and controlled by the operator who may determine what length of the element will be distal to the tether point at the set screw 412. The pusher element will usually not extend beyond the distal end 210 of the introducer catheter 200, or into the target tissue 589, although this may be performed as deemed beneficial by the operator.

Returning now to more details about the guider 338, it is secured rigidly to the board 411 and does not move or have moving parts. As depicted in FIG. 23A, the guider 338 has two inlet ports 345 and one outlet port 346 all of which are in communication with a central hollow lumen 371. Guider 338 is novel in its design and function, since the lumens 371 of the 2 inlet ports 345 join in a manner that wraps the hollow embolic agent 1 around the pusher element 90. The lumen 371 of the inlet port 345 receiving the pusher element 90 is a conventional hole, round in cross section, as in most conventional catheters and tubes. The lumen of the inlet port 345 for the embolic agent 1 is shown in cross section in the magnified drawing indicated by the dashed lines, and is roughly "C" shaped, within the solid, rigid wall 372, causing similar shape for the embolic agent 1. The cross sectional configuration of the inlet port 345 of the guider 338 that accepts the embolic agent 1 is therefore suited for receiving the embolic agent in manner whereby the solid elements of the inlet port 345 are in maximum contact with the inside and outside surfaces of the wall 2 of the embolic agent 1. The C-shaped wall 2 (in cross section) of the embolic agent 1 fits into the C-shaped lumen 371 of the guider 338. This serves to precisely control the position and orientation of the longitudinal slit 17 of the embolic agent 1 for optimum smooth opening and wrapping around the pusher element 90 that occurs at the bifurcation 375 region of the guider 338. Moving to the cross-sectional drawing of the inlet port 345 for the embolic agent 1 corresponding to a location closer to the bifurcation 375 as indicated by the dashed lines, the configuration has changed somewhat as shown. There has been a transition from the above description to a more open shaped lumen 371, more like a sideways "U", and the cross-sectional diameter of the wall 372 has increased slightly. This serves to correspondingly open the longitudinal slit 17 of the embolic agent 1 to prepare it for acceptance of the pusher element 90 at the bifurcation 375. Referring now to the third and upper cross-sectional drawing of the guider 338, corresponding to the level of the outlet port 346 where the two lumens 371 of the two inlet ports 345 are now joined into one lumen 371 containing the embolic agent 1 which is wrapped around the pusher element 90. Now the lumen 371 of the guider 338 is seen to be round and conventional in cross section.

The pusher element 90 in this depiction is a standard metal wire type, flexible with substantial, providing the columnar strength and resistance to buckling and kinking that facilitate the pushing of itself and the embolic agent 1 forward through the system elements into the target tissue 589, overcoming the resistances along the way. It is well known in the art that a highly flexible micro catheter, similar in many ways to the highly flexible embolic agent 1 in this example, is more easily advanced through catheters when a stiffer wire is positioned inside its lumen. Such forward motion is enhanced further by the simultaneous advancement of both elements, facilitating the advancement of the embolic agent 1 which can be quite floppy and difficult to advance alone.

Inevitably, there will be some undesired friction between the embolic agent 1 and the pusher element 90 within its lumen 7 upon the downward linear motion of each cycle when such friction could adversely cause a downward motion of the embolic agent 1. In the depicted invention, this is prevented by stronger frictional forces on the embolic agent 1 at several locations including the body 580, against the internal walls 208 of the introducer catheter 200 and side port adaptor 530, against the O-ring 537 of the side port adaptor 530 which may be adjusted accordingly, against the internal walls 372 of the guider 338, and at the bifurcation 375 of the guider 338 where a downward force upon the embolic agent 1 would not result in downward motion of the embolic agent 1 unless it were strong enough to overcome the forces that would be required to cause un-wrapping of the embolic agent 1 from the pusher element 90 and force it downwards through the guider 338. Prevention of this unwanted motion could also be facilitated by the use of materials and/or coatings of the surfaces of the inside wall 2 of the embolic agent 1 and the pusher element 90 so that the frictional forces between them are much less (when not gripped by the cam mechanism) than the opposing forces described above. Thus their synchronous motion would only occur when grasped together by the cam mechanism as described herein. Further mechanisms for prevention of this unwanted motion are further described in FIGS. 23 F-H.

In FIGS. 23B-E the system is depicted at four quarter phases during its cycle. FIG. 23B depicts the phase of the cycle when the linear motion elements are in their maximally retracted (downward) position. At this point in time, linear motion is transitioning from downward to upward in direction. The maximum retraction of the third linkage arm 394 is associated with maximally counterclockwise rotated cam 407 and absence of grasp of the embolic agent 1 and pusher element 90 by cam 407 and cam block 408. The solid curved arrow depicts the counterclockwise rotation of the drive shaft 332, which is always in this direction.

Progressing to FIG. 23C, the first linkage arm 341 has been rotated into a horizontal direction as shown, thus lifting and partially rotating the second linkage arm 393, thus pushing the linear trolley 410 upwards in a pure linear motion through half of its course. This has also pushed the third linkage arm 394 upward, which at first instant rotates the cam 407 slightly clockwise as depicted by the solid curved arrow, and then to push it upward linearly, bringing the cam block 408 upwards linearly with the cam 407. The pusher element 90 was pushed upward by virtue of its attachment to the linear trolley 410, as well as due to the gripping forces and motion of the cam mechanism, and its distal end 92 is depicted closer to the distal end 210 of the introducer catheter 200. The embolic agent 1 was moved upwards by the gripping forces and motion of the cam mechanism, as well as the frictional forces against the pusher element 90, and is seen to be passing further into the target tissue 589.

Progressing to FIG. 23D, the linear motion components are now at their full upward extent, and the cam mechanism remains closed, with the cam 407 gripped against the embolic agent 1 and cam block 408. The pusher element 90 is maximally forward in the introducer catheter 200 as seen by its distal end 92 being very close to the distal end 210 of the introducer catheter 200. The embolic agent 1 has been pushed maximally into the target cavity 589 until the cycle repeats.

Progressing to FIG. 23E, the first 341 and second 393 linkage arms are oriented as shown, and the linear motion is now retracted halfway through its downward course. The downward forces caused the cam 407 to rotate slightly counterclockwise as shown by solid curved arrow, releasing its grip on the embolic agent 1 which does not move substantially during this portion of the cycle when the linear elements are moving downward. The pusher element 90 is retracted due to its rigid attachment to the linear trolley 410, but does not cause retraction of the embolic agent 1 for reasons detailed herein. The cycle repeats when the elements reach the position of FIG. 23B in another quarter of a cycle.

FIGS. 23F-H depict variations of the above, in part to address the potential adverse backward slippage of the embolic agent 1 during the portion of the cycle when the linear motion elements are being retracted downward, as was described in FIG. 23A. A modification of the guider 338 may include the addition of a constricting O-ring 537 that is similar to the O-ring 537 that is part of a conventional side port adaptor 530. This is depicted in FIG. 23F in crude form, and not depicted in more detail here because it is well described elsewhere in this invention and is commonly available and conventional in various forms currently. FIG. 23F is a frontal view of the guider 338 with cross section view of the portion designated by dashed line, depicting a possible location of a constricting O-ring 537 which has the function of constricting the device very slightly, increasing the frictional forces against the embolic agent (not depicted here) as it moves through. This O-ring 537 may be operator controlled for optimum friction, and may be easily changed during the procedure as needed. If there is back-slip of the embolic agent 1, the O-ring 537 may be tightened until back-slip ceases, without excessive tightening that could lead to difficulties with proper advancement of embolic agent 1 during portion of cycle when this is intended.

Another mechanism for prevention of back-sliding of embolic agent 1 is depicted in FIGS. 23G-H, which depict some select relevant elements from FIGS. 23A-E with new elements added to help accomplish the said purpose. Many elements, including the pusher element 90 of FIGS. 23A-E, are omitted from the drawing to help show the new elements, however all elements of FIGS. 23A-E would be present in this embodiment. The elements seen in FIGS. 23G-H that were already described in FIGS. 23A-E include a board 411, a cam 407, a guider 338, an upper rotational joint 414 for the cam 407, and an embolic agent 1. New elements include a cam arm 417 which is a rigid, hard component rigidly attached to the cam 407, and whose motions are purely determined by the motions of the cam 407, and a wheel 418 which can rotate freely about its shaft 333, with said shaft connected to the cam arm 417 as shown, allowing only rotational motion of the wheel 418 relative to the cam arm 417. Additional new elements include two spring mounts 419 which are rigidly attached to the board 411, a first spring 421 and a second spring 423 attached to their spring mounts 419, 4 simple guiders 416, a gripper 420, and a swing arm 422 attached to a rotational joint 342, which is attached to the board 411.

The cam 407 and its upper rotational joint 414 and the guider 338 are configured and attached to the board 411 as already described in FIGS. 23A-E. In FIG. 23G, the system is shown during its downward (Y axis) linear motion as described earlier, when it is desirable for the embolic agent 1 to remain stationary and not be dragged down (Y-axis) by the frictional forces of the pusher element within it (not shown here). The cam has rotated counter clockwise as previously described, and this has swung the cam arm 417 towards the swing arm 422, which is now engaged by the wheel 418 that rotates freely and passively on its shaft 333 which is connected to the swing arm 422. This forces the rigid swing arm 422 to swing counter clockwise into the position shown, against the opposing force of the first spring 421. This first spring 421 is a tension spring, pulling the swing arm 422 rather than pushing on it. The swing arm is shown pressed against the numerous simple guiders 416, which are rigid structures in the shape of a torus in this example although many different shapes or pluralities could provide similar function. The simple guiders 416 are rigidly attached to the board 411 and will not move. The swing arm 422 is pushing the gripper 420, which is slidably mounted to the board 411 so that it may move sideways (in the X-axis) slightly. When pushed by the swing arm 422 as shown, the center of the gripper 420 is aligned eccentrically along the Y axis with the centers of the simple guiders 416 so that there is compression of the embolic agent 1 and increase in frictional force on the embolic agent 1 which passes through all of them. The embolic agent 1 is therefore held in position during this portion of the cycle, so that back-slippage is minimized while the pusher element is retracted.

Of note in FIG. 23G is that the swing arm 422 is in a directly vertical position, parallel to the linear motion along the Y-axis of some elements such as the cam arm 417 and wheel 418. The wheel 418 rolls along the surface of the swing arm 422 so that the two may always be in contact despite their different motions in the Y-axis. This will keep the swing arm 422 pressed against the simple guiders 416 and gripper 420 as shown during this linear motion cycle so long as the cam 407 and cam arm 417 are rotated in this position.

Moving to FIG. 23H, the same elements are shown, and are therefore not labeled again. However, they are in different positions as shown, corresponding to the opposing phase of the cycle when the linear elements, such as the cam 407 and cam arm 417, are moving upwards along the Y-axis. As reviewed previously, this is when the pusher element and embolic agent 1 are being advanced upward simultaneously as indicated by the nearby solid arrow. In FIG. 23H, the cam 407 has rotated clockwise, swinging the cam arm 417 as shown, permitting the swing arm 422 to be pulled to the left by the first spring 421. The cam arm 417 has moved upward with the cam 407 in the Y-axis, but the swing arm has not since it is secured to the board by the rotational joint 342. The gripper 420 is no longer under the influence of the swing arm 422 and is therefore pushed by the attached second spring 423 rightward towards the spring mount 419. This second spring 423 is an extension spring, meaning it pushes the gripper 420 rather than pulling it. The gripper is mounted in such a manner, using a conventional detention mechanism (not depicted), that it may not be pushed any farther to the left than as depicted in the figure. As shown, its center is now in alignment with the centers of the many simple guiders, so that in this position, there is little if any gripping force exerted on the embolic agent 1, which may therefore freely move upwards as determined by the mechanisms described in FIGS. 23A-E.

Another mechanism that could be employed to prevent back-sliding of the embolic agent 1 during part of the cycle is accomplished by the use of directional traction elements on the pusher element 90, embolic agent 1, or both. These elements and their functions are described in detail elsewhere in this invention, and will therefore be mentioned only briefly here. The traction elements may be configured in a manner that promotes low friction when the pusher element 90 is retracted downward (Y-axis) and it is desirable for the embolic agent 1 to remain stationary. The traction elements would however increase friction between the two elements when they are advanced upward together, so that motion of the pusher element 90 results in upward motion of the embolic agent 1. This mechanism may obviate the need for the variations described in FIGS. 23F-H. Variations on the above may occur and remain within the scope of the invention. The track mechanism may be of any other conventional type including rollers, wheels, or use of different track and track pin configurations that provide similar purely linear motion of the linear trolley 410. Instead of using a cam, a simpler lever or arm could be substituted, which would press against the embolic agent 1 similarly, but would simply have a different shape than the depicted cam.

FIG. 23I depicts one embodiment of the embolic delivery system 324 shown in FIG. 23A-E. It performs essentially the same functions, however uses a different mechanism from the cam and cam block to provide unidirectional grip of the embolic delivery system 324, providing incremental forward motion of the embolic agent 1 when the system moves upward, while avoiding pulling the embolic agent 1 downward when the system moves downward, in a manner that employs a different method of automatic grasping during one direction and automatic release of friction during other direction. In FIG. 23I, automatic grasping of the embolic agent 1, which may also contain a pusher element (not depicted) as in FIGS. 23A-E, is achieved with one or more encircling structures, herein termed gripping rings 424, which have a large enough hole to permit free passage of the embolic agent 1 when oriented orthogonally to its long axis. Each gripping ring 424 is rigidly integrated with a long segment 425 that connects via a rotational joint 342 to a rigid push-rod 426. The rotational joint allows rotational motion between the long segment 425 of the gripping ring 424 and the push-rod 426, with free motion intended to have low friction. There is a detention element 427 that is rigidly attached to the push-rod 426 that prevents the long segment 425 from rotating any higher than the "3 o'clock" position shown on the left. However, the long segment 425 may rotate downward as shown on the right, prevented from rotating further only by the effect of the embolic agent 1 occupying the hole of the gripping ring 424 and preventing further rotation, since the push-rod 426 and embolic agent 1 are both restrained from motion in the x axis by mechanisms already depicted in FIGS. 23A-E to keep them oriented parallel to each other with only linear motion in the Y-axis possible. The push-rod 426 is attached to a linear track system (not depicted) similarly to that for the cam block in FIGS. 23A-E.

On the left in FIG. 23I, the system is shown during the phase where the push-rod is moving downward, as similar to the cam in FIG. 23A-E, and as indicated by the solid arrow. There is no substantial motion of the embolic agent 1, because there is enough space within the hole of the gripping rings 424 to permit their easy sliding motion over the embolic agent 1. This configuration is also seen in the cross section drawing. The detention elements 427 prevent the gripping rings 424 from being pushed by frictional forces from the embolic agent 1 into an angled orientation that would result in gripping of the embolic agent 1. Moving to the figure on the right of FIG. 23I, the phase is shown whereby the push-rod 426 is being pushed upward linearly as shown by the solid arrow. Frictional forces from the embolic agent 1 cause the gripping rings 424 to assume the angles shown, in the absence of detention elements 427 to prevent such direction of motion, and resulting in a narrowing of the effective diameter of the gripping rings 424 in the X-axis, in turn resulting in a gripping action (high friction) against the embolic agent, which is further enhanced by greater force of the push-rod 426. This results in an upward motion of the embolic agent 1 as shown by the solid arrow. Many of the elements of this system are not depicted, but are similar to the elements of FIGS. 23A-E and are therefore not shown again here for brevity, as they can be easily modified slightly using conventional techniques standard in the art to assimilate the novel elements and mechanism of FIG. 23I.

Figure 24A:
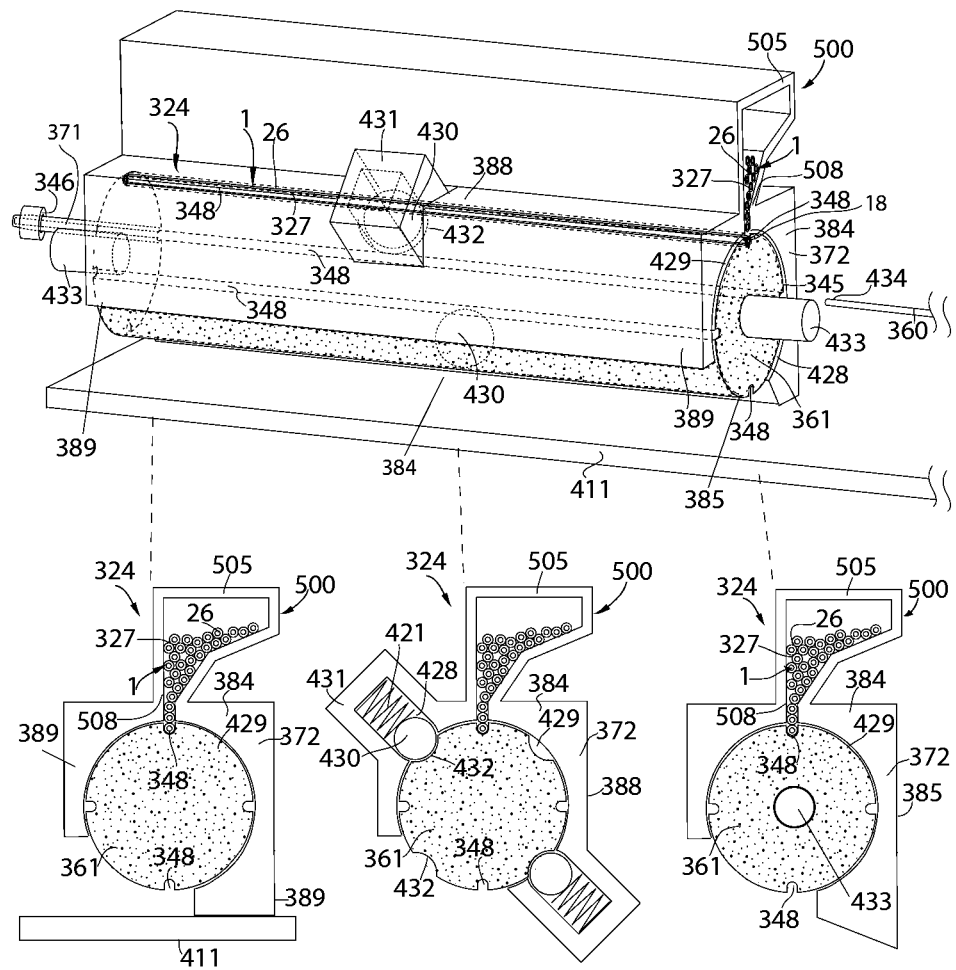
FIGS. 24A-G depicts embodiments of a novel embolic delivery system that combines a linear feeding mechanism with a revolving mechanism to provide rapid sequential delivery of a plurality of embolic agents of short or medium length as described herein.
Figure 24B:
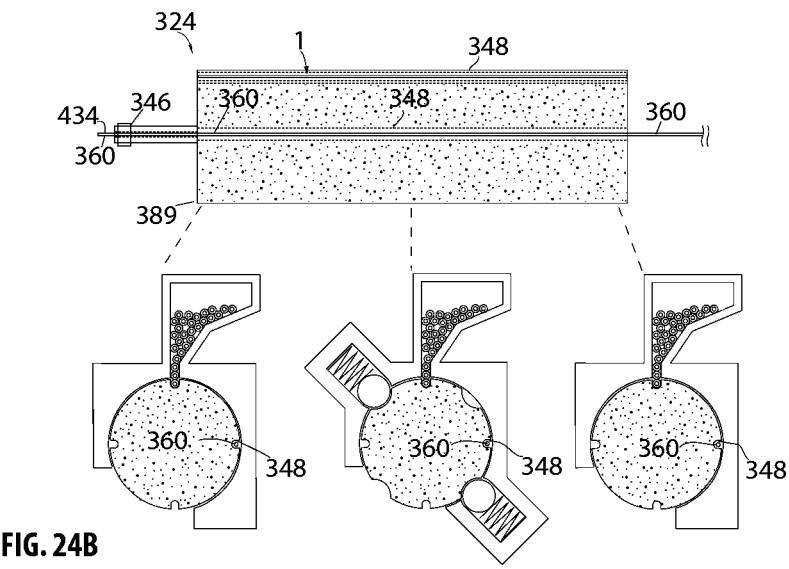
Figure 24C:
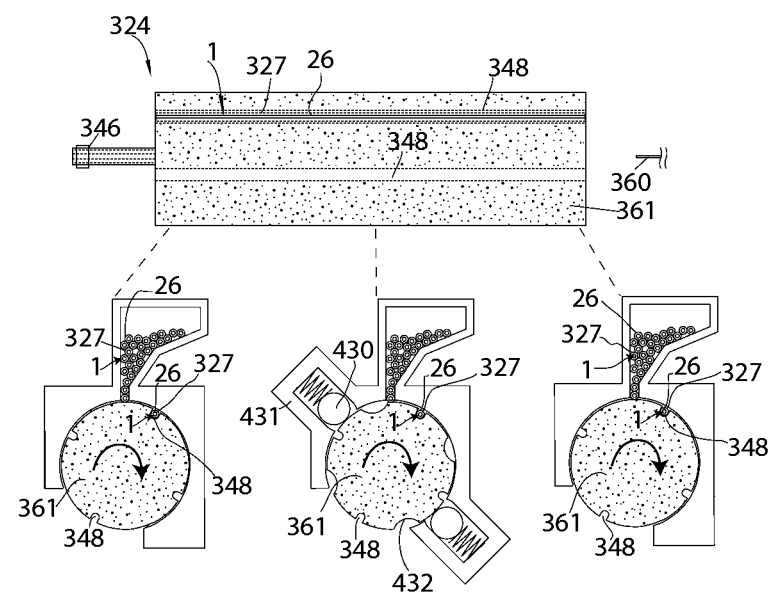

FIG. 24A introduces an embodiment of embolic delivery system 324 that has the novel capacity of rapid sequential delivery of multiple embolic agents 1 of a more conventional length, that are much shorter than most of the other embodiments described in this invention, and which may have memory for a coiled or complex configuration. The embolic delivery system 324 has a proximal portion 385, a middle portion 388, and a distal end 389. It includes a housing 384 with a wall 372, a hollow core 428, and a cylinder hole 429, springs 421, ball bearings 430, a ball housing 431, and a piston 360 with a distal end 434. It also includes a cylinder 361 which includes concavities running its length called feeder chutes 348, and rounded concavities called ball concavities 432 that mate with a portion of the surfaces of the ball bearings 430. The location of entry of the piston 360 into the feeder chute 348 in the three O'clock position is called the inlet port 345. The wall 372 of the embolic delivery system 324 is integrated with the wall 505 of the embolic containment apparatus 500, which includes a delivery channel 508. Other elements of this embolic delivery system 324 pertaining to the drive apparatus for the piston 360, and elements that accept the embolic agent 1 after it is advanced beyond this embolic delivery system 324 will be described in more detail in later figures. The housing 384 of the apparatus, and the cylinder shaft 433 are mounted to the rigid board 411 that is common to other elements in other figures described herein that relate to this current invention in order to maintain constant positioning of elements in relation to each other. The cylinder shaft 433 are mounted to the board 411 using conventional pillow mounts (not depicted) that permit free rotation of the shaft 433.

The embolic agent 1 is similar to that previously described in FIG. 4C or FIG. 9D. In FIG. 24A, the embolic agent 1 is packaged slidably inside an introducer sleeve 327, the combination being called a cartridge 26. The embolic agent 1 may be of any filamentous variety described in this invention, including the type shown in FIG. 2M-O, or FIG. 2A-D as well as many other pushable embolic agents lacking special detachment mechanisms. The embolic agent 1 is straight when packaged inside the rigid or semi-rigid introducer sleeve 327, but may assume a coiled or other variant configuration when unconstrained. In FIG. 24A, the cartridges 26 are seen loosely contained and longitudinally oriented within the walls of the embolic containment apparatus 500, and falling by gravity (as shown) or by a spring loading mechanism (variation not depicted) through the delivery channel 508 to the integrated embolic delivery system 324, where one cartridge 26 at a time may come to rest within the feeder chute 348 of the cylinder 361. The ends of the feeder chutes 348 may have slight tapers (not shown) beyond the ends of the cartridges 26 to prevent longitudinal sliding of the cartridges 26 during piston 360 travel. In this embodiment, there are 4 feeder chutes 348 equally spaced around the cylinder 361 as shown. The cylinder 361 may be rotated about its long axis within the cylinder hole 429, and each quarter turn will place the next feeder chute 348 into position under the delivery channel 508. The rotation may occur as the cylinder shaft 433 is forcibly rotated clockwise by a drive mechanism (shown in later figures). The cylinder shaft 433 is rigidly connected to the cylinder 361. Although the drive mechanism (shown in FIG. 24G) may perform precise quarter rotations of the cylinder 361, the precision may be enhanced by the mechanism shown. In the middle portion 388 of the embolic delivery system 324 there is a ball housing 431 which contains in its hollow core 428, a spring 421 and a ball bearing 430, best seen in the cross section view. The ball bearing 430 may move up and down within the hollow core 428 of the ball housing 431 where it and the spring 421 are contained. The spring 421 is an extension spring, meaning it pushes on the ball bearing 430 against the cylinder 361 as shown. The cylinder 361 has four ball concavities 432 in its mid portion, equally spaced around the cylinder 361 between the feeder chutes 348 as shown. Each ball concavity 432 is a bowl-shaped depression which matches the outer convex surface of the ball bearing 430 in contour. When the cylinder 361 is positioned so that one of its four ball concavities 432 is under the ball bearing 430, the ball bearing 430 is pushed by the spring 421 into the ball concavity 432 and locking the cylinder 361 into the optimum position within housing 384 to line up the delivery channel 508 with the feeder chute 348 for seamless transfer of cartridge 26. Since the ball is spherical in shape, it will help to maintain the cylinder 361 in the proper longitudinal position as well as rotational position. In the depicted embodiment, an identical mechanism is located 180 degrees across the system, to further facilitate the said function by providing opposing forces of similar magnitude, thus stabilizing the cylinder 361 within the housing 384 by substantially removing the burden on the cylinder shaft 433 with regard to providing stabilizing force.

The force of the spring 421 is not great enough to prevent active rotation of the cylinder 361 once sufficient rotational force is applied to the cylinder shaft 433 by the drive mechanism (depicted in later figures). When rotational force is applied, it may overcome the force of the spring 421 that is pushing the ball bearing 430, which will roll or slide against the ball concavity 432 as it moves backwards against the force of the spring 421 within the ball housing 431. Once a ¼ turn has been achieved, the ball bearing 430 will once again lock into the next ball concavity 432 and maintain stability and precise positioning of cylinder 361 within housing 384.

In FIGS. 24A-F, the function of this system is further described and depicted. FIG. 24A consists of a 3-dimensional frontal perspective view with 2-dimensional cross section views at levels as indicated by dashed lines. FIGS. 24B-F consists of a 2-dimensional side projection views with 2-dimensional cross section views at levels as indicated by dashed lines. The drive mechanism will be described in detail in FIG. 24G. FIG. 24A corresponds to the beginning of the cycle. The cartridge 26 containing the embolic agent 1 inside an introducer sleeve 327 is seen loaded in the feeder chute 348 at the 12 o'clock position, with the other 3 feeder chutes 348 empty. In the next phase of the cycle, in FIG. 24B, the piston 360 has been thrust forward through the feeder chute 348 in the 3 o'clock position. The distal end 434 of the piston 360 has passed beyond the distal end 389 of the embolic delivery system 324 and through the lumen 371 of the outlet port 346, and may be capable of further excursion as will be discussed later. The mechanism that keeps the piston precisely aligned, and moves it forward, will be described later. In this phase of the first cycle, the piston 360 has entered an empty feeder chute 348 and therefore does not push anything. In the next phase of the cycle, in FIG. 24C, the system is depicted after a 30 degree clockwise rotation of the cylinder 361. Prior to this rotation of the cylinder 361, the piston 360 is situated outside of the feeder chute 348 as shown. The cylinder 361 will always turn in ¼ rotation increments, so this figure is showing it in mid phase during active rotation of the cylinder 361 for purposes of teaching. The feeder chute 348 containing the cartridge 26 bearing the embolic agent 1 and the introducer sleeve 327 is now seen in approximately the one o'clock position. The rotation of the cylinder 361 has caused the ball concavity 432 to rotate away from the ball bearing 430, pushing the ball bearing 430 backwards in the ball housing 431. It may now roll or slide against the cylinder 361 surface, and over the next feeder chute 348 to come its way, since the feeder chute 348 radius is small relative to that of the ball bearing 430.

Figure 24D:
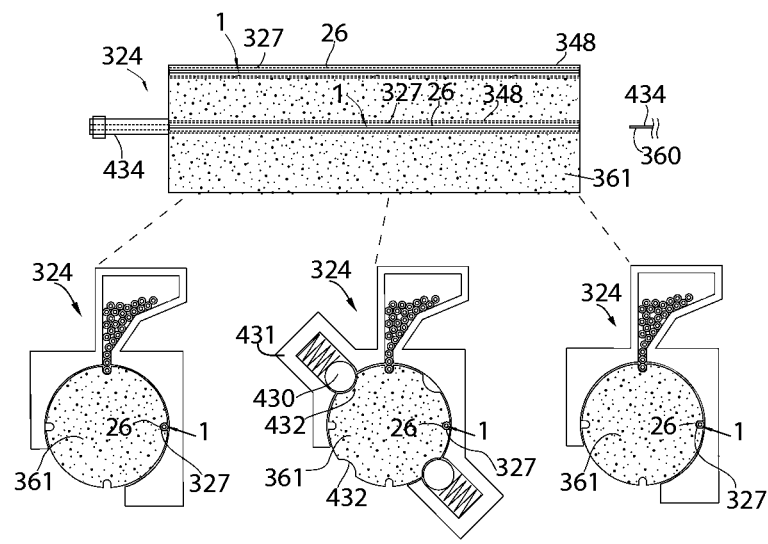
Figure 24E:
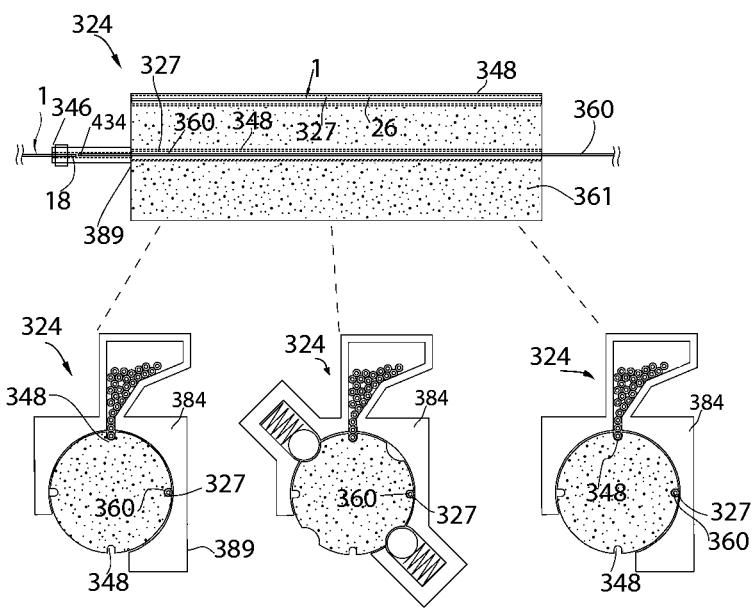

Moving to the next phase in the sequence, in FIG. 24D, the system has come to rest momentarily now that a ¼ turn relative to FIG. 24A has been achieved. It has come to rest because the drive mechanism (shown in FIG. 24G) that turns the cylinder shaft 433 performs quarter turns. The ball bearings 430 have settled into the ball concavities 432 to maintain the precise position of cylinder 361. Progressing to the next phase, in FIG. 24E, the piston 360 has been driven forward into the feeder chute 348 in the direction towards the distal portion 389. Since a cartridge 26 containing embolic agent 1 inside an introducer sleeve 327 was rotated previously to the 3 o'clock position where the piston advances, the piston 360 is seen pushing the embolic agent 1 forward in the direction of the distal portion 389 of the embolic delivery system 324. At the moment of this depiction, the distal end 434 of the piston 360 is at the distal end 389 of the embolic delivery system 324, and is pushing the proximal end 18 of the embolic agent 1, which can be seen extending beyond the outlet port 346. Further excursion is possible and would result in subsequent pushing of proximal end 18 of the embolic agent 1 into a receiving catheter or side-port adaptor (not shown) which will then feed it to the introducer catheter (not shown) and finally into the body, as will be discussed further later. The piston 360, whose diameter is approximately similar to that of the embolic agent 1 and smaller than the diameter of the introducer sleeve 327, is aligned precisely by mechanisms depicted later, to enter the center of the cartridge 26, in the hollow center of the introducer sleeve 327, to push the embolic agent 1 forward. Thus the embolic agent 1 and the piston 360 are both sliding inside the introducer sleeve 327, which is kept in place by a detention mechanism at the end, which can be of conventional type, and is not shown clearly in this figure, but can be as simple as a narrowing at the distal end 389 of the system that is large enough to allow passage of the embolic agent 1 but not of the larger caliber introducer sleeve 327, which will therefore remain substantially motionless in the feeder chute 348 during this phase.

Figure 24F:
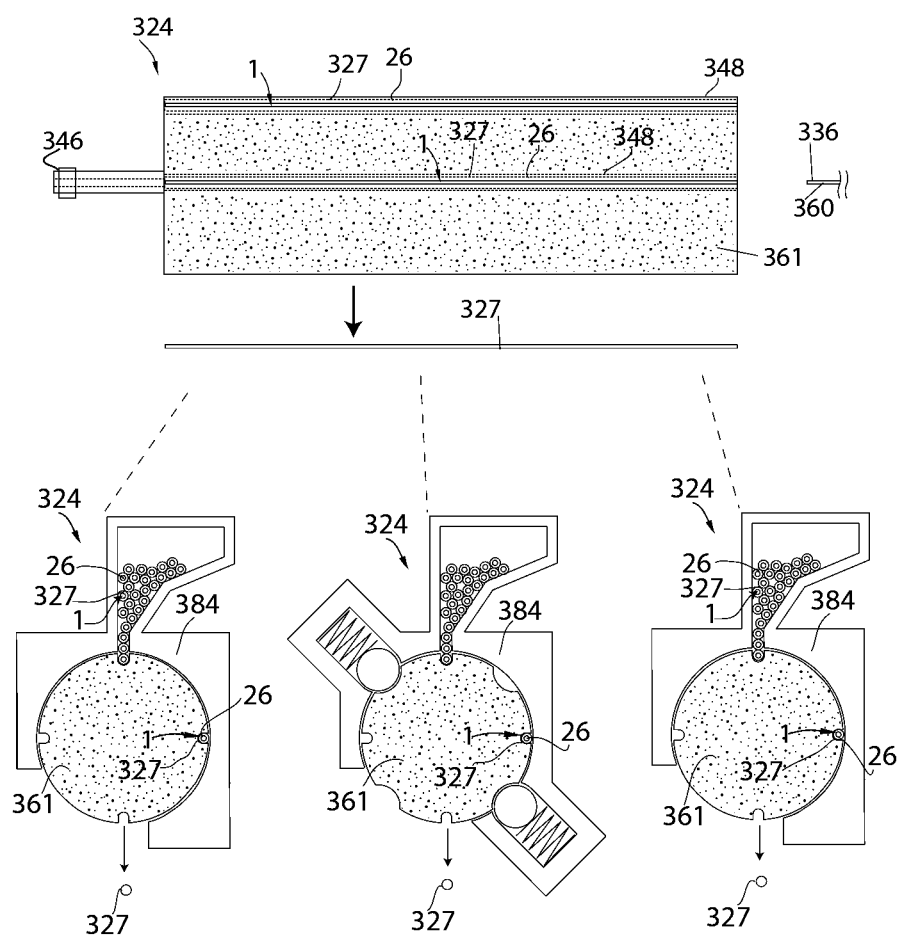

Once the distal end 434 of the piston 360 has traveled its course until it has pushed the embolic agent 1 completely out of the embolic delivery system 324 and into the receiving elements (not shown), then it may be withdrawn back to the position as shown in the next drawing in the cycle shown in FIG. 24F. Upon its withdrawal, the now empty introducer sleeve 327 may have a tendency to stick to the piston 360 enough to be dislodged backwards. Such motion of the introducer sleeve 327 could be prevented by a caliber narrowing (not shown) at the proximal end of the embolic delivery system 324 that, like the one at the distal end 389 already described, is large enough to accept the piston 360 but not the larger caliber introducer sleeve 327.

After the full withdrawal of the piston 360 to the position depicted, the cylinder 361 has rotated another quarter turn so that the empty introducer sleeve 327 that was previously in the three o'clock position is now in the six o'clock position where the housing 384 is incomplete and there is nothing to hold the introducer sleeve 327 in the feeder chute 348, as seen in FIG. 24F. It may drop out due to gravity, or it may be dislodged by a small probe or conventional flat or sharp element (not shown) as it rotates by. Also shown is the cartridge 26 containing an embolic agent 1 inside an introducer sleeve 327 is now in the feeder chute 348 in the 3 o'clock position, having just rotated over from the twelve O'clock position.

As all future cycles are repeated, the same actions of the elements of the embolic delivery system 324 will occur with each phase: First, the cylinder 361 will rotate a quarter turn, resulting in a new cartridge 26 loading into the feeder chute 348 at the twelve O'clock position, a loaded cartridge 26 being positioned at 3 o'clock, and an empty introducer sleeve 327 being ejected at the six o'clock position. Second, once the cylinder 361 has come to rest during each phase, the piston 360 will push the embolic agent 1 out of its introducer sleeve 327 and out of the embolic delivery system 324, and then, third, the piston 360 will retract. These actions described in this paragraph are represented by a continuous cycling from FIG. 24F to FIG. 24E, to FIG. 24F to FIG. 24 E, in ongoing fashion as required by the operator. With each cycle, a new embolic agent 1 is delivered forward into the introducer catheter or intermediate elements (not shown), and a new loaded cartridge 26 comes into place for another delivery of embolic agent 1.

As shown in FIG. 24A, a rigid board 411 serves as a framework for attachment of all components that must be maintained rigidly fixed in position relative to each other, including the cylinder housing 384 and the cylinder shaft 433 mounts. These are un-depicted conventional shaft mounts that allow rotation of the shaft 433 without allowing other substantial motion of the shaft. Also mounted rigidly to the board 411 is the linear track to be described in FIG. 24G, which will maintain the proper relationship between elements described in FIGS. 24A-F and other drive elements in FIG. 24G.

Figure 24G:
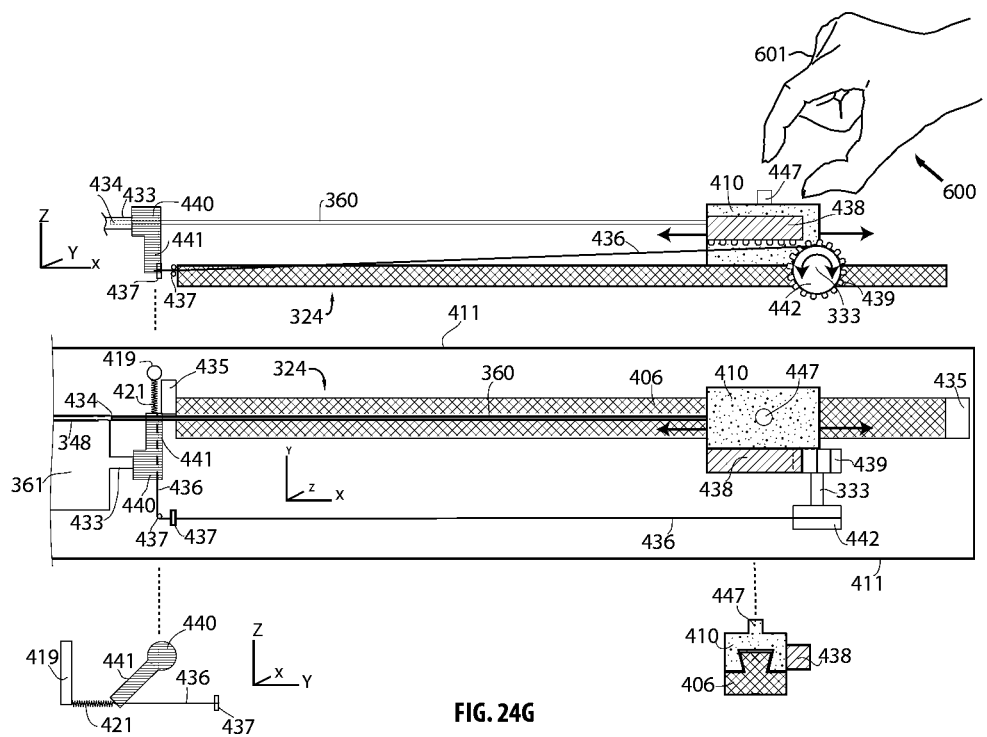

These novel functions and elements are controlled by drive mechanisms described in FIG. 24G. Importantly, all of the actions described in FIGS. 24 A-F are very simply accomplished by two basic linear hand motions of the operator 600. A forward linear hand motion will advance the piston, thus delivering the embolic agent 1, and then without changing grip or hand position on the device, a backwards linear hand motion will result in the withdrawal of the piston, followed by rotation of the cylinder 361 and all other functions described above in FIGS. 24 A-F, so that the system is now in readiness for another cycle upon repeated linear motion of her hand. The system will allow the operator 600 to have exquisite control over the speed and force of advancement of the embolic agent, which can be important for safe delivery. The tactile sense of the resistance to advancement of the embolic agent 1 will be preserved, as is often desired by experienced operators. Thus the novel functions of automation and greatly enhanced expedience of repeated embolic delivery may be accomplished while preserving desirable control aspects in this novel invention.

In variation, the ball bearing 430 may be replaced with a pin or cylinder with its long axis oriented along the long axis of the cylinder 361, and likewise instead of a ball concavity 432, a longer groove that mated with the pin or cylinder could be utilized, and still be in keeping with the overall important and novel features of the invention. In another variation, the feeding mechanism of the embolic agents 1 from the embolic containment apparatus 500 to the embolic delivery system 324 would not rely on gravity, but instead could utilize a spring loaded system more similar to that depicted in FIG. 25A or of other design with similar function. Many other variations in specific element design and configuration are possible that would still be in keeping with the novel and important functional aspects of this invention as outlined herein.

FIG. 24G depicts the driving mechanism of the embolic delivery system 324 that was partially described in FIGS. 24A-F, and includes a side view (top drawing), overhead view (middle drawing), and frontal (cross sectional) view, with further explanation of view indicated by the labeled coordinates. The dashed lines indicate the locations where the views correspond to each other. As described in detail previously, the main functions of this sub-system are, in very simplified form, to push the embolic agent through the embolic delivery system 324 and on to the receiving elements beyond (not shown), as well as to cause quarter rotation increments of the cylinder 361, in sequence and repeatedly. The rigid, cylindrical piston 360 is attached rigidly to the linear trolley 410 which may move only linearly and slidably along a linear track 406, which is rigidly attached to a rigid board 411 that provides a rigid framework for attachment of all elements that need to be secured rigidly in position. The board 411 is depicted on the overhead view only for simplification. The track 406 is attached to the same board 411 as are the cylinder housing 384 and the mounts for the cylinder shaft 433 (see FIGS. 24A-F). Other elements are attached to the board as described individually. As depicted in FIG. 24G, the mechanism for slidability of the linear trolley 410 on the track 406 is a simple sliding function, aided by use of low friction surfaces and precision construction of mating surfaces. However, in variation, this linear motion could be enhanced by addition of conventional roller elements such as bearings or wheels that are not depicted.

The hand 601 of the operator 600 may grasp the handle 447 to move the linear trolley 410 along the linear track 406 in either direction. "Forward" will refer to a leftward direction in the top and side views, and "backward" will be the opposite, and this will correspond to the same descriptions put forth in FIGS. 24A-F. In another contemplated embodiment (not depicted), a conventional automated system may perform the same function of to-and-fro linear motion in a repeated manner, in lieu of the operator's hand 601, and this system may be controllable by the operator 600 using conventional control mechanisms. In FIG. 24G, a forward motion of the linear trolley 410 will move the attached piston 360 forward. The piston's 360 further functions of pushing the embolic agent through the cylinder 361 were described previously and not repeated in detail here. The piston distal end 434 is indicated, and in FIG. 24G is seen to be located immediately outside of the confines of the cylinder 361. Any further forward motion of the piston 360 would place it in the feeder chute 348 of the cylinder 361 as described previously. Any backward motion from this position will simply move it farther away from the cylinder 361, but it will remain aligned linearly along the axis of the cylinder 361 so that subsequent re-advancement will again place it into the feeder chute 348 of the cylinder 361. Also shown on the top view of FIG. 24G are the trolley end stops 435 on both ends of the linear track 406. These are rigidly attached to the track 406 and define the limits of travel of the linear 410 that cannot move beyond the edge of the trolley end stops 435. Also shown on side and top views, and incompletely on the frontal view, are the elements that facilitate cylinder 361 rotation including the rack 438, pinion 439, pinion shaft 333, reel 442, tether 436, tether guides 437, clutch 440, clutch arm 441, spring 421, and spring mount 419. The pinion 439 is attached rigidly to its shaft 333, which is also attached rigidly to a reel 442 as shown. The shaft 333 is attached to the board 411 using conventional mount (not depicted) that allows conventional rotation of the shaft, but allows no other motion of the shaft. Therefore any force that causes rotation of the pinion 439 will rotate the reel 442 in the same manner. Rotation of the pinion 439 is caused by the rack 438 which is rigidly attached to the linear trolley 410, which slides linearly along the linear track 406, as when the operator 600 moves the linear trolley 410. The tether 436 is attached to the reel 442 as shown, so that rotation of the reel 442 will shorten or lengthen the tether 436 depending on direction of rotation. The tether 436 is a filament, of many possible compounds that provide flexibility like a string or thin wire or thin wire rope, and that is substantially resistant to longitudinal stretching. The other end of the tether 436 is attached to the clutch arm 441 so that tension on the tether will pull the clutch arm 441 and cause rotation of the clutch 440 to which it is rigidly attached. The clutch 440 is attached to the cylinder shaft 433 as shown. The clutch 440 permits unidirectional rotation between its outer member rigidly attached to the clutch arm 441 and its inner member rigidly attached to the cylinder shaft 433. The details of the workings of the clutch 440 are not depicted as it is a conventional element well known in the art of automation machines. It permits free clockwise (frontal view) rotation of the outer member (and attached clutch arm 441) relative to inner, but locks the inner and outer members rigidly upon counterclockwise rotation of the clutch arm 441. Therefore, clockwise rotation of the clutch arm 441 would cause no rotation of the cylinder shaft 433 or cylinder 361, whereas counterclockwise rotation of the clutch arm 441 would cause similar rotation of cylinder shaft 433 and cylinder 361. This latter motion would correspond to the 'clockwise' rotation described during normal function of the cylinder 361 in FIGS. 24A-F because the perspective is different in those figures. Repeated oscillation of the clutch arm 441 between the approximate seven thirty o'clock position seen in FIG. 24G and the four thirty o'clock position results in incremental quarter rotations of the cylinder 361 in the counterclockwise direction without any rotation in the clockwise direction, which is the desired rotation sequence described previously in FIGS. 24A-F. The currently described elements in FIG. 24G provide this functionality, in addition to others to be described. Also, depicted are three tether guides 437. These are simple cylindrical rigid objects attached rigidly to the board 411 and do not move. They have low friction surface, permitting sliding of the tether 436 around it, and guiding the course of the tether 436. They are oriented as shown, with two in parallel and those two orthogonal to the third, to perform said function. Of note, the tip of the clutch arm 441 where the tether 436 attaches will move somewhat up and down in the Z-axis as it rotates about the cylinder shaft 433, and therefore these guides will also permit the corresponding expected sliding motion of the tether 436 to occur. In variation the depicted tether guides 437 may be replaced by a single ring.

Therefore, by way of summary, a backward motion of the operator's hand 601 and linear trolley 410 from the position depicted will cause similar backwards linear motion of the rack 438, which will cause rotation of the pinion, thus rotating the reel clockwise as would be seen in side view. This will take up (shorten) the tether 436, thus pulling tension on the clutch arm 441, which will pull it rightward of the depicted seven thirty o'clock position (frontal view) towards its final location in the four thirty o'clock position. The length of the rack 438, circumferences of pinion 439 and reel 442, length of clutch arm 441 are all designed to result in one pass of the rack 438 over the pinion 439 to result in quarter rotation of the cylinder 361. Once the rack 438 has completely passed backwards over the pinion 439, the pinion will stop moving, and the linear trolley 410 will reach the trolley end stop 435. The same backward motion of operator's hand 601 also results in linear backwards motion of the piston 360 as described in FIGS. 24A-F.

Forward motion of the linear trolley 410 from the final position described immediately above will therefore result in the opposite motion of the pinion 439, rotating it counterclockwise (side view), and slackening the tether 436. The spring 421 is attached on one of its ends to the spring mount 419 which is rigidly attached to the board 411, and on its other end to the end of the clutch arm 441. Since it is a tension spring, it will pull the clutch arm 441 towards the spring mount 419. This may now occur since the tether 436 has been slackened, so the clutch arm 441 will rotate back to its seven thirty o'clock position as depicted, once the rack 438 has passed over the pinion 439 to return to the position depicted in FIG. 24G. Importantly, due to the function of the clutch 440, the cylinder 361 did not move upon this last motion of the clutch arm 441.

Further forward motion of the linear trolley 410 along the track 406 will advance the piston 360 into the feeder chute 348 of the cylinder 361 and perform the functions described in more detail in FIGS. 24A-F that result in deployment of embolic agent. Referring again to FIG. 24G, since the rack 438 and pinion 439 are no longer engaged, there is no effect on cylinder 361 rotation during this portion of the excursion. Upon full forward motion, the linear trolley 410 is stopped by the trolley end stop 435, and motion may now be reversed by the operator 600 to retract the piston, until the rack 438 and pinion 439 engage again and the cycle is repeated.

Thus described is an embolic delivery system 324 in FIGS. 24 A-G that performs the novel function of converting a simple to-and-fro hand 601 motion into the many complex functions described, which ultimately have the novel effect of very rapidly and repeatedly delivering embolic agents 1 to a body cavity via an introducer catheter, allowing rapid delivery of a great many embolic agents to treat sizable cavities in an expedient and controlled manner, while maintaining the tactile sense of control by the operator 600 during the delicate process of passing the embolic agent 1 into the tissues without causing harm due to excessive force or excessive bulk of embolic agent. Once the set-up is accomplished, the to-and-fro hand 601 motions are all that are required to repeatedly deliver embolic agent, as opposed to the current standard practice that involves many steps by the operator 600 in loading individual embolic agents and pushing them through the catheters. Although not outlined in detail herein, this standard process has numerous steps and takes longer per each embolic delivery by a very large factor, such that the described invention could shorten a prolonged procedure by an hour or even more in some situations, and make a procedure which is currently impractical become practical, thus expanding the possibilities of what diseases may be treated with embolic technique.

Figure 25A:
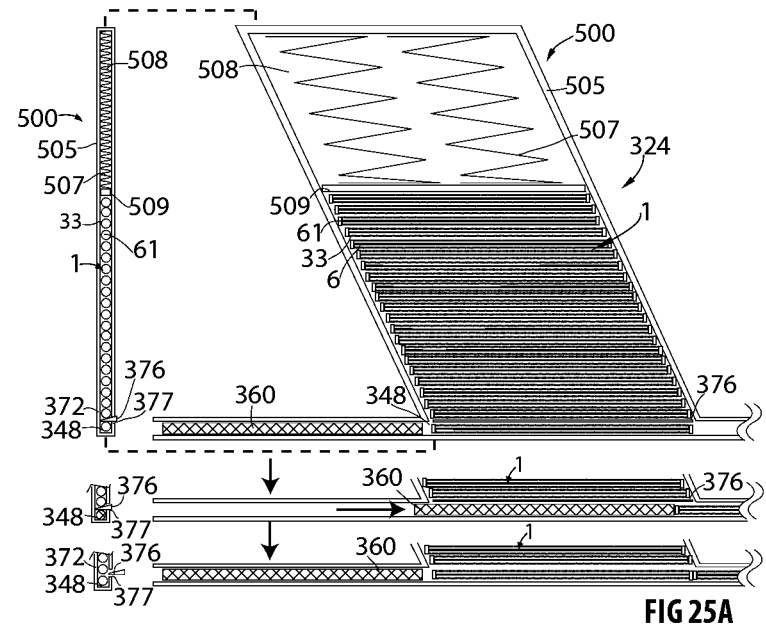
FIGS. 25A-C depict embodiments of a novel embolic delivery system using a non-revolving mechanism to provide rapid sequential delivery of a plurality of embolic agents of short or medium length as described herein.

FIG. 25A include views of an embolic delivery device 324 that can deliver multiple embolic agents 1 in rapid sequence, without introducer sleeves. In this embodiment, the embolic agents 1 are composed of a helical wire 33 with end pieces 61 tethered to a central wire 6, are substantially straight and cylindrical in their resting state, so they do not need to be constrained inside an introducer sleeve to be easily handled in a straight configuration. The embolic agents 1 are stored in an embolic containment apparatus 500 consisting of a wall 505, and a hollow delivery channel 508 where the embolic agents 1 reside and pass towards the feeder chute 348 of the embolic delivery device 324. The embolic agents 1 feed to the feeder chute 348 by an extension spring 507 in the embolic containment apparatus 500 which presses down on a plate 509 as shown, said plate 509 being slidably mounted within the delivery channel 508 so that it may incrementally move towards the feeder chute 348 of the embolic delivery system 324. In the second drawing of the sequence, a substantially cylindrical piston 360 of the embolic delivery system 324 is moved forward by a mechanical linkage (not depicted here) or by the operator's hand motions, to push the embolic agent 1 within the feeder chute 348 forward, to a connection between the embolic delivery system 324 and introducer catheter 200 (not shown) or intermediate elements as described in this invention. Once the piston 360 is withdrawn to its original position as seen in the third drawing of the sequence, another embolic agent 1 is allowed to fill the now empty space in the feeder chute 348, and the cycle may be repeated. Also shown is a movable retainer 376, which is a long, narrow rigid plate. It is shown in the top drawing positioned over the embolic agent 1 in the feeder chute 348. It functions to more precisely align the embolic agent 1 in the feeder chute 348 for smooth forward motion beyond the feeder chute 348, and to maintain the semi-rigid or flexible embolic agent 1 in a very straight configuration within the feeder chute 348 so that forward motion of the piston 360 translates well as forward motion of the embolic agent 1. In the second drawing in the sequence, the movable retainer 376 is in same position as the piston 360 has been advanced forward, pushing embolic agent 1. In the third drawing, the movable retainer 376 has retracted outwards through the opening 377 in the wall 372 of the embolic delivery system 324 just above the feeder chute 348. This allows the next embolic agent 1 to drop into the feeder chute 348 as shown, ready for the next cycle to be repeated. The mechanical driver for the motion of the movable retainer 376 is not depicted in this simple figure, but may use conventional motion systems widely known in the art, and importantly, may be linked with the motion of the piston 360 so that withdrawing the piston also results in the outward motion of the movable retainer 376 without the need for additional manipulations by the operator.

It is well known in the art that conventional wire-coil type embolic agents do not always serve well in pushing other similar embolic agents through a catheter. I.e., they are usually pushed through one at a time by a pusher element until the embolic agent is completely extruded from the introducer catheter. It is known that attempts to push them in series may result in jamming within the catheter when the proximal portion of one agent overlaps with the distal end of the other. However in FIG. 25A, each embolic agent 1 serves to push the former one through the introducer catheter. They must therefore be designed to accomplish this task without failing as described, i.e., the ends must not overlap, and a smooth flow of agents must occur. To this end, such a device will require embolic agents as described elsewhere herein with features to permit serial delivery. In this embodiment, the end pieces 61 are disc shaped instead of the conventional rounded configuration as seen in FIG. 9D. Many different types of embolic agent 1 may be used with this embolic delivery system 324. They may have microfibers attached to promote thrombogenicity. They may be composed of polymer, or be similar to shown in FIGS. 3A-B where agents particularly suited for serial delivery are shown.

Figure 25B:
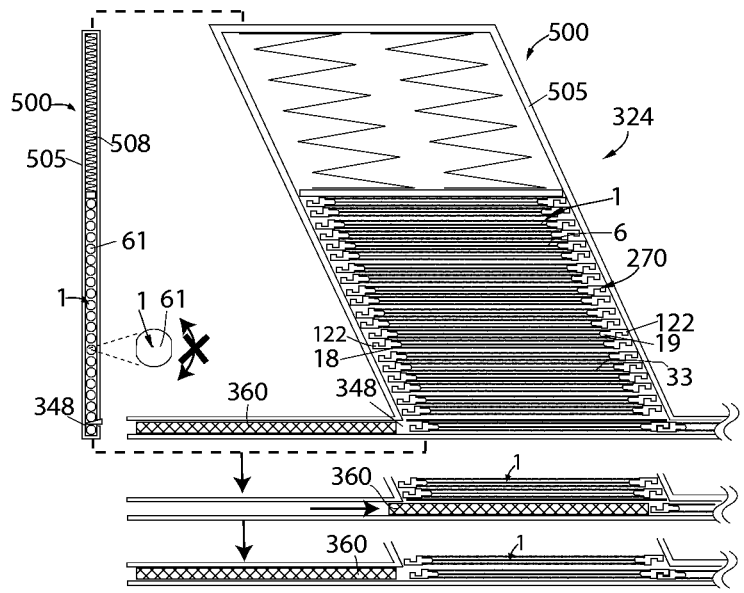

FIG. 25B is a variation of the embodiment shown in FIG. 25A that adds functionality of detachability and added control. The major difference being the use of embolic agent 1 that has traction elements 270 consisting of bidirectional locking elements 122 as described elsewhere herein. Otherwise there are no substantial differences in the embolic delivery system 1 or embolic containment apparatus 500 from FIG. 25A. In FIG. 25B, when the embolic agent 1 falls or is pushed into the feeder chute 348, its bidirectional locking element 122 automatically engages with the bidirectional locking element 122 of the embolic agent 1 preceding it. The bidirectional locking element 122 on the distal end 19 of the embolic agent 1 is oriented as a mirror image with the bidirectional locking element 122 on the proximal end 18, so they engage as shown. In order to orient them for proper matching, rotation of the embolic agents 1 around their long axes is prevented while they are still within the embolic delivery system 324, as indicated by the rotational arrow stricken with an "X". This is accomplished in this example by altering the cross-sectional shape of the embolic agent 1 as shown, where it is not completely round, but instead has partially straight sides as seen best in the magnified image denoted by the dashed lines. The walls 505 of the delivery channel 508 and the feeder chute 348 are narrow enough to prevent rotation of the embolic agents 1 along their long axes, so they will maintain the same orientation that was given to them at the time of manufacture when they were loaded into the embolic containment apparatus 500. Once they are attached together, the embolic agents 1 will function as described in FIG. 8B permitting functions of detachability at the tip of the introducer catheter (not shown here), and ability of operator to advance or retract the series of attached embolic agents 1 by manipulation of the proximal embolic agents 1 in the operating field. By disconnecting the embolic delivery system 324 from the introducer catheter (not shown), manual control of the proximal embolic agents 1 may be achieved. They may be retracted, or manually advanced using a conventional pusher element (not shown) in a conventional manner.

Figure 25C:
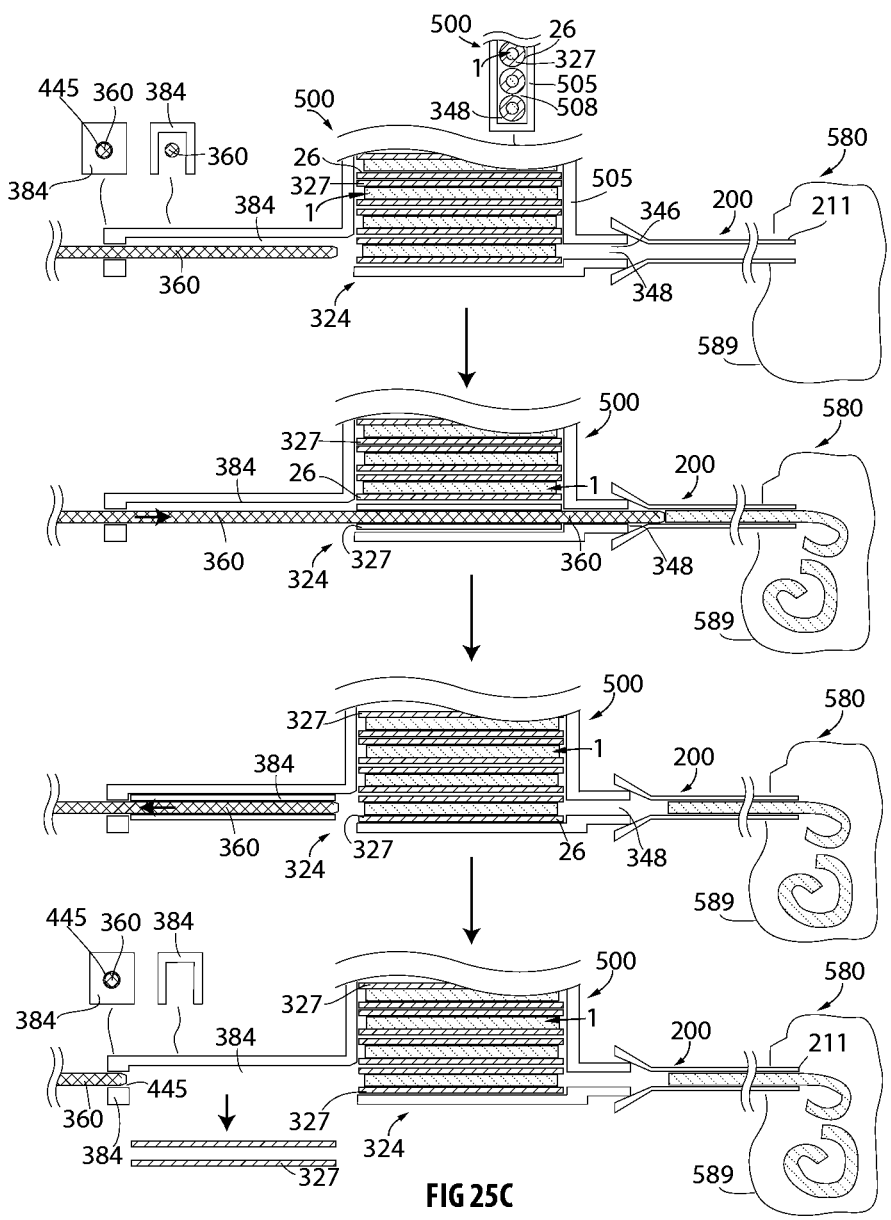

FIG. 25C is a sequential set of two dimensional longitudinal sections, with cross sections in three locations designated by the lines corresponding to the top drawing. It depicts an embolic delivery system 324 that delivers, in a rapidly repeating manner, numerous separate embolic agents 1 that may be relatively short in total length, and that may be straight when inside an introducer catheter 200 or introducer sleeve 327, and may assume any of the shapes described elsewhere herein when in their free state or when unconstrained in the target tissues 589 in the body 580. A major difference with FIGS. 25A-B is that it can work with embolic agents 1 within introducer sleeves 327 as a loaded cartridge 26, which may facilitate serial delivery of embolic agents 1 with memory for shapes other than linear, such as loops or coils, since they will be constrained within their introducer sleeves 327 or introducer catheter 200 or other elements described in this invention which maintain embolic agents 1 in straight configurations until deployed into the target tissues 589. Beginning from the top drawing, the embolic containment apparatus 500 has a wall 505 that houses numerous embolic agents 1, each of which is contained in its own introducer sleeve 327, the assembled combination being called a cartridge 26. The walls 505 form a delivery channel 508 that the embolic agents 1 travel down incrementally towards the feeder chute 348 of the embolic delivery system 324. The cartridges 26 are stacked in the embolic containment apparatus 500 and delivered to the feeder chute 348 by mechanisms not depicted here, but were represented in FIGS. 25A-B. In FIG. 25C, in the top drawing, the system has not yet commenced its action. A cartridge 26 is situated in the feeder chute 348, and the piston 360 is partially retracted. An introducer catheter 200 is attached to the embolic delivery system 324 at its outlet port 346, and the tip of the introducer catheter 211 is in the target tissues 589. The piston 360 is capable of only linear motion using conventional mechanical linkages not shown here.

Progressing to the second drawing in FIG. 25C, the piston 360 has moved linearly forward, entering the introducer sleeve 327 which is too small to be pushed forward. The piston 360 is very slightly greater in diameter than the embolic agent 1, and approximately the same as the inner diameter of the hollow introducer sleeve 327. Therefore, the described action pushes the embolic agent 1 through the feeder chute 348 into the introducer catheter 200 as shown. In this drawing, several cycles of action have already been performed and the embolic agents 1, in series, have begun to deploy into the target tissues 589 as shown. In the third drawing of FIG. 25C, the piston 360 has partially retracted, pulling the introducer sleeve 327 backward out of the feeder chute 348 due to friction between the piston 360 and the introducer sleeve 327. The feeder chute 348 received a new loaded cartridge 26. In the fourth drawing, the piston 360 has retracted further, resulting in the introducer sleeve 327 shearing off of the piston 360 due to the small hole 445 in the housing 384 whose diameter is less than that of the outer diameter of the introducer sleeve 327. The used introducer sleeve 327 falls away into a receptacle (not shown) or the environment as waste. The cycle may be repeated, resulting in more embolic agents 1 deployed in target tissues 589. When the desired endpoint of embolization has been achieved, any residual embolic agent 1 still remaining in the introducer catheter 200 may simply be removed by withdrawing the catheter with the embolic agents 1 still inside, or by the passage of a long pusher element (not shown) through the entire introducer catheter 200 to push all embolic agents 1 still contained within it, into the tissues beyond its tip 211. Any embolic agents 1 that can't or shouldn't be passed may then be withdrawn with the introducer catheter 200, which may be detached from the embolic delivery system 324. If the introducer catheter 200 is a microcatheter which is co-axially passed through a larger introducer catheter as commonly practiced in the art, then catheter access to the target tissues 589 is not lost even upon withdrawal of the introducer catheter 200 and embolic agents 1 within.

FIGS. 26A-G depict several varieties of embolic detachment tools 160 that may be used by the operator in this invention to modify the embolic agent as needed intraprocedurally. FIG. 26A is a perspective view which schematically depicts a wire-stripper 177 that may be applied to the embolic agent 1 as shown to mechanically strip away a short segment of capsule 43, leaving a bare area 39 of wire 6. It has a hinge 178 on one side to allow opening and closing. FIG. 26B is a cut-away view showing the internal workings of a wire stripper 177 which includes a sharp round blade 162 that can open and close with the housing 179. FIG. 26C is a cut-away view showing embolic detachment tool 160 with a sanding element 180 which is round in cross section, that may be squeezed around the embolic agent 1 by the housing 179, and used to abrade the surface of the embolic agent to remove capsule or coating from it. FIG. 26D is a frontal view that depicts a heating element 181 within the housing 179, which may be applied in contact with the embolic agent to melt away material of low melting point, such as easily removable seal as described in a variation of FIG. 6J. FIG. 26E is a perspective view of a wire loop heater 182, which resembles a conventional item in operating suites sometimes called cautery pens. The wire 174 becomes hot and may be used to manually burn off a small segment of capsule or coating from an embolic agent, leaving the metallic components intact. FIG. 26F shows a tool with electrodes 183 attached to a high voltage electrical power source 176, which may be pulsed, causing sparks to burn through the dielectric coating or capsule of some embolic agents, creating an exposed bare area of wire. FIG. 26G is a cut-away and frontal view of a dissolution chamber 184. Its housing 179 has a hub 186 where a syringe may attach to inject liquid into a fluid-tight chamber 184 formed by the housing 179 and two gaskets 185 which may open and close with the housing 179 around the embolic agent. Filling of the chamber and expulsion of air is facilitated by releasing or replacing the vent cap 187 onto the vent 188 in the housing 179. Solvent in the chamber 184, a small segment of embolic agent 1 may result in dissolution of the enclosed segment of capsule.

Figure 27A:
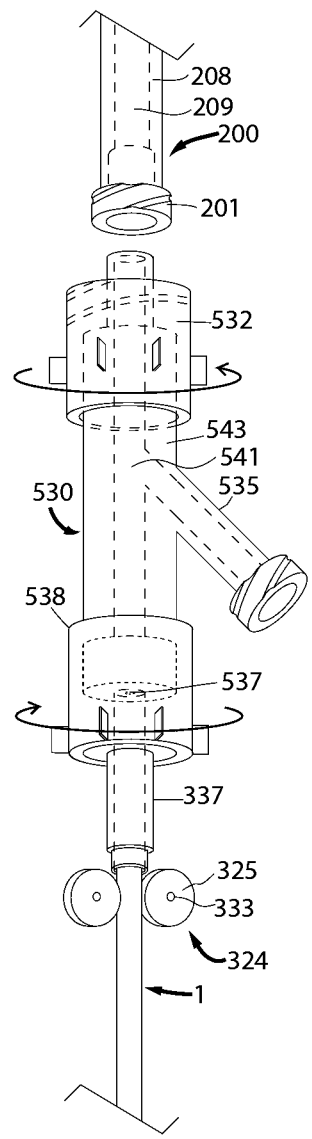
FIG. 27A-B depict embodiments of introducer elements and adaptors which may be used in connection with invention disclosed herein.
Figure 27B:
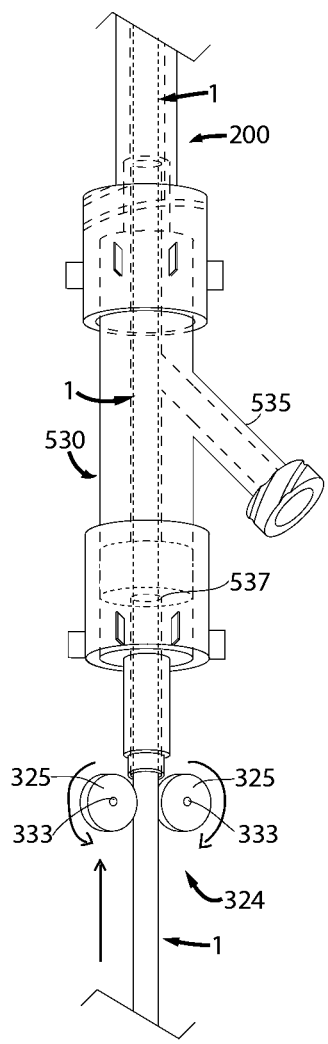

Details of an example of the interfaces between components such as embolic delivery systems 324 using feeder rollers 325 rotating on shafts 333, side port adaptors 530, and introducer catheters 200 are shown in 3 frontal views in FIGS. 27A-B. FIG. 27A shows a modified side port adaptor 530 with a rotating locking hub 532 that can connect detachably with the hub 201 of an introducer catheter 200 that has a wall 208 and lumen 209. The side port adaptor 530 has a wall 543 and lumen 541 and a side port 535, as well as an internal constricting O-ring 537 that is controlled by a rotating O-ring constrictor 538 accessible to the operator. There is an introducer element 347 which is a tube-like extension that accepts the embolic agent 1 and may have two different outer diameters as shown, to provide a small outer diameter that allows it to be positioned in very close proximity to the feeder rollers 325 that rotate on their shafts, with said close positioning serving to prevent kinking or buckling of the embolic agent 1. Discussion of introducer element and embodiments were shown also in FIGS. 16D-G. The O-ring constrictor 538 is a conventional element which is used in this novel device here to maintain fluid-tight seal when desired, while being adjustable to find the best balance between seal and friction of sufficiently small degree against the embolic agent 1 so as to permit its useful motion through the system. Here it is shown constricted, without embolic agent inside its core, such as might occur when the system is being flushed with fluid through the side port 535. FIG. 27B shows the same device with the introducer catheter 200 attached, the O-ring 537 opened, and the embolic agent 1 moving forward through the system as indicated by the solid arrow and the curved arrows showing feeder roller 325 rotation. This system represents a relatively simple and economical system from manufacturing aspect that nevertheless provides many of the useful aspects of the invention including ability to deliver very long embolic agent 1, flush the system, and detach members for introduction of other elements or performance of various other maneuvers commonly performed in practice. In one contemplated embodiment, a hemostatic valve (not shown) may be substituted for the O-ring constrictor 538. Whichever type of seal is used, it is advantageous to be capable of withstanding the hydraulic force of forceful injection of fluid into the side port 535 without allowing backflow.

FIGS. 28A-D details a concept of coil shape utilizing the thermal memory properties of nickel titanium alloy, or nitinol, which can be used to facilitate the objectives of this invention, with regard to the feeding of the embolic agent 1 through the system, which favors a straight filamentous shape, while also having the benefits of more complex geometries as described herein once the embolic agent 1 is within the body cavity. Nitinol may be formulated to be relatively straight or with very weak shape memory at room temperature, but resume a more robust shape memory, of geometry determined at manufacture, at body temperature. This remarkable property has been used with success for a commercial intravenous filter that passed through a catheter as a single wire and formed a complex functional shape in the body. FIG. 28A includes sequential frontal views of an embolic agent 1 with a Nitinol wire 6 in a capsule 43 of polymer, which is substantially straight at room temperature and when constrained within an introducer catheter (not shown), but when introduced into the warm body (not shown), as indicated by the arrow, resumes its pre-determined memory shape, in this case a series of loops. This embolic agent 1 may be modified by the operator and undergo electrolytic detachment as described herein. Nearly any variation of embolic agent 1 composed of an encapsulated wire described herein could be made using Nitinol substituting for stainless steel. The Nitinol will not usually be used to serve the functions often described for metals such as platinum or gold as markers or electrical contacts. FIG. 28B includes sequential frontal views depicting a variation whereby a small diameter strand of stainless steel wire 6 is used as described previously, to permit electrolytic detachment. It is centrally located in the capsule 43. A second wire 62, composed of Nitinol, is eccentrically located in the capsule and never touches the central wire 6. The arrow indicates modification by the operator using embolic detachment tools (not shown) which removes a portion of the capsule 43 as previously described, creating a bare portion 39 of wire 6, and also cut the eccentric second wire 62 of Nitinol. Electrolytic detachment or mechanical detachment may occur using means described in this invention. In the body cavity, the second wire 62 of Nitinol provides the shape memory function described above, causing the embolic agent 1 to be looped at body temperature as shown in FIG. 28A. FIG. 28C includes sequential frontal views showing the concept being applied to a helical wire 33 made of Nitinol. The embolic agent 1 is substantially straight or with weak shape memory at room temperature on the left, but as shown by the arrow, assumes a looped memory shape once deployed in the body. FIG. 28D includes sequential views and frontal view showing an embolic agent 1 composed of a helical wire 33 which need not have shape memory, with a Nitinol wire 6 centrally attached at proximal end 18 and distal end 19 of the embolic agent 1, and which is substantially straight at room temperature and assumes a memory shape at body temperature, creating loops as seen on the right. In other contemplated embodiments, any of the embolic agents in FIGS. 28A-D may also combine other described aspects of this invention, and may have a variety of possible memory shapes they assume.

Various embodiments of the invention disclosed herein are further described as follows.

An embolic agent apparatus, comprising an embolic agent with at least two or more segments, each segment of the embolic agent having a proximal end, a middle portion, and a distal end; and, a detachment element separating each embolic agent segment operable to provide a detachment site selectable by the operator. The apparatus as above further comprising a linking element operable to connect the proximal end of the embolic agent to a detachment element associated with the distal end of a pusher element operable to allow the operator to orient the embolic agent with bi-directional motion. The apparatus of as above further comprising a linking element operable to link the proximal end of the embolic agent with the distal end of the detachment element operable to advance the detachment site of the embolic agent intracorporeally.

The apparatus as above wherein the embolic agent includes at least one node located between the distal and proximate ends of at least one segment of the embolic agent. The apparatus as above wherein the embolic agent includes at least one notch located between the distal and proximate ends of at least one segment of the embolic agent. The apparatus as above wherein the detachment element is selected from the group consisting of a mechanical detachment element, an electrolytic detachment element, a bi-directional locking element, a heat sensitive adhesive, a heat deformable metal, a corrodible metal, a dissolvable metal, and a dissolvable polymer. The apparatus as above wherein the embolic agent is selected from the group consisting of a monofilament, a multifilament, a helical wire, an encapsulated wire, a coated helical wire, a chemically dissolvable polymer, an electrolytically corrodible wire, a polymer, a metal wire, a polyglycolide, a polylactide, a poly L-lactide, a poly DL-lactide, a poly-caprolactone, and a copolymer. The apparatus as above wherein at least one segment of the embolic agent includes a removable seal. The apparatus as above wherein the embolic agent further comprises a wire within the body of the embolic agent capable of conducting electrical current. The apparatus as above wherein the embolic agent further comprises a traction element located on a surface of the embolic agent. The apparatus as above further comprising a linking element with an attachment pin and the linking element positioned between the embolic agent and the detachment element. The apparatus as above wherein the linking element includes a traction element applied to the attachment pin wherein the traction element is selected from the group consisting of a barb, a ridge, an attachment pin, a curved attachment pin, a frictional roughness, and a threaded connection. The apparatus as above wherein the detachment element is one selected from the group consisting of an adhesive, a sealant, a chemically corrodible polymer, an electrolytically corrodible metal, a polymer, polyglycolide, a polylactide, a poly L-lactide, a poly DL-lactide, a poly-caprolactone, and a copolymer. The apparatus as above wherein the detachment element or embolic agent is modified with an embolic detachment tool selected from the group consisting of a spark generator, a heat gun, a sander, a shaper, a wire stripper, a dissolution chamber, a swage tool, an adhesive, a heat chamber, a scissor or a blade. The apparatus as above wherein the comprising a catheter for guiding the embolic agent to the target tissue wherein the catheter includes an electrical current conducting wire secured within the wall of the catheter up to the catheter tip, operable to allow the operator to place the tip of the catheter at the desired detachment element and electrolytically detach the embolic agent intracorporeally. The apparatus as above wherein the comprising a catheter for guiding the embolic agent to the target tissue wherein the catheter delivers a solvent to the selected detachment element, operable to allow the operator to place the tip of the catheter at the desired detachment element and chemically detach the embolic agent intracorporeally.

A catheter apparatus comprising a lumen and a wall forming a tube structure with a proximal end, a middle portion and a distal end; at least one wire encapsulated within the wall portion capable of conducting electricity; and, a contact attached to the proximal end of the tube and a contact attached to the distal end of the tube so as to provide electrical energy to an embolic agent, a detachment element or the local ionic medium.

An embolic delivery system, comprising a drive pulley attached to a drive shaft, a timing pulley and a feeder roller attached to a pulley shaft; a catheter or embolic agent oriented between at least two feeder rollers; and, a timing belt in mechanical communication with the drive pulley and timing pulley operable to bi-directionally move the catheter or embolic agent toward a target tissue.

An embolic delivery system, comprising a drive pulley attached to a drive shaft, a timing pulley and a feeder belt attached to a pulley shaft; a catheter or embolic agent oriented between at least two feeder belts; and, a timing belt in mechanical communication with the drive pulley and timing pulley operable to bi-directionally move the catheter or embolic agent toward a target tissue.

The apparatus as above wherein at least one feeder roller includes a groove around its circumference to assist in feeding and providing traction between the feeder roller and the catheter or embolic agent.

An embolic delivery system, comprising a rotatable cylinder with at least one feeder chute is on the surface of the cylinder with an inlet port for accepting an embolic agent; and, a concentric wall opposing the cylinder surface operable to retain the embolic agent inside the feeder chute as the cylinder is rotated.

A method for implanting an embolic agent, comprising inserting an embolic agent securably linked to a detachment element into an introducer catheter; propelling the embolic agent to the target tissue; and, detaching the embolic agent at the target tissue. The method as above further comprising securing a pusher element and the embolic agent with a traction element. The method as above further comprising propelling the embolic agent with a mechanical embolic delivery system. The method as above further comprising propelling the embolic agent with a hydraulic embolic delivery system. The method as above of further comprising modifying the embolic agent with an embolic detachment tool. The method as above wherein the embolic detachment tool is selected from the group consisting of a spark generator, a heat gun, a sander, a shaper, a wire stripper, a dissolution chamber, a swage tool, an adhesive, a heat chamber, a scissor or a blade.

An embolic delivery apparatus, comprising a cylindrical piston operable to push an embolic agent along a track; a trolley in mechanical communication with the piston via a rack, a pinion, a pinion shaft, a reel, a tether, a tether guide, a clutch, a clutch arm, a spring and a spring mount operable to translate the bi-directional motion of the trolley by the operator's hand movement.

An embolic agent apparatus, comprising a non-segmented variable length embolic agent with a proximal end, a middle portion, and a distal end; and, at least one detachment element located continuously along the length of the embolic agent at which the operator may select the detachment site at any location along the length of the embolic agent.

An embolic agent apparatus, comprising a thermally reactive wire incorporated into an embolic agent wherein the thermal wire includes shape memory such that the embolic agent is substantially linear in the extracorporeal environment and upon introduction into the intracorporeal environment at elevated temperature the embolic agent assumes a complex memory shape. An embolic delivery apparatus, comprising a cam gripper providing a grip around the circumference of the embolic agent in the forward linear direction for advancement of the embolic agent and releasing the grip on the embolic agent when the cam gripper is moving in the opposite linear direction. An embolic agent apparatus, comprising an embolic agent with a distal end, a middle portion, and a proximal end, including a larger surface contact area on the proximal end and the distal end of the embolic agent providing for axial movement of the embolic agent.

While the invention has been particularly shown and described with reference to a various embodiments, it will be understood by those skilled in the art that various changes in form and detail may be made therein without departing from the spirit and scope of the invention.

I claim:

1. An embolic agent apparatus adapted for use with an electrical system having a first polarity and an opposite polarity, the embolic agent apparatus comprising:
    an embolic agent with at least two or more segments, each segment of the embolic agent having a proximal end, a middle portion, and a distal end;
    a detachment element containing an electrolytically corrodible metal separating each embolic agent segment providing a plurality of electrolytic detachment sites along the embolic agent; and
    a catheter for guiding the embolic agent to the target tissue, wherein the catheter defines a lumen adapted to pass the embolic agent, wherein the catheter includes an opposite polarity electrical current conducting wire secured within a wall of the catheter up to an opposite polarity electrical contact located near the distal end of the catheter but spaced radially outside the lumen, the electrical contact operable to allow the operator to position a particular detachment element near the opposite polarity electrical contact without the opposite polarity electrical contact directly contacting any part of the embolic agent and electrolytically detach the embolic agent intracorporeally.

2. The embolic agent apparatus of claim 1, further comprising:
    a drive pulley attached to a drive shaft, a timing pulley and a feeder roller attached to a pulley shaft;
    wherein the embolic agent is oriented between at least two feeder rollers; and,
    a timing belt in mechanical communication with the drive pulley and timing pulley operable to bi-directionally move the embolic agent toward a target tissue.

3. The apparatus of claim 2 wherein at least one feeder roller includes a groove around its circumference to assist in feeding and providing traction between the feeder roller and the catheter or embolic agent.

4. The embolic agent apparatus of claim 1, further comprising:
    a drive pulley attached to a drive shaft, a timing pulley and a feeder belt attached to a pulley shaft;

wherein the embolic agent is oriented between at least two feeder belts; and, a timing belt in mechanical communication with the drive pulley and timing pulley operable to bi-directionally move the embolic agent toward a target tissue.

5. The embolic agent apparatus of claim 1, further comprising:

a cam gripper providing a grip around the circumference of the embolic agent in the forward linear direction for advancement of the embolic agent and releasing the grip on the embolic agent when the cam gripper is moving in the opposite linear direction.

6. The apparatus of claim 1, wherein the embolic agent is selected from the group consisting of a monofilament, a multifilament, a helical wire, an encapsulated wire, a coated helical wire, a chemically dissolvable polymer, an electrolytically corrodible wire, a polymer, a metal wire, a polyglycolide, a polylactide, a poly L-lactide, a poly DL-lactide, a poly-caprolactone, and a copolymer.

7. The apparatus of claim 1, wherein the embolic agent further comprises:

a wire within the body of the embolic agent, wherein the wire has a contiguous length capable of conducting electrical current, wherein the contiguous length of the wire is longer than a length between a proximal end of the catheter and the opposite polarity electrical contact.

8. The apparatus of claim 7, wherein the contiguous length of wire is encapsulated in an electrical insulator.

9. The apparatus of claim 8, wherein the electrical insulator further comprises a plurality of seals that can be selectively removed to bare portions of the contiguous length of wire.

10. The apparatus of claim 1 wherein the catheter further comprises a first polarity electrical current conducting wire secured within the wall of the catheter and electrically coupled to a first polarity electrical contact located near but spaced apart from the first opposite polarity electrical contact, wherein the first polarity electrical contact is adapted to physically contact the embolic agent.

11. The apparatus of claim 10, wherein the opposite polarity electrical contact is adapted to contact an ionic fluid such as blood or saline present in the catheter when the embolic agent is guided through the catheter to the target tissue facilitating selectively electrolytically corroding the detachment element by selectively applying an electrical current that passes through the first polarity and opposite polarity electrical contacts and the detachment element.

12. The method of claim 11, further comprising, before applying the first polarity electric current to the first polarity wire, exposing the electrolytically corrodible detachment element.

13. The apparatus of claim 10, wherein each segment of the embolic agent further comprises a conductive contact point adapted to receive and conduct a first polarity electrical current from the first polarity electrical contact to the electrolytically corrodible metal of one of the plurality of electrolytic detachment sites.

14. The apparatus of claim 10, wherein the embolic agent further comprises:

a plurality of embolic agent contacts each electrically coupled to one of the plurality of electrolytic detachment sites, each embolic agent contact adapted to physically contact the first polarity electrical contact when adjacent, wherein the plurality of electrolytic detachment sites are electrically insulated from each other.

15. The apparatus of claim 1, wherein the embolic agent further comprises:

a contiguous conducting wire within the body of the embolic agent running from a proximal end of the embolic agent to a distal end of the embolic agent.

16. A method for implanting an embolic agent using an electrical system having a first polarity and an opposite polarity, the method comprising:

inserting a continuous embolic agent having a plurality of segments separated by electrolytically corrodible detachment elements defining multiple electrolytic detachment sites on the embolic agent through a lumen of a catheter positioned in a target tissue;

propelling the continuous embolic agent into the target tissue until a desired length of embolic agent is inserted into the target tissue;

selecting a particular electrolytic detachment site to detach;

positioning the selected electrolytic detachment site near an opposite polarity electrical contact located near a distal end of the catheter, wherein the opposite polarity electrical contact is spaced apart from the lumen and does not physically contact the embolic agent;

once the desired length of embolic agent is inserted into the target tissue, applying an electric current to the selected electrolytic detachment site whereby the electric current flows through an ionic fluid, the opposite polarity electrical contact and a opposite polarity electrical current conducting wire secured within the wall of the catheter that is electrically coupled to the opposite polarity electrical contact thereby corroding the selected electrolytic detachment site and truncating the embolic agent to the desired length intracorporeally.

17. The method of claim 16 further comprising:

modifying the detachment element or embolic agent with an embolic detachment tool.

18. The method of claim 17 wherein the embolic detachment tool is selected from the group consisting of a spark generator, a heat gun, a sander, a shaper, a wire stripper, a dissolution chamber, a swage tool, an adhesive, a heat chamber, a scissor or a blade.

19. The method of claim 16, further comprising:

applying the electric current to a first polarity electrical current conducting wire secured within the wall of the catheter that is electrically coupled to a first polarity electrical contact that is located near but is spaced apart from the first polarity electrical contact, wherein the first polarity electrical contact is adapted to physically contact the embolic agent.

20. The method of claim 16, wherein the electrolytically corrodible detachment elements are metallic.

21. The method of claim 16, further comprising applying the electric current to a first polarity wire located within the embolic agent, wherein the first polarity wire has a contiguous length longer than a length between a proximal end of the catheter and the opposite polarity electrical contact, the wire adapted to conduct electrical energy and wherein the first polarity electric current is applied to a portion of the first polarity wire positioned outside a proximal end of the catheter.

22. The method of claim 21, further comprising, before applying the first polarity electric current to the first polarity wire, exposing the portion of the first polarity wire positioned outside the proximal end of the catheter.

23. A catheter apparatus adapted for use with an electrical system having a first polarity and an opposite polarity, the catheter apparatus also adapted for use with an embolic agent having an electrolytically corrodible detachment element, the catheter comprising: a tubular structure with an outer surface and an inner surface defining a lumen, the tubular structure having a proximal end, a middle portion and a distal end; an opposite polarity electrically conductive wire encapsulated within the tubular structure; an opposite polarity electrical contact electrically coupled to the opposite polarity wire and positioned near the distal end of the tubular structure but spaced radially outside the lumen, the opposite polarity electrical contact adapted to conduct electrical energy from an ionic fluid positioned between the electrolytically corrodible detachment element and the opposite polarity electrical contact; a first polarity electrically conductive wire encapsulated within the tubular structure; and a first polarity electrical contact electrically coupled to the first polarity wire and located inside the tubular structure near the distal end of the tubular structure, wherein the first polarity electrical contact is adapted to contact the embolic agent.

24. The catheter apparatus of claim 23, wherein the opposite polarity electrical contact is recessed within the tubular structure and spaced apart from the inner surface of the tubular structure.

25. The catheter apparatus of claim 23, wherein the first polarity electrical contact is substantially flush with the inner surface of the tubular structure.

26. The catheter apparatus of claim 23, wherein the first polarity electrical contact is positioned on the opposite side of the tubular structure relative to the opposite polarity electrical contact.

27. The catheter apparatus of claim 23, further comprising a source of direct current having first polarity and opposite polarity that can be selectively electrically coupled to the first polarity and opposite polarity wires.

28. The catheter apparatus of claim 23, wherein the first polarity electrical contact protrudes internally with respect to the inner surface of the tubular structure.

29. The catheter apparatus of claim 23, wherein the embolic agent comprises a first polarity wire that is located within the embolic agent having a contiguous conductive length longer than a length between a proximal end of the tubular structure and the opposite polarity electrical contact to conduct first polarity electrical energy to the electrolytically corrodible detachment element.

* * * * *